United States Patent
Uesaka et al.

(10) Patent No.: US 7,928,098 B2
(45) Date of Patent: Apr. 19, 2011

(54) THERAPEUTIC AND/OR PREVENTIVE AGENTS FOR A SLEEP DISORDER

(75) Inventors: Noriaki Uesaka, Sunto-gun (JP); Shunji Ichikawa, Tagata-gun (JP); Takao Nakajima, Fujisawa (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 560 days.

(21) Appl. No.: 11/997,585

(22) PCT Filed: Aug. 2, 2006

(86) PCT No.: PCT/JP2006/315328
§ 371 (c)(1),
(2), (4) Date: Feb. 1, 2008

(87) PCT Pub. No.: WO2007/015528
PCT Pub. Date: Feb. 8, 2007

(65) Prior Publication Data
US 2010/0152162 A1    Jun. 17, 2010

(30) Foreign Application Priority Data
Aug. 2, 2005  (JP) .................. 2005-223547

(51) Int. Cl.
| | |
|---|---|
| *A61K 31/555* | (2006.01) |
| *A61K 31/54* | (2006.01) |
| *A61K 31/535* | (2006.01) |
| *A61K 31/4965* | (2006.01) |
| *A61K 31/44* | (2006.01) |
| *A61K 31/425* | (2006.01) |

(52) U.S. Cl. ............... 514/211.15; 514/227; 514/232; 514/236; 514/255.05; 514/333; 514/370

(58) Field of Classification Search ........... 514/211.15, 514/227, 232, 236, 255.05, 333, 370
See application file for complete search history.

(56) References Cited

U.S. PATENT DOCUMENTS

| | | |
|---|---|---|
| 6,436,966 B1 | 8/2002 | Ohkawa et al. |
| 6,620,825 B1 | 9/2003 | Ohkawa et al. |
| 7,101,899 B1 | 9/2006 | Ohkawa et al. |
| 7,276,527 B2 | 10/2007 | Ohkawa et al. |
| 2004/0053973 A1 | 3/2004 | Ohkawa et al. |
| 2004/0053982 A1 | 3/2004 | Press et al. |
| 2004/0097526 A1 | 5/2004 | Gillespie et al. |
| 2005/0004134 A1 | 1/2005 | Tsutsumi et al. |
| 2006/0135566 A1 | 6/2006 | Ohkawa et al. |
| 2006/0154974 A1 | 7/2006 | Sams et al. |
| 2007/0105919 A1 | 5/2007 | Nakajima et al. |

FOREIGN PATENT DOCUMENTS

| | | |
|---|---|---|
| EP | 1 180 518 | 2/2002 |
| EP | 1 894 930 | 3/2008 |
| WO | 99/21555 | 5/1999 |
| WO | 99/64418 | 12/1999 |
| WO | 01/74811 | 10/2001 |
| WO | 02/79204 | 10/2002 |
| WO | 2005/063743 | 7/2005 |
| WO | 2006/032273 | 3/2006 |

OTHER PUBLICATIONS

Huang, et al., "Adenosine A2A, but not A1, receptors mediate the arousal effect of caffeine", Nature Neuroscience, vol. 8, No. 7 (2005) 858-59.

*Primary Examiner* — Raymond J Henley, III
(74) *Attorney, Agent, or Firm* — Fitzpatrick, Cella, Harper & Scinto

(57) ABSTRACT

The present invention provides a therapeutic and/or preventive agent for a sleep disorder comprising, as an active ingredient, a thiazole derivative represented by the general formula (I),

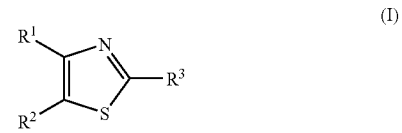

[wherein $R^1$ represents a five-membered aromatic heterocyclic group including at least one oxygen atom, or the like, $R^2$ represents halogen or the like, and $R^3$ represents $-NR^{10}R^{11}$ (wherein $R^{10}$ and $R^{11}$ may be the same or different, and each represents a hydrogen atom or the like), or the like] or a pharmaceutically acceptable salt thereof.

29 Claims, No Drawings

THERAPEUTIC AND/OR PREVENTIVE AGENTS FOR A SLEEP DISORDER

TECHNICAL FIELD

The present invention relates to therapeutic and/or preventive agents for a sleep disorder comprising a thiazole derivative or a pharmaceutically acceptable salt thereof.

BACKGROUND ART

Various classifications have been proposed for sleep disorders based on symptoms and causes, as given below for example.

(i) The Diagnostic Classification of Sleep and Arousal Disorders (DSCAD) was proposed in 1979 by the Association of Sleep Disorders Centers (ASDC) of the United States (*Sleep*, Vol. 2, p. 1-154, 1979). This is the earliest classification that grouped sleep disorders in view of "Disorders of Initiating and Maintaining Sleep (DIMS)".

DSCAD classifies sleep disorders broadly into nine categories: (1) psychophysiological insomnia; (2) sleep disorders associated with mental disorders; (3) sleep disorders associated with a regular use of drugs and alcohol; (4) insomnias associated with sleep-induced breathing disorders; (5) sleep disorders associated with nocturnal myoclonus and restless legs syndrome (RLS); (6) sleep disorders by other disorders, drugs, and environmental conditions; (7) childhood onset insomnias; (8) other types of insomnia; and (9) sleep abnormalities with no symptoms of insomnia. Each of these categories is based on the state of disorder.

(ii) The International Classification of Sleep Disorders (ICSD) was reported in 1990 by the American Sleep Disorders Association (ASDA) (ICSD-International classification of sleep disorders: Diagnostic and coding manual, Diagnostic Classification Steering Committee, Thorpy M J, Chairman. Rochester, Minn.: American Sleep Disorders Association, 1990), and was revised in 2000.

ICSD classifies sleep disorders broadly into four categories: (1) dyssomnias comprising disorders that are primarily disorders of sleep per se [for example, intrinsic sleep disorders such as narcolepsy, extrinsic sleep disorders, and circadian rhythm sleep disorders]; (2) parasomnias comprising disorders of abnormal behaviors that occur during sleep (also known as abnormal behavior during sleep) [arousal disorders, sleep-wake transition disorders, parasomnias usually associated with REM sleep, and other parasomnias]; (3) sleep disorders associated with medical/psychiatric disorders [sleep disorders associated with mental disorders, sleep disorders associated with neurologic disorders, and sleep disorders associated with other medical disorders]; and (4) proposed sleep disorders [for example, short sleeper, long sleeper, subwakefulness syndrome, and the like]. To this date, this classification includes about 90 categories of sleep disorders. Currently, further classifications have been made continuously based on etiology.

(iii) According to the International Classification of Diseases, Tenth Edition (ICD-10) (1992), which have been published by World Health Organization (WHO), sleep disorders are classified into (1) nonorganic sleep disorders (F51: for example, nonorganic insomnia, nonorganic hypersomnia, sleep walking, sleep terrors, nonorganic disorder of the sleep-wake schedule, nightmares, and the like); (2) sleep disorders [G47: for example, sleep apnoea, disorders of initiating and maintaining sleep (insomnias), disorders of excessive somnolence (hypersomnia), cataplexy, narcolepsy, cataplexy attacks, disorders of the sleep-wake schedule (such as irregular sleep pattern, sleep rhythm disorder, and delayed sleep phase syndrome), and the like]; (3) other respiratory conditions originating in the perinatal period (P28: for example, primary sleep apnoea of newborn, and the like); and (4) personal history of risk-factors, not elsewhere classified (Z91: for example, personal history of unhealthy sleep-wake schedule, and the like).

(iv) The Merck Manual, Seventeenth Edition, Section 14, Chapter 173 defines sleep disorders as disorders that affect the ability to fall asleep, stay asleep, or stay awake or that produce sleep-related abnormal behaviors, and the like. According to the Manual, sleep disorders are classified into the following symptoms: (1) insomnia (disorders falling asleep, difficulty staying asleep, or a disturbance in sleep patterns that causes inadequate sleep, and the like; for example, sleep-onset insomnia (difficulty falling asleep), early morning awakening, sleep-wake reversals, rebound insomnia, and the like); (2) hypersomnia (defined as a pathological increase of at least 25% in total sleeping time; for example, narcolepsy, sudden episode of sleep, and the like); (3) sleep apnoea syndromes, parasomnias (based on patients' chief complaints); and the like.

(v) In actual clinical treatment, sleep disorders are broadly classified into (1) insomnias, (2) hypersomnia, (3) parasomnias, and (4) disorders of sleep-wake schedule (corresponding to the circadian rhythm sleep disorders of ICSD). These classifications are made symptomatically based on patients' chief complaints, separately from the international classifications described above. Depending on etiology, a different medical treatment is given to each type of the sleep disorder.

Given a wide variety of symptoms and etiology of sleep disorders, a holistic approach has been proposed for the adjustment of sleep-wake schedules depending on symptoms and etiology, using non-drug therapy in combination with, for example, (i) for the symptoms of insomnia, drugs that help induce sleep or deepen sleep at nighttime, and the like (for example, sedative hypnotics, psychoactive drugs, antidepressants, and the like such as barbiturates and benzodiazepines), and (ii) for the symptoms of hypersomnia, drugs that have stimulant activity for daytime sleepiness (for example, such as psychoanaleptics).

Meanwhile, the stimulant activity of caffeine has been known for long. Recently, it has been reported that the stimulant activity of caffeine is regulated by adenosine $A_{2A}$ receptor [see Non-Patent Document 1].

Also, a thiazole derivative having antagonistic activity against adenosine $A_3$ receptor (see Patent Documents 1 and 2), a thiazole derivative having antagonistic activity against adenosine $A_{2B}$ receptor and adenosine $A_3$ receptor (see Patent Documents 3 and 4), a thiazole derivative having antagonistic activity against adenosine $A_1$ receptor and adenosine $A_{2A}$ receptor (see Patent Document 5), a thiazole derivative having antagonistic activity against adenosine $A_{2A}$ receptor (see Patent Documents 6 to 8), and the like are known.

Patent Document 1: WO 99/21555

Patent Document 2: Japanese Published Unexamined Patent Application No. 114779/2001

Patent Document 3: WO99/64418

Patent Document 4: US Published Patent Application No. 20040053982

Patent Document 5: WO03/039451

Patent Document 6: WO2005/039572

Patent Document 7: WO2005/063743

Patent Document 8: WO2006/032273

Non-Patent Document 1: Nature Neuroscience, p. 1, 2005

DISCLOSURE OF THE INVENTION

Problems to be Solved by the Invention

An object of the present invention is to provide therapeutic and/or preventive agents for a sleep disorder such as hypersomnia [for example, narcolepsy, recurrent hypersomnia (periodic hypersomnia), idiopathic hypersomnia, posttraumatic hypersomnia, a circadian rhythm sleep disorder, or the like], comprising a thiazole derivative or a pharmaceutically acceptable salt thereof, as an active ingredient, medicaments for improving daytime sleepiness, and the like.

Means for Solving the Problems (1) A therapeutic and/or preventive agent for a sleep disorder, which comprises a thiazole derivative represented by the general formula (I):

[Chemical Formula 1]

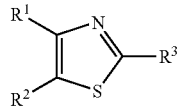

(I)

<wherein $R^1$ represents a substituted or unsubstituted five-membered aromatic heterocyclic group having at least one oxygen atom,
$R^2$ represents halogen, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, substituted or unsubstituted aromatic heterocyclic alkyl, —$NR^4R^5$ (wherein $R^4$ and $R^5$ may be the same or different, and each represents a hydrogen atom, substituted or unsubstituted lower alkyl, substituted or unsubstituted lower alkenyl, substituted or unsubstituted lower alkynyl, substituted or unsubstituted lower alkanoyl, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, or substituted or unsubstituted aromatic heterocyclic alkyl, or $R^4$ and $R^5$ are combined together with the adjacent nitrogen atom thereto to represent a substituted or unsubstituted nitrogen-containing heterocyclic group), —$COR^6$ (wherein $R^6$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, substituted or unsubstituted aromatic heterocyclic alkyl, —$NR^7R^8$ (wherein $R^7$ and $R^8$ may be the same or different, and each represents a hydrogen atom, substituted or unsubstituted lower alkyl, substituted or unsubstituted lower alkenyl, substituted or unsubstituted lower alkynyl, substituted or unsubstituted lower alkanoyl, substituted or unsubstituted lower alkoxy, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, or substituted or unsubstituted aromatic heterocyclic alkyl, or $R^7$ and $R^8$ are combined together with the adjacent nitrogen atom thereto to represent a substituted or unsubstituted nitrogen-containing heterocyclic group), or —$OR^9$ (wherein $R^9$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, or substituted or unsubstituted aromatic heterocyclic alkyl), and
$R^3$ represents —$NR^{10}R^{11}$ (wherein $R^{10}$ and $R^{11}$ may be the same or different, and each represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted aliphatic heterocyclic alkyl, substituted or unsubstituted aromatic heterocyclic alkyl, —$COR^{12}$ [wherein $R^{12}$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, substituted or unsubstituted aromatic heterocyclic alkyl, —$NR^{13}R^{14}$ (wherein $R^{13}$ and $R^{14}$ may be the same or different, and each represents a hydrogen atom, substituted or unsubstituted lower alkyl, substituted or unsubstituted lower alkenyl, substituted or unsubstituted lower alkynyl, substituted or unsubstituted lower alkanoyl, substituted or unsubstituted lower alkoxy, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, or substituted or unsubstituted aromatic heterocyclic alkyl, or $R^{13}$ and $R^{14}$ are combined together with the adjacent nitrogen atom thereto to represent a substituted or unsubstituted nitrogen-containing heterocyclic group), or —$OR^{15}$ (wherein $R^{15}$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, or substituted or unsubstituted aromatic heterocyclic alkyl)], or $R^{10}$ and $R^{11}$ are combined together with the adjacent nitrogen atom thereto to represent a substituted or unsubstituted nitrogen-containing heterocyclic group), —$CONHR^{16}$ (wherein $R^{16}$ represents a hydrogen atom, substituted or unsubstituted lower alkyl, substituted or unsubstituted lower alkenyl, substituted or unsubstituted lower alkynyl, substituted or unsubstituted lower alkanoyl, substituted or unsubstituted cycloalkyl, substituted or unsubstituted aryl, substituted or unsubstituted aralkyl, substituted or unsubstituted aroyl, a substituted or unsubstituted aliphatic heterocyclic group, a substituted or unsubstituted aromatic heterocyclic group, substituted or unsubstituted aliphatic heterocyclic alkyl, or substituted or unsubstituted aromatic heterocyclic alkyl), or the general formula (II)

[Chemical Formula 2]

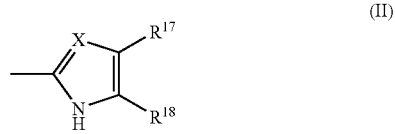

(II)

(wherein =X— represents =CH— or =N—, and $R^{17}$ and $R^{18}$ may be the same or different, and each represents a hydrogen atom, halogen, hydroxy, nitro, azido, amino, cyano, carboxy, formyl, substituted or unsubstituted lower alkyl, substituted or unsubstituted lower alkenyl, substituted or unsubstituted lower alkynyl, substituted or unsubstituted lower alkanoyl, substituted or unsubstituted lower alkoxy, substituted or unsubstituted cycloalkyl, substituted or unsubstituted lower alkylamino, substituted or unsubstituted di-(lower alkyl)amino, substituted or unsubstituted aryl, substituted or unsubstituted aralkyl, substituted or unsubstituted aroyl, a substituted or unsubstituted aliphatic heterocyclic group, a substituted or unsubstituted aromatic heterocyclic group, substituted or unsubstituted aliphatic heterocyclic alkyl, or substituted or unsubstituted aromatic heterocyclic alkyl, or $R^{17}$ and $R^{18}$ are combined together with the respectively adjacent two carbon atoms thereto to form a substituted or unsubstituted carbon ring or a substituted or unsubstituted heterocyclic ring)>,
or a pharmaceutically acceptable salt thereof, as an active ingredient.

(2). The therapeutic and/or preventive agent for a sleep disorder according to (1), wherein $R^1$ is substituted or unsubstituted furyl.

(3) The therapeutic and/or preventive agent for a sleep disorder according to (1) or (2), wherein $R^2$ is —$COR^6$ (wherein $R^6$ has the same meaning as defined above).

(4) The therapeutic and/or preventive agent for a sleep disorder according to (1) or (2), wherein $R^2$ is a substituted or unsubstituted aliphatic heterocyclic group.

(5) The therapeutic and/or preventive agent for a sleep disorder according to (1) or (2), wherein $R^2$ is a substituted or unsubstituted aromatic heterocyclic group.

(6) The therapeutic and/or preventive agent for a sleep disorder according to (3), wherein $R^6$ is substituted or unsubstituted cycloalkyl, substituted or unsubstituted aryl, a substituted or unsubstituted aromatic heterocyclic group, or a substituted or unsubstituted aliphatic heterocyclic group.

(7) The therapeutic and/or preventive agent for a sleep disorder according to (3), wherein $R^6$ is a substituted or unsubstituted aromatic heterocyclic group.

(8) The therapeutic and/or preventive agent for a sleep disorder according to (3), wherein $R^6$ is a substituted or unsubstituted aliphatic heterocyclic group.

(9) The therapeutic and/or preventive agent for a sleep disorder according to (3), wherein $R^6$ is a substituted or unsubstituted aliphatic heterocyclic group having at least one oxygen atom.

(10) The therapeutic and/or preventive agent for a sleep disorder according to (3), wherein $R^6$ is substituted or unsubstituted lower alkyl.

(11) The therapeutic and/or preventive agent for a sleep disorder according to any one of (1) to (10), wherein $R^3$ is —$NR^{10}R^{11}$ (wherein $R^{10}$ and $R^{11}$ have the same meanings as defined above, respectively).

(12) The therapeutic and/or preventive agent for a sleep disorder according to any one of (1) to (10), wherein $R^3$ is —$NHR^{11}$ (wherein $R^{11}$ has the same meaning as defined above).

(13) The therapeutic and/or preventive agent for a sleep disorder according to (11) or (12), wherein $R^{11}$ is —$COR^{12}$ (wherein $R^{12}$ has the same meaning as defined above).

(14) The therapeutic and/or preventive agent for a sleep disorder according to (13), wherein $R^{12}$ is substituted or unsubstituted aryl.

(15) The therapeutic and/or preventive agent for a sleep disorder according to (13), wherein $R^{12}$ is a substituted or unsubstituted aromatic heterocyclic group.

(16) The therapeutic and/or preventive agent for a sleep disorder according to (13), wherein $R^{12}$ is —$OR^{15}$ (wherein $R^{15}$ has the same meaning as defined above).

(17) The therapeutic and/or preventive agent for a sleep disorder according to (13), wherein $R^{12}$ is substituted or unsubstituted aromatic heterocyclic alkyl.

(18) The therapeutic and/or preventive agent for a sleep disorder according to (13), wherein $R^{12}$ is substituted or unsubstituted aliphatic heterocyclic alkyl.

(19) The therapeutic and/or preventive agent for a sleep disorder according to any one of (1) to (10), wherein $R^3$ is —$CONHR^{16}$ (wherein $R^{16}$ has the same meaning as defined above).

(20) The therapeutic and/or preventive agent for a sleep disorder according to any one of (1) to (10), wherein $R^3$ is the general formula (II)

[Chemical Formula 3]

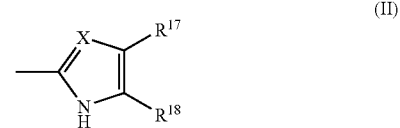

(II)

(wherein X, $R^{17}$, and $R^{18}$ have the same meanings as defined above, respectively).

(21) The therapeutic and/or preventive agent for a sleep disorder according to any one of (1) to (20), wherein the sleep disorder is hypersomnia.

(22) The therapeutic and/or preventive agent for a sleep disorder according to any one of (1) to (20), wherein the sleep disorder is a sleep disorder selected from narcolepsy, recurrent hypersomnia (periodic hypersomnia), idiopathic hypersomnia, and posttraumatic hypersomnia.

(23) The therapeutic and/or preventive agent for a sleep disorder according to any one of (1) to (20), wherein the sleep disorder is a circadian rhythm sleep disorders.

(24) A medicament for improving daytime sleepiness, which comprises the thiazole derivative or the pharmaceutically acceptable salt thereof according to any one of (1) to (20).

(25) A method for treating and/or preventing a sleep disorder, which comprises administering an effective amount of the thiazole derivative or the pharmaceutically acceptable salt thereof according to any one of (1) to (20).

(26) The method according to (25) wherein the sleep disorder is hypersomnia.

(27) The method according to (25), wherein the sleep disorder is a sleep disorder selected from narcolepsy, recurrent hypersomnia (periodic hypersomnia), idiopathic hypersomnia, and posttraumatic hypersomnia.

(28) The method according to (25), wherein the sleep disorder is a circadian rhythm sleep disorders.

(29) A method for improving daytime sleepiness, which comprises administering an effective amount of the thiazole derivative or the pharmaceutically acceptable salt thereof according to any one of (1) to (20).

(30) Use of the thiazole derivative or the pharmaceutically acceptable salt thereof according to any one of (1) to (20) for the manufacture of a therapeutic and/or preventive agent for a sleep disorder.

(31) The use according to (30), wherein the sleep disorder is hypersomnia.

(32) The use according to (30), wherein the sleep disorder is a sleep disorder selected from narcolepsy, recurrent hypersomnia (periodic hypersomnia), idiopathic hypersomnia, and posttraumatic hypersomnia.

(33) The use according to (30), wherein the sleep disorder is a circadian rhythm sleep disorders.

(34) Use of the thiazole derivative or the pharmaceutically acceptable salt thereof according to any one of (1) to (20) for the manufacture of a medicament for improving daytime sleepiness.

Effect of the Invention

The present invention provides therapeutic and/or preventive agents for a sleep disorder, particularly hypersomnia and/or a sleep disorder accompanying daytime sleepiness [for example, narcolepsy, recurrent hypersomnia (periodic hypersomnia), idiopathic hypersomnia, posttraumatic hypersomnia, a circadian rhythm sleep disorder, or the like], comprising a thiazole derivative or a pharmaceutically acceptable salt thereof as an active ingredient.

BEST MODE FOR CARRYING OUT THE INVENTION

In the following, the compounds represented by general formula (I) will be referred to as Compound (I). The compounds having the other formula numbers are referred in the same manner.

The respective groups of general formula (I) defined above are further defined as follows:

(i) Examples of a lower alkyl moiety of the lower alkyl, the lower alkanoyl, the lower alkoxy, the lower alkylamino, and the di-(lower alkyl)amino include linear or branched alkyl each having 1 to 10 carbon atoms. Specific examples include methyl, ethyl, propyl, isopropyl, butyl, isobutyl, sec-butyl, tert-butyl, pentyl, isopentyl, neopentyl, hexyl, heptyl, octyl, nonyl, decyl, and the like. The two lower alkyl moieties of the di-(lower alkyl)amino may be the same or different.

(ii) Examples of the lower alkenyl include linear or branched alkenyl each having 2 to 10 carbon atoms. Specific examples include vinyl, allyl, 1-propenyl, butenyl, pentenyl, hexenyl, heptenyl, octenyl, nonenyl, decenyl, and the like.

(iii) Examples of the lower alkynyl include linear or branched alkynyl each having 2 to 10 carbon atoms. Specific examples include ethynyl, propynyl, butynyl, pentynyl, hexynyl, heptynyl, octynyl, nonynyl, decynyl, and the like.

(iv) Examples of the cycloalkyl include cycloalkyl having 3 to 8 carbon atoms, a bridged cyclic hydrocarbon group having 4 to 8 carbon atoms, a bicyclic or tricyclic spiro hydrocarbon group having spiro-linked cycloalkyl having 3 to 8 carbon atoms, and the like. Specific examples include cyclopropyl, cyclobutyl, cyclopentyl, cyclohexyl, cycloheptyl, cyclooctyl, adamantyl, noradamantyl, bicyclo[2.2.1]heptyl, spiro[4.5]decanyl, and the like.

(v) Examples of an aryl moiety of the aryl and the aroyl include aryl having 6 to 10 carbon atoms. Specific examples include phenyl, naphthyl, and the like.

(vi) Examples of an aromatic heterocyclic group moiety of the aromatic heterocyclic group and the aromatic heterocyclic alkyl include: a five-membered or six-membered monocyclic aromatic heterocyclic group having at least one atom selected from a nitrogen atom, an oxygen atom, and a sulfur atom; a fused bicyclic or tricyclic aromatic heterocyclic group with four- to eight-membered rings fused together, having at least one atom selected from a nitrogen atom, an oxygen atom, and a sulfur atom, and the like. Specific examples include furyl, thienyl, pyrrolyl, pyridyl, N-oxopyridyl, pyrazinyl, imidazolyl, pyrazolyl, triazolyl, thiazolyl, isothiazolyl, thiadiazolyl, oxazolyl, isooxazolyl, oxadiazolyl, pyrimidinyl, pyridazinyl, indolyl, isoindolyl, benzothienyl, benzofuranyl, benzothiazolyl, benzoimidazolyl, benzothiadiazolyl, benzotriazolyl, quinolyl, isoquinolyl, quinazolynyl, furo[2,3-b]pyridyl, and the like.

(vii) Examples of the five-membered aromatic heterocyclic group having at least one oxygen atom include the five-membered monocyclic aromatic heterocyclic group having at least one oxygen atom exemplified above as a five-membered monocyclic aromatic heterocyclic group in the aromatic heterocyclic group (vi). Specific examples include furyl, oxazolyl, isooxazolyl, oxadiazolyl, and the like.

(viii) Examples of an aliphatic heterocyclic group moiety of the aliphatic heterocyclic group and the aliphatic heterocyclic alkyl include: a three- to eight-membered monocyclic aliphatic heterocyclic group having at least one atom selected from a nitrogen atom, an oxygen atom, and a sulfur atom; a fused bicyclic or tricyclic aliphatic heterocyclic group with four- to eight-membered rings fused together, having at least one atom selected from a nitrogen atom, an oxygen atom, and a sulfur atom; a bridged heterocyclic group with five- to ten-membered rings having two bridgehead carbon atoms forming bridges, having at least one atom selected from a nitrogen atom, an oxygen atom, and a sulfur atom; a bicyclic or tricyclic spiro aliphatic heterocyclic group with spiro-linked four- to eight-membered rings, having at least one atom selected from a nitrogen atom, an oxygen atom, and a sulfur atom; and the like. Specific examples include pyrrolidinyl, imidazolidinyl, thiazolidinyl, piperidinyl, piperazinyl, morpholinyl, thiomorpholinyl, piperidino, morpholino, thiomorpholino, oxazolynyl, dioxolanyl, dioxanyl, dioxepanyl, dihydropyridyl, tetrahydropyridyl, pyranyl, dihydropyranyl, tetrahydropyranyl, tetrahydroisoquinolinyl, tetrahydroquinolinyl, indolynyl, isoindolynyl, octahydropyrazino[2,1-c][1,4]oxadinyl, dihydropyridazinyl, oxyranyl, oxetanyl, oxolanyl, thiolanyl, thianyl, aziridinyl, azetidinyl, azolidinyl, perhydrooxazepinyl, perhydrothiazepinyl, perhydroazepinyl, perhydroazocinyl, perhydrodiazepinyl, succinimido, phthalimido, glutarimido, 1,3-benzodioxolyl, 1,4-benzodioxanyl, 3,4-dihydro-2H-1,5-benzodioxepinyl, 1,4-dioxaspiro[4.5]decanyl, 1,4-dioxa-8-azaspiro[4.5]decanyl, octahydropyrrolo[1,2-a]pyrazinyl, octahydropyrazino[2,1-c][1,4]oxadinyl, octahydropyrazino[2,1-c][1,4]thiadinyl, 1-oxaspiro[4.5]decanyl, 1-oxa-8-azaspiro[4.5]decanyl, 8-oxa-3-azabicyclo[3.2.1]octanyl, 7-oxa-bicyclo[2.2.1]heptyl, 2-oxa-5-azabicyclo[2.2.1]heptyl, and the like.

(ix) Examples of an alkylene moiety of the aromatic heterocyclic alkyl and the aliphatic heterocyclic alkyl include linear or branched alkylene each having 1 to 10 carbon atoms. Specific examples include methylene, ethylene, trimethylene, propylene, tetramethylene, pentamethylene, hexamethylene, heptamethylene, octamethylene, nonamethylene, decamethylene, and the like.

(x) Examples of the aralkyl include aralkyl having 7 to 16 carbon atoms. Specific examples include benzyl, phenethyl, phenylpropyl, phenylbutyl, phenylpentyl, phenylhexyl, phenylheptyl, phenyloctyl, phenylnonyl, phenyldecyl, naphthylmethyl, naphthylethyl, naphthylpropyl, naphthylbutyl, naphthylpentyl, naphthylhexyl, anthrylmethyl, anthrylethyl, and the like.

(xi) Examples of the nitrogen-containing heterocyclic group formed together with the adjacent nitrogen atom include a five-membered or six-membered monocyclic heterocyclic group having at least one nitrogen atom (the monocyclic heterocyclic group may include another nitrogen atom(s), (an) oxygen atom(s), or (a) sulfur atom(s)), and a fused bicyclic or tricyclic heterocyclic group with three- to eight-membered rings fused together, having at least one nitrogen atom (the fused heterocyclic group may include another nitrogen atom(s), (an) oxygen atom(s), or (a) sulfur atom(s)). Specific examples include aziridinyl, azetidinyl, pyrrolidinyl, piperidino, azepanyl, pyrrolyl, imidazolidinyl, imidazolyl, pyrazolidinyl, pyrazolinyl, pyrazolyl, piperazinyl, homopiperazinyl, oxazolidinyl, 2H-thioxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzoxazolyl, dihydrobenzothioxazolyl, benzoimidazolidinyl benzoimidazolyl, dihydroindazolyl, indazolyl, benzotriazolyl, pyrrolopyridinyl, pyrrolopyrimidinyl, imidazopyridinyl, purinyl, and the like.

(xii) Examples of a carbocyclic moiety of the carbon ring formed together with the respectively adjacent two carbon atoms include a three- to eight-membered alicyclic or aromatic carbon ring. Specific examples include cyclopropene, cyclobutene, cyclopentene, cyclohexene, cycloheptene, cyclooctene, benzene, and the like.

(xiii) Examples of a heterocyclic moiety of the heterocyclic ring formed together with the respectively adjacent two carbon atoms include a three- to eight-membered aliphatic heterocyclic or aromatic heterocyclic ring. Specific examples include: a three- to eight-membered monocyclic aliphatic or aromatic heterocyclic ring, having at least one atom selected from a nitrogen atom, an oxygen atom, and a sulfur atom; a fused bicyclic or tricyclic, aliphatic or aromatic heterocyclic ring, with four- to eight-membered rings fused together, having at least one atom selected from a nitrogen atom, an oxygen atom, and a sulfur atom. Specific examples include pyrrolidine, imidazolidine, thiazolidine, piperidine, piperazine, morpholine, thiomorpholine, oxazoline, dioxolan, dioxane, dioxepane, dihydropyridine, tetrahydropyridine, pyran, dihydropyran, tetrahydropyran, tetrahydroisoquinoline, tetrahydroquinoline, indoline, isoindoline, octahydropyrazino[2,1-c][1,4]oxazine, dihydropyridazine, oxirane, oxetane, oxolane, thiorane, thiane, aziridine, azetidine, azolidine, perhydrooxazepine, perhydrothiazepine, perhydroazepine, perhydroazocine, perhydrodiazepine, succinimide, phthalimide, glutarimide, 1,3-benzodioxone, 1,4-benzodioxane, 3,4-dihydro-2H-1,5-benzodioxepine, furan, thiophene, pyrrole, pyridine, N-oxopyridine, pyrazine, imidazole, pyrazole, triazole, thiazole, isothiazole, thiadiazole, oxazole, isooxazole, oxadiazole, pyrimidine, pyridazine, indoline, isoindoline, benzothiophene, benzofuran, benzothiazole, benzoimidazole, benzothiadiazole, benzotriazole, quinoline, isoquinoline, quinazoline, and the like.

(xiv) The halogen means each atom of fluorine, chlorine, bromine, and iodine.

(xv) Examples of the aliphatic heterocyclic group having at least one oxygen atom include the aliphatic heterocyclic group having at least one oxygen atom exemplified above in the aliphatic heterocyclic group (viii). Specific examples include morpholinyl, morpholino, oxazolynyl, dioxolanyl, dioxanyl, dioxepanyl, pyranyl, dihydropyranyl, tetrahydropyranyl, octahydropyrazino[2,1-c][1,4]oxadinyl, oxiranyl, oxetanyl, oxolanyl, perhydrooxazepinyl, 1,3-benzodioxolyl, 1,4-benzodioxanyl, 3,4-dihydro-2H-1,5-benzodioxepinyl, 1,4-dioxaspiro[4.5]decanyl, 1,4-dioxa-8-azaspiro[4.5]decanyl, octahydropyrazino[2,1-c][1,4]oxadinyl, and the like.

(xvi) Examples of substituent (A) of the substituted lower alkyl include substituents which may be the same or different and in number of, for example, 1 to 3. Specific examples include halogen, hydroxy, nitro, azido, cyano, carboxy, formyl, substituted or unsubstituted lower alkoxy, substituted or unsubstituted lower alkanoyloxy, substituted or unsubstituted lower alkylsulfanyl, —NR$^x$R$^y$ (wherein R$^x$ and R$^y$ may be the same or different, and each represents a hydrogen atom, substituted or unsubstituted lower alkyl, substituted or unsubstituted adamantyl, substituted or unsubstituted aralkyl, substituted or unsubstituted aromatic heterocyclic alkyl, or substituted or unsubstituted aliphatic heterocyclic alkyl), substituted or unsubstituted cycloalkyl, substituted or unsubstituted aryloxy, substituted or unsubstituted aromatic heterocyclic oxy, substituted or unsubstituted aliphatic heterocyclic oxy, substituted or unsubstituted aralkyloxy, substituted or unsubstituted aralkylsulfanyl, substituted or unsubstituted aromatic heterocyclic alkyloxy, substituted or unsubstituted aromatic heterocyclic alkylsulfanyl, substituted or unsubstituted aliphatic heterocyclic alkyloxy, substituted or unsubstituted aliphatic heterocyclic alkylsulfanyl, and the like.

Examples of substituent (a) of the substituted lower alkoxy, the substituted lower alkanoyloxy, the substituted lower alkylsulfanyl, and the substituted lower alkyl of —NR$^x$R$^y$ as exemplified in substituent (A) include substituents which may be the same or different and in number of, for example, 1 to 3. Specific examples include halogen, hydroxy, hydroxyimino, methoxyimino, nitro, azido, amino, cyano, carboxy, cycloalkyl, substituted or unsubstituted lower alkoxy, substituted or unsubstituted substituted lower alkanoyloxy, substituted or unsubstituted lower alkylamino, substituted or unsubstituted di-(lower alkyl)amino, aryloxy, aromatic heterocyclic oxy, aliphatic heterocyclic oxy, aralkyloxy, aralkylamino, aromatic heterocyclic alkyloxy, aromatic heterocyclic alkylamino, aliphatic heterocyclic alkyloxy, aliphatic heterocyclic alkylamino, and the like.

Examples of substituent (b) of the substituted lower alkoxy, the substituted lower alkanoyloxy, the substituted lower alkylamino, and the substituted di-(lower alkyl)amino as exemplified in substituent (a) include substituents which may be the same or different and in number of, for example, 1 to 3. Specific examples include halogen, hydroxy, amino, lower alkoxy, lower alkylamino, di-(lower alkyl)amino, and the like.

Examples of substituent (c) of the substituted adamantyl defined as R$^x$ and R$^y$ of —NR$^x$R$^y$ as exemplified in substituent (A) include substituents which may be the same or different and in number of, for example, 1 to 3. Specific examples include lower alkyl, lower alkoxy, hydroxy, oxo, formyl, and the like.

Examples of substituent (d) of the substituted cycloalkyl, the substituted aliphatic heterocyclic alkyloxy, the substituted aliphatic heterocyclic alkylsulfanyl, and the substituted aliphatic heterocyclic alkyl defined as R$^x$ and R$^y$ of —NR$^x$R$^y$ as exemplified in substituent (A) include substituents which may be the same or different and in number of, for example, 1 to 3. Specific examples include the groups exemplified in substituent (a), lower alkyl, oxo, formyl, and the like.

Examples of substituent (e) of the substituted aryloxy, the substituted aromatic heterocyclic oxy, the substituted aliphatic heterocyclic oxy, the substituted aralkyloxy, the substituted aralkylsulfanyl, the substituted aromatic heterocyclic alkyloxy, the substituted aromatic heterocyclic alkylsulfanyl, and the substituted aralkyl and the substituted aromatic heterocyclic alkyl defined as $R^x$ and $R^y$ of —$NR^xR^y$ as exemplified in substituent (A) include substituents which may be the same or different and in number of, for example, 1 to 3. Specific examples include halogen, hydroxy, nitro, azido, amino, cyano, carboxy, formyl, substituted or unsubstituted lower alkyl, substituted or unsubstituted lower alkanoyl, cycloalkyl, lower alkoxy, lower alkylsulfanyl, lower alkylsulfonyl, lower alkoxycarbonyl, lower alkylaminocarbonyl, di-(lower alkyl)aminocarbonyl, lower alkylamino, di-(lower alkyl)amino, aryl, an aliphatic heterocyclic group, an aromatic heterocyclic group, aryloxy, aromatic heterocyclic oxy, aliphatic heterocyclic oxy, aralkyl, aromatic heterocyclic alkyl, aliphatic heterocyclic alkyl, aralkylcarbonyl, aromatic heterocyclic alkylcarbonyl, aliphatic heterocyclic alkylcarbonyl, and the like.

Examples of a substituent of the substituted lower alkyl and the substituted lower alkanoyl as exemplified in substituent (e) include substituents which may be the same or different and in number of, for example, 1 to 3. Specific examples include the groups exemplified in substituent (b), and the like.

More preferable examples of substituents as substituent (A) include 1 to 3 substituents selected from the group consisting of: halogen; hydroxy; cyano; carboxy; formyl; lower alkoxy which may be substituted with 1 to 3 substituents selected from halogen, hydroxy, lower alkoxy, amino, lower alkylamino, and di-(lower alkyl)amino; lower alkanoyloxy; lower alkylsulfanyl; —$NR^{x1}R^{y1}$ (wherein $R^{x1}$ and $R^{y1}$ may be the same or different, and each represents a hydrogen atom; lower alkyl which may be substituted with 1 to 3 substituents selected from hydroxy, lower alkoxy, amino, lower alkylamino, and di-(lower alkyl)amino; adamantyl which may be substituted with 1 to 3 substituents selected from oxo, hydroxy, and lower alkoxy; aralkyl which may be substituted with 1 to 3 substituents selected from halogen, hydroxy, and lower alkoxy; aromatic heterocyclic alkyl which may be substituted with 1 to 3 substituents selected from hydroxy, lower alkoxy, and lower alkyl; or aliphatic heterocyclic alkyl which may be substituted with 1 to 3 substituents selected from oxo, hydroxy, lower alkoxy, and lower alkyl); cycloalkyl; aryloxy which may be substituted with 1 to 3 substituents selected from halogen, hydroxy, and lower alkoxy; aromatic heterocyclic oxy which may be substituted with 1 to 3 substituents selected from hydroxy, lower alkoxy, and lower alkyl; aralkyloxy which may be substituted with 1 to 3 substituents selected from halogen, hydroxy, and lower alkoxy; aromatic heterocyclic alkyloxy which may be substituted with 1 to 3 substituents selected from hydroxy, lower alkoxy, and lower alkyl; and aliphatic heterocyclic alkyloxy which may be substituted with 1 to 3 substituents selected from oxo, hydroxy, lower alkoxy, and lower alkyl.

Examples of more preferable substituents as substituent (A) include 1 to 3 substituents selected from the group consisting of: halogen; hydroxy; lower alkoxy; —$NR^{X1}R^{Y1}$ (wherein $R^{X1}$ and $R^{Y1}$ may be the same or different, and each represents a hydrogen atom; lower alkyl which may be substituted with 1 to 3 substituents selected from hydroxy and lower alkoxy; or adamantyl which may be substituted with hydroxy); aryloxy; and aromatic heterocyclic oxy.

(xvii) Examples of substituent (B) of the substituted lower alkanoyl, the substituted lower alkenyl, the substituted lower alkynyl, the substituted lower alkoxy, the substituted lower alkylamino, and the substituted di-(lower alkyl)amino include substituents which may be the same or different and in number of, for example, 1 to 3. Specific examples include the groups exemplified in substituent (A), substituted or unsubstituted aryl, a substituted or unsubstituted aliphatic heterocyclic group, a substituted or unsubstituted aromatic heterocyclic group, and the like.

Examples of substituent (f) of the substituted aryl and substituted aromatic heterocyclic group exemplified in substituent (B) include substituents which may be the same or different and in number of, for example, 1 to 3. Specific examples include the groups exemplified in substituent (a), lower alkyl, and the like.

Examples of substituent (g) of the substituted aliphatic heterocyclic group exemplified in substituent (B) include substituents which may be the same or different and in number of, for example, 1 to 3. Specific examples include the groups exemplified in substituent (a), lower alkyl, oxo, formyl, and the like.

More preferable examples of substituents as substituent (B) include 1 to 3 substituents selected from the group consisting of halogen; hydroxy; cyano; carboxy; formyl; lower alkoxy which may be substituted with 1 to 3 substituents selected from halogen, hydroxy, lower alkoxy, amino, lower alkylamino, and di-(lower alkyl)amino; lower alkanoyloxy; lower alkylsulfanyl; —$NR^{x1}R^{y1}$ (wherein $R^{x1}$ and $R^{y1}$ have the same meanings as described above, respectively); cycloalkyl; aryloxy which may be substituted with 1 to 3 substituents selected from halogen, hydroxy, and lower alkoxy; aromatic heterocyclic oxy which may be substituted with 1 to 3 substituents selected from hydroxy, lower alkoxy, and lower alkyl; aralkyloxy which may be substituted with 1 to 3 substituents selected from halogen, hydroxy, and lower alkoxy; aromatic heterocyclic alkyloxy which may be substituted with 1 to 3 substituents selected from hydroxy, lower alkoxy, and lower alkyl; aliphatic heterocyclic alkyloxy which may be substituted with 1 to 3 substituents selected from oxo, hydroxy, lower alkoxy, and lower alkyl; aryl; and an aromatic heterocyclic group.

Examples of further more preferable substituents as substituent (B) include 1 to 3 substituents selected from the group consisting of hydroxy, lower alkoxy, and aryl.

(xviii) Examples of substituent (C) of the substituted cycloalkyl and the substituted carbon ring formed by combining together with the respectively adjacent two carbon atoms include substituents which may be the same or different and in number of, for example, 1 to 3. Specific examples include the groups exemplified in substituent (A), lower alkyl, oxo, methylenedioxy, ethylenedioxy, trimethylenedioxy, and the like.

More preferable examples of substituents as substituent (C) include lower alkyl; oxo; methylenedioxy; ethylenedioxy; trimethylenedioxy; halogen; hydroxy; cyano; carboxy; formyl; lower alkoxy which may be substituted with 1 to 3 substituents selected from halogen, hydroxy, lower alkoxy, amino, lower alkylamino, and di-(lower alkyl)amino; lower alkanoyloxy; lower alkylsulfanyl; —$NR^{x1}R^{y1}$ (wherein $R^{x1}$ and $R^{y1}$ have the same meanings as described above, respectively); cycloalkyl; aryloxy which may be substituted with 1 to 3 substituents selected from halogen, hydroxy, and lower alkoxy; aromatic heterocyclic oxy which may be substituted with 1 to 3 substituents selected from hydroxy, lower alkoxy, and lower alkyl; aralkyloxy which may be substituted with 1 to 3 substituents selected from halogen, hydroxy, and lower alkoxy; aromatic heterocyclic alkyloxy which may be substituted with 1 to 3 substituents selected from hydroxy, lower alkoxy, and lower alkyl; and aliphatic heterocyclic alkyloxy which may be substituted with 1 to 3 substituents selected from oxo, hydroxy, lower alkoxy, and lower alkyl.

Examples of further more preferable substituents include 1 to 3 substituents selected from the group consisting of lower alkyl, oxo, hydroxy, lower alkoxy, ethylenedioxy, and trimethylenedioxy.

(xix) Examples of substituent (D) of the substituted aryl, the substituted aralkyl, the substituted aroyl, the substituted aromatic heterocyclic group, the substituted five-membered aromatic heterocyclic group having at least one oxygen atom, the substituted furyl, the substituted aromatic heterocyclic alkyl, and the heterocyclic ring formed together with the respectively adjacent two carbon atoms include substituents which may be the same or different and in number of, for example, 1 to 4. Specific examples include oxo, hydroxyimino, methoxyimino, halogen, hydroxy, nitro, azido, cyano, carboxy, formyl, substituted or unsubstituted lower alkyl, substituted or unsubstituted lower alkanoyl, substituted or unsubstituted lower alkenyl, substituted or unsubstituted lower alkynyl, substituted or unsubstituted cycloalkyl, substituted or unsubstituted lower alkoxy, substituted or unsubstituted lower alkanoyloxy, —$NR^{x2}R^{y2}$ (wherein $R^{x2}$ and $R^{y2}$ may be the same or different, and each represents a hydrogen atom, substituted or unsubstituted lower alkyl, substituted or unsubstituted aralkyl, substituted or unsubstituted aromatic heterocyclic alkyl, or substituted or unsubstituted aliphatic heterocyclic alkyl), substituted or unsubstituted lower alkylsulfanyl, substituted or unsubstituted lower alkylsulfonyl, sulfamoyl, substituted or unsubstituted lower alkylaminosulfonyl, substituted or unsubstituted di-(lower alkyl)aminosulfonyl, substituted or unsubstituted lower alkoxycarbonyl, substituted or unsubstituted lower alkylcarbamoyl, substituted or unsubstituted di-(lower alkyl)carbamoyl, aromatic heterocyclic carbonyl, aliphatic heterocyclic carbonyl, substituted or unsubstituted aryl, a substituted or unsubstituted aliphatic heterocyclic group, a substituted or unsubstituted aromatic heterocyclic group, substituted or unsubstituted aryloxy, substituted or unsubstituted aromatic heterocyclic oxy, substituted or unsubstituted aliphatic heterocyclic oxy, tri (lower alkyl)silyl, substituted or unsubstituted aralkyl, substituted or unsubstituted aromatic heterocyclic alkyl, substituted or unsubstituted aliphatic heterocyclic alkyl, substituted or unsubstituted aralkyloxy, substituted or unsubstituted aralkylsulfanyl, substituted or unsubstituted aromatic heterocyclic alkyloxy, substituted or unsubstituted aromatic heterocyclic alkylsulfanyl, substituted or unsubstituted aliphatic heterocyclic alkyloxy, substituted or unsubstituted aliphatic heterocyclic alkylsulfanyl, and the like.

Examples of a substituent of the substituted lower alkyl, the substituted lower alkenyl, the substituted lower alkynyl, the substituted lower alkanoyl, the substituted lower alkoxy, the substituted lower alkanoyloxy, the substituted lower alkyl defined as $R^{x2}$ and $R^{y2}$ of —$NR^{x2}R^{y2}$, the substituted lower alkylsulfanyl, the substituted lower alkylsulfonyl, the substituted lower alkylaminosulfonyl, the substituted di-(lower alkyl)aminosulfonyl, the substituted lower alkoxycarbonyl, the substituted lower alkylcarbamoyl, and the substituted di-(lower alkyl)carbamoyl as exemplified in substituent (D) include substituents which may be the same or different and in number of, for example, 1 to 3. Specific examples include the groups exemplified in substituent (a), and the like.

Examples of a substituent of the substituted aryl, the substituted aryloxy, the substituted aromatic heterocyclic group, the substituted aromatic heterocyclic oxy, the substituted aliphatic heterocyclic oxy, the substituted aralkyl, the substituted aromatic heterocyclic alkyl, the substituted aralkyloxy, the substituted aralkylsulfanyl, the substituted aromatic heterocyclic alkyloxy, the substituted aromatic heterocyclic alkylsulfanyl, the substituted aralkyl and the substituted aromatic heterocyclic alkyl defined as $R^{x2}$ and $R^{y2}$ of —$NR^{x2}R^{y2}$, as exemplified in substituent (D) include substituents which may be the same or different and in number of, for example, 1 to 3. Specific examples include the groups exemplified in substituent (e), and the like.

Examples of substituent (h) of the substituted cycloalkyl, the substituted aliphatic heterocyclic group, the substituted aliphatic heterocyclic alkyl, the substituted aliphatic heterocyclic alkyloxy, the substituted aliphatic heterocyclic alkylsulfanyl, and the substituted aliphatic heterocyclic alkyl defined as $R^{x2}$ and $R^{y2}$ of —$NR^{x2}R^{y2}$ as exemplified in substituent (D) include substituents which may be the same or different and in number of, for example, 1 to 3. Specific examples include the groups exemplified in substituent (a), lower alkyl, oxo, and the like.

More preferable examples of substituents as substituent (D) include 1 to 3 substituents selected from the group consisting of: oxo; hydroxyimino; methoxyimino; halogen; hydroxy; nitro; cyano; carboxy; formyl; lower alkyl which may be substituted with 1 to 3 substituents selected from halogen, —$OR^{z1}$ [wherein $R^{z1}$ represents a hydrogen atom; lower alkyl which may be substituted with 1 to 3 substituents selected from hydroxy, lower alkoxy, and —$NR^{x3}R^{y3}$ (wherein $R^{x3}$ and $R^{y3}$ may be the same or different, and each represents a hydrogen atom; or lower alkyl which may be substituted with hydroxy, lower alkoxy, amino, lower alkylamino, or di-(lower alkyl)amino); aralkyl which may be substituted with 1 to 3 substituents selected from halogen, hydroxy, and lower alkoxy; or aromatic heterocyclic alkyl which may be substituted with 1 to 3 substituents selected from lower alkyl, hydroxy, and lower alkoxy], and —$NR^{x4}R^{y4}$ (wherein $R^{x4}$ and $R^{y4}$ may be the same or different, and each represents a hydrogen atom; or lower alkyl which may be substituted with hydroxy, lower alkoxy, amino, lower alkylamino, or di-(lower alkyl)amino); cycloalkyl; aryl which may be substituted with 1 to 3 substituents selected from hydroxy and lower alkoxy; an aromatic heterocyclic group which may be substituted with 1 to 3 substituents selected from lower alkyl, hydroxy, and lower alkoxy; an aliphatic heterocyclic group which may be substituted with 1 to 3 substituents selected from oxo, lower alkyl, hydroxy, and lower alkoxy; lower alkanoyl; lower alkoxycarbonyl; carbamoyl; lower alkylcarbamoyl; di-(lower alkyl)carbamoyl; aralkyl which may be substituted with 1 to 3 substituents selected from hydroxy and lower alkoxy; aromatic heterocyclic alkyl which may be substituted with 1 to 3 substituents selected from lower alkyl, hydroxy, and lower alkoxy; aliphatic heterocyclic alkyl which may be substituted with 1 to 3 substituents selected from oxo, lower alkyl, hydroxy, and lower alkoxy; lower alkoxy which may be substituted with 1 to 3 substituents selected from halogen, hydroxy, and lower alkoxy; aralkyloxy which may be substituted with 1 to 3 substituents selected from hydroxy and lower alkoxy; aromatic heterocyclic alkyloxy which may be substituted with 1 to 3 substituents selected from lower alkyl, hydroxy, and lower alkoxy; —$NR^{x5}R^{y5}$ (wherein $R^{x5}$ and $R^{y5}$ may be the same or different, and each represents a hydrogen atom; lower alkyl which may be substituted with 1 to 3 substituents selected from hydroxy, lower alkoxy, amino, lower alkylamino, and di-(lower alkyl)amino; aralkyl which may be substituted with 1 to 3 substituents selected from hydroxy and lower alkoxy; aromatic heterocyclic alkyl which may be substituted with 1 to 3 substituents selected from lower alkyl, hydroxy, and lower alkoxy; or aliphatic heterocyclic alkyl which may be substituted with 1 to 3 substituents selected from oxo, lower alkyl, hydroxy, and lower alkoxy); lower alkylsulfonyl; and tri(lower alkyl)silyl.

Examples of further more preferable substituents include oxo; hydroxyimino; halogen; hydroxy; nitro; cyano; carboxy; formyl; lower alkyl which may be substituted with 1 to 3 substituents selected from halogen, —OR$^{Z1}$ [wherein R$^{Z1}$ represents a hydrogen atom or lower alkyl which may be substituted with —NR$^{X3}$R$^{Y3}$ (wherein R$^{X3}$ and R$^{Y4}$ may be the same or different, and each represents a hydrogen atom or lower alkyl)], and —NR$^{X4}$R$^{Y4}$ (wherein R$^{X4}$ and R$^{Y4}$ may be the same or different, and each represents a hydrogen atom; or lower alkyl which may be substituted with lower alkoxy or di-(lower alkyl)amino); cycloalkyl; aryl which may be substituted with 1 to 3 substituents selected from hydroxy and lower alkoxy; an aromatic heterocyclic group which may be substituted with 1 to 3 substituents selected from hydroxy and lower alkoxy; aliphatic heterocyclic alkyl which may be substituted with 1 to 3 substituents selected from oxo, lower alkyl, hydroxy, and lower alkoxy; lower alkanoyl; lower alkylcarbamoyl; di-(lower alkyl)carbamoyl; aralkyl; aromatic heterocyclic alkyl; aliphatic heterocyclic group; lower alkoxy; —NR$^{X5}$R$^{Y5}$ (wherein R$^{X5}$ and R$^{Y5}$ may be the same or different, and each represents a hydrogen atom; or lower alkyl which may be substituted with hydroxy); lower alkylsulfonyl; and tri(lower alkyl)silyl.

(xx) Examples of substituent (E) of the substituted aliphatic heterocyclic group, the substituted aliphatic heterocyclic alkyl, the substituted nitrogen-containing heterocyclic group formed together with the adjacent nitrogen atom, and the substituted aliphatic heterocyclic group having at least one oxygen atom include substituents which may be the same or different and in number of, for example, 1 to 3. Specific examples include the groups exemplified in substituent (D), methylenedioxy, ethylenedioxy, trimethylenedioxy, oxo, and the like.

More preferable examples of substituents as substituent (E) include 1 to 3 substituents selected from the group consisting of: methylenedioxy; ethylenedioxy; trimethylenedioxy; oxo; hydroxyimino; methoxyimino; halogen; hydroxy; nitro; cyano; carboxy; formyl; lower alkyl which may be substituted with cycloalkyl, halogen, —OR$^{z2}$ [wherein R$^{z2}$ represents a hydrogen atom; lower alkyl which may be substituted with 1 to 3 substituents selected from hydroxy, lower alkoxy, and —NR$^{x6}$R$^{y6}$ (wherein R$^{x6}$ and R$^{y6}$ may be the same or different, and each represents a hydrogen atom; or lower alkyl which may be substituted with 1 to 3 substituents selected from hydroxy, lower alkoxy, amino, lower alkylamino, and di(lower alkyl)amino); aralkyl which may be substituted with 1 to 3 substituents selected from halogen, hydroxy, and lower alkoxy; or aromatic heterocyclic alkyl which may be substituted with 1 to 3 substituents selected from lower alkyl, hydroxy, and lower alkoxy], and —NR$^{x7}$R$^{y7}$ (wherein R$^{x7}$ and R$^{y7}$ may be the same or different, and each represents a hydrogen atom; or lower alkyl which may be substituted with hydroxy, lower alkoxy, amino, lower alkylamino, or di-(lower alkyl)amino); cycloalkyl; aryl which may be substituted with 1 to 3 substituents selected from hydroxy and lower alkoxy; an aromatic heterocyclic group which may be substituted with 1 to 3 substituents selected from lower alkyl, hydroxy, and lower alkoxy; an aliphatic heterocyclic group which may be substituted with 1 to 3 substituents selected from oxo, lower alkyl, hydroxy, and lower alkoxy; lower alkanoyl; lower alkoxycarbonyl; carbamoyl; lower alkylcarbamoyl; di-(lower alkyl)carbamoyl; aralkyl which may be substituted with 1 to 3 substituents selected from hydroxy and lower alkoxy; aromatic heterocyclic alkyl which may be substituted with 1 to 3 substituents selected from lower alkyl, hydroxy, and lower alkoxy; aliphatic heterocyclic alkyl which may be substituted with oxo, lower alkyl, hydroxy, or lower alkoxy; lower alkoxy which may be substituted with 1 to 3 substituents selected from halogen, hydroxy, and lower alkoxy; aralkyloxy which may be substituted with 1 to 3 substituents selected from hydroxy and lower alkoxy; aromatic heterocyclic alkyloxy which may be substituted with 1 to 3 substituents selected from lower alkyl, hydroxy, and lower alkoxy; —NR$^{x8}$R$^{y8}$ (wherein R$^{x8}$ and R$^{y8}$ may be the same or different, and each represents a hydrogen atom; lower alkyl which may be substituted with 1 to 3 substituents selected from hydroxy, lower alkoxy, amino, lower alkylamino, and di-(lower alkyl)amino; aralkyl which may be substituted with 1 to 3 substituents selected from hydroxy and lower alkoxy; aromatic heterocyclic alkyl which may be substituted with 1 to 3 substituents selected from lower alkyl, hydroxy, and lower alkoxy; or aliphatic heterocyclic alkyl which may be substituted with 1 to 3 substituents selected from oxo, lower alkyl, hydroxy, and lower alkoxy); lower alkylsulfonyl; lower alkylaminosulfonyl; and di-(lower alkyl)aminosulfonyl.

Examples of further more preferable substituents as substituent (E) include 1 to 3 substituents selected from the group consisting of: ethylenedioxy; oxo; halogen; hydroxy; cyano; lower alkyl which may be substituted with 1 to 3 substituents selected from cycloalkyl, halogen, hydroxy, and lower alkoxy; aryl; an aromatic heterocyclic group; an aliphatic heterocyclic group; lower alkoxycarbonyl; di-(lower alkyl) carbamoyl; aromatic heterocyclic alkyl; lower alkoxy; —NR$^{x9}$R$^{y9}$ (wherein R$^{x9}$ and R$^{y9}$ may be the same or different, and each represents a hydrogen atom or lower alkyl); lower alkylsulfonyl; and di-(lower alkyl)aminosulfonyl.

The lower alkyl moiety of the lower alkyl, the lower alkoxy, the lower alkanoyl, the lower alkanoyloxy, the lower alkylsulfanyl, the lower alkoxycarbonyl, the lower alkylcarbamoyl, the di-(lower alkyl)carbamoyl, the lower alkylsulfonyl, the lower alkylaminosulfonyl, the di-(lower alkyl)aminosulfonyl, and the tri(lower alkyl)silyl exemplified above in (xvi) to (xx) has the same meaning as described above the lower alkyl(i). The two lower alkyl moieties of the di-(lower alkyl) amino, the di-(lower alkyl)carbamoyl, and the di-(lower alkyl)aminosulfonyl may be the same or different, and the three lower alkyl moieties of the tri(lower alkyl)silyl may be the same or different. The aralkyl moiety of the aralkyl, the aralkyloxy, the aralkylamino, and the aralkylsulfanyl has the same meaning as described above the aralkyl (x). The halogen and the cycloalkyl have the same meanings as described above the halogen (xiv) and the cycloalkyl (iv), respectively. The aryl moiety of the aryl and the aryloxy has the same meaning as described above the aryl (v). The aromatic heterocyclic group moiety of the aromatic heterocyclic group, the aromatic heterocyclic oxy, the aromatic heterocyclic alkyloxy, the aromatic heterocyclic alkylamino, the aromatic heterocyclic alkylsulfanyl, and the aromatic heterocyclic alkyl, and the aliphatic heterocyclic group moiety of the aliphatic heterocyclic group, the aliphatic heterocyclic oxy, the aliphatic heterocyclic alkyloxy, the aliphatic heterocyclic alkylamino, the aliphatic heterocyclic alkylsulfanyl, and the aliphatic heterocyclic alkyl have the same meanings as described above the aromatic heterocyclic group (vi) and the aliphatic heterocyclic group (viii), respectively. The alkylene moiety of the aromatic heterocyclic alkyloxy, the aromatic heterocyclic alkylamino, the aromatic heterocyclic alkylsulfanyl, and the aromatic heterocyclic alkyl, and the alkylene moiety of the aliphatic heterocyclic alkyloxy, the aliphatic heterocyclic alkylamino, the aliphatic heterocyclic alkylsulfanyl, and the aliphatic heterocyclic alkyl have the same meanings as described above the alkyl moiety (ix).

In each group of Compound (I):

(1) R$^1$ is preferably a furyl group, and more preferably a 2-furyl group, and the like, for example.

(2) R$^2$ is preferably a substituted or unsubstituted aliphatic heterocyclic group, a substituted or unsubstituted aromatic heterocyclic group, —COR⁶ (wherein R⁶ has the same meaning as described above), and the like, and more preferably a substituted or unsubstituted aromatic heterocyclic group, —COR⁶ (wherein R⁶ has the same meaning as described above), and the like, for example. In above —COR⁶, R⁶ is preferably substituted or unsubstituted aryl, substituted or unsubstituted cycloalkyl, a substituted or unsubstituted aromatic heterocyclic group, a substituted or unsubstituted aliphatic heterocyclic group, and the like, and more preferably substituted or unsubstituted aryl, a substituted or unsubstituted aromatic heterocyclic group, a substituted or unsubstituted aliphatic heterocyclic group, and the like, and further preferably a substituted or unsubstituted aromatic heterocyclic group, a substituted or unsubstituted aliphatic heterocyclic group, and the like, and even more preferably a substituted or unsubstituted aliphatic heterocyclic group having at least one oxygen atom, and the like, for example. Substituted or unsubstituted lower alkyl is also preferable as R⁶, for example. Specific examples are preferably pyridyl; morpholino; and —COR⁶ᴬ (wherein R⁶ᴬ represents phenyl which may be substituted with lower alkyl, lower alkoxy, halogen, cyano, and the like; cycloalkyl which may be substituted with oxo and the like; pyridyl which may be substituted with lower alkyl, lower alkoxy, halogen, dimethylamino, an aliphatic heterocyclic group, and the like; or an aliphatic heterocyclic group having at least one oxygen atom, such as dioxolanyl, dioxanyl, dioxepanyl, pyranyl, dihydropyranyl, and tetrahydropyranyl, which may be substituted with lower alkyl, lower alkoxy, and the like), and more preferably pyridyl, —COR⁶ᴬ (wherein R⁶ᴬ has the same meaning as described above), and the like. In above —COR⁶ᴬ, preferable examples of R⁶ᴬ include phenyl which may be substituted with lower alkyl, lower alkoxy, halogen, cyano, and the like; pyridyl which may be substituted with lower alkyl, lower alkoxy, halogen, dimethylamino, an aliphatic heterocyclic group, and the like; an aliphatic heterocyclic group having at least one oxygen atom, such as oxolanyl, dioxanyl, dioxepanyl, pyranyl, dihydropyranyl, and tetrahydropyranyl, which may be substituted with lower alkyl, lower alkoxy, and the like; and the like. More preferable examples are pyridyl which may be substituted with lower alkyl, lower alkoxy, halogen, dimethylamino, an aliphatic heterocyclic group, and the like; an aliphatic heterocyclic group having at least one oxygen atom, such as oxolanyl, dioxanyl, dioxepanyl, pyranyl, dihydropyranyl, and tetrahydropyranyl, which may be substituted with lower alkyl, lower alkoxy, and the like; and the like. An even more preferable example is an aliphatic heterocyclic group having at least one oxygen atom, such as oxolanyl, dioxanyl, dioxepanyl, pyranyl, dihydropyranyl, and tetrahydropyranyl, which may be substituted with lower alkyl, lower alkoxy, and the like; and the like.

(3) R³ is preferably —NR¹⁰R¹⁰ (wherein R¹⁰ and R¹⁰ have the same meanings as described above, respectively), —CONHR¹⁶ (wherein R¹⁶ has the same meaning as described above), and general formula (II)

[Chemical Formula 4]

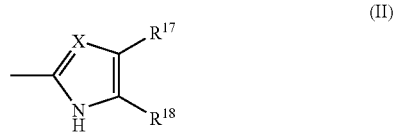

(II)

(wherein X, R¹⁷, and R¹⁸ have the same meanings as described above, respectively), and more preferably —NHR¹¹ (wherein R¹¹ has the same meaning as described above), for example. In above —NHR¹¹, R¹¹ is preferably —COR¹² (wherein R¹² has the same meaning as described above), and more preferably —COR¹²ᴬ [wherein R¹²ᴬ represents substituted or unsubstituted aryl, a substituted or unsubstituted aromatic heterocyclic group, —OR¹⁸ (wherein R¹⁵ has the same meaning as described above), substituted or unsubstituted aliphatic heterocyclic alkyl, substituted or unsubstituted aromatic heterocyclic alkyl, and the like], and further preferably —COR¹²ᴮ (wherein R¹²ᴮ represents substituted or unsubstituted aryl, a substituted or unsubstituted aromatic heterocyclic group, substituted or unsubstituted aliphatic heterocyclic alkyl, substituted or unsubstituted aromatic heterocyclic alkyl, and the like), and even more preferably —COR¹²ᶜ (wherein R¹²ᶜ represents substituted or unsubstituted aryl, a substituted or unsubstituted aromatic heterocyclic group, and the like), for example. Further, —COR¹²ᴰ (wherein R¹²ᴰ represents a substituted or unsubstituted aromatic heterocyclic group), —COR¹²ᴱ (wherein R¹²ᴱ represents substituted or unsubstituted aliphatic heterocyclic alkyl), and the like are also even more preferable.

The foregoing preferable groups for R¹, R², and R³ have the same meanings as described above in corresponding (i) to (xv). Examples of substituents of the each group include the groups as exemplified above in corresponding substituents (A), (B), (C), (D), and (E).

Also, for example, on the adenosine $A_{2A}$ receptor binding assay described in Test Example 1 below, Compound (I) is preferably a compound having an inhibitory effect of 50% or greater at a Compound (I) concentration of $3 \times 10^{-8}$ mol/L, more preferably a compound having an inhibitory effect of 50% or greater at a Compound (I) concentration of $1 \times 10^{-8}$ mol/L, further preferably a compound having an inhibitory effect of 50% or greater at a Compound (I) concentration of $3 \times 10^{-9}$ mol/L, and even more preferably a compound having an inhibitory effect of 50% or greater at a Compound (I) concentration of $1 \times 10^{-9}$ mol/L. In terms of Ki value obtained in the same assay, a compound having an inhibitory effect at 30 nmol/L or less is preferable, a compound having an inhibitory effect at 10 nmol/L or less is more preferable, a compound having an inhibitory effect at 3 nmol/L or less is further preferable, and a compound having an inhibitory effect at 1 nmol/L or less is even more preferable.

Further, Compound (I) is a compound with affinity to adenosine $A_{2A}$ receptor preferably at least 10 times, more preferably at least 50 times, further preferably at least 100 times, even more preferably at least 500 times, and most preferably at least 1000 times greater than that to adenosine $A_1$ receptor, for example. Affinity can be determined according to the conventional manner, for example, by the method according to Test Example 1 described below, or by the methods described in, for example, Naunyn Schmiedebergs Arch Pharmacol. 1987, 355(1), p. 59-63; Naunyn Schmiedebergs Arch Pharmacol. 1987, 355(2), p. 204-210; Br. J. Pharmacol. 1996, 117(8), p. 1645-1652; and the like.

The pharmaceutically acceptable salts of Compound (I) include, for example, acid addition salts, metal salts, ammonium salts, organic amine addition salts, amino acid addition salts, and the like that are pharmaceutically acceptable. The pharmaceutically acceptable acid addition salts of Compound (I) include, for example, inorganic acid salts such as hydrochloride, sulfate, and phosphate, and organic acid salts such as acetate, maleate, fumarate, and citrate, and the like. Examples of pharmaceutically acceptable metal salts include: alkali metal salts such as sodium salt and potassium salt; alkaline earth metal salts such as magnesium salt and calcium salt; aluminum salt; zinc salt; and the like. Examples of pharmaceutically acceptable ammonium salts include salts of ammonium, tetramethylammonium, or the like. Examples of pharmaceutically acceptable organic amine addition salts include addition salts of morpholine, piperidine, or the like. Examples of pharmaceutically acceptable amino acid addition salts include addition salts of lysine, glycine, phenylalanine, aspartic acid, glutamic acid, or the like.

The sleep disorder treated and/or prevented by therapeutic and/or preventive agents for a sleep disorder of the present invention, or the sleep disorder improved by the improver of daytime sleepiness of the present invention may be any of the sleep disorders given in ICSD; ICD-10; the Merck Manual, 17th Edition; the DSM-III-R or DSM-IV of the American Psychiatric Association; and the like (for classification of sleep disorders, refer to *Seishin Shinkei Yakuri*, Yasuo Hishikawa, Vol. 18, No. 2, p. 65-72). A sleep disorder that is preferable among these sleep disorders are those in which symptoms are expected to be treated and/or prevented, or improved by the stimulant activity or sleepiness improving activity, and specifically sleep disorders that involve excessive sleep and/or daytime sleepiness, and the like.

More specifically, by use of therapeutic and/or preventive agents for a sleep disorder of the present invention, a sleep disorder including narcolepsy; hypersomnia such as recurrent hypersomnia (periodic hypersomnia), idiopathic hypersomnia, and posttraumatic hypersomnia; circadian rhythm sleep disorder such as time zone change syndrome (jet lag syndrome, jet lag), shift work sleep disorder, irregular sleep-wake pattern, delayed sleep phase syndrome, and non-24-hour sleep-wake disorder; and the like can be treated and/or prevented, or improved.

The following will describe preparation methods of Compound (I). The compounds included in Compound (I) may be prepared by the method described in WO2005/063743 and the like, or modified methods thereof, or alternatively by the methods described below.

Note that, in the preparation methods below, in the case where the defined groups undergo changes under the conditions of the each preparation method or are inappropriate for performing the methods, the desired compound can be prepared by employing the method of introducing and removing protective groups commonly used in organic synthetic chemistry, as described in, for example, *Protective Groups in Organic Synthesis*, T. W. Greene, John Wiley & Sons Inc., 1999, and the like. As required, the order of reaction steps, such as introduction of substituents may be changed as well.

Compound (I) can be prepared according to the following steps.

Preparation Method 1

Among Compound (I), Compound (Ia-i) in which $R^3$ is $-NH_2$, Compound (Ia-ii) in which $R^3$ is $-NHR^{11a}$ (wherein $R^{11a}$ represents any of the groups defined above as $R^{11}$ except for hydrogen atom), or Compound (Ia-iii) in which $R^3$ is $-NR^{10a}R^{11a}$ (wherein $R^{10a}$ represents any of the groups defined above as $R^{10}$ except for hydrogen atom, and $R^{11a}$ has the same meaning as described above) can be prepared by the methods described in, for example, Japanese Published Unexamined Patent Application No. 5-155871, Japanese Published Unexamined Patent Application No. 11-193281, and the like, or similar methods thereof. For example, Compound (I) can be prepared according to the following steps.

[Chemical Formula 5]

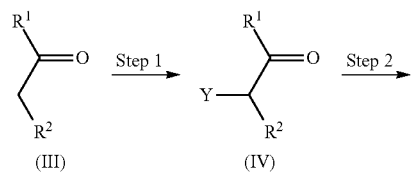

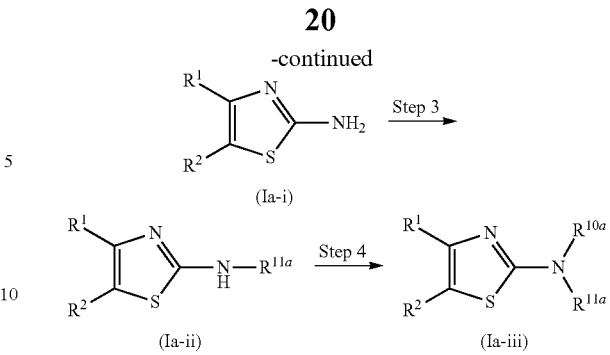

(Wherein, $R^1$, $R^2$, $R^{10a}$, and $R^{11a}$ have the same meanings as described above, respectively, and Y represents a chlorine atom, a bromine atom, or an iodine atom)

Step 1

Compound (IV) can be prepared by reacting Compound (III) with 1 to 200 equivalents of, preferably, 1 to 5 equivalents of halogenating agent without solvent or in a solvent inert to the reaction, at a temperature between −30° C. and 150° C., preferably between 0° C. and 100° C., for 5 minutes to 72 hours.

Compound (III) can be obtained either commercially or by the methods described in, for example, WO03/35639, Japanese Published Unexamined Patent Application No. 11-193281, and the like or similar methods thereof.

Examples of the hydrogenating agent include chlorine, bromine, iodine, N,N,N,N-tetra-n-butylammonium tribromide, pyridinium tribromide, and the like.

Examples of the solvent inert to the reaction include acetone, 1,4-dioxane, acetonitrile, chloroform, dichloromethane, tetrahydrofuran (THF), ethyl acetate, N,N-dimethylformamide (DMF), acetic acid, water, and the like, which may be used alone or in combination.

Step 2

Compound (Ia-i) can be prepared by reacting Compound (IV) with preferably 1 to 20 equivalents of thiourea in a solvent inert to the reaction, at a temperature between −30° C. and 150° C., preferably between room temperature and 100° C., for 5 minutes to 72 hours.

Examples of the solvent inert to the reaction include toluene, hexane, THF, DMF, ethanol, acetonitrile, and the like, which may be used alone or in combination.

Step 3

Compound (Ia-ii) can be prepared by reacting Compound (Ia-i) with preferably 1 to 100 equivalents of $R^{11a}Y$ (wherein $R^{11a}$ and Y have the same meanings as described above, respectively), if necessary, in the presence of preferably 1 to 100 equivalents of base, without solvent or in a solvent inert to the reaction, at a temperature between −30° C. and 150° C. for 5 minutes to 72 hours. When $R^{11a}$ is $-COR^{12}$ (wherein $R^{12}$ has the same meaning as described above), $R^{11a}-O-R^{11a}$ (wherein $R^{11a}$ has the same meaning as described above) may be used instead of $R^{11a}Y$.

Examples of the solvent inert to the reaction include acetonitrile, dichloromethane, 1,2-dichloroethane, chloroform, 1,2-dimethoxyethane, DMF, N,N-dimethyl acetamide (DMA), 1,4-dioxane, THF, diethyl ether, diisopropyl ether, benzene, toluene, xylene, pyridine, N,N-dimethyl imidazolidinone (DMI), N-methylpyrrolidone (NMP), sulfolane, and the like, which may be used alone or in combination.

Examples of the base include pyridine, triethylamine, diisopropylethylamine, N-methylmorpholine, N-methylpiperidine, 1,8-diazabicyclo[5.4.0]undec-7-ene (DBU), N,N-dimethylaminopyridine (DMAP), potassium acetate, potassium carbonate, cesium carbonate, sodium carbonate, sodium bicarbonate, sodium hydroxide, lithium hydroxide, potassium hydroxide, potassium phosphate, and the like.

Step 4

Compound (Ia-iii) can be prepared by reacting Compound (Ia-ii) in the same manner as in Step 3 with preferably 1 to 100 equivalents of $R^{10a}Y$ (wherein $R^{10a}$ and Y have the same meanings as described above, respectively). When $R^{10a}$ is —$COR^{12}$ (wherein $R^{12}$ has the same meaning as described above), $R^{10a}$—O—$R^{10a}$ (wherein $R^{10a}$ has the same meaning as described above) may be used instead of $R^{10a}Y$.

Preparation Method 2

Among Compound (I), Compound (Id) in which $R^2$ is —$COR^6$ (wherein $R^6$ has the same meaning as described above), and $R^3$ is —$NR^{10}R^{11}$ (wherein $R^{10}$ and $R^{11}$ have the same meanings as described above, respectively) can be prepared according to the following steps.

[Chemical Formula 6]

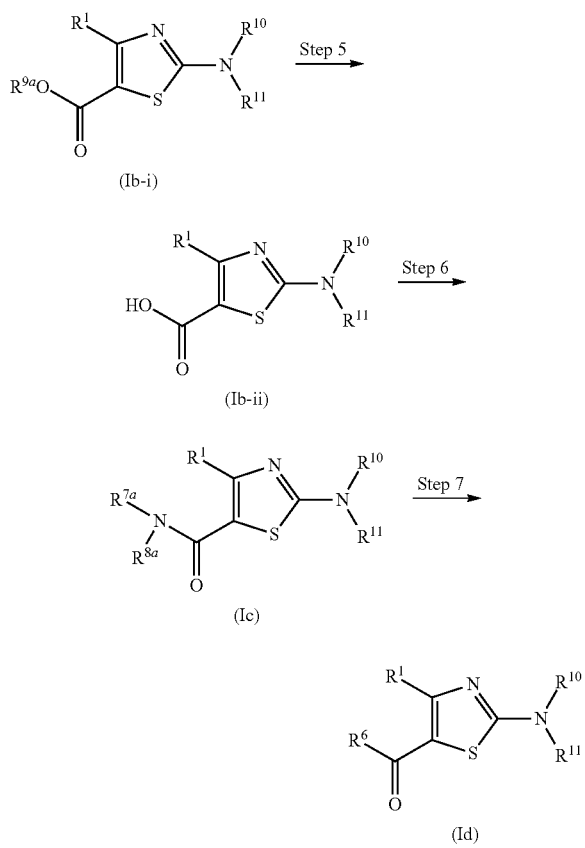

(Wherein $R^1$, $R^6$, $R^{10}$ and $R^{11}$ have the same meanings as described above, respectively, $R^{9a}$ represents lower alkyl or substituted or unsubstituted aralkyl as defined for $R^9$, $R^{7a}$ represents lower alkyl as defined for $R^7$, and $R^{8a}$ represents lower alkoxy as defined for $R^8$)

Step 5

Compound (Ib-ii) can be prepared from Compound (Ib-i) obtained by the method described in Preparation Method 1, according to the method of removing protective groups described in, for example, *Protective Groups in Organic Synthesis*, T. W. Greene, John Wiley & Sons Inc., 1981, and the like.

For example, when $R^{9a}$ is methyl or ethyl, Compound (Ib-ii) can be prepared by treating Compound (Ib-i) with preferably 1 equivalent to a large excess amount of base in a water-containing solvent, at a temperature between 0° C. and the boiling point of the solvent used, for 5 minutes to 72 hours.

Examples of the water-containing solvent include water-containing methanol, water-containing ethanol, water-containing propanol, water-containing THF, water-containing 1,4-dioxane, water-containing 1,2-dimethoxyethane, water-containing toluene, water-containing dichloromethane, water-containing DMF, and the like, which may be used alone or in combination.

Examples of the base include sodium hydroxide, potassium hydroxide, lithium hydroxide, and the like.

Also, when $R^{9a}$ is tert-butyl for example, Compound (Ib-ii) can be prepared by treating Compound (Ib-i) with 1 equivalent to a large excess amount of acid without solvent or in a solvent inert to the reaction, at a temperature between −30° C. and 100° C. for 5 minutes to 72 hours.

Examples of the solvent inert to the reaction include methanol, ethanol, propanol, THF, 1,4-dioxane, 1,2-dimethoxyethane, toluene, ethyl acetate, dichloromethane, DMF, water, and the like, which may be used alone or in combination.

Examples of the acid include trifluoroacetic acid, hydrochloric acid, sulfuric acid, and the like.

Step 6

Compound (Ic) can be prepared by reacting Compound (Ib-ii) with preferably 1 to 100 equivalents of $HNR^{7a}R^{8a}$ (wherein $R^{7a}$ and $R^{8a}$ have the same meanings as described above, respectively) in the presence of preferably 1 to 30 equivalents of condensing agent, and in the presence of preferably 1 to 30 equivalents of additive if necessary, without solvent or in a solvent inert to the reaction, at a temperature between −30° C. and 100° C. for 5 minutes to 72 hours.

Examples of the solvent inert to the reaction include acetonitrile, dichloromethane, 1,2-dichloroethane, chloroform, 1,2-dimethoxyethane, DMF, DMA, 1,4-dioxane, THF, diethyl ether, diisopropyl ether, benzene, toluene, xylene, pyridine, DMI, NMP, sulfolane, water, and the like, which may be used alone or in combination.

Examples of the condensing agent include dicyclohexylimide (DCC), diisopropylcarbodiimide, N-(3-dimethylaminopropyl)-W-ethylcarbodiimide (EDC), EDC hydrochloride, benzotriazole-1-yl-tris(dimethylamino)phosphonium hexafluorophosphate (BOP), benzotriazole-1-yl-tripyrrolidino-phosphonium hexafluorophosphate (PyBOP), diphenylphosphoryl azide (DPPA), and the like.

Examples of the additive include 1-hydroxybenzotriazole hydrate, triethylamine, and the like.

Step 7

Compound (Id) can be prepared by reacting Compound (Ic) with preferably 1 to 50 equivalents of $R^6M$ (wherein $R^6$ has the same meaning as described above, and M represents a metal group such as MgCl, MgBr, MgI, Li, $ZnCH_3$, $ZnCH_2CH_3$, and $Ti(OCH(CH_3)_2)_3$, in a solvent inert to the reaction, at a temperature between −78° and the boiling point of the solvent used, for 5 minutes to 72 hours.

Examples of the solvent inert to the reaction include diethyl ether, THF, 1,4-dioxane, 1,2-dimethoxyethane, toluene, and the like, which may be used alone or in combination.

Preparation Method 3

Compound (Id) can also be prepared according to the following steps.

[Chemical Formula7]

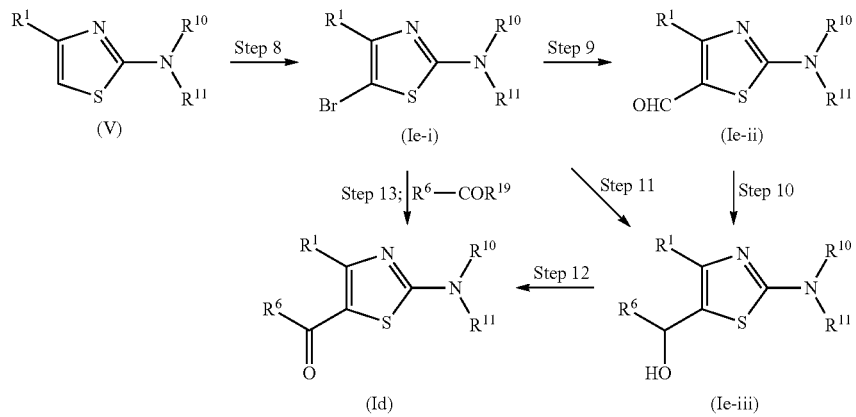

[Wherein $R^1$, $R^6$, $R^{10}$ and $R^{11}$ have the same meanings as described above, respectively, $R^{19}$ represents: lower alkoxy such as methoxy, ethoxy, propanoxy, and t-butoxy; phenoxy; phenoxy substituted with one to five fluorine atoms, chlorine atoms, bromine atoms, methoxy, ethoxy, methyl, and the like; or —$NR^{20}R^{21}$ (wherein $R^{20}$ represents lower alkyl such as methyl and ethyl, and $R^{21}$ represents lower alkoxy such as methoxy and ethoxy)]

Step 8

Compound (Ie-i) can be prepared using Compound (V), by the method described in, for example, *Journal of the Chemical Society* (J. Chem. Soc.), p. 114, 1947, and the like, or similar methods thereof.

Specifically, Compound (Ie-i) can be prepared by reacting Compound (V) with preferably 1 to 20 equivalents of brominating agent in a solvent inert to the reaction, at a temperature between −30° C. and the boiling point of the solvent used, for 5 minutes to 72 hours.

Compound (V) can be obtained either commercially or by the method described in, for example, *Journal of the American Chemical Society* (J. Am. Chem. Soc.), Vol. 72, p. 3722, 1953, and the like, or similar methods thereof. Compound (V) can also be obtained according to the method described in Preparation Method 1.

Examples of the solvent inert to the reaction include dichloromethane, chloroform, 1,2-dichloroethane, and the like, which may be used alone or in combination.

Examples of the brominating agent include N-bromosuccinimide, bromine, N,N,N,N-tetra-n-butylammonium tribromide, pyridinium tribromide, and the like.

Step 9

Compound (Ie-ii) can be prepared by reacting Compound (Ie-i) with preferably 1 to 100 equivalents of formylating agent in a solvent inert to the reaction, in the presence of preferably 1 to 20 equivalents of base, at a temperature between −78° C. and room temperature for 5 minutes to 72 hours.

Examples of the solvent inert to the reaction include THF, diethyl ether, 1,4-dioxane, 1,2-dimethoxyethane, hexane, and the like, which may be used alone or in combination.

Examples of the formylating agent include DMF, N-methyl-N-phenylformamide, N-methyl-N-(2-pyridyl)formamide, morpholinoformamide, and the like. DMF is preferable among these examples.

Examples of the base include lithium diisopropylamide, lithium bis(trimethylsilyl)amide, methyllithium, n-butyl lithium, lithium hydride, sodium hydride, potassium hydride, methyl magnesium bromide, ethyl magnesium bromide, isopropyl magnesium chloride, and the like.

Step 10

Compound (Ie-iii) can be prepared by reacting Compound (Ie-ii) with preferably 1 to 50 equivalents of $R^6M$ (wherein $R^6$ and M have the same meanings as described above, respectively) in a solvent inert to the reaction, at a temperature between −78° C. and the boiling point of the solvent used, for 5 minutes to 72 hours.

Examples of the solvent inert to the reaction include diethyl ether, THF, 1,4-dioxane, 1,2-dimethoxyethane, toluene, and the like, which may be used alone or in combination.

Step 11

Alternatively, Compound (Ie-iii) can also be prepared by reacting Compound (Ie-i) with preferably 1 to 100 equivalents of $R^6CHO$ (wherein $R^6$ has the same meaning as described above) in a solvent inert to the reaction, in the presence of preferably 1 to 20 equivalents of base, at a temperature between −78° C. and room temperature for 5 minutes to 72 hours.

Examples of the solvent inert to the reaction include THF, diethyl ether, 1,4-dioxane, 1,2-dimethoxyethane, hexane, and the like, which may be used alone or in combination.

Examples of the base include lithium diisopropylamide, lithium bis(trimethylsilyl)amide, methyllithium, n-butyl lithium, lithium hydride, sodium hydride, potassium hydride, methyl magnesium bromide, ethyl magnesium bromide, isopropyl magnesium chloride, and the like.

Step 12

Compound (Id) can be prepared by treating Compound (Ie-iii) with preferably 1 to 100 equivalents of oxidizing agent without solvent or in a solvent inert to the reaction, at a temperature between −78° C. and the boiling point of the solvent for 5 minutes to 72 hours.

Examples of the solvent inert to the reaction include acetonitrile, dichloromethane, 1,2-dichloroethane, chloroform, 1,2-dimethoxyethane, DMF, DMA, 1,4-dioxane, THF, diethyl ether, diisopropyl ether, benzene, toluene, xylene, pyridine, DMI, NMP, sulfolane, water, and the like, which may be used alone or in combination.

Examples of the oxidizing agent include chromic acid, pyridinium chlorochromate (PCC), pyridinium dichlorochromate (PDC), dimethyl sulfoxide (DMSO)-oxalyl chloride, DMSO-DCC, tetrapropylammonium perruthenate (TPAP), Dess-Martin reagent (DMP: 1,1,1-triacetoxy-1,1-dihydro-1,2-benziodoxol-3(1H)-one, *Jikken Kagaku Kouza*, 5th Edition, Vol. 15, p. 27, Nihon Kagaku-Kai, Maruzen, 2003), 2-iodoxybenzoic acid (IBX), 2,2,6,6-tetramethylpiperidine-N-oxide (TEMPO), manganese dioxide, and the like.

Step 13

Compound (Id) can also be prepared by reacting Compound (Ie-i) with preferably 1 to 100 equivalents of $R^6$—$COR^{19}$ (wherein $R^6$ and $R^{19}$ have the same meanings as described above, respectively) in a solvent inert to the reaction, in the presence of preferably 1 to 20 equivalents of base, at a temperature between −78° C. and room temperature for 5 minutes to 72 hours.

Examples of the solvent inert to the reaction include THF, diethyl ether, 1,4-dioxane, 1,2-dimethoxyethane, hexane, and the like, which may be used alone or in combination.

Examples of the base include lithium diisopropylamide, lithium bis(trimethylsilyl)amide, methyllithium, n-butyl lithium, lithium hydride, sodium hydride, potassium hydride, methyl magnesium bromide, ethyl magnesium bromide, isopropyl magnesium chloride, and the like.

Preparation Method 4

Among Compound (I), Compound (Ia-v) in which $R^2$ is —$NR^4R^5$ (wherein $R^4$ and $R^5$ have the same meanings as described above, respectively), and $R^3$ is —$NR^{10}R^{11}$ (wherein $R^{10}$ and $R^{11}$ have the same meanings as described above, respectively) can be prepared according to the following step.

[Chemical Formula 8]

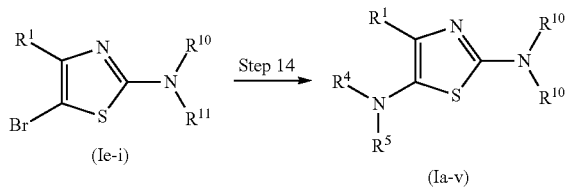

(Wherein $R^1$, $R^2$, $R^{10}$ and $R^{11}$ have the same meanings as described above, respectively).

Step 14

Compound (Ia-v) can be prepared using Compound (Iei) obtained in Step 8 of Preparation Method 3, by the method described in, for example, EP518731, or similar methods thereof.

Specifically, Compound (Ia-v) can be prepared by reacting Compound (Ie-i) with preferably 1 to 200 equivalents of $HNR^4R^5$ (wherein $R^4$ and $R^5$ have the same meanings as described above, respectively) without solvent or in a solvent inert to the reaction, in the presence of preferably 1 to 100 equivalents of base if necessary, at a temperature between −30° C. and 150° C. for 5 minutes to 72 hours.

Examples of the solvent inert to the reaction include acetonitrile, methanol, ethanol, dichloromethane, chloroform, 1,2-dichloroethane, 1,2-dimethoxyethane, DMF, DMA, 1,4-dioxane, THF, diethyl ether, diisopropyl ether, benzene, toluene, xylene, DMI, NMP, sulfolane, water, and the like, which may be used alone or in combination. DMF or DMA is preferable among these examples.

Examples of the base include triethylamine, diisopropylethylamine, DBU, potassium carbonate, sodium hydroxide, and the like.

Preparation Method 5

Among Compound (I), Compound (If) in which $R^2$ is —$CH_2NR^{22}R^{23}$ (wherein $R^{22}$ and $R^{23}$ represent $R^x$ and $R^y$ of the substituent —$NR^xR^y$ (wherein $R^x$ and $R^y$ have the same meanings as described above, respectively) of the substituted lower alkyl defined for $R^2$, or are combined together with the adjacent nitrogen atom thereto to represent an aliphatic heterocyclic group of the substituted or unsubstituted aliphatic heterocyclic alkyl defined for $R^2$) can be prepared according to the following step.

[Chemical Formula 9]

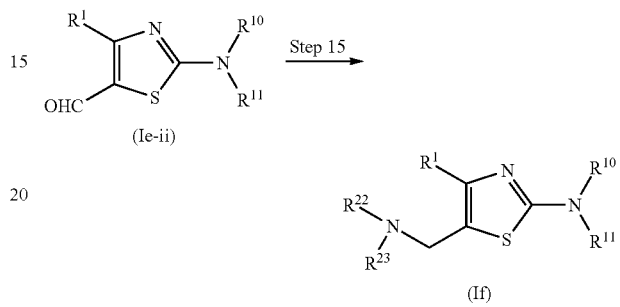

(Wherein $R^1$, $R^{10}$, $R^{11}$, $R^{22}$ and $R^{23}$ have the same meanings as described above, respectively)

Step 15

Compound (If) can be prepared by reacting Compound (Ie-ii) obtained in Step 9 of Preparation Method 3 with preferably 1 to 200 equivalents of $HNR^{22}R^{23}$ (wherein $R^{22}$ and $R^{23}$ have the same meanings as described above, respectively) in a solvent inert to the reaction, in the presence of preferably 1 to 50 equivalents of reducing agent, at a temperature between −30° C. and the boiling point of the solvent used, for 5 minutes to 72 hours.

Examples of the reducing agent include sodium triacetoxyborohydride, sodium borohydride, sodium cyanogenborohydride, and the like. Sodium triacetoxyborohydride is preferable among these examples.

Examples of the solvent inert to the reaction include, but are not particularly limited to, methanol, ethanol, dichloromethane, chloroform, 1,2-dichloroethane, THF, 1,4-dioxane, diethyl ether, diisopropyl ether, benzene, toluene, xylene, DMF, water, and the like, which may be used alone or in combination.

Preparation Method 6

Among Compound (I), Compound (Ig) in which $R^3$ is —$NHCONR^{13}R^{14}$ (wherein $R^{13}$ and $R^{14}$ have the same meanings as described above, respectively), or —NHCOOR$^{15}$ (wherein $R^{15}$ has the same meaning as described above) can be prepared according to the following steps.

[Chemical Formula 10]

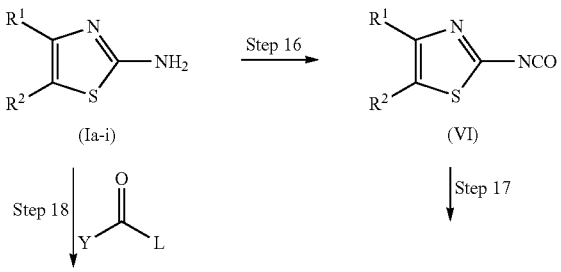

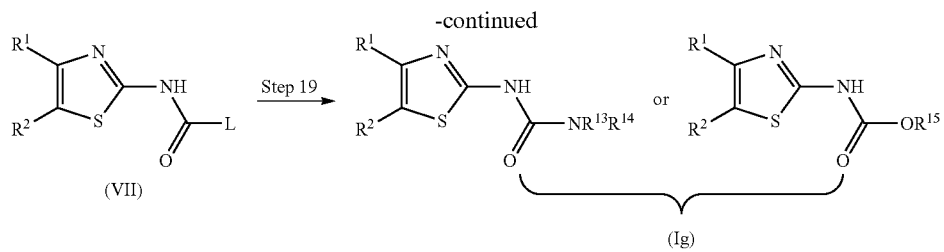

(VII)    (Ig)

[Wherein $R^1$, $R^2$, $R^{13}$, $R^{14}$, $R^{15}$ and Y have the same meanings as described above, respectively, L represents a leaving group including: halogen such as a chlorine atom, a bromine atom, and an iodine atom; lower alkoxy such as methoxy, ethoxy, and t-butoxy; phenoxy; or phenoxy substituted with a fluorine atom, a chlorine atom, a bromine atom, methoxy, ethoxy, methyl, nitro, cyano, and the like]

Step 16

Compound (VI) can be prepared using Compound (Ia-i) obtained by Preparation Methods 1 to 5 and the like, by the methods described in *Jikken Kagaku Kouza*, 4th Edition, Vol. 20, p. 473-483, Nihon Kagaku-Kai, Maruzen, 1992, and the like, or similar methods thereof.

For example, Compound (VI) can be prepared by reacting Compound (Ia-i) with preferably 1 to 20 equivalents of phosgene or isoster thereof without solvent or in a solvent inert to the reaction, in the presence of preferably 1 to 100 equivalents of base if necessary, at a temperature between –30° C. and 150° C. for 5 minutes to 72 hours.

Examples of the solvent inert to the reaction include acetonitrile, methanol, ethanol, dichloromethane, chloroform, 1,2-dichloroethane, 1,2-dimethoxyethane, DMF, DMA, 1,4-dioxane, THF, diethyl ether, diisopropyl ether, benzene, toluene, xylene, DMI, NMP, sulfolane, water, and the like, which may be used alone or in combination.

Examples of the isoster of phosgene include triphosgene, 1,1'-carbonyldiimidazole (CDI), and the like.

Examples of the base include triethylamine, diisopropylethylamine, DBU, potassium carbonate, sodium hydroxide, and the like.

Step 17

Compound (Ig) can be prepared by reacting Compound (VI) with preferably 1 to 200 equivalents of $HR^{13}R^{14}$ (wherein $R^{13}$ and $R^{14}$ have the same meanings as described above, respectively) or $HOR^{15}$ (wherein $R^{15}$ has the same meaning as described above) without solvent or in a solvent inert to the reaction, in the presence of preferably 1 to 100 equivalents of base if necessary, at a temperature between –30° C. and 150° C. for 5 minutes to 72 hours.

Examples of the solvent inert to the reaction include acetonitrile, dichloromethane, chloroform, 1,2-dichloroethane, 1,2-dimethoxyethane, DMF, DMA, 1,4-dioxane, THF, diethyl ether, diisopropyl ether, benzene, toluene, xylene, DMI, NMP, sulfolane, water, and the like, which may be used alone or in combination.

Examples of the base include triethylamine, diisopropylethylamine, DBU, and the like.

Further, Compound (Ig) can also be prepared by performing Step 17 without isolating Compound (VI) in Step 16.

Step 18

Compound (VII) can be prepared by reacting Compound (Ia-i) with preferably 1 to 50 equivalents of YCOL (wherein Y and L have the same meanings as described above, respectively) in a solvent inert to the reaction, in the presence of preferably 1 to 100 equivalents of base if necessary, at a temperature between –30° C. and 150° C. for 5 minutes to 72 hours.

YCOL (wherein Y and L have the same meanings as described above, respectively) can be obtained either commercially or by the method described in *Journal of the American Chemical Society*, 1954, Vol. 76, p. 4458, and the like, or similar methods thereof.

Examples of the solvent inert to the reaction include acetonitrile, dichloromethane, 1,2-dichloroethane, chloroform, 1,2-dimethoxyethane, DMF, DMA, 1,4-dioxane, THF, diethyl ether, diisopropyl ether, benzene, toluene, xylene, pyridine, DMI, NMP, sulfolane, and the like, which may be used alone or in combination.

Examples of the base include pyridine, triethylamine, diisopropylethylamine, N-methylmorpholine, N-methylpiperidine, DBU, DMAP, potassium acetate, potassium carbonate, cesium carbonate, sodium carbonate, sodium bicarbonate, sodium hydroxide, lithium hydroxide, potassium hydroxide, potassium phosphate, and the like.

Step 19

Compound (Ig) can be prepared using Compound (VII), in the same manner as in the method of step 17.

Further, Compound (Ig) can also be prepared by performing Step 19 without isolating Compound (VII) in Step 18.

Preparation Method 7

Among Compound (I), Compound (Ig-i) in which $R^3$ is —NHCONHR$^{14}$ (wherein $R^{14}$ has the same meaning as described above) can be prepared according to the following step.

[Chemical Formula 11]

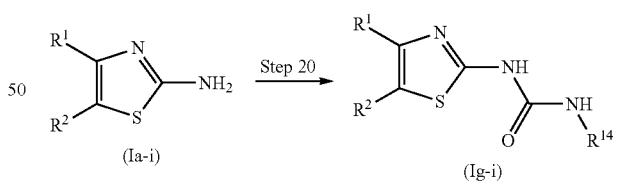

(Ia-i)    (Ig-i)

(Wherein $R^1$, $R^2$ and $R^{14}$ have the same meanings as described above, respectively)

Step 20

Compound (Ig-i) can be prepared by reacting Compound (Ia-i) obtained by preparation methods 1 to 5 and the like, with preferably 1 to 20 equivalents of $R^{14}$—NCO (wherein $R^{14}$ has the same meaning as described above) in a solvent inert to the reaction at a temperature between 0° C. and the boiling point of the solvent used, for 5 minutes to 72 hours.

$R^{14}$—NCO (wherein $R^{14}$ has the same meaning as described above) can be obtained either commercially or by the method described in *Jikken Kagaku Kouza*, 4th Edition, Vol. 20, p. 473-483, Nihon Kagaku-Kai, Maruzen, 1992, and the like, or similar methods thereof.

Examples of the solvent inert to the reaction include acetonitrile, THF, 1,4-dioxane, DMF, dichloromethane, 1,2-dichloroethane, diethyl ether, benzene, toluene, water, and the like.

Preparation Method 8

Among Compound (I), Compound (Ih) in which $R^3$ is —CONHR$^{16}$ (wherein $R^{16}$ has the same meaning as described above) can be prepared according to the following steps.

[Chemical Formula 12]

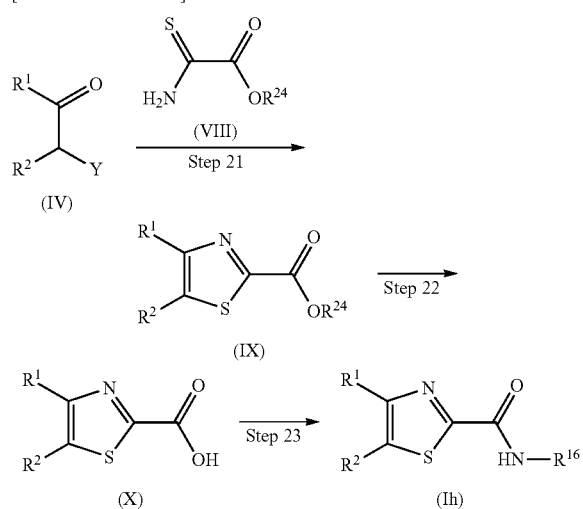

(Wherein $R^1$, $R^2$, $R^{16}$ and Y have the same meanings as described above, respectively, and $R^{24}$ represents lower alkyl such as methyl, ethyl, propyl, and t-butyl) Step 21

Compound (IX) can be prepared using Compound (IV) obtained by Preparation Method 1, by the method described in *Journal of Medicinal and Pharmaceutical Chemistry*, 1959, Vol. 2, p. 588, and the like, or similar methods thereof.

For example, Compound (IX) can be prepared by reacting Compound (IV) with preferably 1 to 20 equivalents of Compound (VIII) in a solvent inert to the reaction at a temperature between room temperature and 100° C. for 5 minutes to 72 hours.

Examples of the solvent inert to the reaction include toluene, hexane, THF, DMF, methanol, ethanol, diethyl ether, acetonitrile, and the like, which may be used alone or in combination.

Compound (VIII) can be obtained either commercially or by the method described in *Journal of Medicinal and Pharmaceutical Chemistry*, 1959, Vol. 2, p. 588, and the like, or similar methods thereof.

Further, Compound (IX) can also be prepared by successively performing Step 21, without isolating Compound (IV) from $R^1COCH_2R^2$ as in Step 1 of Preparation Method 1.

Step 22

Compound (X) can be prepared using Compound (IX), in the same manner as in the method in Step 5 of Preparation Method 2.

Step 23

Compound (Ih) can be prepared using Compound (X) and $H_2NR^{16}$ (wherein $R^{16}$ has the same meaning as described above), in the same manner as in the method in Step 6 of Preparation Method 2.

Preparation Method 9

Compound (Ih) can also be prepared according to the following steps.

[Chemical Formula 13]

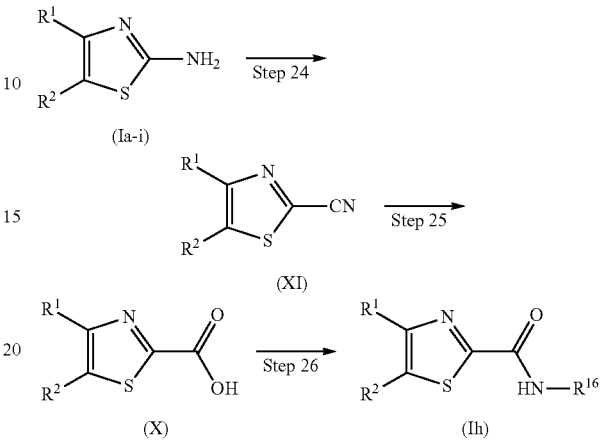

(Wherein $R^1$, $R^2$ and $R^{16}$ have the same meanings as described above, respectively) Step 24

Compound (XI) can be prepared by reacting Compound (Ia-i) with preferably 1 to 20 equivalents of cyanating agent in a solvent inert to the reaction, in the presence of preferably 1 to 20 equivalents of nitrite compound, at a temperature between −30° C. and 150° C. for 5 minutes to 72 hours.

Examples of the nitrite compound include sodium nitrite, tert-butyl nitrite, isoamyl nitrite, and the like.

Examples of the cyanating agent include copper(I) cyanide, sodium cyanide, potassium cyanide, tetrabutylammonium cyanide, zinc cyanide, copper(I) potassium cyanide, and the like.

Examples of the solvent inert to the reaction include toluene, acetonitrile, dimethyl sulfoxide, water, and the like, which may be used alone or in combination.

Step 25

Compound (X) can be prepared from Compound (XI) by the method described in *Jikken Kagaku Kouza*, 5th Edition, Vol. 15, p. 15, Nihon Kagaku-Kai, Maruzen, 2003, and the like, or similar methods thereof.

For example, Compound (X) can be prepared by treating Compound (XI) with 1 equivalent to a large excess amount of base in a water-containing solvent, at a temperature between 0° C. and the boiling point of the solvent used, for 5 minutes to 72 hours.

Examples of the base include sodium hydroxide, potassium hydroxide, lithium hydroxide, and the like.

Examples of the water-containing solvent include water-containing methanol, water-containing ethanol, water-containing propanol, water-containing THF, water-containing 1,4-dioxane, water-containing 1,2-dimethoxyethane, water-containing toluene, water-containing dichloromethane, water-containing DMF, and the like, which may be used either alone or in combination.

Step 26

Compound (Ih) can be prepared using Compound (X) and $H_2NR^{16}$ (wherein $R^{16}$ has the same meaning as described above), in the same manner as in Step 23 of Preparation Method 8.

Preparation Method 10

Among Compound (I), Compound (Ii) in which $R^3$ is represented by the foregoing formula (II) can be prepared according to the following steps.

[Chemical Formula 14]

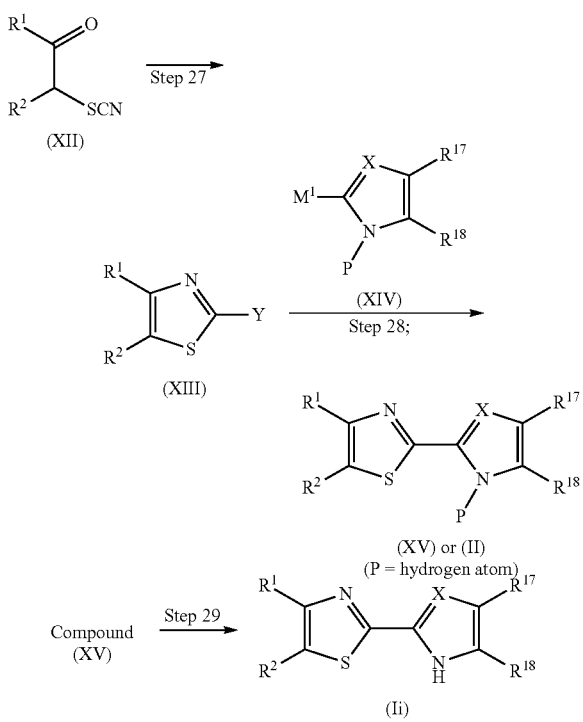

[Wherein $R^1$, $R^2$, $R^{17}$, $R^{18}$, X and Y have the same meanings as described above, respectively, P represents a hydrogen atom or a protective group (examples of the protective group including tert-butoxycarbonyl (Boc group), benzyloxycarbonyl (Z group), benzyl, acetyl, benzoyl, and the like), and $M^1$ represents trimethyl tin, tributyl tin, triphenyl tin, —$B(OR^{25})OR^{26}$ (wherein $R^{25}$ and $R^{26}$ may be the same or different, and each represents a hydrogen atom or lower alkyl such as methyl, ethyl, propyl, isopropyl, and butyl), or 4,4,5,5-tetramethyl-1,3,2-dioxaborolan]

Step 27

Compound (XIII) can be prepared by reacting Compound (XII) with preferably 1 equivalent to an excess amount of hydrogen halide (YH) in a solvent inert to the reaction, at a temperature between −30° C. and the boiling point of the solvent used, for 5 minutes to 72 hours.

Compound (XII) can be obtained by the method described in, for example, *Journal of Organic Chemistry*, 1948, Vol. 13, p. 722, and the like, or similar methods thereof.

Examples of the hydrogen halide include hydrogen chloride, hydrogen bromide, hydrogen iodide, and the like.

Examples of the solvent inert to the reaction include dichloromethane, chloroform, 1,2-dichloroethane, 1,4-dioxane, THF, diethyl ether, diisopropyl ether, acetonitrile, acetic acid, ethyl acetate, and the like, which may be used alone or in combination.

Step 28

Compound (XV) or (Ii) can be prepared by reacting Compound (XIII) with Compound (XIV) in a solvent inert to the reaction in the presence of a catalytic amount of palladium compound, at a temperature between room temperature and 140° C. for 5 minutes to 72 hours.

Compound (XV) can be obtained by the methods described in *Journal of Organic Chemistry*, 2002, Vol. 67, p. 7551; Synlett, 1992, p. 805; WO03/053925, and the like, or similar methods thereof.

The reaction may be performed by adding preferably 0.2 to 5 equivalents of, for example, inorganic salts such as lithium chloride, potassium chloride, silver oxide, copper oxide, silver nitrate, and silver acetate, or bases such as triethylamine, sodium ethoxide, sodium carbonate, and sodium hydroxide, preferably sodium carbonate.

Examples of the palladium compound include bis(triphenylphosphine)palladium(II) chloride, tetrakis(triphenylphosphine)palladium(0), [1,2-bis(diphenylphosphino)ethane]palladium(II) chloride, [1,1'-bis(diphenylphosphino)ferrocene]palladium(II) chloride, and the like.

Examples of the solvent inert to the reaction include diethyl ether, THF, 1,4-dioxane, DMF, DMA, DMSO, benzene, toluene, xylene, dichloromethane, chloroform, carbon tetrachloride, 1,2-dichloroethane, acetonitrile, ethyl acetate, methyl acetate, methylethyl ketone, methanol, ethanol, propanol, isopropyl alcohol, butanol, hexane, water, and the like, which may be used alone or in combination.

Step 29

Compound (Ii) can be prepared by removing protecting group P from Compound (XV) using the method of removing protective groups commonly used in organic synthetic chemistry [for example, the methods described in *Protective Groups in Organic Synthesis*, T. W. Greene, John Wiley & Sons Inc., 1999, and the like].

For example, when P is a Boc group, Compound (Ii) can be prepared by treating Compound (XV) with hydrochloric acid, trifluoroacetic acid, and the like. When P is a Z group or a benzyl group, Compound (Ii) can be prepared by subjecting Compound (XV) to a reduction reaction such as a hydrogenation reaction, for example.

Preparation Method 11

Among Compound (I), Compound (Ii-i) in which $R^3$ is represented by the foregoing formula (II) and X is a nitrogen atom can be prepared according to the following steps.

[Chemical Formula 15]

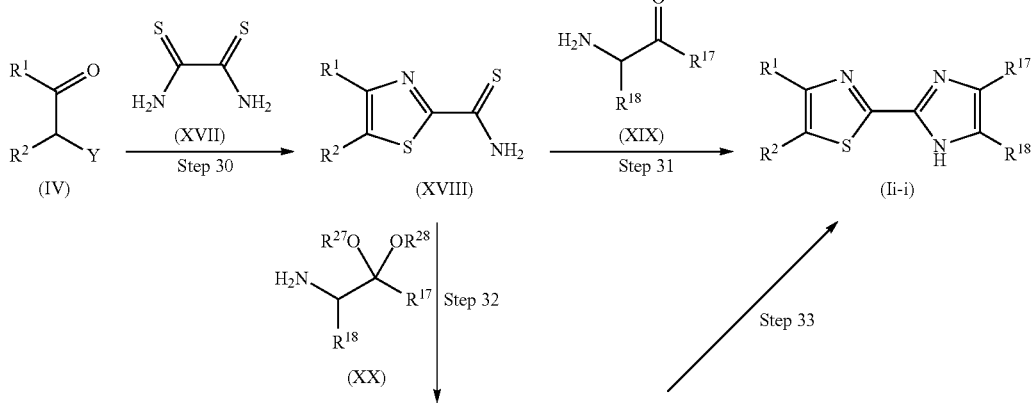

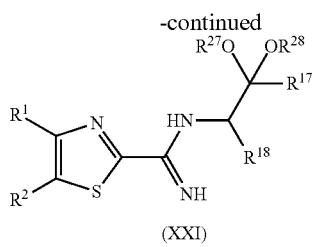

(XXI)

[Wherein $R^1$, $R^2$, $R^{17}$, $R^{18}$ and Y have the same meanings as described above, respectively, $R^{27}$ and $R^{28}$ may be the same or different, and each represents lower alkyl such as methyl, ethyl, propyl, or represent —$(CH_2)_2$— or —$(CH_2)_3$— together with each other]

Step 30

Compound (XVIII) can be prepared by the method described in *Synthetic Communications*, 2001, Vol. 31, p. 3747, and the like, or similar methods thereof.

For example, Compound (XVIII) can be prepared by reacting Compound (IV) obtained in Step 1 of Preparation Method 1 with preferably 1 to 20 equivalents of rubeanic acid (Compound (XVII)) in a solvent inert to the reaction, at a temperature between room temperature and 100° C., for 5 minutes to 72 hours.

Examples of the solvent inert to the reaction include toluene, hexane, THF, DMF, methanol, ethanol, diethyl ether, acetonitrile, and the like, which may be used alone or in combination.

Step 31

Compound (Ii-i) can be prepared by reacting Compound (XVIII) with an excess amount of methyl iodide in a solvent inert to the reaction, at a temperature between 0° C. and 40° C. for 5 minutes to 72 hours, and then with Compound (XIX) in a solvent inert to the reaction, at temperature between room temperature and the boiling point of the solvent used, for 5 minutes to 72 hours.

Compound (XIX) can be obtained either commercially or by the methods described in *Journal of the Chemical Society*, 1949, Vol. 71, p. 2473; *Synthetic Communications*, 2000, Vol. 30, p. 2287; and the like, or similar methods thereof.

Examples of the solvent inert to the reaction include toluene, hexane, THF, DMF, methanol, ethanol, diethyl ether, acetonitrile, acetone, and the like, which may be used alone or in combination.

Compound (Ii-i) can also be prepared via the following two steps.

Step 32

Compound (XXI) can be prepared using Compound (XVIII) and Compound (XX), in the same manner as in the method of Step 31.

Compound (XX) can by obtained either commercially or by the method described in *Tetrahedron*, 1995, Vol. 51, p. 5147, and the like, or similar methods thereof.

Step 33

Compound (Ii-i) can be prepared using Compound (XXI), by the method of removing protective groups described in, for example, *Protective Groups in Organic Synthesis*, T. W. Greene, John Wiley & Sons Inc., 1981, and the like, or similar methods thereof.

For example, Compound (Ii-i) can be prepared by treating Compound (XXI) with preferably 1 equivalent to a large excess amount of acid in a solvent inert to the reaction, at a temperature between 0° C. and the boiling point of the solvent used, for 5 minutes to 72 hours.

Examples of the acid include hydrochloric acid, sulfuric acid, acetic acid, trifluoroacetic acid, and the like.

Examples of the solvent inert to the reaction include dichloromethane, chloroform, acetone, diethyl ether, THF, water, and the like, which may be used alone or in combination.

Further, Compound (Ii-i) can also be prepared by successively performing Step 33 without isolating Compound (XXI) obtained in Step 32.

Preparation Method 12

Compound (Ii-1) can also be prepared according to the following steps.

[Chemical Formula 16]

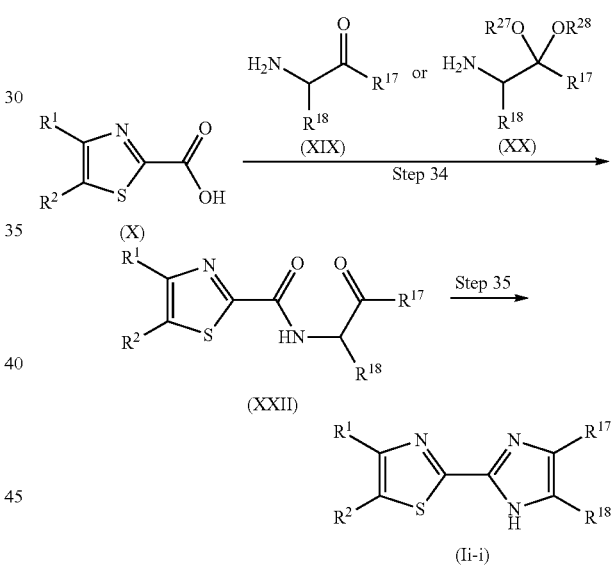

(Wherein $R^1$, $R^2$, $R^{17}$, $R^{18}$, $R^{27}$, and $R^{28}$ have the same meanings as described above, respectively)

Step 34

Compound (XXII) can be prepared using Compound (X) and Compound (XIX) or (XX) by performing Step 26 of Preparation Method 9, and if necessary successively Step 33 of Preparation Method 11.

Step 35

Compound (Ii-i) can be prepared by reacting Compound (XXII) with preferably 1 equivalent to an excess amount of ammonia compound without solvent or in a solvent inert to the reaction, at a temperature between room temperature and 150° C. for 5 minutes to 72 hours.

Examples of the ammonia compound include ammonia, ammonium formate, ammonium acetate, ammonium trifluoroacetate, and the like.

Examples of the solvent inert to the reaction include acetic acid, DMF, water, and the like, which may be used alone or in combination.

Preparation Method 13

Compound (Ii-i) can also be prepared according to the following steps.

[Chemical Formula 17]

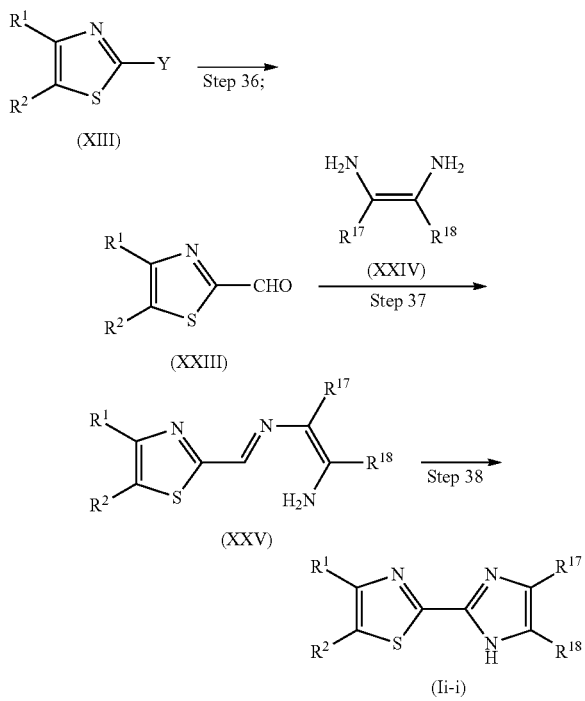

(Wherein $R^1$, $R^2$, $R^{17}$, $R^{18}$, and Y have the same meanings as described above, respectively)

Step 36

Compound (XXIII) can be prepared using Compound (XIII) obtained in Step 27 of Preparation Method 10, in the same manner as in the method in Step 9 of Preparation Method 3.

Step 37

Compound (XXV) can be prepared by reacting Compound (XXIII) with preferably 1 to 200 equivalents of Compound (XXIV) in a solvent, at a temperature between −30° C. and the boiling point of the solvent used, for 5 minutes to 72 hours.

Compound (XXIV) can be obtained either commercially or by the methods described in *Journal of the Chemical Society*, 1957, p. 2197; *Journal of Organic Chemistry*, 1960, Vol. 25, p. 1752; and the like, or similar methods thereof.

Examples of the solvent include methanol, ethanol, dichloromethane, chloroform, 1,2-dichloroethane, THF, 1,4-dioxane, diethyl ether, diisopropyl ether, benzene, nitrobenzene, toluene, xylene, DMF, water, and the like, which may be used alone or in combination.

In the case where nitrobenzene is used as the solvent in this step, Compound (Ii-i), which is the desired compound of the next Step 38 can be directly prepared from Compound (XXIII).

Step 38

Compound (Ii-1) can be prepared by treating Compound (XXV) with preferably 1 to 100 equivalents of oxidizing agent in a solvent inert to the reaction, at a temperature between −78° C. and the boiling point of the solvent used, for 5 minutes to 72 hours.

Examples of the oxidizing agent include m-chloroperbenzoic acid, 2,3-dichloro-5,6-dicyano-1,4-benzoquinone (DDQ), benzofuroxan, potassium permanganate, hydrogen peroxide, peracetic acid, tert-butyl hydroperoxide, and the like.

Examples of the solvent inert to the reaction include acetonitrile, dichloromethane, 1,2-dichloroethane, chloroform, 1,2-dimethoxyethane, DMF, DMA, 1,4-dioxane, THF, diethyl ether, diisopropyl ether, benzene, toluene, xylene, pyridine, DMI, NMP, sulfolane, water, and the like, which may be used either alone or in combination.

The intermediates and desired compounds of the foregoing preparation methods may be isolated and purified by separation and purification methods commonly used in organic synthetic chemistry, for example, such as filtration, extraction, washing, drying, condensation, recrystallization, and various types of chromatography. The intermediates may be supplied to the next reaction without any purification.

Among Compound (I), it may exist as stereoisomers such as regioisomer, geometrical isomer, and optical isomer, or tautomers. These and all other possible isomers and mixtures thereof can also be used for therapeutic and/or preventive agents for sleep disorder of the present invention.

To obtain a salt of Compound (I), when Compound (I) is obtained in the form of a salt, it may be purified as it is. Further, when Compound (I) is obtained in a free form, Compound (I) may be dissolved or suspended in a suitable solvent, followed by addition of an acid or a base to form a salt. Then, the resulting salt may be isolated and purified.

Compound (I) and a pharmaceutically acceptable salt thereof may exist as an adduct with water or various solvents. Such adducts can also be used for therapeutic and/or preventive agents for sleep disorder of the present invention.

Table 1-1 through Table 4 below show specific examples of Compound (I) obtained by the present invention. It should be noted however that the compounds used in the present invention are not limited to these examples.

TABLE 1-1

(I)

| Compound Number | $R^2$ | $R^{11}$ |
|---|---|---|
| 1 | 4-pyridyl | —C(O)-3-pyridyl |
| 2 | 4-pyridyl | —C(O)—CH$_3$ |
| 3 | 4-pyridyl | —C(O)—CH$_2$OCH$_3$ |
| 4 | 4-pyridyl | —C(O)-cyclohexyl |
| 5 | 4-pyridyl | —C(O)-2-pyridyl |

TABLE 1-1-continued
(I)
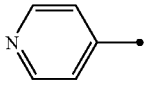
| Compound Number | R² | R¹¹ |
|---|---|---|
| 6 | 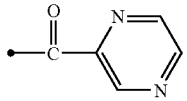 | 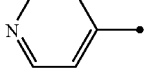 |
| 7 | 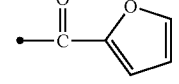 | 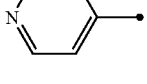 |
| 8 | 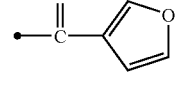 | 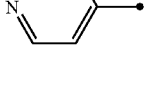 |
| 9 | 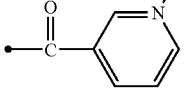 | 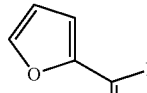 |
| 10 | 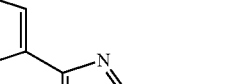 | 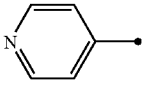 |
| 11 | 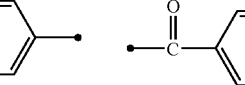 | 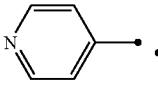 |
| 12 | 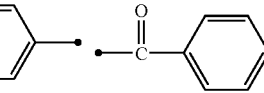 | 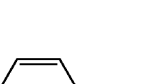 |
TABLE 1-2
(I)
| Compound Number | R² | R¹¹ |
|---|---|---|
| 13 | 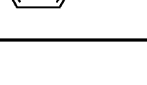 |  |
| 14 | 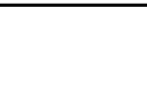 | 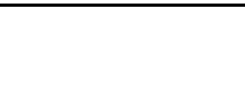 |
| 15 | 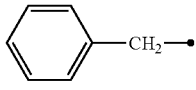 | 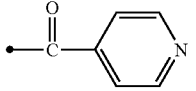 |
| 16 | 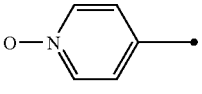 | 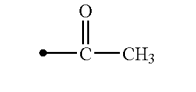 |
| 17 | 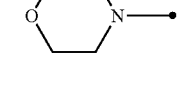 | 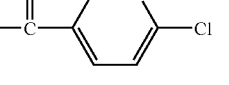 |

TABLE 1-2-continued
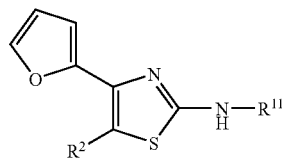
(I)
| Compound Number | R² | R¹¹ |
|---|---|---|
| 18 | 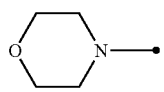 | 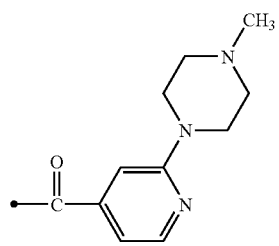 |
| 19 | 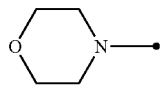 | 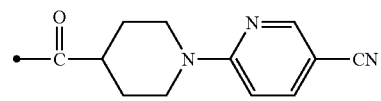 |
| 20 | 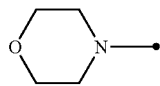 | 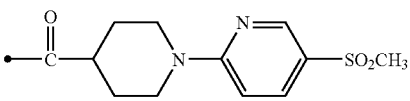 |
| 21 | 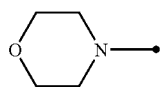 | 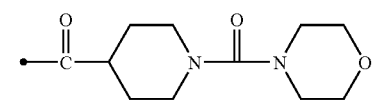 |
| 22 | 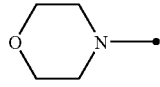 | 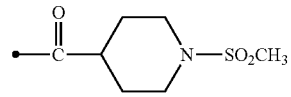 |
| 23 | 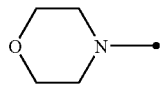 | 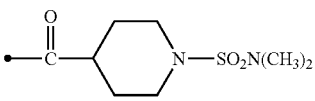 |
| 24 | 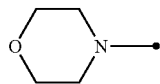 | 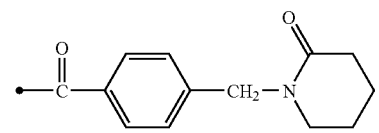 |

TABLE 1-3
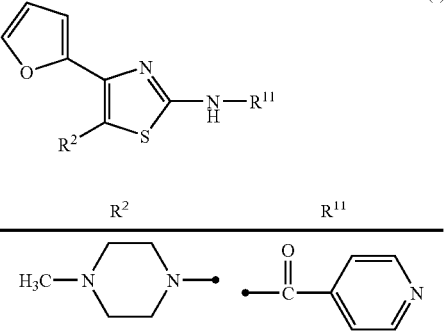
| Compound Number | R² | R¹¹ |
|---|---|---|
| 25 | 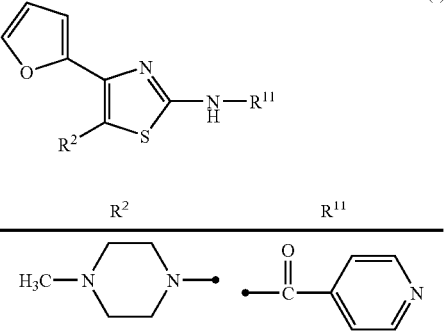 | 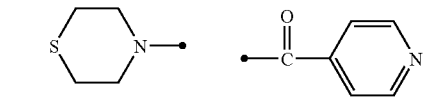 |
| 26 | 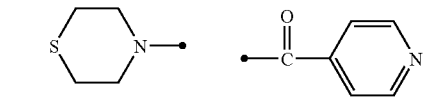 | 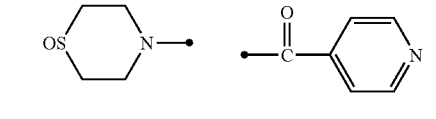 |
| 27 | 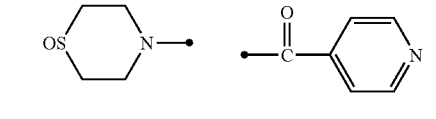 | 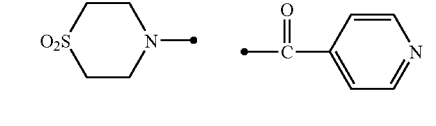 |
| 28 | 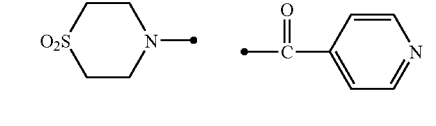 | 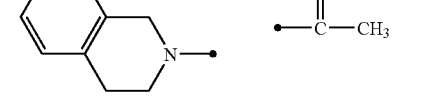 |
| 29 | 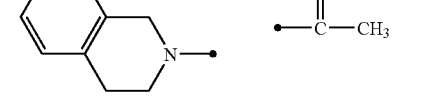 | 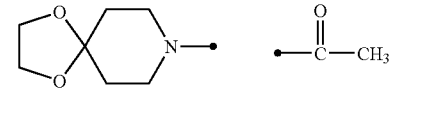 |
| 30 | 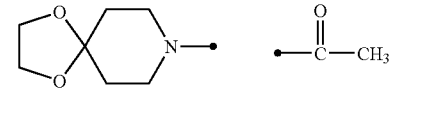 | 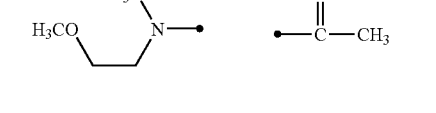 |
| 31 | 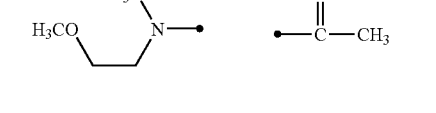 |  |
| 32 |  | 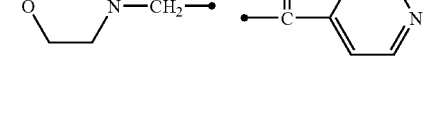 |
| 33 | 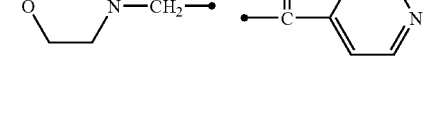 | 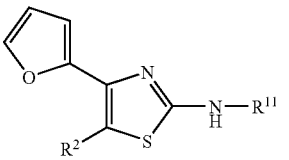 |
TABLE 1-3-continued
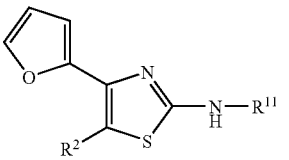
| Compound Number | R² | R¹¹ |
|---|---|---|
| 34 | 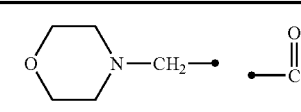 | 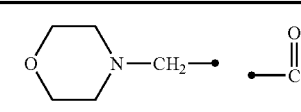 |
| 35 | 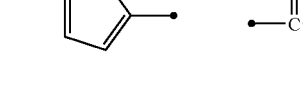 | 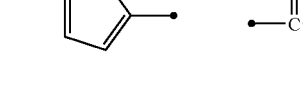 |
| 36 | 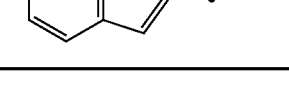 | 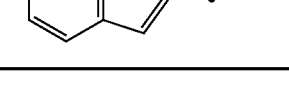 |
TABLE 1-4
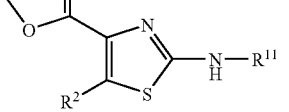
| Compound Number | R² | R¹¹ |
|---|---|---|
| 37 | 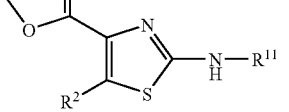 | 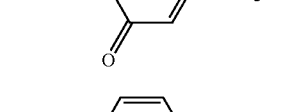 |
| 38 | 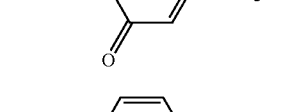 | 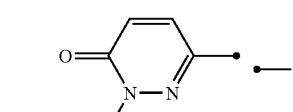 |
| 39 | 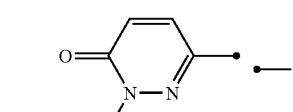 |  |

TABLE 2-1
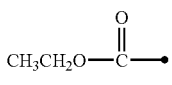
(I)
| Compound Number | R² | R¹¹ |
|---|---|---|
| 40 | CH₃CH₂O−C(=O)−• | •−C(=O)−O−C(CH₃)₃ |
| 41 | HO−C(=O)−• | •−C(=O)−O−C(CH₃)₃ |
| 42 | CH₃O−N(CH₃)−C(=O)−• | •−C(=O)−O−C(CH₃)₃ |
| 43 | Ph−C(=O)−• | •−C(=O)−O−C(CH₃)₃ |
| 44 | Ph−C(=O)−• | •−H |
| 45 | Ph−C(=O)−• | •−C(=O)−C(CH₃)₂−OH |
| 46 | Ph−C(=O)−• | •−C(=O)−C(cyclopropyl)(OH) |
| 47 | Ph−C(=O)−• | •−C(=O)−(3-C₆H₄)−C(=O)N(CH₃)₂ |
| 48 | Ph−C(=O)−• | •−C(=O)−(4-pyridyl, 2-CH₂Cl) |
| 49 | Ph−C(=O)−• | •−C(=O)−(4-pyridyl, 2-CH₂N(CH₃)₂) |

TABLE 2-1-continued
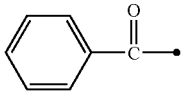
(I)
| Compound Number | R² | R¹¹ |
|---|---|---|
| 50 | 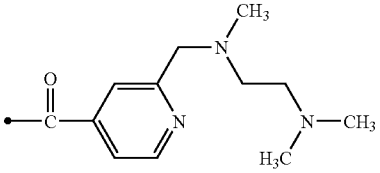 | 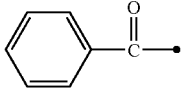 |
TABLE 2-2
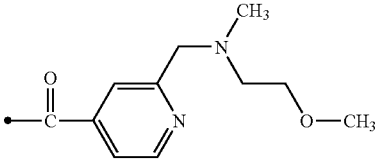
(I)
| Compound Number | R² | R¹¹ |
|---|---|---|
| 51 | 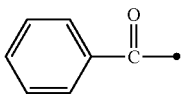 | 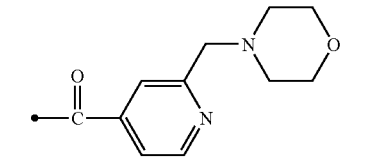 |
| 52 | 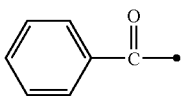 | 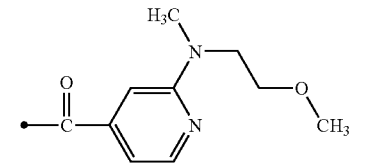 |
| 53 | 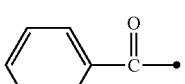 | 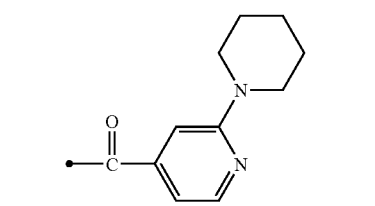 |
| 54 | | |

TABLE 2-2-continued (I)

| Compound Number | R² | R¹¹ |
|---|---|---|
| 55 | phenyl-C(=O)– | 6-chloropyridin-3-yl-C(=O)– |
| 56 | phenyl-C(=O)– | 6-morpholinopyridin-3-yl-C(=O)– |
| 57 | phenyl-C(=O)– | 6-oxo-1H-pyridin-3-yl-C(=O)– |
| 58 | phenyl-C(=O)– | 1-methyl-6-oxo-pyridin-3-yl-C(=O)– |
| 59 | phenyl-C(=O)– | 1-ethyl-6-oxo-pyridin-3-yl-C(=O)– |

TABLE 2-3

(I)

| Compound Number | R² | R¹¹ |
|---|---|---|
| 60 | phenyl-C(=O)– | 1-(pyridin-4-ylmethyl)-6-oxo-pyridin-3-yl-C(=O)– |
| 61 | phenyl-C(=O)– | pyridazin-4-yl-C(=O)– |

TABLE 2-3-continued (I) Structure: furan-thiazole core with R² at 5-position and NH-R¹¹ at 2-position.

| Compound Number | R² | R¹¹ |
|---|---|---|
| 62 | 2-methylbenzoyl (–C(O)–C₆H₄–2-CH₃) | –C(O)–O–C(CH₃)₃ |
| 63 | 2-methylbenzoyl | –H |
| 64 | 2-methylbenzoyl | –C(O)–(4-pyridyl) |
| 65 | 3-methylbenzoyl | –C(O)–O–C(CH₃)₃ |
| 66 | 3-methylbenzoyl | –H |
| 67 | 3-methylbenzoyl | –C(O)–(4-pyridyl) |
| 68 | 4-methylbenzoyl | –C(O)–(4-pyridyl) |

TABLE 2-4
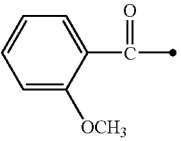
| Compound Number | R² | R¹¹ |
|---|---|---|
| 69 | 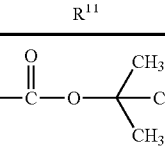 | 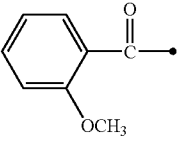 |
| 70 |  | —H |
| 71 | 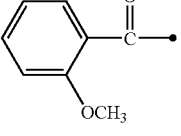 | 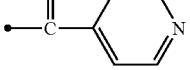 |
| 72 | 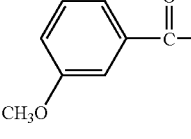 | 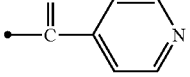 |
| 73 | 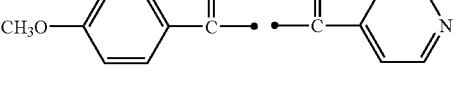 | 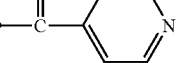 |
| 74 | 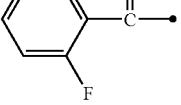 | 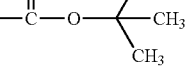 |
| 75 | 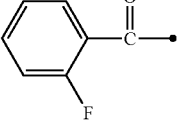 | —H |
| 76 |  | 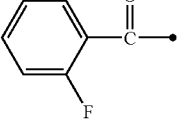 |
| 77 | 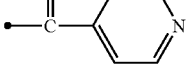 | 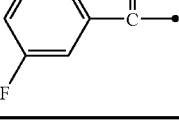 |
TABLE 2-5
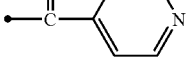
| Compound Number | R² | R¹¹ |
|---|---|---|
| 78 | 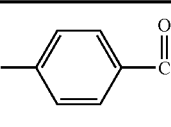 | 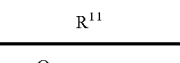 |
| 79 | 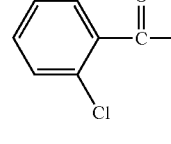 | 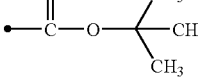 |
| 80 | 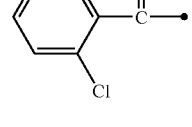 | —H |
| 81 |  | 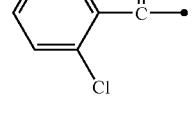 |
| 82 | 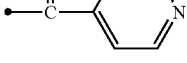 | 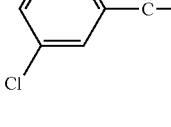 |
| 83 | 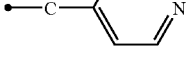 | 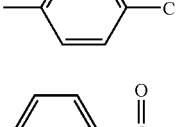 |
| 84 | 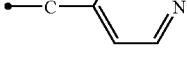 | 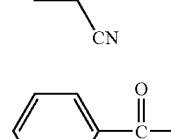 |
| 85 |  | —H |
| 86 | 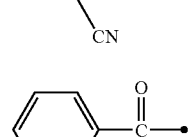 |  |

TABLE 2-6

Structure (I): 2-(furan-2-yl)-5-R²-N-R¹¹-thiazol-2-amine

| Compound Number | R² | R¹¹ |
|---|---|---|
| 87 | 3-cyanobenzoyl | tert-butoxycarbonyl (Boc) |
| 88 | 3-cyanobenzoyl | H |
| 89 | 3-cyanobenzoyl | isonicotinoyl (pyridine-4-carbonyl) |
| 90 | 4-cyanobenzoyl | tert-butoxycarbonyl (Boc) |
| 91 | 4-cyanobenzoyl | H |
| 92 | 4-cyanobenzoyl | isonicotinoyl (pyridine-4-carbonyl) |
| 93 | pyridine-2-carbonyl | tert-butoxycarbonyl (Boc) |
| 94 | pyridine-2-carbonyl | H |
| 95 | pyridine-2-carbonyl | isonicotinoyl (pyridine-4-carbonyl) |
| 96 | pyridine-2-carbonyl | acetyl |

TABLE 2-7

Structure (I): 2-(furan-2-yl)-5-R²-N-R¹¹-thiazol-2-amine

| Compound Number | R² | R¹¹ |
|---|---|---|
| 97 | pyridine-2-carbonyl | butanoyl (–C(O)CH₂CH₂CH₃) |
| 98 | pyridine-2-carbonyl | pivaloyl (–C(O)C(CH₃)₃) |
| 99 | pyridine-2-carbonyl | cyclopropanecarbonyl |

TABLE 2-7-continued
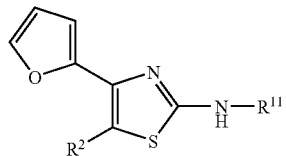
(I)
| Compound Number | R² | R¹¹ |
|---|---|---|
| 100 | 2-pyridyl-C(=O)- | 1-methylcyclopropyl-C(=O)- |
| 101 | 2-pyridyl-C(=O)- | cyclobutyl-C(=O)- |
| 102 | 2-pyridyl-C(=O)- | (tetrahydropyran-4-yl)-C(=O)- |
| 103 | 2-pyridyl-C(=O)- | [1-(tert-butoxycarbonyl)piperidin-4-yl]-C(=O)- |
| 104 | 2-pyridyl-C(=O)- | (piperidin-4-yl)-C(=O)- |
| 105 | 2-pyridyl-C(=O)- | [1-(pyridin-3-ylmethyl)piperidin-4-yl]-C(=O)- |
| 106 | 2-pyridyl-C(=O)- | [1-(pyridin-4-ylmethyl)piperidin-4-yl]-C(=O)- |
| 107 | 2-pyridyl-C(=O)- | phenyl-C(=O)- |

TABLE 2-8
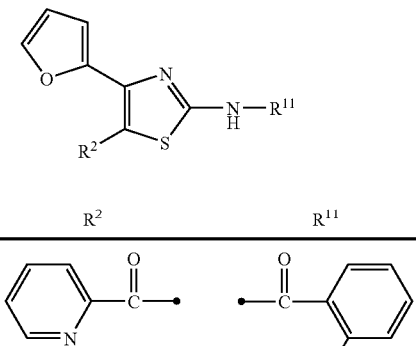
(I)
| Compound Number | R² | R¹¹ |
|---|---|---|
| 108 | 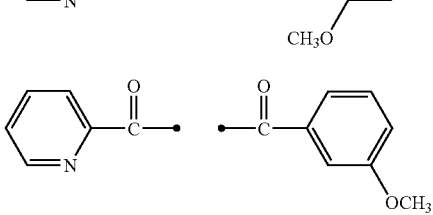 |  |
| 109 |  |  |
| 110 |  |  |
| 111 | 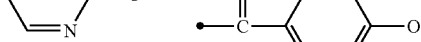 |  |
| 112 |  | 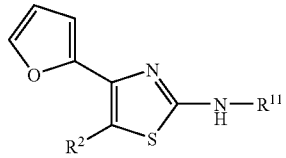 |
TABLE 2-8-continued
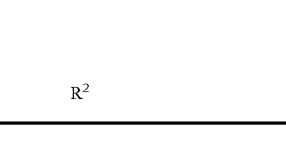
(I)
| Compound Number | R² | R¹¹ |
|---|---|---|
| 113 | 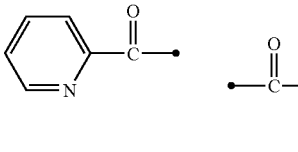 | 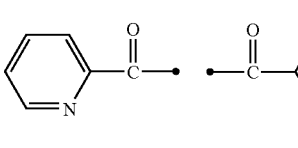 |
| 114 | 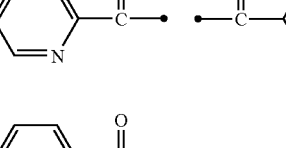 | 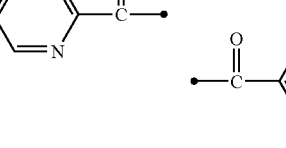 |
| 115 | 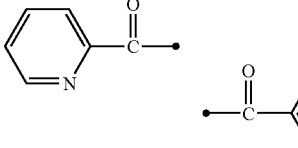 | 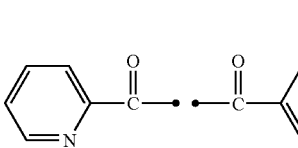 |
| 116 | 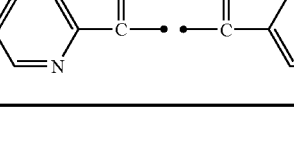 | 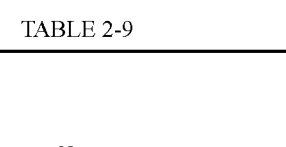 |
TABLE 2-9
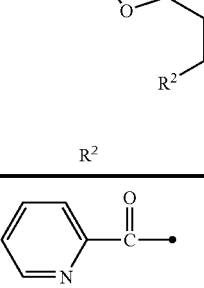
(I)
| Compound Number | R² | R¹¹ |
|---|---|---|
| 117 | 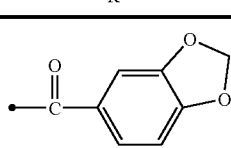 | 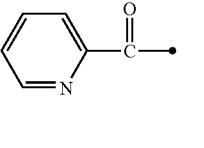 |
| 118 | 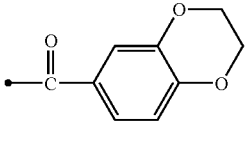 | |

TABLE 2-9-continued (I)

| Compound Number | R² | R¹¹ |
|---|---|---|
| 119 | 2-pyridyl-C(O)- | 2,3-dihydro-1,4-benzodioxin-2-yl-C(O)- |
| 120 | 2-pyridyl-C(O)- | (2-methylpyridin-4-yl)-C(O)- |
| 121 | 2-pyridyl-C(O)- | [2-(4-methoxybenzyloxy)pyridin-4-yl]-C(O)- |
| 122 | 2-pyridyl-C(O)- | (2-chloropyridin-4-yl)-C(O)- |
| 123 | 2-pyridyl-C(O)- | (3-chloropyridin-4-yl)-C(O)- |
| 124 | 2-pyridyl-C(O)- | (2,6-dichloropyridin-4-yl)-C(O)- |

TABLE 2-10
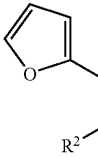
| Compound Number | R² | R¹¹ |
|---|---|---|
| 125 | 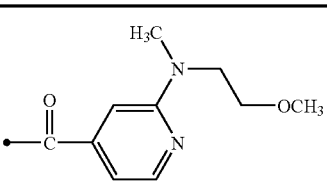 | 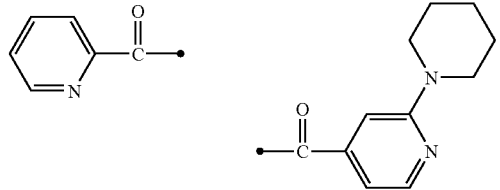 |
| 126 | 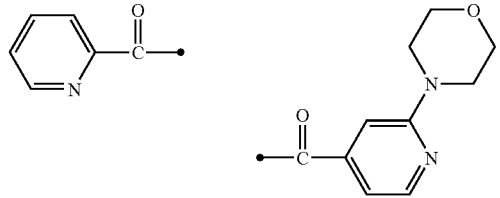 |  |
| 127 |  |  |
| 128 |  | 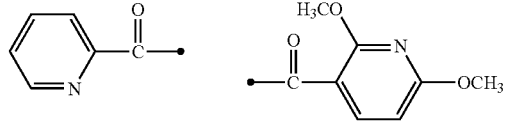 |
| 129 | | |
| 130 | | |
| 131 | | |
| 132 | | |

TABLE 2-10-continued
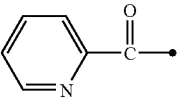
(I)
| Compound Number | R² | R¹¹ |
|---|---|---|
| 133 | 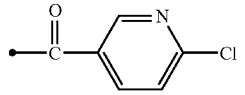 | 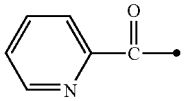 |
TABLE 2-11
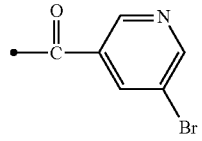
(I)
| Compound Number | R² | R¹¹ |
|---|---|---|
| 134 | 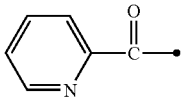 | 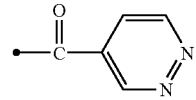 |
| 135 | 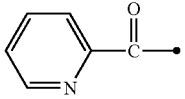 | 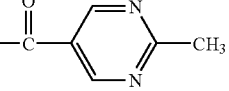 |
| 136 | 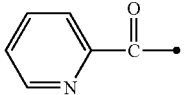 | 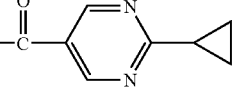 |
| 137 | 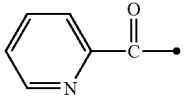 | 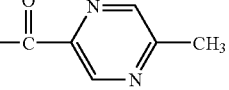 |
| 138 | 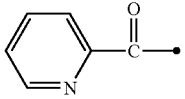 | 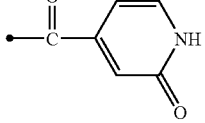 |
| 139 | | |

TABLE 2-11-continued
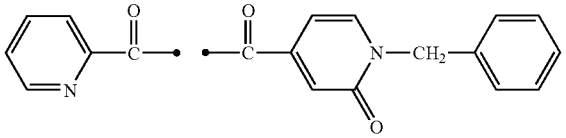
(I)
| Compound Number | R² | R¹¹ |
|---|---|---|
| 140 | 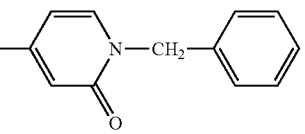 | 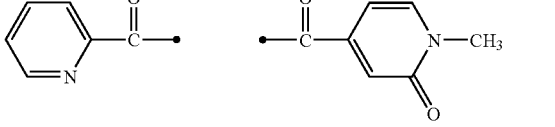 |
| 141 | 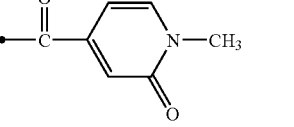 | 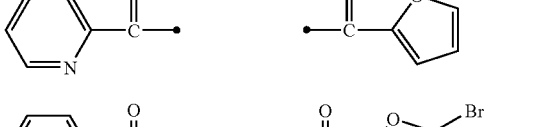 |
| 142 | 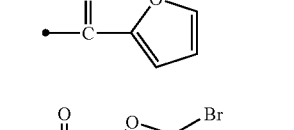 | 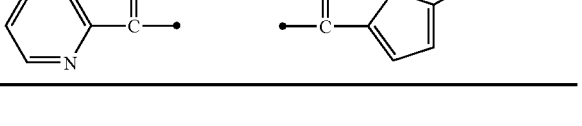 |
| 143 | 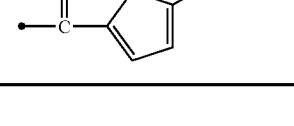 | 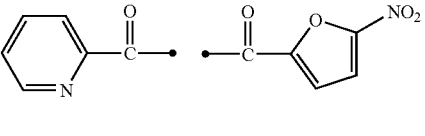 |
TABLE 2-12
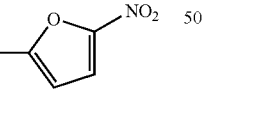
(I)
| Compound Number | R² | R¹¹ |
|---|---|---|
| 144 | 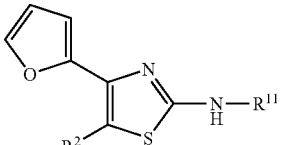 | 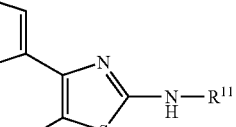 |
| 145 | 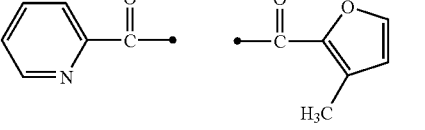 | 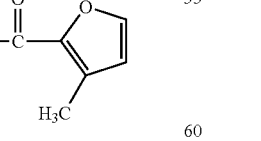 |
| 146 | 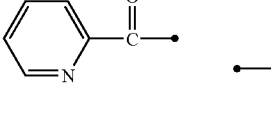 | 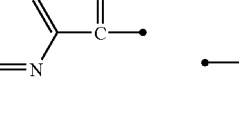 |
TABLE 2-12-continued
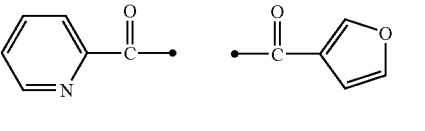
(I)
| Compound Number | R² | R¹¹ |
|---|---|---|
| 147 | 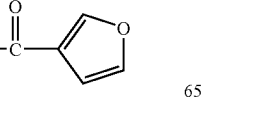 | 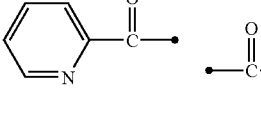 |
| 148 | 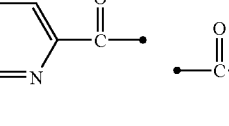 | 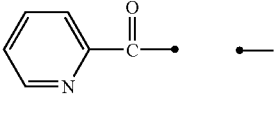 |
| 149 | 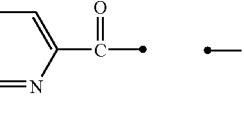 | |

TABLE 2-12-continued

Structure (I): 4-(furan-2-yl)-N-R¹¹-5-R²-thiazol-2-amine

| Compound Number | R² | R¹¹ |
|---|---|---|
| 150 | pyridin-2-yl-C(O)- | isoxazol-5-yl-C(O)- |
| 151 | pyridin-2-yl-C(O)- | 5-methylisoxazol-3-yl-C(O)- |
| 152 | pyridin-2-yl-C(O)- | benzo[1,2,3]thiadiazol-5-yl-C(O)- |
| 153 | pyridin-2-yl-C(O)- | 1-methyl-1H-benzotriazol-6-yl-C(O)- |

TABLE 2-13

Structure (I): 4-(furan-2-yl)-N-R¹¹-5-R²-thiazol-2-amine

| Compound Number | R² | R¹¹ |
|---|---|---|
| 154 | pyridin-2-yl-C(O)- | 2-(1-hydroxyethyl)benzofuran-5-yl-C(O)- |
| 155 | pyridin-2-yl-C(O)- | 2-(2-hydroxypropan-2-yl)benzofuran-5-yl-C(O)- |
| 156 | pyridin-2-yl-C(O)- | furo[2,3-b]pyridin-5-yl-C(O)- |
| 157 | pyridin-2-yl-C(O)- | -C(O)-OCH₃ |
| 158 | pyridin-2-yl-C(O)- | -C(O)-OCH₂CH₃ |
| 159 | pyridin-2-yl-C(O)- | -C(O)-O-cyclobutyl |
| 160 | pyridin-2-yl-C(O)- | -C(O)-O-cyclopentyl |
| 161 | pyridin-2-yl-C(O)- | -C(O)-O-(tetrahydropyran-4-yl) |
| 162 | pyridin-2-yl-C(O)- | -C(O)-O-(1-methylpiperidin-4-yl) |
| 163 | pyridin-2-yl-C(O)- | -C(O)-O-CH(CH₂F)₂ |
| 164 | pyridin-2-yl-C(O)- | -C(O)-morpholin-4-yl |

TABLE 2-14

Structure (I): 2-(furan-2-yl)-5-R²-N-R¹¹-thiazol-2-amine

| Compound Number | R² | R¹¹ |
|---|---|---|
| 165 | pyridin-2-yl-C(O)- | -C(O)-N(piperidine) |
| 166 | pyridin-2-yl-C(O)- | -C(O)-NH-CH(CH₃)₂ |
| 167 | pyridin-2-yl-C(O)- | -C(O)-NH-C(CH₃)₃ |
| 168 | pyridin-2-yl-C(O)- | -C(O)-NH-CH₂CH₂-OCH₃ |
| 169 | pyridin-2-yl-C(O)- | -C(O)-NH-CH₂CH₂CH₂-OCH₃ |

TABLE 2-14-continued

Structure (I)

| Compound Number | R² | R¹¹ |
|---|---|---|
| 170 | pyridin-2-yl-C(O)- | -C(O)-CH₂-Cl |
| 171 | pyridin-2-yl-C(O)- | -C(O)-CH₂-Br |
| 172 | pyridin-2-yl-C(O)- | -C(O)-CH₂-N(morpholine) |
| 173 | pyridin-2-yl-C(O)- | -C(O)-CH₂-N(2,6-dimethylmorpholine) |
| 174 | pyridin-2-yl-C(O)- | -C(O)-CH₂-N(4-methylpiperidine) |

TABLE 2-15

Structure (I)

| Compound Number | R² | R¹¹ |
|---|---|---|
| 175 | pyridin-2-yl-C(O)- | -C(O)-CH₂-N(4-methoxypiperidine) |
| 176 | pyridin-2-yl-C(O)- | -C(O)-CH₂-N(3-(N,N-diethylcarbamoyl)piperidine) |

TABLE 2-15-continued

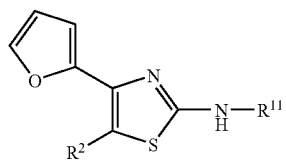
(I)

| Compound Number | R² | R¹¹ |
|---|---|---|
| 177 | pyridin-2-yl-C(=O)– | –C(=O)–CH₂–N(1,4-dioxa-8-azaspiro[4.5]decan-8-yl) |
| 178 | pyridin-2-yl-C(=O)– | –C(=O)–CH₂–N(4-piperidin-1-yl-piperidin-1-yl) |
| 179 | pyridin-2-yl-C(=O)– | –C(=O)–CH₂–N(4-morpholin-4-yl-piperidin-1-yl) |
| 180 | pyridin-2-yl-C(=O)– | –C(=O)–CH₂–N(4-methylpiperazin-1-yl) |
| 181 | pyridin-2-yl-C(=O)– | –C(=O)–CH₂–N(4-ethylpiperazin-1-yl) |
| 182 | pyridin-2-yl-C(=O)– | –C(=O)–CH₂–N(4-isopropylpiperazin-1-yl) |
| 183 | pyridin-2-yl-C(=O)– | –C(=O)–CH₂–N(4-acetylpiperazin-1-yl) |
| 184 | pyridin-2-yl-C(=O)– | –C(=O)–CH₂–N(4-phenylpiperazin-1-yl) |
| 185 | pyridin-2-yl-C(=O)– | –C(=O)–CH₂–N(4-pyridin-2-yl-piperazin-1-yl) |

TABLE 2-16
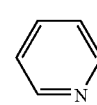
| Compound Number | R² | R¹¹ |
|---|---|---|
| 186 | 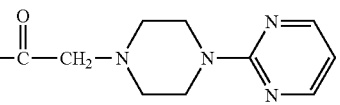 | 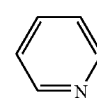 |
| 187 | 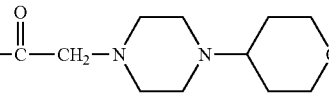 | 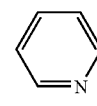 |
| 188 | 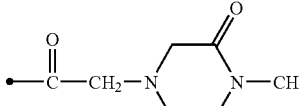 | 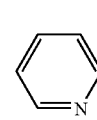 |
| 189 | 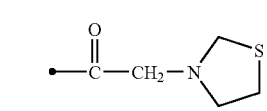 | 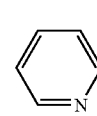 |
| 190 | 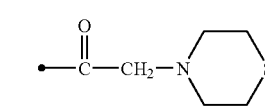 | 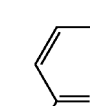 |
| 191 | 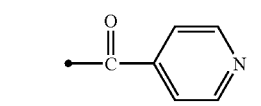 | 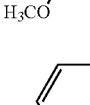 |
| 192 | 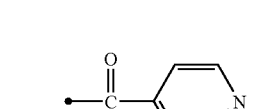 | 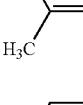 |
| 193 | 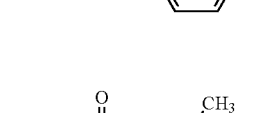 | 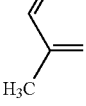 |
| 194 | 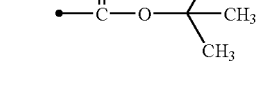 | 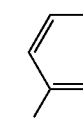 |
| 195 | 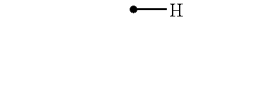 | |

TABLE 2-16-continued
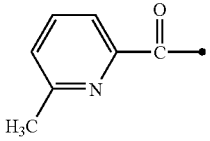
(I)
| Compound Number | R² | R¹¹ |
|---|---|---|
TABLE 2-17
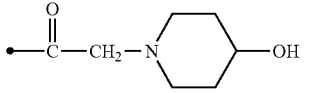
(I)
| Compound Number | R² | R¹¹ |
|---|---|---|
| 196 | 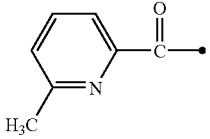 | 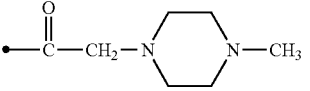 |
| 197 | 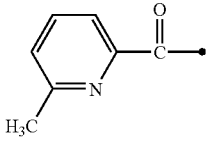 | 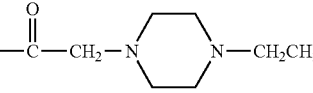 |
| 198 | 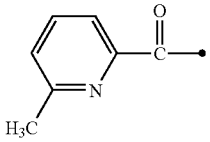 | 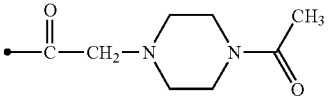 |
| 199 | 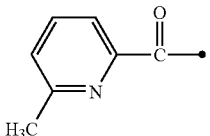 |  |
| 200 | 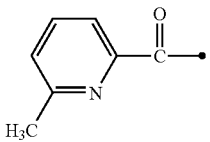 |  |
| 201 | | |

TABLE 2-17-continued

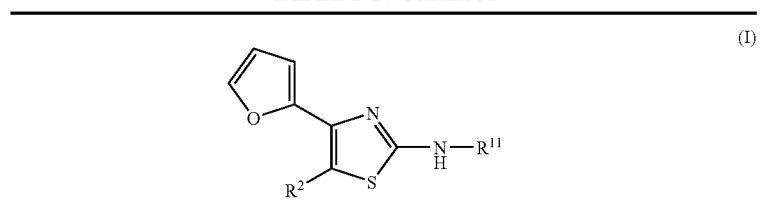

| Compound Number | R² | R¹¹ |
|---|---|---|
| 202 | 5-methylpyridin-2-yl-C(=O)- | -C(=O)-pyridin-4-yl |
| 203 | 4-methylpyridin-2-yl-C(=O)- | -C(=O)-pyridin-4-yl |
| 204 | 5-methoxypyridin-2-yl-C(=O)- | -C(=O)-O-C(CH₃)₃ |

TABLE 2-18

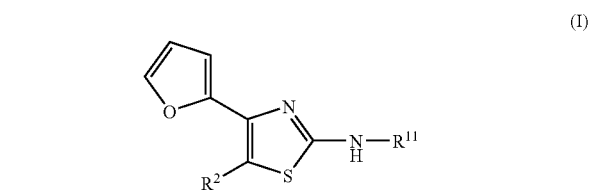

| Compound Number | R² | R¹¹ |
|---|---|---|
| 205 | 5-methoxypyridin-2-yl-C(=O)- | -H |
| 206 | 5-methoxypyridin-2-yl-C(=O)- | -C(=O)-pyridin-4-yl |
| 207 | 6-bromopyridin-2-yl-C(=O)- | -C(=O)-pyridin-4-yl |

TABLE 2-18-continued

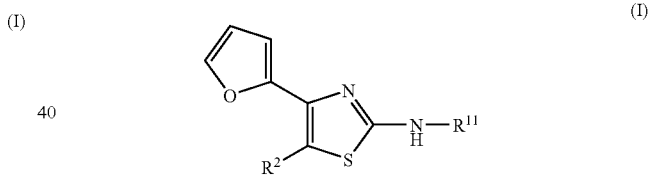

| Compound Number | R² | R¹¹ |
|---|---|---|
| 208 | 6-morpholinopyridin-2-yl-C(=O)- | -C(=O)-pyridin-4-yl |
| 209 | pyridin-3-yl-C(=O)- | -C(=O)-O-C(CH₃)₃ |
| 210 | pyridin-3-yl-C(=O)- | -H |

TABLE 2-18-continued
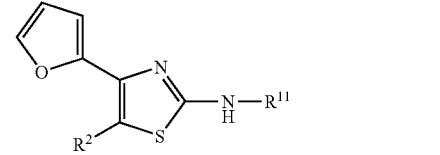
(I)
| Compound Number | R² | R¹¹ |
|---|---|---|
| 211 |  |  |
| 212 | 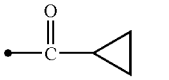 | 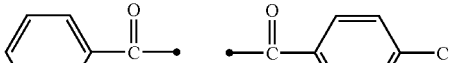 |
| 213 | 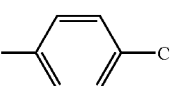 |  |
| 214 | 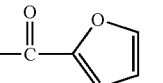 | 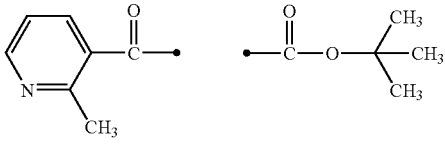 |
TABLE 2-19
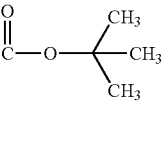
(I)
| Compound Number | R² | R¹¹ |
|---|---|---|
| 215 | 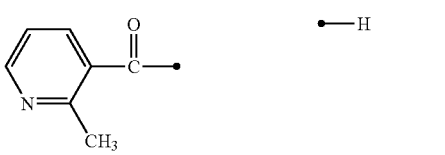 |  |
| 216 | 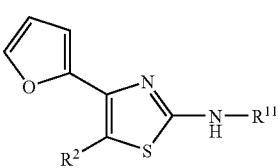 | —H |
| 217 | 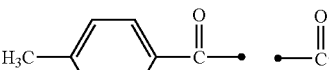 | 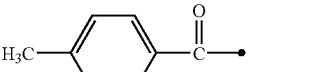 |
| 218 | 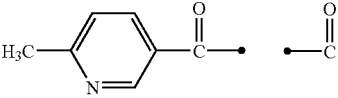 | 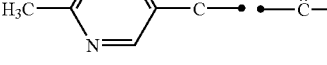 |
| 219 |  | —H |
| 220 |  | 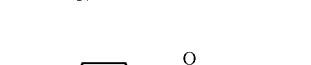 |
| 221 | 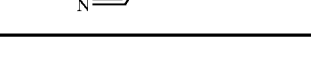 | |

TABLE 2-20

(I)

| Compound Number | R² | R¹¹ |
|---|---|---|
| 226 | 6-methoxypyridin-3-yl-C(=O)- | -C(=O)-pyridin-4-yl |
| 227 | 6-chloropyridin-3-yl-C(=O)- | -C(=O)-O-C(CH₃)₃ |
| 228 | 6-chloropyridin-3-yl-C(=O)- | -H |
| 229 | 6-chloropyridin-3-yl-C(=O)- | -C(=O)-pyridin-4-yl |
| 230 | 6-(dimethylamino)pyridin-3-yl-C(=O)- | -C(=O)-pyridin-4-yl |
| 231 | 6-morpholinopyridin-3-yl-C(=O)- | -C(=O)-pyridin-4-yl |
| 232 | 6-(4-methylpiperazin-1-yl)pyridin-3-yl-C(=O)- | -C(=O)-pyridin-4-yl |
| 233 | 2-(4-hydroxypiperidin-1-yl)pyrimidin-5-yl-C(=O)- | -C(=O)-pyridin-4-yl |
| 234 | pyridin-4-yl-C(=O)- | -C(=O)-O-C(CH₃)₃ |
| 235 | pyridin-4-yl-C(=O)- | -H |
| 236 | pyridin-4-yl-C(=O)- | -C(=O)-pyridin-4-yl |

TABLE 2-21

TABLE 2-22

(Structure I: 4-(furan-2-yl)-thiazole with R² at 5-position and NH-R¹¹ at 2-position)

| Compound Number | R² | R¹¹ |
|---|---|---|
| 237 | 2-methylpyridin-4-yl carbonyl | tert-butoxycarbonyl |
| 238 | 2-methylpyridin-4-yl carbonyl | H |
| 239 | 2-methylpyridin-4-yl carbonyl | pyridin-4-yl carbonyl |
| 240 | 2-methylpyridin-4-yl carbonyl | 2-methylpyridin-4-yl carbonyl |
| 241 | 2-methoxypyridin-4-yl carbonyl | tert-butoxycarbonyl |
| 242 | 2-methoxypyridin-4-yl carbonyl | H |
| 243 | 2-methoxypyridin-4-yl carbonyl | pyridin-4-yl carbonyl |
| 244 | 2-morpholinopyridin-4-yl carbonyl | tert-butoxycarbonyl |
| 245 | 2-morpholinopyridin-4-yl carbonyl | H |
| 246 | 2-morpholinopyridin-4-yl carbonyl | pyridin-4-yl carbonyl |
| 247 | furan-2-yl carbonyl | tert-butoxycarbonyl |
| 248 | furan-2-yl carbonyl | H |
| 249 | furan-2-yl carbonyl | pyridin-4-yl carbonyl |
| 250 | 5-methylfuran-2-yl carbonyl | pyridin-4-yl carbonyl |
| 251 | furan-3-yl carbonyl | tert-butoxycarbonyl |
| 252 | furan-3-yl carbonyl | H |
| 253 | furan-3-yl carbonyl | pyridin-4-yl carbonyl |
| 254 | thiophen-2-yl carbonyl | pyridin-4-yl carbonyl |

TABLE 2-23
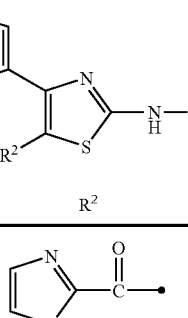
| Compound Number | R² | R¹¹ |
|---|---|---|
| 255 | 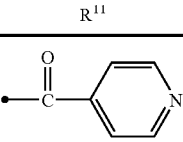 | 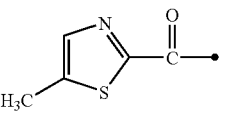 |
| 256 | 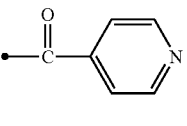 | 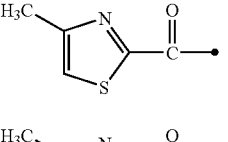 |
| 257 | 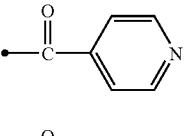 | 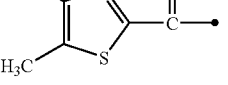 |
| 258 | 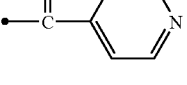 | 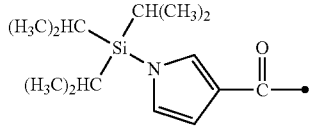 |
| 259 | 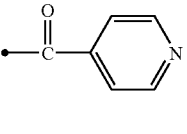 | 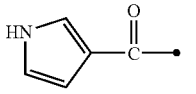 |
| 260 | 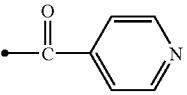 | 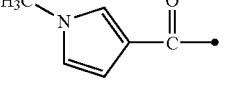 |
| 261 | 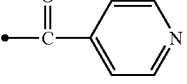 | 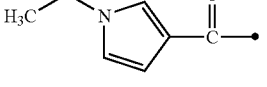 |
| 262 | 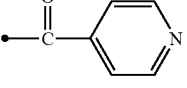 | 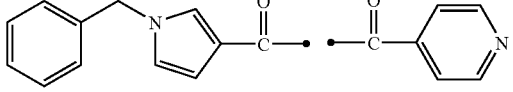 |
| 263 | 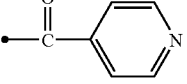 | 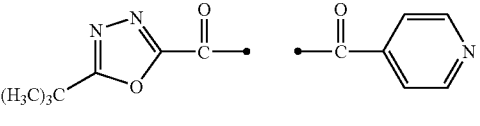 |
| 264 | 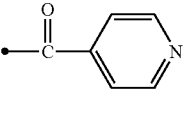 | 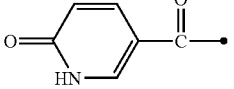 |
| 265 |  | •—H |

TABLE 2-24

(I)

![Structure I: furan-thiazole-NH-R11 with R2]

| Compound Number | R² | R¹¹ |
|---|---|---|
| 266 | 1-methyl-2-oxo-1,2-dihydropyridin-5-yl-C(=O)– | –H |
| 267 | 1-methyl-2-oxo-1,2-dihydropyridin-5-yl-C(=O)– | –C(=O)-pyridin-4-yl |
| 268 | 1-ethyl-2-oxo-1,2-dihydropyridin-5-yl-C(=O)– | –H |
| 269 | 1-ethyl-2-oxo-1,2-dihydropyridin-5-yl-C(=O)– | –C(=O)-pyridin-4-yl |
| 270 | 1-benzyl-2-oxo-1,2-dihydropyridin-5-yl-C(=O)– | –H |
| 271 | 1-benzyl-2-oxo-1,2-dihydropyridin-5-yl-C(=O)– | –C(=O)-pyridin-4-yl |
| 272 | 2-oxo-1,2-dihydropyridin-4-yl-C(=O)– | –H |
| 273 | 1-methyl-2-oxo-1,2-dihydropyridin-4-yl-C(=O)– | –H |

TABLE 2-24-continued
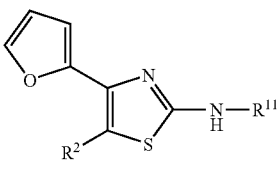
(I)
| Compound Number | R² | R¹¹ |
|---|---|---|
| 274 | 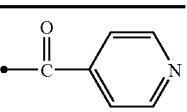 | 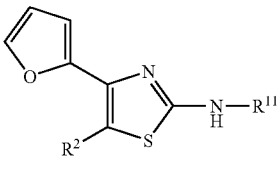 |
TABLE 2-25
(I)
| Compound Number | R² | R¹¹ |
|---|---|---|
| 275 | 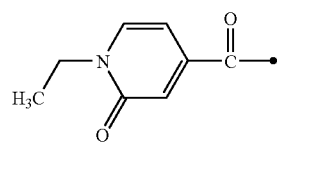 | •—H |
| 276 | 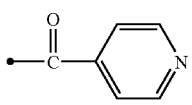 | 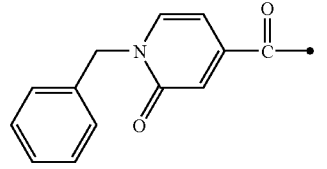 |
| 277 |  | •—H |
| 278 | 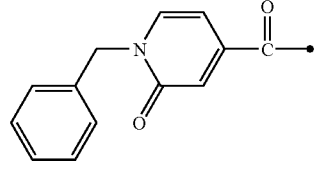 | 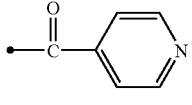 |
| 279 | 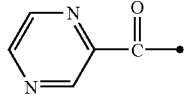 | 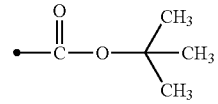 |

TABLE 2-25-continued

Structure (I): furan-thiazole with R² at 5-position and NH-R¹¹ at 2-position

| Compound Number | R² | R¹¹ |
|---|---|---|
| 280 | pyrazin-2-yl-C(=O)- | -H |
| 281 | pyrazin-2-yl-C(=O)- | -C(=O)-pyridin-4-yl |
| 282 | pyrimidin-4-yl-C(=O)- | -C(=O)-pyridin-4-yl |
| 283 | pyridazin-3-yl-C(=O)- | -C(=O)-pyridin-4-yl |
| 284 | H₃C-C(=O)- | -C(=O)-pyridin-4-yl |

TABLE 2-26

Structure (I): furan-thiazole with R² at 5-position and NH-R¹¹ at 2-position

| Compound Number | R² | R¹¹ |
|---|---|---|
| 285 | F₃C-C(=O)- | -C(=O)-O-C(CH₃)₃ |
| 286 | F₃C-C(=O)- | -H |
| 287 | F₃C-C(=O)- | -C(=O)-pyridin-4-yl |
| 288 | H₃C-CH₂-C(=O)- | -C(=O)-pyridin-4-yl |

TABLE 2-26-continued

Structure (I): furan-thiazole with R² at 5-position and NH-R¹¹ at 2-position

| Compound Number | R² | R¹¹ |
|---|---|---|
| 289 | H₃C-CH₂-CH₂-C(=O)- | -C(=O)-pyridin-4-yl |
| 290 | H₃C-CH₂-CH₂-C(=O)- | -C(=O)-O-C(CH₃)₃ |
| 291 | H₃C-CH₂-CH₂-C(=O)- | -H |
| 292 | H₃C-CH₂-CH₂-C(=O)- | -C(=O)-cyclopropyl |

TABLE 2-26-continued

Structure (I): 4-(furan-2-yl)-N-R¹¹-5-R²-thiazol-2-amine

| Compound Number | R² | R¹¹ |
|---|---|---|
| 293 | H₃C-CH₂-C(=O)- | -C(=O)-(furan-2-yl) |
| 294 | H₃C-CH₂-C(=O)- | -C(=O)-(2-(chloromethyl)pyridin-4-yl) |
| 295 | H₃C-CH₂-C(=O)- | -C(=O)-(2-(methoxymethyl)pyridin-4-yl) |

TABLE 2-27

Structure (I)

| Compound Number | R² | R¹¹ |
|---|---|---|
| 296 | H₃C-CH₂-C(=O)- | -C(=O)-(2-(2-(dimethylamino)ethoxymethyl)pyridin-4-yl) |
| 297 | H₃C-CH₂-C(=O)- | -C(=O)-CH₂-morpholino |
| 298 | (H₃C)₂CH-C(=O)- | -C(=O)-O-C(CH₃)₃ |
| 299 | (H₃C)₂CH-C(=O)- | -H |
| 300 | (H₃C)₂CH-C(=O)- | -C(=O)-(pyridin-4-yl) |
| 301 | (H₃C)₂CH-C(=O)- | -C(=O)-cyclopropyl |

TABLE 2-27-continued
(I)
| Compound Number | R² | R¹¹ |
|---|---|---|
| 302 | 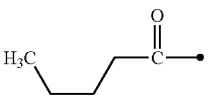 | 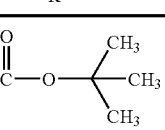 |
| 303 | 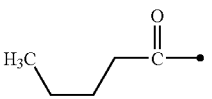 | •—H |
| 304 |  | 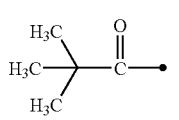 |
| 305 | 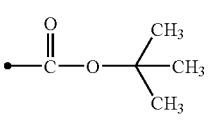 | •—H |
| 306 | 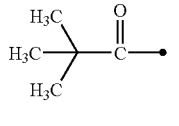 |  |
TABLE 2-28
(I)
| Compound Number | R² | R¹¹ |
|---|---|---|
| 307 | 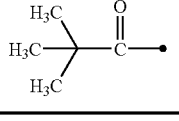 | 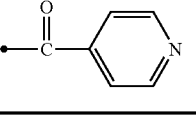 |
| 308 | 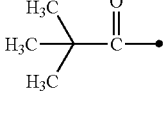 | 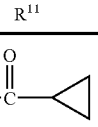 |
| 309 | 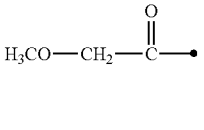 | •—H |
| 310 | 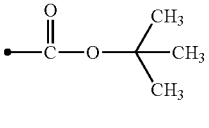 | 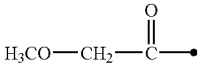 |

TABLE 2-28-continued
(I)
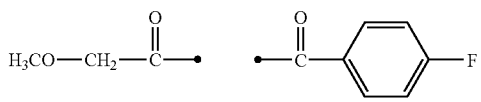
| Compound Number | R² | R¹¹ |
|---|---|---|
| 311 | 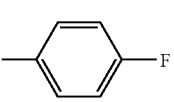 | 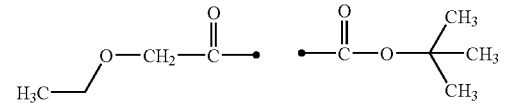 |
| 312 | 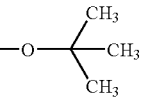 | 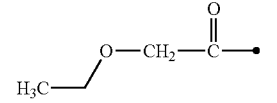 |
| 313 | 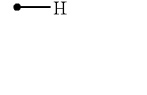 | •—H |
| 314 | 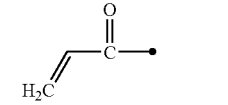 | 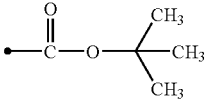 |
| 315 | 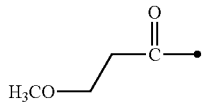 | 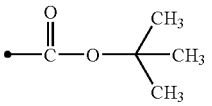 |
| 316 | 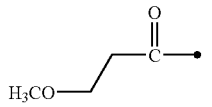 | •—H |
| 317 | 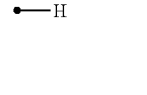 | 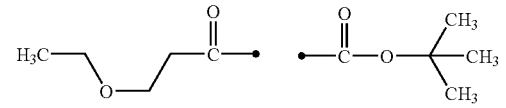 |
TABLE 2-29
(I)
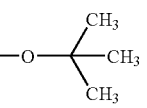
| Compound Number | R² | R¹¹ |
|---|---|---|
| 318 | 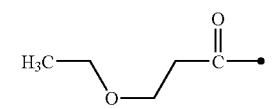 | 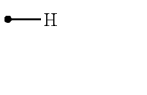 •—H |

TABLE 2-29-continued
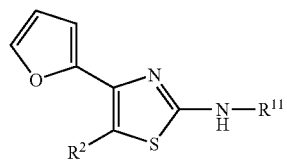
(I)
| Compound Number | $R^2$ | $R^{11}$ |
|---|---|---|
| 319 | H₃CO-CH₂-C≡C-C(=O)- | -C(=O)-(4-pyridyl) |
| 320 | H₃CO-CH₂-C≡C-C(=O)- | -C(=O)-O-C(CH₃)₃ |
| 321 | H₃CO-CH₂CH₂CH₂-C(=O)- | -C(=O)-O-C(CH₃)₃ |
| 322 | H₃CO-CH₂CH₂CH₂-C(=O)- | -H |
| 323 | cyclopropyl-C(=O)- | -C(=O)-(4-pyridyl) |
| 324 | cyclopropyl-C(=O)- | -C(=O)-O-C(CH₃)₃ |
| 325 | cyclopropyl-C(=O)- | -H |
| 326 | cyclopropyl-C(=O)- | -C(=O)-(2-methoxyphenyl) |
| 327 | cyclopropyl-C(=O)- | -C(=O)-CH₂-morpholino |
| 328 | cyclobutyl-C(=O)- | -C(=O)-O-C(CH₃)₃ |

TABLE 2-30

(I) 4-(furan-2-yl)-N-R¹¹-5-R²-thiazol-2-amine structure

| Compound Number | R² | R¹¹ |
|---|---|---|
| 329 | cyclobutyl-C(=O)- | -H |
| 330 | cyclobutyl-C(=O)- | -C(=O)-(pyridin-4-yl) |
| 331 | cyclobutyl-C(=O)- | -C(=O)-(furan-2-yl) |
| 332 | cyclobutyl-C(=O)- | -C(=O)-(4-cyanophenyl) |
| 333 | cyclobutyl-C(=O)- | -C(=O)-cyclopropyl |
| 334 | (3-methyloxetan-3-yl)-C(=O)- | -C(=O)-O-C(CH₃)₃ |

TABLE 2-30-continued

| Compound Number | R² | R¹¹ |
|---|---|---|
| 335 | (3-methyloxetan-3-yl)-C(=O)- | -H |
| 336 | cyclopentyl-C(=O)- | -C(=O)-(pyridin-4-yl) |
| 337 | cyclopentyl-C(=O)- | -C(=O)-O-C(CH₃)₃ |
| 338 | cyclopentyl-C(=O)- | -H |
| 339 | cyclopentyl-C(=O)- | -C(=O)-cyclopropyl |

TABLE 2-31

| Compound Number | R² | R¹¹ |
|---|---|---|
| 340 | cyclopentyl-C(=O)- | -C(=O)-morpholin-4-yl |
| 341 | cyclohexyl-CH(OH)- | -C(=O)-O-C(CH₃)₃ |
| 342 | cyclohexyl-C(=O)- | -C(=O)-O-C(CH₃)₃ |

TABLE 2-31-continued (I)

[Structure: 4-(furan-2-yl)-5-R²-N-R¹¹-thiazol-2-amine]

| Compound Number | R² | R¹¹ |
|---|---|---|
| 343 | cyclohexyl-C(=O)- | —H |
| 344 | cyclohexyl-C(=O)- | -C(=O)-(4-pyridyl) |
| 345 | 4-methoxycyclohexyl-C(=O)- | -C(=O)-O-C(CH₃)₃ |
| 346 | 4-methoxycyclohexyl-C(=O)- | —H |
| 347 | 4-methoxycyclohexyl-C(=O)- | -C(=O)-(4-pyridyl) |
| 348 | 4-methoxycyclohexyl-C(=O)- | -C(=O)-(4-cyanophenyl) |
| 349 | 4-hydroxycyclohexyl-C(=O)- | —H |
| 350 | 1,4-dioxaspiro[4.5]dec-8-yl-C(=O)- | -C(=O)-O-C(CH₃)₃ |

TABLE 2-32

(I)

[Structure: 4-(furan-2-yl)-5-R²-N-R¹¹-thiazol-2-amine]

| Compound Number | R² | R¹¹ |
|---|---|---|
| 351 | 1,4-dioxaspiro[4.5]dec-8-yl-C(=O)- | —H |

TABLE 2-32-continued
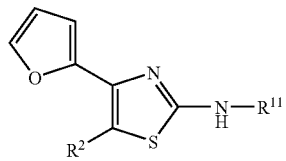
(I)
| Compound Number | R² | R¹¹ |
|---|---|---|
| 352 | 4-oxocyclohexyl-C(O)- | -H |
| 353 | 4-oxocyclohexyl-C(O)- | -C(O)-(pyridin-4-yl) |
| 354 | 4-oxocyclohexyl-C(O)- | -C(O)-(2-methylpyridin-4-yl) |
| 355 | 4-oxocyclohexyl-C(O)- | -C(O)-(furan-2-yl) |
| 356 | 4-oxocyclohexyl-C(O)- | -C(O)-(3-methoxyphenyl) |
| 357 | 4-oxocyclohexyl-C(O)- | -C(O)-(4-cyanophenyl) |
| 358 | tetrahydropyran-4-yl-C(O)- | -C(O)-O-C(CH₃)₃ |
| 359 | tetrahydropyran-4-yl-C(O)- | -H |
| 360 | tetrahydropyran-4-yl-C(O)- | -C(O)-(pyridin-4-yl) |
| 361 | tetrahydropyran-4-yl-C(O)- | -C(O)-cyclopropyl |

TABLE 2-33

TABLE 2-34

(Structural formula (I): 4-(furan-2-yl)-N-R¹¹-5-R²-thiazol-2-amine)

| Compound Number | R² | R¹¹ |
|---|---|---|
| 362 | tetrahydropyran-4-yl-C(=O)- | benzoyl |
| 363 | tetrahydropyran-4-yl-C(=O)- | 2-methylbenzoyl |
| 364 | tetrahydropyran-4-yl-C(=O)- | 3-methylbenzoyl |
| 365 | tetrahydropyran-4-yl-C(=O)- | 4-methylbenzoyl |
| 366 | tetrahydropyran-4-yl-C(=O)- | 2-methoxybenzoyl |
| 367 | tetrahydropyran-4-yl-C(=O)- | 3-methoxybenzoyl |
| 368 | tetrahydropyran-4-yl-C(=O)- | 4-methoxybenzoyl |
| 369 | tetrahydropyran-4-yl-C(=O)- | 3-(dimethylamino)benzoyl |
| 370 | tetrahydropyran-4-yl-C(=O)- | 4-(dimethylamino)benzoyl |
| 371 | tetrahydropyran-4-yl-C(=O)- | 2-fluorobenzoyl |
| 372 | tetrahydropyran-4-yl-C(=O)- | 3-fluorobenzoyl |
| 373 | tetrahydropyran-4-yl-C(=O)- | 4-fluorobenzoyl |
| 374 | tetrahydropyran-4-yl-C(=O)- | 2-chlorobenzoyl |
| 375 | tetrahydropyran-4-yl-C(=O)- | 3-chlorobenzoyl |
| 376 | tetrahydropyran-4-yl-C(=O)- | 4-chlorobenzoyl |
| 377 | tetrahydropyran-4-yl-C(=O)- | 2-cyanobenzoyl |
| 378 | tetrahydropyran-4-yl-C(=O)- | 3-cyanobenzoyl |
| 379 | tetrahydropyran-4-yl-C(=O)- | 4-cyanobenzoyl |
| 380 | tetrahydropyran-4-yl-C(=O)- | 2-(trifluoromethoxy)benzoyl |

TABLE 2-35

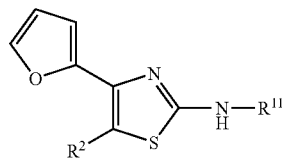

| Compound Number | R² | R¹¹ |
|---|---|---|
| 381 | tetrahydropyran-4-yl-C(O)- | 3-(OCF₃)-C₆H₄-C(O)- |
| 382 | tetrahydropyran-4-yl-C(O)- | 4-(OCF₃)-C₆H₄-C(O)- |
| 383 | tetrahydropyran-4-yl-C(O)- | 4-(CH₂Cl)-C₆H₄-C(O)- |
| 384 | tetrahydropyran-4-yl-C(O)- | 4-(CH₂N(CH₃)₂)-C₆H₄-C(O)- |
| 385 | tetrahydropyran-4-yl-C(O)- | 4-(CH₂-piperidin-1-yl)-C₆H₄-C(O)- |
| 386 | tetrahydropyran-4-yl-C(O)- | 4-(CH₂-(4-hydroxypiperidin-1-yl))-C₆H₄-C(O)- |
| 387 | tetrahydropyran-4-yl-C(O)- | 4-(CH₂-morpholin-4-yl)-C₆H₄-C(O)- |
| 388 | tetrahydropyran-4-yl-C(O)- | 2,3-(OCH₃)₂-C₆H₃-C(O)- |
| 389 | tetrahydropyran-4-yl-C(O)- | 2,4-(OCH₃)₂-C₆H₃-C(O)- |
| 390 | tetrahydropyran-4-yl-C(O)- | 2,5-(OCH₃)₂-C₆H₃-C(O)- |

TABLE 2-36

TABLE 2-37

| Compound Number | R² | R¹¹ |
|---|---|---|
| 391 | tetrahydropyran-4-yl-C(=O)- | 2,6-dimethoxybenzoyl |
| 392 | tetrahydropyran-4-yl-C(=O)- | 3,4-dimethoxybenzoyl |
| 393 | tetrahydropyran-4-yl-C(=O)- | 3,5-dimethoxybenzoyl |
| 394 | tetrahydropyran-4-yl-C(=O)- | 2,3-difluorobenzoyl |
| 395 | tetrahydropyran-4-yl-C(=O)- | 2,4-difluorobenzoyl |
| 396 | tetrahydropyran-3-yl-C(=O)- | 2,5-difluorobenzoyl |
| 397 | tetrahydropyran-4-yl-C(=O)- | 2,6-difluorobenzoyl |
| 398 | tetrahydropyran-4-yl-C(=O)- | 3,4-difluorobenzoyl |

| Compound Number | R² | R¹¹ |
|---|---|---|
| 399 | tetrahydropyran-4-yl-C(=O)- | 3,5-difluorobenzoyl |
| 400 | tetrahydropyran-4-yl-C(=O)- | 2,3-dihydro-1,4-benzodioxin-5-yl-carbonyl |
| 401 | tetrahydropyran-4-yl-C(=O)- | 1,3-benzodioxol-5-yl-carbonyl |
| 402 | tetrahydropyran-4-yl-C(=O)- | 2,2-difluoro-1,3-benzodioxol-4-yl-carbonyl |
| 403 | tetrahydropyran-4-yl-C(=O)- | 2,2-difluoro-1,3-benzodioxol-5-yl-carbonyl |
| 404 | tetrahydropyran-4-yl-C(=O)- | 2-chloropyridin-4-yl-carbonyl |
| 405 | tetrahydropyran-4-yl-C(=O)- | 2-methylpyridin-4-yl-carbonyl |
| 406 | tetrahydropyran-4-yl-C(=O)- | pyridin-3-yl-carbonyl |
| 407 | tetrahydropyran-4-yl-C(=O)- | 6-chloropyridin-3-yl-carbonyl |

TABLE 2-38

(I)

Structure: 4-(furan-2-yl)-thiazole with R² at 5-position and NH-R¹¹ at 2-position.

| Compound Number | R² | R¹¹ |
|---|---|---|
| 408 | tetrahydropyran-4-yl-C(=O)- | -C(=O)-pyridin-3-yl(6-morpholino) |
| 409 | tetrahydropyran-4-yl-C(=O)- | -C(=O)-pyridin-3-yl(6-CH₃) |
| 410 | tetrahydropyran-4-yl-C(=O)- | -C(=O)-pyridin-3-yl(6-CF₃) |
| 411 | tetrahydropyran-4-yl-C(=O)- | -C(=O)-pyridin-3-yl(5-CH₃) |
| 412 | tetrahydropyran-4-yl-C(=O)- | -C(=O)-pyridin-2-yl |
| 413 | tetrahydropyran-4-yl-C(=O)- | -C(=O)-pyrimidin-5-yl(2-CH₃) |
| 414 | tetrahydropyran-4-yl-C(=O)- | -C(=O)-pyrazin-2-yl |
| 415 | tetrahydropyran-4-yl-C(=O)- | -C(=O)-pyrazin-2-yl(5-CH₃) |
| 416 | tetrahydropyran-4-yl-C(=O)- | -C(=O)-furan-2-yl |
| 417 | tetrahydropyran-4-yl-C(=O)- | -C(=O)-furan-2-yl(5-CH₃) |
| 418 | tetrahydropyran-4-yl-C(=O)- | -C(=O)-furan-2-yl(5-CHO) |

TABLE 2-39

(I)

Structure: 4-(furan-2-yl)-thiazole with R² at 5-position and NH-R¹¹ at 2-position.

| Compound Number | R² | R¹¹ |
|---|---|---|
| 419 | tetrahydropyran-4-yl-C(=O)- | -C(=O)-furan-2-yl(5-CH=N-OH) |
| 420 | tetrahydropyran-4-yl-C(=O)- | -C(=O)-furan-2-yl(5-CN) |
| 421 | tetrahydropyran-4-yl-C(=O)- | -C(=O)-furan-3-yl |
| 422 | tetrahydropyran-4-yl-C(=O)- | -C(=O)-thiophen-2-yl |
| 423 | tetrahydropyran-4-yl-C(=O)- | -C(=O)-thiophen-3-yl |
| 424 | tetrahydropyran-4-yl-C(=O)- | -C(=O)-pyrazol-4-yl(1-CH₃) |
| 425 | tetrahydropyran-4-yl-C(=O)- | -C(=O)-pyrazol-4-yl(1-CH₂CH₃) |
| 426 | tetrahydropyran-4-yl-C(=O)- | -C(=O)-pyrazol-4-yl(1-phenyl) |
| 427 | tetrahydropyran-4-yl-C(=O)- | -C(=O)-isoxazol-5-yl |
| 428 | tetrahydropyran-4-yl-C(=O)- | -C(=O)-tetrahydrofuran-2-yl |
| 429 | tetrahydropyran-4-yl-C(=O)- | -C(=O)-tetrahydrofuran-3-yl |

TABLE 2-40

TABLE 2-41

| Compound Number | R² | R¹¹ |
|---|---|---|
| 430 | tetrahydropyran-4-yl-C(=O)- | -C(=O)-CH₂-(tetrahydropyran-4-yl) |
| 431 | tetrahydropyran-4-yl-C(=O)- | -C(=O)-CH₂-phenyl |
| 432 | tetrahydropyran-4-yl-C(=O)- | -C(=O)-CH₂-CH₂-phenyl |
| 433 | tetrahydropyran-4-yl-C(=O)- | -C(=O)-CH=CH-phenyl (trans) |
| 434 | tetrahydropyran-4-yl-C(=O)- | -C(=O)-CH₂-O-phenyl |
| 435 | tetrahydropyran-4-yl-C(=O)- | -C(=O)-CH₂-O-CH₃ |
| 436 | tetrahydropyran-4-yl-C(=O)- | -C(=O)-CH₂-Br |
| 437 | tetrahydropyran-4-yl-C(=O)- | -C(=O)-CH₂-O-CH₂CH₃ |
| 438 | tetrahydropyran-4-yl-C(=O)- | -C(=O)-CH₂-N(CH₃)₂ |
| 439 | tetrahydropyran-4-yl-C(=O)- | -C(=O)-CH₂-N(CH₃)(CH₂CH₂-O-CH₃) |
| 440 | tetrahydropyran-4-yl-C(=O)- | -C(=O)-CH₂-N(CH₂CH₂-O-CH₃)₂ |
| 441 | tetrahydropyran-4-yl-C(=O)- | -C(=O)-CH₂-(pyrrolidin-1-yl) |
| 442 | tetrahydropyran-4-yl-C(=O)- | -C(=O)-CH₂-(2-(methoxymethyl)pyrrolidin-1-yl) |
| 443 | tetrahydropyran-4-yl-C(=O)- | -C(=O)-CH₂-((S)-2-(methoxymethyl)pyrrolidin-1-yl) |
| 444 | tetrahydropyran-4-yl-C(=O)- | -C(=O)-CH₂-(3-(dimethylamino)pyrrolidin-1-yl) |
| 445 | tetrahydropyran-4-yl-C(=O)- | -C(=O)-CH₂-(isoindolin-2-yl) |
| 446 | tetrahydropyran-4-yl-C(=O)- | -C(=O)-CH₂-(thiazolidin-3-yl) |
| 447 | tetrahydropyran-4-yl-C(=O)- | -C(=O)-CH₂-(piperidin-1-yl) |
| 448 | tetrahydropyran-4-yl-C(=O)- | -C(=O)-CH₂-(4-hydroxypiperidin-1-yl) |
| 449 | tetrahydropyran-4-yl-C(=O)- | -C(=O)-CH₂-(3-hydroxypiperidin-1-yl) |
| 450 | tetrahydropyran-4-yl-C(=O)- | -C(=O)-CH₂-(4-methoxypiperidin-1-yl) |

TABLE 2-42

(I)

| Compound Number | R² | R¹¹ |
| --- | --- | --- |
| 451 | tetrahydropyran-4-yl-C(=O)– | –C(=O)–CH₂–N(piperidine-4-methyl-4-OH) |
| 452 | tetrahydropyran-4-yl-C(=O)– | –C(=O)–CH₂–N(piperidine-3-CH₂OH) |
| 453 | tetrahydropyran-4-yl-C(=O)– | –C(=O)–CH₂–N(piperidine-4-CH₂OH) |
| 454 | tetrahydropyran-4-yl-C(=O)– | –C(=O)–CH₂–N(piperidine-4-C(CH₃)₂OH) |
| 455 | tetrahydropyran-4-yl-C(=O)– | –C(=O)–CH₂–N(piperidine-4-CH₂-C(CH₃)₂OH) |
| 456 | tetrahydropyran-4-yl-C(=O)– | –C(=O)–CH₂–N(piperidine-4-pyrrolidin-1-yl) |
| 457 | tetrahydropyran-4-yl-C(=O)– | –C(=O)–CH₂–N(piperidine-4-piperidin-1-yl) |
| 458 | tetrahydropyran-4-yl-C(=O)– | –C(=O)–CH₂–N(piperidine-4-morpholin-4-yl) |
| 459 | tetrahydropyran-4-yl-C(=O)– | –C(=O)–CH₂–N(1,4-dioxa-8-azaspiro[4.5]dec-8-yl) |
| 460 | tetrahydropyran-4-yl-C(=O)– | –C(=O)–CH₂–N(piperidine-4-CN) |
| 461 | tetrahydropyran-4-yl-C(=O)– | –C(=O)–CH₂–N(piperidine-4,4-diF) |

TABLE 2-43

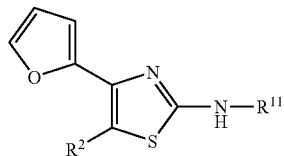

(I)

| Compound Number | R² | R¹¹ |
|---|---|---|
| 462 | tetrahydropyran-4-yl-C(O)– | –C(O)–CH₂–N(3,6-dihydro-2H-pyridin-1-yl) |
| 463 | tetrahydropyran-4-yl-C(O)– | –C(O)–CH₂–N(morpholin-4-yl) |
| 464 | tetrahydropyran-4-yl-C(O)– | –C(O)–CH₂–N(2,6-dimethylmorpholin-4-yl) |
| 465 | tetrahydropyran-4-yl-C(O)– | –C(O)–CH₂–N(piperazin-1-yl)–C(O)–O–C(CH₃)₃ |
| 466 | tetrahydropyran-4-yl-C(O)– | –C(O)–CH₂–N(piperazin-1-yl)–NH |
| 467 | tetrahydropyran-4-yl-C(O)– | –C(O)–CH₂–N(piperazin-1-yl)–N–CH₃ |
| 468 | tetrahydropyran-4-yl-C(O)– | –C(O)–CH₂–N(piperazin-1-yl)–N–CH(CH₃)₂ |
| 469 | tetrahydropyran-4-yl-C(O)– | –C(O)–CH₂–N(piperazin-1-yl)–N–C(O)–O–CH₂CH₃ |
| 470 | tetrahydropyran-4-yl-C(O)– | –C(O)–CH₂–N(piperazin-1-yl)–N–CH₂–C(CH₃)₂–OH |
| 471 | tetrahydropyran-4-yl-C(O)– | –C(O)–CH₂–N(piperazin-1-yl)–N–CH₂–C(CH₃)₂–O–CH₃ |

TABLE 2-44
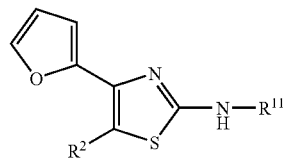
| Compound Number | R² | R¹¹ |
|---|---|---|
| 472 | | |
| 473 | | |
| 474 | | |
| 475 | | |
| 476 | | |
| 477 | | |
| 478 | | |
| 479 | | |
| 480 | | |
| 481 | | |

TABLE 2-45

TABLE 2-46

TABLE 2-47

Structure (I): 4-(furan-2-yl)-5-R²-thiazol-2-yl-NH-R¹¹

| Compound Number | R² | R¹¹ |
|---|---|---|
| 503 | H-C(=O)- | pyridin-3-yl-C(=O)- |
| 504 | HO-C(=O)- | pyridin-3-yl-C(=O)- |
| 505 | morpholin-4-yl-C(=O)- | pyridin-3-yl-C(=O)- |
| 506 | (CH₃)₂N-C(=O)- | pyridin-3-yl-C(=O)- |
| 507 | CH₃O(CH₃)N-C(=O)- | pyridin-3-yl-C(=O)- |
| 508 | phenyl-C(=O)- | pyridin-3-yl-C(=O)- |

TABLE 3-1

Structure (I): 4-(furan-2-yl)-5-R²-thiazol-2-R³

| Compound Number | R² | R³ |
|---|---|---|
| 509 | tetrahydropyran-4-yl-C(=O)- | -NH-C(=O)-N(CH₃)-(7-oxabicyclo[2.2.1]heptan-2-yl) |
| 510 | tetrahydropyran-4-yl-C(=O)- | -(7-oxabicyclo[2.2.1]heptan-2-yl)-CH₂-N(CH₃)-C(=O)-NH- |
| 511 | tetrahydropyran-4-yl-C(=O)- | -NH-C(=O)-morpholin-4-yl |
| 512 | tetrahydropyran-4-yl-C(=O)- | -NH-C(=O)-(2-oxa-5-azabicyclo[2.2.1]heptan-5-yl) |
| 513 | tetrahydropyran-4-yl-C(=O)- | -NH-C(=O)-(1-oxa-8-azaspiro[4.5]decan-8-yl) |
| 514 | tetrahydropyran-4-yl-C(=O)- | -NH-C(=O)-O-(trans-4-hydroxycyclohexyl) |
| 515 | tetrahydropyran-4-yl-C(=O)- | -NH-C(=O)-O-(hydroxy-norbornyl) |
| 516 | tetrahydropyran-4-yl-C(=O)- | 1H-indol-2-yl |
| 517 | tetrahydropyran-4-yl-C(=O)- | 1H-benzimidazol-2-yl |
| 518 | tetrahydropyran-4-yl-C(=O)- | 1H-imidazo[4,5-b]pyridin-2-yl |
| 519 | tetrahydropyran-4-yl-C(=O)- | 1H-imidazo[4,5-c]pyridin-2-yl |

TABLE 3-2

Compounds of formula (I) with furan-thiazole core and R2, R3 substituents.

| Compound Number | R2 | R3 |
|---|---|---|
| 520 | tetrahydropyran-4-yl-C(=O)- | 2-(4-methoxyphenyl)-1H-imidazol-4-yl |
| 521 | tetrahydropyran-4-yl-C(=O)- | 4,5,6,7-tetrahydro-1H-benzimidazol-2-yl |
| 522 | tetrahydropyran-4-yl-C(=O)- | 1,4,6,7-tetrahydropyrano[3,4-d]imidazol-2-yl |
| 523 | tetrahydropyran-4-yl-C(=O)- | 4,5,6,7-tetrahydrothiopyrano[4,3-d]imidazol-2-yl |
| 524 | tetrahydropyran-4-yl-C(=O)- | 4,5,6,7-tetrahydro-3H-imidazo[4,5-c]pyridin-2-yl |
| 525 | 1,4-dioxepan-6-yl-C(=O)- | 2-oxa-5-azabicyclo[2.2.1]heptan-5-yl-C(=O)-NH- |
| 526 | pyridin-2-yl-C(=O)- | 7-oxabicyclo[2.2.1]heptan-2-yl-N(CH3)-C(=O)-NH- |
| 527 | pyridin-2-yl-C(=O)- | 7-oxabicyclo[2.2.1]heptan-2-yl-N(CH3)-C(=O)-NH- |
| 528 | pyridin-2-yl-C(=O)- | morpholin-4-yl-C(=O)-NH- |

TABLE 3-2-continued

| Compound Number | R2 | R3 |
|---|---|---|
| 529 | pyridin-2-yl-C(=O)- | 2-oxa-5-azabicyclo[2.2.1]heptan-5-yl-C(=O)-NH- |

TABLE 3-3

| Compound Number | R2 | R3 |
|---|---|---|
| 530 | pyridin-2-yl-C(=O)- | 1-oxa-8-azaspiro[4.5]decan-8-yl-C(=O)-NH- |
| 531 | pyridin-2-yl-C(=O)- | trans-4-hydroxycyclohexyl-O-C(=O)-NH- |
| 532 | pyridin-2-yl-C(=O)- | hydroxynorbornyl-O-C(=O)-NH- |
| 533 | pyridin-2-yl-C(=O)- | 1H-indol-2-yl |
| 534 | pyridin-2-yl-C(=O)- | 1H-benzimidazol-2-yl |
| 535 | pyridin-2-yl-C(=O)- | 3H-imidazo[4,5-b]pyridin-2-yl |

TABLE 3-3-continued
(I)
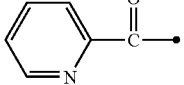
| Compound Number | R² | R³ |
|---|---|---|
| 536 | 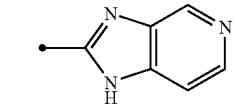 | 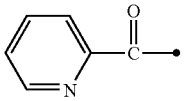 |
| 537 | 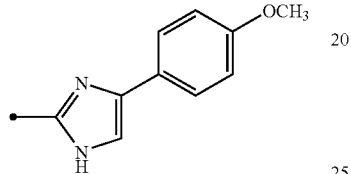 | 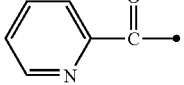 |
| 538 | 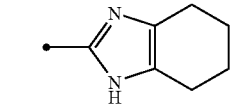 | 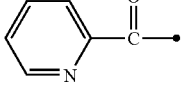 |
| 539 | 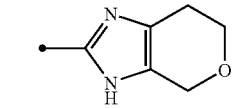 | 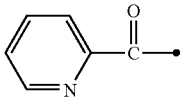 |
| 540 | 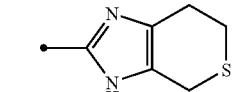 | 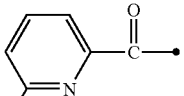 |
TABLE 3-4
(I)
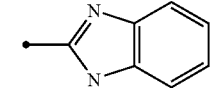
| Compound Number | R² | R⁴ |
|---|---|---|
| 541 | 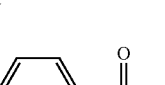 | 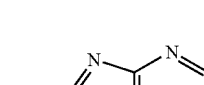 |
| 542 | 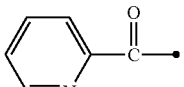 | 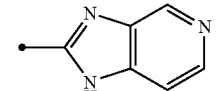 |
TABLE 3-4-continued
(I)
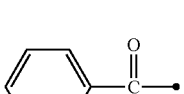
| Compound Number | R² | R⁴ |
|---|---|---|
| 543 | 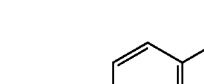 | 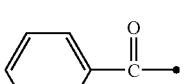 |
| 544 | 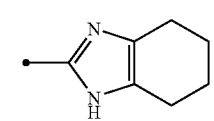 | 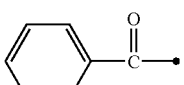 |
| 545 | 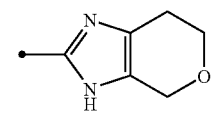 | 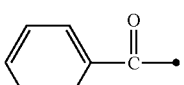 |
| 546 | 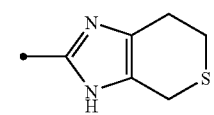 | 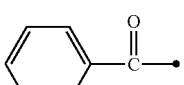 |
| 547 | 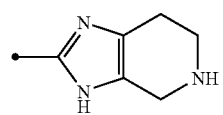 | 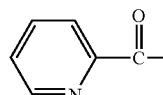 |
| 548 | 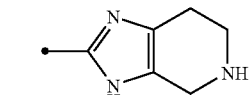 | 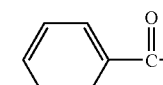 |
| 549 | 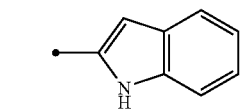 | 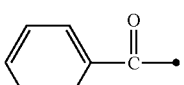 |
| 550 | 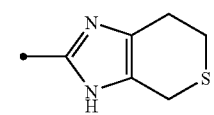 | 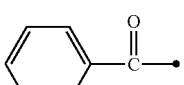 |

TABLE 4

(I) Structure: furan-thiazole core with R³ on thiazole C2 and R² on thiazole C4 (position shown as R² at thiazole; R⁴ labeled in table header)

| Compound Number | R² | R⁴ |
|---|---|---|
| 551 | tetrahydropyran-4-yl-C(=O)– | –C(=O)NH-phenyl |
| 552 | tetrahydropyran-4-yl-C(=O)– | –C(=O)NH–CH(CH₃)₂  (isopropyl, shown as HN–CH with CH₃ and H₃C) |
| 553 | pyridin-2-yl-C(=O)– | –C(=O)NH-phenyl |
| 554 | pyridin-2-yl-C(=O)– | –C(=O)NH–CH(CH₃)₂ |

Test Example 1

Adenosine Receptor Binding Activity (Adenosine $A_{2A}$ Receptor Binding Assay)

The test is performed according to the method of Bruns et al. (Molecular Pharmacology, Vol. 29, p. 331, 1986).

Rat (SD rat, Japan SLC, Inc.) striatum is suspended in 50 mL of ice-cooled tris(hydroxymethyl)-aminomethane hydrochloride (Tris HCl) buffer (50 mmol/L, pH 7.7), using a Polytron homogenizer (Kinematica, Inc.). The suspension is centrifuged (48,000×g, 20 minutes) and the resulting precipitate is resuspended by adding the same amount of Tris HCl buffer (50 mmol/L) thereto, followed by centrifugation under the same conditions. The resulting final precipitate is suspended in Tris HCl buffer (50 mmol/L) [containing magnesium chloride (10 mmol/L), and adenosine deaminase (0.02 unit/mg tissue) (Sigma)] to prepare the suspension at the tissue concentration of 5 mg (wet weight)/mL.

To 100 μl of tissue suspension, 80 μl of tritium-labeled CGS-21680 {³H-2-[p-(2-carboxyethyl)phenethylamino]-5'-(N-ethylcarboxamido)adenosine: 40 Ci/mmol; New England Nuclear [*The Journal of Pharmacology and Experimental Therapeutics*, Vol. 251, p. 888, 1989]} (final concentration of 6.0 mmol/L), and 20 μL of test compound solution ($10^{-7}$ mol/L, DMSO solution of test compound diluted with Tris HCl buffer) are added. The mixture is allowed to stand at 25° C. for 120 minutes, followed by rapid suction filtration using glass-fiber filter paper (GF/C; Whatman), then immediately washed three times with 200 μL of ice-cooled Tris HCl buffer (50 mmol/L). The glass-fiber filter paper is then placed in a vial container, and MicroScinti (PerkinElmer) is added to measure the radioactivity with a TopCount (PerkinElmer).

Percent inhibition of adenosine $A_{2A}$ receptor binding (3H-CGS21680 binding) by the test compound can be calculated by the following equation.

$$\text{Percent Inhibition (\%)} = \left(1 - \frac{\text{Amount of binding in the presence of medicament} - \text{amount of non-specific binding}}{\text{Total amount of binding} - \text{amount of non-specific binding}}\right) \times 100 \quad [\text{Equation 1}]$$

The total bound radioactivity refers to bound radioactivity of ³H-CGS21680 that has bound to the receptors in the absence of the assay compound. The non-specific bound radioactivity refers to bound radioactivity of ³H-CGS21680 in the presence of 100 mmol/L of cyclopentyladenosine (CPA; Sigma). The bound radioactivity in the presence of medicament refers to bound radioactivity of ³H-CGS21680 in presence of $10^{-7}$ mol/L of test compound.

In the above test, percent inhibition for the adenosine $A_{2A}$ receptor by Compound (I) or a pharmaceutically acceptable salt thereof can be determined at different concentrations by appropriately adjusting the concentration of the test compound. According to the test, it is confirmed that Compound (I) has the antagonistic activity to the adenosine $A_{2A}$ receptor.

Test Example 2

The effect of Compound (I) on Pentobarbital Sodium-Induced Sleeping Time

The test was conducted to examine influence of Compound (I) of the present invention on pentobarbital sodium-induced sleeping time, according to the method of *Iyakuhin no Kaihatsu*, Vol. 9, *Iyakuhin no Tansaku I*, "antihypnotic", p. 220-226, Hirokawa Shoten.

(1) Test Material

For the test, ddY male mice (19-21 g body weight; Japan SLC, Inc.) were used. All test compounds were used by suspending in distilled water (Otsuka Pharmaceutical Factory, Inc.) containing 0.5 volume/weight % methylcellulose (0.5% MC: Wako Pure Chemical Industries, Ltd.). A volume of 0.1 mL was administered per 10 g body weight of mice.

(2) Test Method

Groups of seven mice were used. To the control groups were orally administrated 0.5% MC, whereas a suspension of the test compound was orally administered to the test compound administered groups. One hour after the administration, pentobarbital sodium (pentobarbital-Na: Tokyo Chemical Industry Co., Ltd., 25 mg/kg) was administered subcutaneously. Mouse placed in a recumbent position, the mouse immediately returns to a proper upright position (this is known as righting reflex). However, the administration of pentobarbital sodium eliminated the righting reflex in the control groups. The time period in which the administration of test compound eliminated the righting reflex was regarded as a sleeping time. By a measurement of time disappearing righting reflex immediately after the administration, the sleeping time was determined. The results are shown in Table 5-1 and Table 5-2.

TABLE 5-1

| Test compound | Dose (mg/kg, p.o.) | Sleeping time (min) Mean value ± standard deviation |
|---|---|---|
| Control | — | 52.12 ± 5.20 |
| 1 | 10 | 15.58 ± 8.50 **** |
| 5 | 10 | 0.82 ± 0.82 *** |
| 7 | 10 | 6.38 ± 4.58 * |
| 8 | 10 | 4.16 ± 4.16 * |
| 11 | 10 | 22.75 ± 6.63 **** |
| Control | — | 35.56 ± 5.21 |
| 95 | 10 | 0.45 ± 0.45 *** |
| 136 | 10 | 1.89 ± 1.81 *** |
| 361 | 10 | 1.65 ± 1.40 *** |
| 367 | 10 | 0.10 ± 0.10 *** |
| 376 | 10 | 0.00 ± 0.00 *** |
| 416 | 10 | 0.06 ± 0.06 *** |
| 420 | 10 | 0.00 ± 0.00 *** |
| 407 | 10 | 0.00 ± 0.00 *** |

*, , *, and **** mean significant difference over the control groups
* $p < 0.001$, Student's t-test
** $p < 0.01$, Aspin-Welch test
*** $p < 0.001$, Aspin-Welch test
**** $p < 0.01$, Student's t-test

TABLE 5-2

| Test compound | Dose (mg/kg, p.o.) | Sleeping time (min) Mean value ± standard deviation |
|---|---|---|
| Control | — | 40.00 ± 5.32 |
| 508 | 10 | 14.26 ± 4.35 ** |
| 78 | 10 | 8.66 ± 4.67 * |
| 114 | 10 | 0.63 ± 0.53 * |
| 142 | 10 | 4.52 ± 4.41 * |
| 157 | 10 | 9.39 ± 5.68 **** |
| 336 | 10 | 1.60 ± 1.56 *** |
| Control | — | 45.87 ± 4.17 |
| 99 | 10 | 0.05 ± 0.02 *** |
| 360 | 10 | 0.03 ± 0.02 *** |
| 373 | 10 | 0.03 ± 0.02 *** |
| 365 | 10 | 0.05 ± 0.05 *** |
| 463 | 10 | 0.00 ± 0.00 *** |
| 409 | 10 | 0.05 ± 0.05 *** |

*, , *, and **** mean significant difference over the control groups
* $p < 0.001$, Student's t-test
** $p < 0.01$, Aspin-Welch test
*** $p < 0.001$, Aspin-Welch test
**** $p < 0.01$, Student's t-test From the above results, it was shown that Compound (I) or a pharmaceutically acceptable salt thereof had the effect for reducing the sleeping time induced by pentobarbital sodium. In other words, it was shown that Compound (I) suppress sleep induced by hypnotics such as pentobarbital sodium. That is, it is considered that Compound (I) has stimulant activity, and is useful to treating and/or preventing a sleep disorder and improving daytime sleepiness, and the like, for example.

It is therefore considered that Compound (I) can suitably treat and/or prevent or improve sleep disorders, particularly those whose symptoms are expected to be treated and/or prevented, or improved by the stimulant activity or sleepiness improving activity, or more specifically sleep disorders that involve excessive sleep and/or daytime sleepiness.

More specifically, it is considered that by administrating Compound (I), a sleep disorder, particularly narcolepsy; hypersomnia such as recurrent hypersomnia (periodic hypersomnia), idiopathic hypersomnia, and posttraumatic hypersomnia; a circadian rhythm sleep disorder such as time zone change syndrome (jet lag syndrome, jet lag), a shift work sleep disorder, irregular sleep-wake pattern, delayed sleep phase syndrome, or a non-24-hour sleep-wake disorder; and the like can be suitably treated and/or prevented or improved.

Compound (I) or a pharmaceutically acceptable salt thereof can be administered alone. However, usually, Compound (I) or a pharmaceutically acceptable salt thereof is preferably provided in various pharmaceutical preparations. The pharmaceutical preparations may be used for animals or humans.

Pharmaceutical preparations according to the present invention may include Compound (I) or a pharmaceutically acceptable salt thereof as an active ingredient either alone or as a mixture with an active ingredient for any other treatment. Furthermore, these pharmaceutical preparations are prepared by mixing the active ingredient with one or more pharmaceutically acceptable carriers and then subjecting the mixture to any method well-known in the technical field of pharmaceutics.

As for the administration route, it is preferred to select the most effective route of administration. Examples of the administration route include oral administration and parenteral administration such as intravenous administration.

Examples of administration form include tablets, injections, and the like.

Suitable dosage forms for the oral administration, for example, tablets, can be prepared by using excipients such as lactose, disintegrators such as starch, lubricants such as magnesium stearate, binders such as hydroxypropylcellulose, surfactants such as fatty acid ester, and plasticizers such as glycerine, and the like.

Suitable dosage forms for the parenteral administration, for example, injections, can be prepared by using diluents or solvent such as a salt solution, a glucose solution, or a mixture of brine and glucose solution, and the like.

In the above dosage forms for the parenteral administration, one or more additives selected from the excipients, disintegrators, lubricants, binders, surfactants, plasticizers, which are exemplified in the oral administration, diluents, preservatives, flavors, and the like, may be added.

Compound (I) or a pharmaceutically acceptable salt thereof is usually administered systemically or locally by oral or parenteral administration when used for the foregoing purposes. The doses and the frequencies of administration may vary depending upon dosage form, age and body weight of a patient, nature or seriousness of the symptom to be treated, and the like. In the oral administration, in general, a dose of 0.01 to 1000 mg, preferably, 0.05 to 500 mg, is administered to an adult patient once or several times a day. In the parenteral administration such as the intravenous administration, in general, a dose of 0.001 to 1000 mg, preferably, 0.01 to 300 mg, is administered to an adult patient once or several times a day, or continuously to the vein for 1 to 24 hours a day. However, these doses and frequencies of administration may vary by the various conditions described above.

The present invention will be discussed in detail based on Examples and Reference Examples below.

The proton nuclear magnetic resonance spectrum ($^1$H NMR) used in Reference Examples was measured at 270 MHz or 300 MHz, and, depending on the compound and measurement conditions, exchanged protons may not be observed clearly. Signal multiplicity is given by the notation commonly used. The symbol "br" denotes an apparently wide signal.

Example 1

Tablet (Compound 78)

Tablets having the following composition are prepared according to the conventional manner. Compound 78 (40 g), lactose (286.8 g) and potato starch (60 g) are mixed together, and 10% hydroxypropylcellulose aqueous solution (120 g) is added thereto. The mixture is kneaded according to the conventional manner, granulated, dried, and sized into a powder for tabletting. This is followed by addition of magnesium stearate (1.2 g) and mixing. The powders are then punched with a tabletting machine equipped with a punch having a diameter of 8 mm (Kikusui Seisakusho, model RT-15) to obtain tablets (containing 20 mg of active ingredient per tablet).

TABLE 6

| Formulation | Compound 78 | 20 mg |
|---|---|---|
| | Lactose | 143.4 mg |
| | Potato starch | 30 mg |
| | Hydroxypropylcellulose | 6 mg |
| | Magnesium stearate | 0.6 mg |
| | | 200 mg |

Example 2

Injection (Compound 95)

An injection having the following composition is prepared according to the conventional manner. Compound 95 (1 g) and D-mannitol (5 g) are added to distilled water for injection and mixed therewith. This is followed by addition of hydrochloric acid and an aqueous solution of sodium hydroxide to adjust the pH at 6. The total volume is adjusted to 1000 mL with distilled water for injection. Then, 2 mL of the mixture is aseptically charged to each glass vial to obtain an injection (containing 2 mg of active ingredient per vial).

TABLE 7

| Formulation | Compound 95 | 2 mg |
|---|---|---|
| | D-mannitol | 10 mg |
| | Hydrochloric acid | appropriate amount |
| | NaOH aqueous solution | appropriate amount |
| | Distilled water for injection | appropriate amount |
| | | 2.00 mL |

Example 3

Tablet (Compound 376)

Using Compound 376 (40 g), the title tablets (containing 20 mg of active ingredient per tablet) are obtained in the same manner as in Preparation Example 1.

TABLE 8

| Formulation | Compound 376 | 20 mg |
|---|---|---|
| | Lactose | 143.4 mg |
| | Potato starch | 30 mg |
| | Hydroxypropylcellulose | 6 mg |
| | Magnesium stearate | 0.6 mg |
| | | 200 mg |

Example 4

Tablet (Compound 420)

Using Compound 420 (40 g), the title tablets (containing 20 mg of active ingredient per tablet) are obtained in the same manner as in Preparation Example 1.

TABLE 9

| Formulation | Compound 420 | 20 mg |
|---|---|---|
| | Lactose | 143.4 mg |
| | Potato starch | 30 mg |
| | Hydroxypropylcellulose | 6 mg |
| | Magnesium stearate | 0.6 mg |
| | | 200 mg |

Example 5

Injection (Compound 463)

Using Compound 463 (1 g), the title injection (containing 2 mg of active ingredient per vial) is obtained in the same manner as in Preparation Example 2.

TABLE 10

| Formulation | Compound 463 | 2 mg |
|---|---|---|
| | D-mannitol | 10 mg |
| | Hydrochloric acid | appropriate amount |
| | NaOH aqueous solution | appropriate amount |
| | Distilled water for injection | appropriate amount |
| | | 2.00 mL |

Example 6

Tablet (Compound 1)

Using Compound 1 (40 g), the title tablets (containing 20 mg of active ingredient per tablet) are obtained in the same manner as in Preparation Example 1.

TABLE 11

| Formulation | Compound 1 | 20 mg |
|---|---|---|
| | Lactose | 143.4 mg |
| | Potato starch | 30 mg |
| | Hydroxypropylcellulose | 6 mg |
| | Magnesium stearate | 0.6 mg |
| | | 200 mg |

Example 7

Injection (Compound 1)

Using Compound 1 (1 g), the title injection (containing 2 mg of active ingredient per vial) is obtained in the same manner as in Preparation Example 2.

TABLE 12

| Formulation | Compound 1 | 2 mg |
|---|---|---|
| | D-mannitol | 10 mg |
| | Hydrochloric acid | appropriate amount |
| | NaOH aqueous solution | appropriate amount |
| | Distilled water for injection | appropriate amount |
| | | 2.00 mL |

Example 8

Tablet (Compound 407)

Using Compound 407 (40 g), the title tablets (containing 20 mg of active ingredient per tablet) are obtained in the same manner as in Preparation Example 1.

TABLE 13

| Formulation | Compound 407 | 20 mg |
|---|---|---|
| | Lactose | 143.4 mg |
| | Potato starch | 30 mg |
| | Hydroxypropylcellulose | 6 mg |
| | Magnesium stearate | 0.6 mg |
| | | 200 mg |

Example 9

Tablet (Compound 409)

Using Compound 409 (40 g), the title tablets (containing 20 mg of active ingredient per tablet) are obtained in the same manner as in Preparation Example 1.

TABLE 14

| Formulation | Compound 409 | 20 mg |
|---|---|---|
| | Lactose | 143.4 mg |
| | Potato starch | 30 mg |
| | Hydroxypropylcellulose | 6 mg |
| | Magnesium stearate | 0.6 mg |
| | | 200 mg |

Example 10

Tablet (Compound 373)

Using Compound 373 (40 g), the title tablets (containing 20 mg of active ingredient per tablet) are obtained in the same manner as in Preparation Example 1.

TABLE 15

| Formulation | Compound 373 | 20 mg |
|---|---|---|
| | Lactose | 143.4 mg |
| | Potato starch | 30 mg |
| | Hydroxypropylcellulose | 6 mg |
| | Magnesium stearate | 0.6 mg |
| | | 200 mg |

Example 11

Tablet (Compound 416)

Using Compound 416 (40 g), the title tablets (containing 20 mg of active ingredient per tablet) are obtained in the same manner as in Preparation Example 1.

TABLE 16

| Formulation | Compound 416 | 20 mg |
|---|---|---|
| | Lactose | 143.4 mg |
| | Potato starch | 30 mg |
| | Hydroxypropylcellulose | 6 mg |
| | Magnesium stearate | 0.6 mg |
| | | 200 mg |

Example 12

Injection (Compound 5)

Using Compound 5 (1 g), the title injection (containing 2 mg of active ingredient per vial) is obtained in the same manner as in Preparation Example 2.

TABLE 17

| Formulation | Compound 5 | 2 mg |
|---|---|---|
| | D-mannitol | 10 mg |
| | Hydrochloric acid | appropriate amount |
| | NaOH aqueous solution | appropriate amount |
| | Distilled water for injection | appropriate amount |
| | | 2.00 mL |

Example 13

Injection (Compound 360)

Using Compound 360 (1 g), the title injection (containing 2 mg of active ingredient per vial) is obtained in the same manner as in Preparation Example 2.

TABLE 18

| Formulation | Compound 360 | 2 mg |
|---|---|---|
| | D-mannitol | 10 mg |
| | Hydrochloric acid | appropriate amount |
| | NaOH aqueous solution | appropriate amount |
| | Distilled water for injection | appropriate amount |
| | | 2.00 mL |

Compounds 1 to 508 were obtained according to the methods described in WO2005/063743.

Reference Example 1

N-[4-(2-Furyl)-5-(4-pyridyl)thiazol-2-yl]pyridine-4-carboxamide (Compound 1)

$^1$H NMR (DMSO-d$_6$, δ ppm): 6.61 (dd, J=1.8, 3.3 Hz, 1H), 6.74 (dd, J=0.7, 3.3 Hz, 1H), 7.46 (dd, J=1.5, 4.6 Hz, 2H), 7.67 (dd, J=0.7, 1.8 Hz, 1H), 8.02 (dd, J=1.5, 4.6 Hz, 2H), 8.63 (dd, J=1.5, 4.6 Hz, 2H), 8.83 (dd, J=1.5, 4.6 Hz, 2H). ESIMS m/z: [M+H]$^+$ 349.

Reference Example 2

N-[4-(2-Furyl)-5-(4-pyridyl)thiazol-2-yl]acetamide (Compound 2)

$^1$H NMR (DMSO-d$_6$, δ ppm): 2.20 (s, 3H), 6.58 (dd, J=1.8, 3.3 Hz, 1H), 6.68 (dd, J=0.7, 3.3 Hz, 1H), 7.42 (dd, J=1.5, 4.5 Hz, 2H), 7.62 (dd, J=0.7, 1.8 Hz, 1H), 8.58 (dd, J=1.5, 4.5 Hz, 2H), 12.50 (br s, 1H). ESIMS m/z: [M+H]$^+$286.

Reference Example 3

N-[4-(2-Furyl)-5-(4-pyridyl)thiazol-2-yl]methoxyacetamide (Compound 3)

$^1$H NMR (DMSO-d$_6$, δ ppm): 3.34 (s, 3H), 4.20 (s, 2H), 6.59 (dd, J=1.8, 3.3 Hz, 1H), 6.70 (d, J=3.3 Hz, 1H), 7.43 (d, J=6.1 Hz, 2H), 7.65 (d, J=1.8 Hz, 1H), 8.61 (d, J=6.1 Hz, 2H), 12.5 (br s, 1H). APCIMS m/z: [M+H]$^+$ 315.

Reference Example 4

N-[4-(2-Furyl)-5-(4-pyridyl)thiazol-2-yl]cyclohexanecarboxamide (Compound 4)

$^1$H NMR (DMSO-$d_6$, δ ppm): 1.24-1.86 (10H, m), 2.50-2.56 (m, 1H), 6.58 (dd, J=1.8, 3.3 Hz, 1H), 6.69 (d, J=3.3 Hz, 1H), 7.41 (d, J=6.0 Hz, 2H), 7.64 (d, J=1.8 Hz, 1H), 8.56 (d, J=6.0 Hz, 2H), 12.4 (br s, 1H). ESIMS m/z: [M+H]$^+$ 354.

Reference Example 5

N-[4-(2-Furyl)-5-(4-pyridyl)thiazol-2-yl]pyridine-3-carboxamide (Compound 5)

$^1$H NMR (DMSO-$d_6$, δ ppm): 6.61 (dd, J=1.8, 3.3 Hz, 1H), 6.75 (d, J=3.3 Hz, 1H), 7.48 (d, J=6.1 Hz, 2H), 7.59-7.63 (m, 1H), 7.67-7.68 (m, 1H), 8.44-8.48 (m, 1H), 8.64 (d, J=6.1 Hz, 2H), 8.81-8.83 (m, 1H), 9.24-9.25 (m, 1H). APCIMS m/z: [M+H]$^+$ 349.

Reference Example 6

N-[4-(2-Furyl)-5-(4-pyridyl)thiazol-2-yl]pyrazine-2-carboxamide (Compound 6)

$^1$H NMR (DMSO-$d_6$, δ ppm): 6.58 (dd, J=1.8, 3.3 Hz, 1H), 6.74 (d, J=3.3 Hz, 1H), 7.45 (d, J=6.1 Hz, 2H), 7.66 (d, J=1.8 Hz, 1H), 8.61 (d, J=6.1 Hz, 2H), 8.83-8.84 (m, 1H), 8.94-8.95 (m, 1H), 9.30-9.31 (m, 1H), 12.85 (br s, 1H). APCIMS m/z: [M+H]$^+$ 350.

Reference Example 7

N-[4-(2-Furyl)-5-(4-pyridyl)thiazol-2-yl]furan-2-carboxamide (Compound 7)

$^1$H NMR (DMSO-$d_6$, δ ppm): 6.60 (dd, J=1.8, 3.3 Hz, 1H), 6.74 (d, J=3.3 Hz, 1H), 6.77 (dd, J=1.7, 3.5 Hz, 1H), 7.45 (d, J=6.0 Hz, 2H), 7.67 (d, J=1.8 Hz, 1H), 7.76 (d, J=3.5 Hz, 1H), 8.05 (d, J=1.7 Hz, 1H), 8.62 (d, J=6.0 Hz, 2H), 13.02 (br s, 1H). APCIMS m/z: [M+H]$^-$ 338.

Reference Example 8

N-[4-(2-Furyl)-5-(4-pyridyl)thiazol-2-yl]furan-3-carboxamide (Compound 8)

$^1$H NMR (DMSO-$d_6$, δ ppm): 6.59 (dd, J=1.8, 3.3 Hz, 1H), 6.71 (d, J=3.3 Hz, 1H), 7.12-7.13 (m, 1H), 7.42-7.44 (m, 2H), 7.65 (d, J=1.8 Hz, 1H), 7.85-7.86 (m, 1H), 8.30-8.62 (m, 3H), 12.84 (br s, 1H). APCIMS m/z: [M+H]$^+$ 338.

Reference Example 9

N-[4-(2-Furyl)-5-(4-pyridyl)thiazol-2-yl]-1-oxopyridine-3-carboxamide (Compound 9)

$^1$H NMR (DMSO-$d_6$, δ ppm): 6.62 (dd, J=1.7, 3.5 Hz, 1H), 6.77 (dd, J=0.7, 3.5 Hz, 1H), 7.53 (dd, J=1.7, 4.6 Hz, 2H), 7.58-7.63 (m, 1H), 7.68 (dd, J=0.7, 1.7 Hz, 1H), 7.96-7.99 (m, 1H), 8.44-8.46 (m, 1H), 8.66 (dd, J=1.7, 4.6 Hz, 2H), 8.83-8.84 (m, 1H). APCIMS m/z: [M+H]$^+$ 365.

Reference Example 10

N-[4-(2-Furyl)-5-(4-pyridyl)thiazol-2-yl]-2-hydroxypyridine-5-carboxamide (Compound 10)

$^1$H NMR (DMSO-$d_6$, δ ppm): 6.42 (d, J=9.7 Hz, 1H), 6.58 (dd, J=1.7, 3.3 Hz, 1H), 6.70 (d, J=3.3 Hz, 1H), 7.42 (d, J=6.1 Hz, 2H), 7.64 (d, J=1.7 Hz, 1H), 8.03 (dd, J=2.8, 9.7 Hz, 1H), 8.42 (d, J=2.8 Hz, 1H), 8.59 (d, J=6.1 Hz, 2H). APCIMS m/z: [M+H]$^+$ 365.

Reference Example 11

N-[4-(2-Furyl)-5-(4-pyridyl)thiazol-2-yl]-4-(imidazole-1-ylmethyl)benzamide (Compound 11)

$^1$H NMR (DMSO-$d_6$, δ ppm): 5.23 (s, 2H), 6.42 (dd, J=1.9, 3.2 Hz, 1H), 6.57 (dd, J=0.8, 3.2 Hz, 1H), 6.93 (m, 1H), 7.17 (m, 1H), 7.28 (d, J=8.4 Hz, 2H), 7.36 (dd, J=0.8, 1.9 Hz, 1H), 7.42 (dd, J=1.6, 4.6 Hz, 2H), 7.60 (m, 1H), 7.96 (d, J=8.4 Hz, 2H), 8.65 (dd, J=1.6, 4.6 Hz, 2H), 10.15 (br s, 1H). APCIMS m/z: [M+H]$^+$ 428.

Reference Example 12

N-[4-(2-Furyl)-5-phenylthiazol-2-yl]pyridine-4-carboxamide (Compound 12)

$^1$H NMR (DMSO-$d_6$, δ ppm): 6.53-6.55 (m, 2H), 7.43-7.46 (m, 5H), 7.61 (dd, J=0.7, 1.8 Hz, 1H), 8.02 (dd, J=1.7, 4.5 Hz, 2H), 8.82 (dd, J=1.7, 4.5 Hz, 2H), 13.23 (br s, 1H). ESIMS m/z: [M+H]$^+$ 348.

Reference Example 13

N-[5-Benzyl-4-(2-furyl)thiazol-2-yl]pyridine-4-carboxamide (Compound 13)

$^1$H NMR (DMSO-$d_6$, δ ppm): 4.39 (s, 2H), 6.34 (dd, J=1.8, 3.5 Hz, 1H), 6.50 (d, J=3.5 Hz, 1H), 7.26-7.36 (m, 6H), 7.63 (dd, J=1.7, 4.5 Hz, 2H), 8.71 (dd, J=1.7, 4.5 Hz, 2H), 10.90 (br s, 1H). ESIMS m/z: [M−H]$^-$ 360.

Reference Example 14

N-[4-(2-Furyl)-5-(1-oxopyridin-4-yl)thiazol-2-yl]acetamide (Compound 14)

$^1$H NMR (DMSO-$d_6$, δ ppm): 2.18 (s, 3H), 6.59 (dd, J=1.8, 3.3 Hz, 1H), 6.71 (dd, J=0.7, 3.3 Hz, 1H), 7.44 (dd, J=1.5, 4.6 Hz, 2H), 7.66 (dd, J=0.7, 1.8 Hz, 1H), 8.22 (dd, J=1.5, 4.6 Hz, 2H), 12.5 (br s, 1H). ESIMS m/z: [M+H]$^+$ 302.

Reference Example 15

2-Chloro-N-[4-(2-furyl)-5-morpholinothiazol-2-yl]pyridine-5-carboxamide (Compound 15)

$^1$H NMR(CDCl$_3$, δ ppm): 3.04 (t, J=4.3 Hz, 4H), 3.90 (t, J=4.3 Hz, 4H), 6.41 (dd, J=1.6, 3.5 Hz, 1H), 6.79 (d, J=3.5 Hz, 1H), 7.23 (d, J=1.6 Hz, 1H), 7.36 (d, J=8.4 Hz, 1H), 8.11 (dd, J=2.2, 8.4 Hz, 1H), 8.84 (d, J=2.2 Hz, 1H).

Reference Example 16

N-[4-(2-Furyl)-5-morpholinothiazol-2-yl]-2-[(2-hydroxyethyl)amino]pyridine-5-carboxamide (Compound 16)

$^1$H NMR (DMSO-d$_6$, δ ppm): 2.91 (t, J=4.4 Hz, 4H), 3.30-3.43 (m, 2H), 3.51-3.54 (m, 2H), 3.78 (t, J=4.4 Hz, 4H), 4.74 (m, 1H), 6.55 (d, J=8.9 Hz, 1H), 6.60 (dd, J=1.9, 3.2 Hz, 1H), 6.81 (dd, J=0.8, 3.2 Hz, 1H), 7.36 (t, J=8.1 Hz, 1H), 7.68 (dd, J=0.8, 1.9 Hz, 1H), 8.00 (dd, J=2.2, 8.9 Hz, 1H), 8.75 (d, J=2.2 Hz, 1H). APCIMS m/z: [M+H]$^+$ 416.

Reference Example 17

N-[4-(2-Furyl)-5-morpholinothiazol-2-yl]-2-morpholinopyridine-5-carboxamide (Compound 17)

$^1$H NMR (CDCl$_3$, δ ppm): 3.02 (t, J=4.6 Hz, 4H), 3.68 (t, J=4.7 Hz, 4H), 3.82 (t, J=4.7 Hz, 4H), 3.89 (t, J=4.6 Hz, 4H), 6.51 (dd, J=1.9, 3.5 Hz, 1H), 6.66 (d, J=9.2 Hz, 1H), 6.88 (d, J=3.5 Hz, 1H), 7.45 (d, J=1.9 Hz, 1H), 7.98 (dd, J=2.4, 9.2 Hz, 1H), 8.72 (d, J=2.4 Hz, 1H). APCIMS m/z: [M+H]$^+$ 442.

Reference Example 18

N-[4-(2-Furyl)-5-morpholinothiazol-2-yl]-2-(4-methylpiperazin-1-yl)pyridine-4-carboxamide (Compound 18)

$^1$H NMR (CDCl$_3$, δ ppm): 2.37 (s, 3H), 2.55 (t, J=4.9 Hz, 4H), 3.03 (t, J=4.6 Hz, 4H), 3.66 (t, J=4.9 Hz, 4H), 3.90 (t, J=4.6 Hz, 4H), 6.51 (dd, J=1.9, 3.2 Hz, 1H), 6.87 (dd, J=0.8, 3.2 Hz, 1H), 6.90 (dd, J=1.3, 5.1 Hz, 1H), 7.11 (d, J=1.3 Hz, 1H), 7.44 (dd, J=0.8, 1.9 Hz, 1H), 8.32 (d, J=5.1 Hz, 1H), 9.50 (br s, 1H). APCIMS m/z: [M+H]$^+$ 455.

Reference Example 19

1-(5-Cyanopyridin-2-yl)-N-[4-(2-furyl)-5-morpholinothiazol 2-yl]piperidine-4-carboxamide (Compound 19)

$^1$H NMR (CDCl$_3$, δ ppm): 1.70-1.95 (m, 4H), 2.40-2.55 (m, 1H), 2.85-2.95 (m, 2H), 2.99 (t, J=4.6 Hz, 4H), 3.88 (t, J=4.6 Hz, 4H), 4.35-4.45 (m, 2H), 6.52 (dd, J=1.9, 3.5 Hz, 1H), 6.60 (d, J=9.4 Hz, 1H), 6.87 (dd, J=0.8, 3.5 Hz, 1H), 7.45 (dd, J=0.8, 1.9 Hz, 1H), 7.61 (dd, J=2.2, 9.4 Hz, 1H), 8.40 (d, J=2.2 Hz, 1H), 9.76 (br s, 1H). APCIMS m/z: [M+H]$^+$ 465.

Reference Example 20

N-[4-(2-Furyl)-5-morpholinothiazol-2-yl]-1-[5-(methanesulfonyl)pyridin-2-yl]piperidine-4-carboxamide (Compound 20)

1H NMR (CDCl$_3$, δ ppm): 1.70-1.90 (m, 2H), 1.90-2.00 (m, 2H), 2.45-2.55 (m, 1H), 2.99 (t, J=4.7 Hz, 4H), 3.04 (s, 3H), 3.05-3.10 (m, 2H), 3.88 (t, J=4.7 Hz, 4H), 4.41-4.51 (m, 2H), 6.52 (dd, J=1.9, 3.2 Hz, 1H), 6.63 (d, J=9.2 Hz, 1H), 6.87 (d, J=3.2 Hz, 1H), 7.45 (d, J=1.9 Hz, 1H), 7.87 (dd, J=2.4, 9.2 Hz, 1H), 8.63 (d, J=2.4 Hz, 1H), 9.51 (br s, 1H). APCIMS m/z: [M+H]$^+$ 518.

Reference Example 21

N-[4-(2-Furyl)-5-morpholinothiazol-2-yl]-1-morpholinocarbonylpiperidine-4-carboxamide (Compound 21)

$^1$H NMR (CDCl$_3$, δ ppm): 1.60-1.90 (m, 4H), 2.30-2.50 (m, 1H), 2.65-2.85 (m, 2H), 2.99 (t, J=4.3 Hz, 4H), 3.26 (t, J=4.3 Hz, 4H), 3.68 (t, J=4.3 Hz, 4H), 3.66-3.76 (m, 2H), 3.88 (t, J=4.3 Hz, 4H), 6.51 (dd, J=1.9, 3.5 Hz, 1H), 6.87 (d, J=3.5 Hz, 1H), 7.44 (d, J=1.9 Hz, 1H), 9.73 (br s, 1H). APCIMS m/z: [M+H]$^+$ 476.

Reference Example 22

N-[4-(2-Furyl)-5-morpholinothiazol-2-yl]-1-methanesulfonylpiperidine-4-carboxamide (Compound 22)

$^1$H NMR (CDCl$_3$, δ ppm): 1.80-2.00 (m, 4H), 2.35-2.50 (m, 1H), 2.70-2.85 (m, 2H), 2.80 (s, 3H), 2.99 (t, J=4.3 Hz, 4H), 3.76 (ddd, J=3.8, 3.8, 14.6 Hz, 2H), 3.88 (t, J=4.3 Hz, 4H), 6.52 (dd, J=1.9, 3.5 Hz, 1H), 6.87 (d, J=3.5 Hz, 1H), 7.45 (d, J=1.9 Hz, 1H), 9.67 (br s, 1H). APCIMS m/z: [M+H]$^+$ 441.

Reference Example 23

1-(N,N-Dimethylsulfamoyl)-N-[4-(2-furyl)-5-morpholinothiazol-2-yl]piperidine-4-carboxamide (Compound 23)

$^1$H NMR (CDCl$_3$, δ ppm): 1.70-1.95 (m, 4H), 2.25-2.45 (m, 1H), 2.70-2.85 (m, 2H), 2.83 (s, 6H), 2.99 (t, J=4.6 Hz, 4H), 3.78 (ddd, J=3.8, 3.8, 14.8 Hz, 2H), 3.89 (t, J=4.6 Hz, 4H), 6.52 (dd, J=1.9, 3.2 Hz, 1H), 6.87 (d, J=3.2 Hz, 1H), 7.44 (d, J=1.9 Hz, 1H), 9.75 (br s, 1H). APCIMS m/z: [M+H]$^+$ 470.

Reference Example 24

N-[4-(2-Furyl)-5-morpholinothiazol-2-yl]-4-(2-oxopiperidinomethyl)benzamide (Compound 24)

$^1$H NMR (CDCl$_3$, δ ppm): 1.81-1.84 (m, 4H), 2.48-2.51 (m, 2H), 3.03 (t, J=4.6 Hz, 4H), 3.22-3.26 (m, 2H), 3.90 (t, J=4.6 Hz, 4H), 4.66 (s, 2H), 6.51 (dd, J=1.9, 3.5 Hz, 1H), 6.88 (dd, J=0.5, 3.5 Hz, 1H), 7.45 (dd, J=0.5, 1.9 Hz, 1H), 7.67 (d, J=13.5 Hz, 2H), 7.87 (d, J=13.5 Hz, 2H), 9.45 (br s, 1H). APCIMS m/z: [M+H]$^+$ 467.

Reference Example 25

N-[4-(2-Furyl)-5-(4-methylpiperazin-1-yl)thiazol-2-yl]-pyridine-4-carboxamide (Compound 25)

$^1$H NMR (CDCl$_3$, δ ppm): 2.47 (s, 3H), 2.70-2.81 (m, 4H), 3.10-3.19 (m, 4H), 6.40 (dd, J=1.8, 3.3 Hz, 1H), 6.76 (d, J=3.3 Hz, 1H), 7.28 (d, J=1.8 Hz, 1H), 7.66 (d, J=6.1 Hz, 2H), 8.74 (d, J=6.1 Hz, 2H). APCIMS m/z: [M+H]$^+$ 370.

Reference Example 26

N-[4-(2-Furyl)-5-thiomorpholinothiazol-2-yl]pyridine-4-carboxamide (Compound 26)

$^1$H NMR (CDCl$_3$, δ ppm): 2.84-2.87 (m, 4H), 3.25-3.28 (m, 4H), 6.45 (dd, J=1.8, 3.5 Hz, 1H), 6.81 (d, J=3.5 Hz, 1H), 7.34 (d, J=1.8 Hz, 1H), 7.69 (dd, J=1.7, 4.6 Hz, 2H), 8.78 (dd, J=1.7, 4.6 Hz, 2H), 10.2 (br s, 1H). APCIMS m/z: [M+H]$^+$ 373.

Reference Example 27

N-[4-(2-Furyl)-5-(1-oxothiomorpholino)thiazol-2-yl]pyridine-4-carboxamide (Compound 27)

$^1$H NMR (DMSO-d$_6$, δ ppm): 2.93-3.33 (m, 8H), 6.61 (dd, J=1.8, 3.3 Hz, 1H), 6.88 (d, J=3.3 Hz, 1H), 7.70 (d, J=1.8 Hz, 1H), 7.97 (d, J=6.2 Hz, 2H), 8.79 (d, J=6.2 Hz, 2H). APCIMS m/z: [M+H]$^+$ 389.

Reference Example 28

N-[5-(1,1-Dioxothiomorpholino)-4-(2-furyl)thiazol-2-yl]-pyridine-4-carboxamide (Compound 28)

$^1$H NMR (CDCl$_3$, δ ppm): 3.21-3.24 (m, 4H), 3.52-3.56 (m, 4H), 6.47 (dd, J=1.8, 3.3 Hz, 1H), 6.74 (d, J=3.3 Hz, 1H), 7.42 (d, J=1.8 Hz, 1H), 7.76 (d, J=6.1 Hz, 2H), 8.80 (d, J=6.1 Hz, 2H). APCIMS m/z: [M+H]$^+$ 405.

Reference Example 29

N-[4-(2-Furyl)-5-(1,2,3,4-tetrahydroisoquinolin-2-yl)thiazol-2-yl]acetamide (Compound 29)

$^1$H NMR (DMSO-d$_6$, δ ppm): 2.11 (s, 3H), 2.98-3.02 (m, 2H), 3.21-3.25 (m, 2H), 4.13 (s, 2H), 6.55 (dd, J=1.8, 3.3 Hz, 1H), 6.67 (dd, J=0.8, 3.3 Hz, 1H), 7.10-7.19 (m, 4H), 7.67 (dd, J=0.8, 1.8 Hz, 1H), 12.08 (br s, 1H). ESIMS m/z: [M+H]$^+$ 340.

Reference Example 30

N-[5-(1,4-Dioxa-8-azaspiro[4.5]decane-8-yl)-4-(2-furyl)-thiazol-2-yl]acetamide (Compound 30)

$^1$H NMR (CDCl$_3$, δ ppm): 1.87-1.91 (m, 4H), 2.14 (s, 3H), 3.05-3.09 (m, 4H), 3.98 (s, 4H), 6.47 (dd, J=1.8, 3.3 Hz, 1H), 6.80 (dd, J=0.7, 3.3 Hz, 1H), 7.39 (dd, J=0.7, 1.8 Hz, 1H), 10.61 (br s, 1H). APCIMS m/z: [M+H]$^+$ 350.

Reference Example 31

N-{4-(2-Furyl)-5-[N-(2-methoxyethyl)-N-methylamino]thiazol-2-yl}acetamide 0.5 fumarate (Compound 31)

$^1$H NMR (DMSO-d$_6$, δ ppm): 2.09 (s, 3H), 2.72 (s, 3H), 3.03-3.07 (m, 2H), 3.19 (s, 3H), 3.41-3.45 (m, 2H), 6.56 (dd, J=1.8, 3.3 Hz, 1H), 6.60 (s, 1H), 6.77 (dd, J=0.7, 3.3 Hz, 1H), 7.64 (dd, J=0.7, 1.8 Hz, 1H), 12.08 (br s, 1H). APCIMS m/z: [M+H]$^+$ 296.

Reference Example 32

N-[5-Formyl-4-(2-furyl)thiazol-2-yl]pyridine-4-carboxamide (Compound 32)

$^1$H NMR (DMSO-d$_6$, δ ppm): 6.77 (dd, J=1.7, 3.5 Hz, 1H), 7.18 (dd, J=0.7, 3.5 Hz, 1H), 8.00-8.03 (m, 3H), 8.84 (dd, J=1.7, 4.6 Hz, 2H), 10.46 (s, 1H), 13.60 (br s, 1H).

Reference Example 33

N-[4-(2-Furyl)-5-(morpholinomethyl)thiazol-2-yl]pyridine-4-carboxamide (Compound 33)

$^1$H NMR (DMSO-d$_6$, δ ppm): 3.31-3.34 (m, 4H), 3.59-3.62 (m, 4H), 3.95 (s, 2H), 6.62 (dd, J=1.8, 3.3 Hz, 1H), 6.75 (dd, J=0.9, 3.3 Hz, 1H), 7.79 (dd, J=0.9, 1.8 Hz, 1H), 7.99 (dd, J=1.7, 4.4 Hz, 2H), 8.81 (dd, J=1.7, 4.4 Hz, 2H), 13.02 (br s, 1H) ESIMS m/z: [M−H]$^+$ 371.

Reference Example 34

N-[4-(2-Furyl)-5-(morpholinomethyl)thiazol-2-yl]-3-pyridinecarboxamide (Compound 34)

$^1$H NMR (CDCl$_3$, δ ppm): 2.60-2.63 (m, 4H), 3.74-3.77 (m, 4H), 3.94 (s, 2H), 6.42 (dd, J=1.8, 3.3 Hz, 1H), 6.61 (d, J=3.3 Hz, 1H), 7.41 (d, J=1.8 Hz, 1H), 7.42-7.44 (m, 1H), 8.24-8.28 (m, 1H), 8.78-8.83 (m, 1H), 9.18-9.19 (m, 1H). APCIMS m/z: [M−H]$^−$ 369.

Reference Example 35

N-[4-(2-Furyl)-5-(2-thienyl)thiazol-2-yl]benzamide (Compound 35)

$^1$H NMR (CDCl$_3$, δ ppm): 6.33 (dd, J=1.8, 3.3 Hz, 1H), 6.46 (d, J=3.3 Hz, 1H), 7.11 (dd, J=3.7, 5.1 Hz, 1H), 7.27 (dd, J=1.5, 3.7 Hz, 1H), 7.34 (d, J=1.8 Hz, 1H), 7.41 (dd, J=1.5, 5.1 Hz, 1H), 7.43-7.53 (m, 2H), 7.54-7.62 (m, 1H), 7.86-7.94 (m, 2H), 9.59 (br s, 1H). APCIMS m/z: [M+H]$^+$ 353.

Reference Example 36

N-[4-(2-Furyl)-5-(1-methylindol-2-yl)thiazol-2-yl]benzamide (Compound 36)

$^1$H NMR (CDCl$_3$, δ ppm): 3.55 (s, 3H), 6.05 (d, J=3.5 Hz, 1H), 6.29 (dd, J=1.6, 3.5 Hz, 1H), 6.73 (s, 1H), 7.14-7.22 (m, 1H), 7.24-7.41 (m, 2H), 7.35 (d, J=1.6 Hz, 1H), 7.50-7.71 (m, 4H), 7.91-7.97 (m, 2H), 9.76 (br s, 1H). mp: 195-196° C.

Reference Example 37

N-[4-(2-Furyl)-5-(1-methyl-2-oxo-1,2-dihydropyridin-4-yl)thiazol-2-yl]pyridine-4-carboxamide (Compound 37)

$^1$H NMR (DMSO-d$_6$, δ ppm): 3.46 (s, 3H), 6.21 (dd, J=1.6, 7.0 Hz, 1H), 6.46 (d, J=1.6 Hz, 1H), 6.62 (dd, J=1.9, 3.5 Hz, 1H), 6.77 (dd, J=0.8, 3.5 Hz, 1H), 7.74 (d, J=7.0 Hz, 1H), 7.74 (dd, J=0.8, 1.9 Hz, 1H), 8.01 (dd, J=1.6, 4.6 Hz, 2H), 8.82 (dd, J=1.6, 4.6 Hz, 2H), 13.35 (br s, 1H). APCIMS m/z: [M+H]$^+$ 379. mp: 280-282° C.

Reference Example 38

N-[4-(2-Furyl)-5-(1-methyl-2-oxo-1,2-dihydropyridin-5-yl)thiazol-2-yl]pyridine-4-carboxamide (Compound 38)

$^1$H NMR (DMSO-d$_6$, δ ppm): 3.49 (s, 3H), 6.46 (d, J=9.4 Hz, 1H), 6.57 (dd, J=1.9, 3.5 Hz, 1H), 6.66 (dd, J=0.8, 3.5 Hz, 1H), 7.44 (dd, J=2.7, 9.4 Hz, 1H), 7.67 (dd, J=0.8, 1.9 Hz, 1H), 8.00 (d, J=2.7 Hz, 1H), 8.01 (dd, J=1.6, 4.3 Hz, 2H), 8.20

(dd, J=1.6, 4.3 Hz, 2H), 13.22 (br s, 1H). APCIMS m/z: [M+H]⁺ 379. mp: 294-295° C.

Reference Example 39

N-[4-(2-Furyl)-5-(1-isopropyl-6-oxo-1,6-dihydropyridazin-3-yl)thiazol-2-yl]pyridine-4-carboxamide (Compound 39)

¹H NMR (DMSO-d₆, δ ppm): 1.32-1.34 (m, 6H), 5.17-5.22 (m, 1H), 6.66 (dd, J=1.8, 3.3 Hz, 1H), 6.85 (d, J=3.3 Hz, 1H), 6.96 (d, J=9.7 Hz, 1H), 7.45 (d, J=9.7 Hz, 1H), 7.78 (d, J=1.8 Hz, 1H), 8.03 (d, J=4.5 Hz, 2H), 8.85 (d, J=4.5 Hz, 2H), 13.3 (s, 1H). APCIMS m/z: [M+H]⁺ 408. mp: 190-194° C.

Reference Example 40

Ethyl 2-(tert-butoxycarbonylamino)-4-(2-furyl)thiazol-5-carboxylate (Compound 40)

¹H NMR (CDCl₃, δ ppm): 1.37 (t, J=7.0 Hz, 3H), 1.46 (s, 9H), 4.35 (q, J=7.0 Hz, 2H), 6.55 (dd, J=1.6, 3.5 Hz, 1H), 7.52 (dd, J=0.3, 1.6 Hz, 1H), 7.79 (dd, J=0.3, 3.5 Hz, 1H), 9.43 (br s, 1H). ESIMS m/z: [M+H]⁺ 339.

Reference Example 41

2-(tert-Butoxycarbonylamino)-4-(2-furyl)thiazol-5-carboxylic acid (Compound 41)

¹H NMR (DMSO-d₆, δ ppm): 1.50 (s, 9H), 6.61 (dd, J=1.9, 3.2 Hz, 1H), 7.55 (dd, J=0.8, 3.2 Hz, 1H), 7.76 (dd, J=0.8, 1.9 Hz, 1H), 12.00 (br s, 1H). APCIMS m/z: [M+H]⁺ 311.

Reference Example 42

2-(tert-Butoxycarbonylamino)-4-(2-furyl)-N-methoxy-N-methylthiazol-5-carboxamide (Compound 42)

¹H NMR (CDCl₃, δ ppm): 1.46 (s, 9H), 3.34 (s, 3H), 3.67 (s, 3H), 6.47 (dd, J=1.6, 3.5 Hz, 1H), 7.04 (dd, J=0.8, 3.5 Hz, 1H), 7.47 (dd, J=0.8, 1.6 Hz, 1H), 9.23 (br s, 1H).

Reference Example 43 tert-Butyl N-[5-benzoyl-4-(2-furyl)thiazol-2-yl]carbamate (Compound 43)

¹H NMR (CDCl₃, δ ppm): 1.49 (s, 9H), 6.38 (dd, J=1.8, 3.5 Hz, 1H), 7.10 (d, J=3.5 Hz, 1H), 7.27 (d, J=1.8 Hz, 1H), 7.36-7.53 (m, 3H), 7.76-7.78 (m, 2H).

Reference Example 44

2-Amino-4-(2-furyl)thiazol-5-yl Phenyl Ketone (Compound 44)

¹H NMR (DMSO-d₆, δ ppm): 6.40 (dd, J=1.8, 3.5 Hz, 1H), 6.80 (dd, J=0.7, 3.5 Hz, 1H), 7.30 (dd, J=0.7, 1.8 Hz, 1H), 7.31-7.37 (m, 2H), 7.44-7.55 (m, 3H), 8.00 (s, 2H).

Reference Example 45

N-[5-Benzoyl-4-(2-furyl)thiazol-2-yl]-2-hydroxy-2-methylpropanamide (Compound 45)

¹H NMR (CDCl₃, δ ppm): 1.63 (s, 6H), 6.44 (dd, J=1.8, 3.5 Hz, 1H), 7.21 (d, J=0.7, 3.5 Hz, 1H), 7.38 (d, J=0.7, 1.8 Hz, 1H), 7.39-7.53 (m, 3H), 7.78-7.82 (m, 2H), 10.6 (s, 1H). APCIMS m/z: [M+H]⁺ 357. mp: 153-154° C.

Reference Example 46

N-[5-Benzol-4-(2-furyl)thiazol-2-yl]-1-hydroxycyclopropanecarboxamide (Compound 46)

¹H NMR (CDCl₃, δ ppm): 1.26-1.32 (m, 2H), 1.51-1.56 (m, 2H), 6.41 (dd, J=1.8, 3.5 Hz, 1H), 7.13 (dd, J=0.7, 3.5 Hz, 1H), 7.34 (dd, J=0.7, 1.8 Hz, 1H), 7.37-7.42 (m, 2H), 7.49-7.52 (m, 1H), 7.77-7.80 (m, 2H), 10.31 (s, 1H). APCIMS m/z: [M+H]⁺ 355. mp: 202-205° C.

Reference Example 47

N-[5-Benzoyl-4-(2-furyl)thiazol-2-yl]-3-(N,N-dimethylcarbamoyl)benzamide (Compound 47)

¹H NMR (DMSO-d₆, δ ppm): 2.94 (s, 3H), 3.02 (s, 3H), 6.50 (dd, J=1.8, 3.5 Hz, 1H), 6.94 (dd, J=0.8, 3.5 Hz, 1H), 7.45-7.49 (m, 3H), 7.56-7.73 (m, 5H), 8.16-8.20 (m, 2H). APCIMS m/z: [M+H]⁺ 386. mp: 222-224° C.

Reference Example 48

2-Chloromethyl-N-[5-benzoyl-4-(2-furyl)thiazol-2-yl]pyridine-4-carboxamide (Compound 48)

¹H NMR (CDCl₃, δ ppm): 4.69 (s, 2H), 6.22 (dd, J=1.7, 3.3 Hz, 1H), 6.97 (d, J=3.3 Hz, 1H), 7.12 (d, J=1.7 Hz, 1H), 7.39-7.64 (m, 4H), 7.81-7.85 (m, 3H), 8.66-8.68 (m, 1H).

Reference Example 49

N-[5-Benzoyl-4-(2-furyl)thiazol-2-yl]-2-(dimethylaminomethyl)pyridine-4-carboxamide (Compound 49)

¹H NMR (CDCl₃, δ ppm): 2.30 (s, 6H), 3.65 (s, 2H), 6.30 (dd, J=1.8, 3.3 Hz, 1H), 7.06 (d, J=3.3 Hz, 1H), 7.21 (d, J=1.8 Hz, 1H), 7.39-7.44 (m, 2H), 7.52-7.57 (m, 1H), 7.65 (dd, J=1.5, 5.0 Hz, 1H), 7.80 (d, J=1.5 Hz, 1H), 7.81-7.87 (m, 2H), 8.72 (d, J=5.0 Hz, 1H). APCIMS m/z: [M+H]⁺ 433. mp: 205-209° C.

Reference Example 50

N-[5-Benzoyl-4-(2-furyl)thiazol-2-yl]-2-[N-(2-dimethylaminoethyl)-N-methylaminomethyl]pyridine-4-carboxamide (Compound 50)

¹H NMR (DMSO-d₆, δ ppm): 2.31 (s, 3H), 2.48 (s, 3H), 2.49 (s, 3H), 2.70 (t, J=6.2 Hz, 2H), 2.84 (t, J=6.2 Hz, 2H), 3.78 (s, 2H), 6.42 (dd, J=1.9, 3.2 Hz, 1H), 6.88 (dd, J=0.8, 3.2 Hz, 1H), 7.35-7.44 (m, 3H), 7.47-7.55 (m, 1H), 7.64-7.69 (m, 2H), 7.88 (dd, J=1.9, 5.1 Hz, 1H), 8.06 (m, 1H), 8.62 (dd, J=0.8, 5.1 Hz, 1H). APCIMS m/z: [M+H]⁺ 490.

Reference Example 51

N-[5-Benzoyl-4-(2-furyl)thiazol-2-yl]-2-[N-(2-methoxyethyl)-N-methylaminomethyl]pyridine-4-carboxamide Dihydrochloride (Compound 51)

¹H NMR (DMSO-d₆, δ ppm): 2.87 (s, 3H), 3.31 (s, 3H), 3.41 (t, J=5.4 Hz, 2H), 3.77 (t, J=5.4 Hz, 2H), 4.59 (s, 2H), 6.48 (dd, J=1.6, 3.2 Hz, 1H), 6.89 (dd, J=0.8, 3.2 Hz 1H), 7.41-7.49 (m, 3H), 7.55-7.61 (m, 1H), 7.70-7.76 (m, 2H), 8.11 (dd, J=1.6, 5.1 Hz, 1H), 8.21 (d, J=1.6 Hz, 1H), 8.90 (d, J=5.1 Hz, 1H). APCIMS m/z: [M+H]$^+$ 477.

Reference Example 52

N-[5-Benzoyl-4-(2-furyl)thiazol-2-yl]-2-(morpholinomethyl)pyridine-4-carboxamide (Compound 52)

$^1$H NMR (CDCl$_3$, δ ppm): 2.52-2.53 (m, 4H), 3.71 (s, 2H), 3.72-3.75 (m, 4H), 6.29 (dd, J=1.8, 3.5 Hz, 1H), 7.04 (d, J=3.5 Hz, 1H), 7.21 (d, J=1.8 Hz, 1H), 7.39-7.45 (m, 2H), 7.53-7.58 (m, 1H), 7.62 (dd, J=1.8, 5.1 Hz, 1H), 7.80 (d, J=1.8 Hz, 1H), 7.83-7.87 (m, 2H), 8.72 (d, J=5.1 Hz, 1H). APCIMS m/z: [M+H]$^+$ 475. mp: 212-213° C.

Reference Example 53

N-[5-Benzoyl-4-(2-furyl)thiazol-2-yl]-2-[N-(2-methoxyethyl)-N-methylamino]pyridine-4-carboxamide (Compound 53)

$^1$H NMR (DMSO-d$_6$, δ ppm): 3.13 (s, 3H), 3.35 (s, 3H), 3.59 (t, J=5.5 Hz, 2H), 3.79 (t, J=5.5 Hz, 2H), 6.35 (dd, J=1.8, 3.5 Hz, 1H), 6.89 (dd, J=1.3, 5.1 Hz, 1H), 7.01 (d, J=1.8 Hz, 1H), 7.07 (d, J=3.5 Hz, 1H), 7.38-7.43 (m, 2H), 7.51-7.56 (m, 1H), 7.79-7.82 (m, 2H), 8.06 (d, J=1.3 Hz, 1H), 8.26 (d, J=5.1 Hz, 1H), 10.70 (br s, 1H). APCIMS m/z: [M+H]$^+$ 463. mp: 145-147° C.

Reference Example 54

N-[5-Benzoyl-4-(2-furyl)thiazol-2-yl]-2-piperdinopyridine-4-carboxamide (Compound 54)

$^1$H NMR (DMSO-d$_6$, δ ppm): 1.55-1.64 (m, 6H), 3.61-3.65 (m, 4H), 6.51 (dd, J=1.8, 3.5 Hz, 1H), 6.96 (d, J=3.5 Hz, 1H), 7.12 (d, J=5.0 Hz, 1H), 7.43-7.51 (m, 4H), 7.58-7.63 (m, 1H), 7.72-7.74 (m, 2H), 8.27 (d, J=5.0 Hz, 1H), 13.38 (br s, 1H). APCIMS m/z: [M+H]$^+$ 459. mp: 195-198° C.

Reference Example 55

2-Chloro-N-[5-benzoyl-4-(2-furyl)thiazol-2-yl]pyridine-5-carboxamide (Compound 55)

$^1$H NMR (CDCl$_3$, δ ppm): 6.31 (dd, J=1.8, 3.3 Hz, 1H), 7.02 (d, J=3.3 Hz, 1H), 7.21 (d, J=1.8 Hz, 1H), 7.39-7.46 (m, 3H), 7.52-7.57 (m, 1H), 7.79-7.82 (m, 2H), 8.16 (dd, J=2.6, 8.1 Hz, 1H), 8.93 (d, J=2.6 Hz, 1H).

Reference Example 56

N-[5-Benzoyl-4-(2-furyl)thiazol-2-yl]-2-morpholino-5-pyridinecarboxamide (Compound 56)

$^1$H NMR (CDCl$_3$, δ ppm): 3.67-3.70 (m, 4H), 3.80-3.83 (m, 4H), 6.37 (dd, J=1.8, 3.7 Hz, 1H), 6.62 (d, J=9.2 Hz, 1H), 7.14 (d, J=3.7 Hz, 1H), 7.30 (d, J=1.8 Hz, 1H), 7.38-7.43 (m, 2H), 7.51-7.56 (m, 1H), 7.80-7.83 (m, 2H), 7.97 (dd, J=2.6, 9.2 Hz, 1H), 8.73 (d, J=2.6 Hz, 1H), 10.02 (br s, 1H). APCIMS m/z: [M+H]$^+$ 461.

Reference Example 57

N-[5-Benzol-4-(2-furyl)thiazol-2-yl]-2-oxo-1,2-dihydropyridine-5-carboxamide (Compound 57)

$^1$H NMR (DMSO-d$_6$, δ ppm): 6.41 (d, J=9.7 Hz, 1H), 6.48 (dd, J=1.8, 3.5 Hz, 1H), 6.93 (d, J=3.5 Hz, 1H), 7.41-7.46 (m, 3H), 7.55-7.60 (m, 1H), 7.68-7.70 (m, 2H), 8.02 (dd, J=2.8, 9.7 Hz, 1H), 8.44 (d, J=2.8 Hz, 1H). APCIMS m/z: [M+H]$^+$ 392. mp: >300° C.

Reference Example 58

N-[5-Benzoyl-4-(2-furyl)thiazol-2-yl]-1-methyl-2-oxo-1,2-dihydropyridine-5-carboxamide (Compound 58)

$^1$H NMR (DMSO-d$_6$, δ ppm): 3.99 (s, 3H), 6.45 (dd, J=1.8, 3.5 Hz, 1H), 6.91 (d, J=3.5 Hz, 1H), 7.38-7.43 (m, 3H), 7.51-7.57 (m, 1H), 7.65-7.67 (m, 2H), 7.94 (d, J=5.0 Hz, 1H), 8.09 (s, 1H), 8.71 (d, J=5.0 Hz, 1H). APCIMS m/z: [M+H]$^+$ 406. mp: 220-225° C.

Reference Example 59

N-[5-Benzoyl-4-(2-furyl)thiazol-2-yl]-1-ethyl-2-oxo-1,2-dihydropyridine-5-carboxamide (Compound 59)

$^1$H NMR (DMSO-d$_6$, δ ppm): 1.36 (t, J=7.1 Hz, 3H), 4.00 (q, J=7.1 Hz, 2H), 6.27 (dd, J=1.8, 3.3 Hz, 1H), 6.50 (d, J=9.5 Hz, 1H), 6.95 (d, J=3.3 Hz, 1H), 7.17 (d, J=1.8 Hz, 1H), 7.37-7.42 (m, 2H), 7.50-7.56 (m, 1H), 7.69 (dd, J=2.6, 9.5 Hz, 1H), 7.78-7.82 (m, 2H), 8.23 (d, J=2.6 Hz, 1H), 11.28 (br s, 1H). APCIMS m/z: [M+H]$^+$ 420. mp: 109-114° C.

Reference Example 60

N-[5-Benzoyl-4-(2-furyl)thiazol-2-yl]-2-oxo-1-(pyridin-4-ylmethyl)-1,2-dihydropyridine-5-carboxamide (Compound 60)

$^1$H NMR (DMSO-d$_6$, δ ppm): 5.22 (s, 2H), 6.49 (dd, J=1.8, 3.5 Hz, 1H), 6.55 (d, J=9.6 Hz, 1H), 6.92 (d, J=3.5 Hz, 1H), 7.28 (d, J=5.9 Hz, 2H), 7.41-7.47 (m, 3H), 7.56-7.61 (m, 1H), 7.68-7.72 (m, 2H), 8.10 (dd, J=2.5, 9.6 Hz, 1H), 8.54 (d, J=5.9 Hz, 2H), 8.91 (d, J=2.5 Hz, 1H), 13.01 (br s, 1H). APCIMS m/z: [M+H]$^+$ 483. mp: 270-275° C.

Reference Example 61

N-[5-Benzoyl-4-(2-furyl)thiazol-2-yl]pyridazine-4-carboxamide (Compound 61)

$^1$H NMR (DMSO-d$_6$, δ ppm): 6.49 (dd, J=1.8, 3.5 Hz, 1H), 6.94 (d, J=3.5 Hz, 1H), 7.41-7.47 (m, 3H), 7.56-7.59 (m, 1H), 7.69-7.72 (m, 2H), 8.22-8.25 (m, 1H), 9.51-9.53 (m, 1H), 9.71-9.73 (m, 1H). APCIMS m/z: [M+H]$^+$ 377. mp: 225-248° C.

Reference Example 62 tert-Butyl N-[4-(2-furyl)-5-(2-methylbenzoyl)thiazol-2-yl]carbamate (Compound 62)

$^1$H NMR (CDCl$_3$, δ ppm): 1.48 (s, 9H), 2.42 (s, 3H), 6.45 (dd, J=1.6, 3.5 Hz, 1H), 7.13-7.40 (m, 5H), 7.50-7.55 (m, 1H), 8.86 (br s, 1H). APCIMS m/z: [M+H]$^+$ 385.

Reference Example 63

2-Amino-4-(2-furyl)thiazol-5-yl 2-methylphenyl ketone (Compound 63)

$^1$H NMR (DMSO-d$_6$, δ ppm): 2.37 (s, 3H), 6.40 (dd, J=1.6, 3.2 Hz, 1H), 7.05-7.30 (m, 4H), 7.39 (dd, J=0.5, 1.6 Hz, 1H), 8.05 (br s, 2H). APCIMS m/z: [M+H]$^+$ 285.

Reference Example 64

N-[4-(2-Furyl)-5-(2-methylbenzoyl)thiazol-2-yl]pyridine-4-carboxamide (Compound 64)

$^1$H NMR (DMSO-d$_6$, δ ppm): 2.31 (s, 3H), 6.52 (dd, J=1.9, 3.5 Hz, 1H), 6.95 (d, J=3.5 Hz, 1H), 7.30-7.45 (m, 2H), 7.51 (d, J=1.9 Hz, 1H), 7.52-7.55 (m, 2H), 8.02 (dd, J=1.6, 4.6 Hz, 2H), 8.83 (dd, J=1.6, 4.6 Hz, 2H), 13.58 (br s, 1H). APCIMS m/z: [M+H]$^+$ 390.

Reference Example 65 tert-Butyl N-[4-(2-furyl)-5-(3-methylbenzoyl)thiazol-2-yl]carbamate (Compound 65)

$^1$H NMR (CDCl$_3$, δ ppm): 1.52 (s, 9H), 2.35 (s, 3H), 6.39 (dd, J=1.9, 3.5 Hz, 1H), 7.09 (d, J=3.5 Hz, 1H), 7.26-7.33 (m, 3H), 7.53-7.59 (m, 2H), 8.55 (br s, 1H). APCIMS m/z: [M+H]$^+$ 385.

Reference Example 66

2-Amino-4-(2-furyl)thiazol-5-yl 3-methylphenyl ketone (Compound 66)

$^1$H NMR (DMSO-d$_6$, δ ppm): 2.25 (s, 3H), 6.41 (dd, J=1.6, 3.2 Hz, 1H), 6.80 (d, J=3.2 Hz, 1H), 7.18-7.36 (m, 6H), 7.98 (br s, 2H). APCIMS m/z: [M+H]$^+$ 285.

Reference Example 67

N-[4-(2-Furyl)-5-(3-methylbenzoyl)thiazol-2-yl]pyridine-4-carboxamide (Compound 67)

$^1$H NMR (DMSO-d$_6$, δ ppm): 2.35 (s, 3H), 6.54 (dd, J=1.6, 3.5 Hz, 1H), 7.17-7.21 (m, 1H), 7.23 (dd, J=0.8, 3.5 Hz, 1H), 7.30-7.43 (m, 3H), 7.62 (dd, J=0.8, 1.6 Hz, 1H), 8.00 (dd, J=1.6, 4.6 Hz, 2H), 8.83 (dd, J=1.6, 4.6 Hz, 2H), 13.61 (br s, 1H). APCIMS m/z: [M+H]$^+$ 390.

Reference Example 68

N-[4-(2-Furyl)-5-(4-methylbenzoyl)thiazol-2-yl]pyridine-4-carboxamide (Compound 68)

$^1$H NMR (DMSO-d$_6$, δ ppm): 2.37 (s, 3H), 6.53 (dd, J=1.8, 3.3 Hz, 1H), 6.95 (d, J=3.3 Hz, 1H), 7.28 (d, J=8.1 Hz, 2H), 7.54 (d, J=1.8 Hz, 1H), 7.66 (d, J=8.1 Hz, 2H), 8.03 (dd, J=1.5, 4.5 Hz, 2H), 8.84 (dd, J=1.5, 4.5 Hz, 2H), 13.58 (br s, 1H). APCIMS m/z: [M+H]$^+$ 390.

Reference Example 69 tert-Butyl N-[4-(2-furyl)-5-(2-methoxybenzoyl)thiazol-2-yl]carbamate (Compound 69)

$^1$H NMR (CDCl$_3$, δ ppm): 1.48 (s, 9H), 3.74 (s, 3H), 6.45 (dd, J=1.9, 3.5 Hz, 1H), 6.83-6.92 (m, 1H), 6.97 (ddd, J=0.8, 7.3, 7.3 Hz, 1H), 7.35-7.37 (m, 1H), 7.39-7.43 (m, 2H), 7.54-7.57 (m, 1H), 8.78 (br s, 1H). APCIMS m/z: [M+H]$^+$ 401.

Reference Example 70

2-Amino-4-(2-furyl)thiazol-5-yl 2-methoxyphenyl ketone (Compound 70)

$^1$H NMR (DMSO-d$_6$, δ ppm): 3.64 (s, 3H), 6.42 (dd, J=1.6, 3.2 Hz, 1H), 6.88-7.04 (m, 3H), 7.19-7.23 (m, 1H), 7.30-7.40 (m, 1H), 7.41-7.43 (m, 1H), 7.97 (br s, 2H). APCIMS m/z: [M+H]$^+$ 301.

Reference Example 71

N-[4-(2-Furyl)-5-(2-methoxybenzoyl)thiazol-2-yl]pyridine-4-carboxamide (Compound 71)

$^1$H NMR (DMSO-d$_6$, δ ppm): 3.67 (s, 3H), 6.56 (dd, J=1.6, 3.2 Hz, 1H), 7.03 (dd, J=7.5, 7.5 Hz, 1H), 7.09 (d, J=8.6 Hz 1H), 7.28 (dd, J=0.5, 3.2 Hz, 1H), 7.40 (dd, J=1.6, 7.5 Hz, 1H), 7.50 (ddd, J=1.6, 7.5, 8.6 Hz, 1H), 7.53 (dd, J=0.5, 1.6 Hz, 1H), 8.00 (dd, J=1.6, 4.3 Hz, 2H), 8.82 (dd, J=1.6, 4.3 Hz, 2H), 13.55 (br s, 1H). APCIMS m/z: [M+H]$^+$ 406.

Reference Example 72

N-[4-(2-Furyl)-5-(3-methoxybenzoyl)thiazol-2-yl]pyridine-4-carboxamide (Compound 72)

$^1$H NMR (DMSO-d$_6$, δ ppm): 3.75 (s, 3H), 6.53 (dd, J=1.6, 3.5 Hz, 1H), 6.97 (dd, J=0.5, 3.5 Hz, 1H), 7.17 (ddd, J=1.1, 2.7, 7.5 Hz, 1H), 7.22-7.32 (m, 2H), 7.30-7.40 (m, 1H), 7.52 (dd, J=0.5, 1.6 Hz, 1H), 8.03 (dd, J=1.6, 4.6 Hz, 2H), 8.84 (dd, J=1.6, 4.6 Hz, 2H), 13.59 (br s, 1H). APCIMS m/z: [M+H]$^+$ 406.

Reference Example 73

N-[4-(2-Furyl)-5-(4-methoxybenzoyl)thiazol-2-yl]pyridine-4-carboxamide (Compound 73)

$^1$H NMR (DMSO-d$_6$, δ ppm): 3.09 (s, 3H), 6.53 (dd, J=1.6, 3.5 Hz, 1H), 6.89 (dd, J=0.8, 3.5 Hz, 1H), 7.00 (dd, J=2.2, 8.9 Hz, 2H), 7.55 (dd, J=0.8, 1.6 Hz, 1H), 7.76 (dd, J=2.2, 8.9 Hz, 2H), 8.03 (dd, J=1.6, 4.6 Hz, 2H), 8.84 (dd, J=1.6, 4.6 Hz, 2H), 13.54 (br s, 1H). APCIMS m/z: [M+H]$^+$ 406.

Reference Example 74 tert-Butyl N-[5-(2-fluorobenzoyl)-4-(2-furyl)thiazol-2-yl]carbamate (Compound 74)

$^1$H NMR (CDCl$_3$, δ ppm): 1.51 (s, 9H), 6.43 (dd, J=1.6, 3.5 Hz, 1H), 7.06 (ddd, J=1.1, 8.7, 9.5 Hz, 1H), 7.18 (ddd, J=1.1, 7.6, 7.6 Hz, 1H), 7.35 (d, J=3.5 Hz, 1H), 7.39-7.48 (m, 2H), 7.53 (ddd, J=1.6, 7.6, 7.6 Hz, 1H), 8.56 (br s, 1H). APCIMS m/z: [M+H]$^+$ 389.

Reference Example 75

2-Amino-4-(2-furyl)thiazol-5-yl 2-fluorophenyl ketone (Compound 75)

$^1$H NMR (DMSO-d$_6$, δ ppm): 6.40 (dd, J=1.9, 3.5 Hz, 1H), 6.88 (dd, J=0.8, 3.5 Hz, 1H), 7.14 (d, J=8.1 Hz, 1H), 7.18 (dd, J=3.0, 3.8 Hz, 1H), 7.34 (dd, J=0.8, 1.9 Hz, 1H), 7.36-7.49 (m, 2H), 8.17 (br s, 2H). APCIMS m/z: [M+H]$^+$ 289.

Reference Example 76

N-[5-(2-Fluorobenzoyl)-4-(2-furyl)thiazol-2-yl]pyridine-4-carboxamide (Compound 76)

$^1$H NMR (DMSO-d$_6$, δ ppm): 6.46 (dd, J=1.9, 3.2 Hz, 1H), 7.15-7.25 (m, 3H), 7.36-7.46 (m, 2H), 7.49 (dd, J=0.8, 1.9 Hz, 1H), 7.96 (d, J=5.4 Hz, 2H), 8.63 (d, J=5.4 Hz, 2H). APCIMS m/z: [M+H]$^+$ 394.

Reference Example 77

N-[5-(3-Fluorobenzoyl)-4-(2-furyl)thiazol-2-yl]pyridine-4-carboxamide (Compound 77)

$^1$H NMR (DMSO-d$_6$, δ ppm): 6.53 (dd, J=1.8, 3.6 Hz, 1H), 6.97 (d, J=3.6 Hz, 1H), 7.40-7.55 (m, 5H), 8.03 (dd, J=1.5, 4.2 Hz, 2H), 8.84 (dd, J=1.5, 4.2 Hz, 2H), 13.64 (br s, 1H). ESIMS m/z: [M+H]$^+$ 394.

Reference Example 78

N-[5-(4-Fluorobenzoyl)-4-(2-furyl)thiazol-2-yl]pyridine-4-carboxamide (Compound 78)

$^1$H NMR (DMSO-d$_6$, δ ppm): 6.53 (dd, J=1.6, 3.5 Hz, 1H), 6.92 (dd, J=0.8, 3.5 Hz, 1H), 7.28 (ddd, J=1.9, 8.9, 8.9 Hz, 2H), 7.51 (dd, J=0.8, 1.6 Hz, 1H), 7.81 (dd, J=1.9, 5.4, 8.9 Hz, 2H), 8.03 (dd, J=1.9, 4.6 Hz, 2H), 8.84 (dd, J=1.9, 4.6 Hz, 2H), 13.60 (br s, 1H). ESIMS m/z: [M+H]$^+$ 394.

Reference Example 79 tert-Butyl N-[5-(2-chlorobenzoyl)-4-(2-furyl)thiazol-2-yl]carbamate (Compound 79)

$^1$H NMR (CDCl$_3$, δ ppm): 1.48 (s, 9H), 6.48 (dd, J=1.6, 3.2 Hz, 1H), 7.20-7.42 (m, 6H), 7.68 (d, J=1.6 Hz, 1H), 8.87 (br s, 1H). APCIMS m/z: [$^{35}$ClM+H]$^+$ 405, [$^{37}$ClM+H]$^+$ 407.

Reference Example 80

2-Amino-4-(2-furyl)thiazol-5-yl 2-chlorophenyl ketone (Compound 80)

$^1$H NMR (DMSO-d$_6$, δ ppm): 6.42 (dd, J=1.6, 3.2 Hz, 1H), 7.03 (d, J=3.2 Hz, 1H), 7.26-7.47 (m, 5H), 8.19 (br s, 2H). APCIMS m/z: [$^{35}$ClM+H]$^+$ 305, [$^{37}$ClM+H]$^+$ 307.

Reference Example 81

N-[5-(2-Chlorobenzoyl)-4-(2-furyl)thiazol-2-yl]pyridine-4-carboxamide (Compound 81)

$^1$H NMR (DMSO-d$_6$, δ ppm): 6.58 (dd, J=1.6, 3.5 Hz, 1H), 7.36 (dd, J=0.8, 3.5 Hz, 1H), 7.42 (ddd, J=3.2, 6.5, 7.8 Hz, 1H), 7.51-7.59 (m, 3H), 7.65 (dd, J=0.8, 1.6 Hz, 1H), 8.00 (dd, J=1.6, 4.6 Hz, 2H), 8.83 (dd, J=4.6 Hz, 2H), 13.69 (br s, 1H). APCIMS m/z: [$^{35}$ClM+H]$^+$ 410, [$^{37}$ClM+H]$^+$ 412.

Reference Example 82

N-[5-(3-Chlorobenzoyl)-4-(2-furyl)thiazol-2-yl]pyridine-4-carboxamide (Compound 82)

$^1$H NMR (DMSO-d$_6$, δ ppm): 6.53 (dd, J=1.6, 3.5 Hz, 1H), 6.98 (d, J=3.5 Hz 1H), 7.44-7.51 (m, 2H), 7.63 (d, J=1.6 Hz, 1H), 7.65-7.69 (m, 2H), 8.03 (dd, J=1.6, 4.6 Hz, 2H), 8.84 (dd, J=1.6, 4.6 Hz, 2H), 13.63 (br s, 1H). ESIMS on/z: [$^{35}$ClM+H]$^+$ 410, [$^{37}$ClM+H]$^+$ 412.

Reference Example 83

N-[5-(4-Chlorobenzoyl)-4-(2-furyl)thiazol-2-yl]pyridine-4-carboxamide (Compound 83)

$^1$H NMR (DMSO-d$_6$, δ ppm): 6.54 (dd, J=1.8, 3.6 Hz, 1H), 6.95 (d, J=3.6 Hz, 1H), 7.52 (d, J=1.8 Hz, 1H), 7.52 (d, J=8.4 Hz, 2H), 7.73 (d, J=8.4 Hz, 2H), 8.03 (d, J=6.0 Hz, 2H), 8.84 (d, J=6.0 Hz, 2H), 13.63 (br s, 1H). ESIMS m/z: [$^{35}$ClM–H]$^-$ 408, [$^{37}$ClM–H]$^-$ 410.

Reference Example 84 tert-Butyl N-[5-(2-cyanobenzoyl)-4-(2-furyl)thiazol-2-yl]carbamate (Compound 84)

$^1$H NMR (CDCl$_3$, δ ppm): 1.52 (s, 9H), 6.39 (dd, J=1.9, 3.5 Hz, 1H), 7.19-7.22 (m, 1H), 7.26-7.28 (m, 1H), 7.50-7.65 (m, 3H), 7.67-7.75 (m, 1H), 8.54 (br s, 1H). APCIMS m/z: [M+H]$^+$ 396.

Reference Example 85

2-Amino-4-(2-furyl)thiazol-5-yl 2-cyanophenyl ketone (Compound 85)

$^1$H NMR (DMSO-d$_6$, δ ppm): 6.38 (dd, J=1.9, 3.5 Hz, 1H), 6.80 (dd, J=0.8, 3.5 Hz, 1H), 7.22 (dd, J=0.8, 1.9 Hz, 1H), 7.47-7.52 (m, 1H), 7.55-7.60 (m, 2H), 7.83-7.88 (m, 1H), 8.29 (br s, 2H). APCIMS m/z: [M+H]$^+$ 296.

Reference Example 86

N-[5-(2-Cyanobenzoyl)-4-(2-furyl)thiazol-2-yl]pyridine-4-carboxamide (Compound 86)

$^1$H NMR (DMSO-d$_6$, δ ppm): 6.50 (dd, J=1.6, 3.5 Hz, 1H), 7.04 (dd, J=0.8, 3.5 Hz, 1H), 7.45 (dd, J=0.8, 1.6 Hz, 1H), 7.67-7.73 (m, 3H), 7.95-8.00 (m, 1H), 8.03 (dd, J=1.6, 4.3 Hz, 2H), 8.84 (dd, J=1.6, 4.3 Hz, 2H), 13.70 (br s, 1H). APCIMS m/z: [M+H]$^+$ 401.

Reference Example 87 tert-Butyl N-[5-(3-cyanobenzoyl)-4-(2-furyl)thiazol-2-yl]carbamate (Compound 87)

$^1$H NMR (CDCl$_3$, δ ppm): 1.54 (s, 9H), 6.40 (dd, J=1.9, 3.5 Hz, 1H), 7.05 (d, J=3.5 Hz, 1H), 7.18 (d, J=1.9 Hz, 1H), 7.50 (dd, J=7.8, 7.8 Hz, 1H), 7.75 (ddd, J=1.3, 1.3, 7.8 Hz, 1H), 7.94 (ddd, J=1.3, 1.3, 7.8 Hz, 1H), 7.95-7.99 (m, 1H), 8.51 (br s, 1H). APCIMS m/z: [M+H]$^+$ 396.

Reference Example 88

2-Amino-4-(2-furyl)thiazol-5-yl 3-cyanophenyl ketone (Compound 88)

$^1$H NMR (DMSO-d$_6$, δ ppm): 6.41 (dd, J=1.9, 3.5 Hz, 1H), 6.78 (dd, J=0.8, 3.5 Hz, 1H), 7.27 (dd, J=0.8, 1.9 Hz, 1H), 7.54 (dd, J=7.8, 7.8 Hz, 1H), 7.79 (ddd, J=1.3, 1.3, 7.8 Hz, 1H), 7.85 (ddd, J=1.3, 1.3, 7.8 Hz, 1H), 7.89 (ddd, J=1.3, 1.3, 7.8 Hz, 1H), 8.17 (br s, 2H). APCIMS m/z: [M+H]$^+$ 296.

Reference Example 89

N-[5-(3-Cyanobenzoyl)-4-(2-furyl)thiazol-2-yl]pyridine-4-carboxamide (Compound 89)

$^1$H NMR (DMSO-d$_6$, δ ppm): 6.51 (dd, J=1.9, 3.5 Hz, 1H), 6.96 (d, J=3.5 Hz, 1H), 7.46 (d, J=1.9 Hz, 1H), 7.65 (dd, J=7.8, 7.8 Hz, 1H), 7.96-8.08 (m, 5H), 8.84 (d, J=5.9 Hz, 2H), 13.66 (br s, 1H). APCIMS m/z: [M+H]$^+$ 401.

Reference Example 90 tert-Butyl N-[5-(4-cyanobenzoyl)-4-(2-furyl)thiazol-2-yl]carbamate (Compound 90)

$^1$H NMR (CDCl$_3$, δ ppm): 1.51 (s, 9H), 6.39 (dd, J=1.9, 3.5 Hz, 1H), 7.07 (d, J=3.5, Hz, 1H), 7.17 (d, J=1.9 Hz, 1H), 7.65 (dd, J=1.9, 8.6 Hz, 2H), 7.79 (dd, J=1.9, 8.6 Hz, 2H), 8.79 (br s, 1H). APCIMS m/z: [M+H]$^+$ 396.

Reference Example 91

2-Amino-4-(2-furyl)thiazol-5-yl 4-cyanophenyl ketone (Compound 91)

$^1$H NMR (DMSO-d$_6$, δ ppm): 6.41 (dd, J=1.6, 3.2 Hz, 1H), 6.90 (dd, J=0.5, 3.2 Hz, 1H), 7.27 (dd, J=0.5, 1.6 Hz, 1H), 7.62 (dd, J=1.9, 8.1 Hz, 2H), 7.78 (dd, J=1.9, 8.1 Hz, 2H), 8.18 (br s, 2H). APCIMS m/z: [M+H]$^+$ 296.

Reference Example 92

N-[5-(4-Cyanobenzoyl)-4-(2-furyl)thiazol-2-yl]pyridine-4-Carboxamide (Compound 92)

$^1$H NMR (DMSO-d$_6$, δ ppm): 6.52 (dd, J=1.9, 3.5 Hz, 1H), 6.98 (dd, J=0.8, 3.5 Hz, 1H), 7.46 (dd, J=0.8, 1.9 Hz, 1H), 7.82 (dd, J=2.2, 8.6 Hz, 2H), 7.91 (dd, J=2.2, 8.6 Hz, 2H), 8.03 (dd, J=1.9, 4.6 Hz, 2H), 8.84 (dd, J=1.9, 4.6 Hz, 2H), 13.67 (br s, 1H). ESIMS m/z: [M+H]$^+$ 401.

Reference Example 93 tert-Butyl N-[4-(2-furyl)-5-(pyridin-2-ylcarbonyl)thiazol-2-yl]carbamate (Compound 93)

$^1$H NMR(CDCl$_3$, δ ppm): 1.46 (s, 9H), 6.53 (dd, J=1.8, 3.7 Hz, 1H), 7.43-7.47 (m, 1H), 7.48 (d, J=1.8 Hz, 1H), 7.84 (d, J=3.7 Hz, 1H), 7.84-7.89 (m, 1H), 8.14-8.17 (m, 1H), 8.70-8.71 (m, 1H).

Reference Example 94

2-Amino-4-(2-furyl)thiazol-5-yl 2-pyridyl ketone (Compound 94)

$^1$H NMR (CDCl$_3$, δ ppm): 6.03 (br s, 2H), 6.53 (dd, J=1.8, 3.5 Hz, 1H), 7.43-7.46 (m, 1H), 7.51 (d, J=1.8 Hz, 1H), 7.86-7.89 (m, 1H), 7.95 (d, J=3.5 Hz, 1H), 8.14-8.17 (m, 1H), 8.60-8.61 (m, 1H).

Reference Example 95

N-[4-(2-Furyl)-5-(pyridin-2-ylcarbonyl)thiazol-2-yl]pyridine-4-carboxamide (Compound 95)

$^1$H NMR (DMSO-d$_6$, δ ppm): 6.65 (dd, J=1.7, 3.5 Hz, 1H), 7.47 (d, J=3.5 Hz, 1H), 7.67-7.71 (m, 1H), 7.73 (d, J=1.7 Hz, 1H), 8.05 (d, J=6.1 Hz, 2H), 8.09-8.11 (m, 2H), 8.71-8.74 (m, 1H), 8.84 (d, J=6.1 Hz, 2H), 13.5 (br s, 1H). APCIMS m/z: [M+H]$^+$ 377. mp: 218-227° C.

Reference Example 96

N-[4-(2-Furyl)-5-(pyridin-2-ylcarbonyl)thiazol-2-yl]-acetamide (Compound 96)

$^1$H NMR (CDCl$_3$, δ ppm): 2.20 (s, 3H), 6.57 (dd, J=1.8, 3.6 Hz, 1H), 7.49 (dd, J=7.2, 11.3 Hz, 1H), 7.54 (d, J=1.8 Hz, 1H), 7.85 (d, J=3.6 Hz, 1H), 7.90 (dd, J=11.3, 11.5 Hz, 1H), 8.19 (d, J=11.5 Hz, 1H), 8.74 (d, J=7.2 Hz, 1H), 9.72 (br s, 1H). APCIMS m/z: [M+H]$^+$ 314. mp: 216-217° C.

Reference Example 97

N-[4-(2-Furyl)-5-(pyridin-2-ylcarbonyl)thiazol-2-yl]-butanamide (Compound 97)

$^1$H NMR (CDCl$_3$, δ ppm): 0.98 (t, J=7.3 Hz, 3H), 1.68-1.84 (m, 2H), 2.37 (t, J=7.3 Hz, 2H), 6.57 (dd, J=1.9, 3.5 Hz, 1H), 7.49 (dd, J=4.9, 7.6 Hz, 1H), 7.53 (d, J=1.9 Hz, 1H), 7.86 (d, J=3.5 Hz, 1H), 7.89 (dd, J=7.6, 7.8 Hz, 1H), 8.19 (d, J=7.8 Hz, 1H), 8.73 (d, J=4.9 Hz, 1H), 9.60 (br s, 1H). APCIMS m/z: [M+H]$^+$ 342. mp: 148-149° C.

Reference Example 98

N-[4-(2-Furyl)-5-(pyridin-2-ylcarbonyl)thiazol-2-yl]-2,2-dimethylpropanamide (Compound 98)

$^1$H NMR (CDCl$_3$, δ ppm): 1.36 (s, 9H), 6.58 (dd, J=1.6, 3.2 Hz, 1H), 7.48 (dd, J=4.9, 7.6 Hz, 1H), 7.57 (d, J=1.6 Hz, 1H), 7.89 (dd, J=7.6, 8.1 Hz, 1H), 7.92 (d, J=3.2 Hz, 1H), 8.19 (d, J=8.1 Hz, 1H), 8.74 (d, J=4.9 Hz, 1H), 9.10 (br s, 1H). APCIMS m/z: [M+H]$^+$ 356. mp: 186-187° C.

Reference Example 99

N-[4-(2-Furyl)-5-(pyridin-2-ylcarbonyl)thiazol-2-yl] cyclopropanecarboxamide (Compound 99)

$^1$H NMR (CDCl$_3$, δ ppm): 0.82-0.92 (m, 2H), 1.12-1.21 (m, 2H), 1.37-1.48 (m, 1H), 6.55 (dd, J=1.6, 3.5 Hz, 1H), 7.46 (dd, J=4.9, 7.6 Hz, 1H), 7.53 (dd, J=0.8, 1.6 Hz, 1H), 8.17 (d, J=7.8 Hz, 1H), 8.7 (d, J=4.9 Hz, 1H), 10.91 (br s, 1H). APCIMS m/z: [M+H]$^+$ 340. mp: 191-192° C.

Reference Example 100

N-[4-(2-Furyl)-5-(pyridin-2-ylcarbonyl)thiazol-2-yl]-1-methylcyclopropanecarboxamide (Compound 100)

$^1$H NMR (DMSO-d$_6$, δ ppm): 0.77-0.84 (m, 2H), 1.25-1.31 (m, 2H), 1.44 (s, 3H), 6.61 (dd, J=1.9, 3.5 Hz, 1H), 7.39 (dd, J=0.5, 3.5 Hz, 1H), 7.60-7.69 (m, 1H), 7.68 (dd, J=0.5, 1.9 Hz, 1H), 8.01-8.10 (m, 2H), 8.64-8.69 (m, 1H), 12.14 (br s, 1H). APCIMS m/z: [M+H]$^+$ 354. mp: 195-196° C.

Reference Example 101

N-[4-(2-Furyl)-5-(pyridin-2-ylcarbonyl)thiazol-2-yl]cyclobutanecarboxamide (Compound 101)

$^1$H NMR (CDCl$_3$, δ ppm): 1.77-2.38 (m, 6H), 3.33-3.48 (m, 1H), 6.61 (dd, J=1.6, 3.2 Hz, 1H), 7.40 (d, J=3.2 Hz, 1H), 7.61-7.71 (m, 1H), 7.67 (d, J=1.6 Hz, 1H), 8.01-8.10 (m, 2H), 8.68 (d, J=4.6 Hz, 1H), 12.56 (br s, 1H). APCIMS m/z: [M+H]$^+$ 354.
mp: 165-170° C.

Reference Example 102

N-[4-(2-Furyl)-5-(pyridin-2-ylcarbonyl)thiazol-2-yl]tetrahydropyran-4-carboxamide (Compound 102)

$^1$H NMR (CDCl$_3$, δ ppm): 1.62-1.98 (m, 4H), 2.44-2.64 (m, 1H), 3.33-3.46 (m, 2H), 3.95-4.07 (m, 2H), 6.57 (dd, J=1.9, 3.8 Hz, 1H), 7.48 (ddd, J=1.1, 4.9, 7.6 Hz, 1H), 7.54 (dd, J=1.6, 1.9 Hz, 1H), 7.88 (ddd, J=1.6, 7.6, 7.8 Hz, 1H), 7.88 (dd, J=1.6, 3.8 Hz, 1H), 8.19 (ddd, J=0.8, 1.1, 7.8 Hz, 1H), 8.72 (ddd, J=0.8, 1.6, 4.9 Hz, 1H), 9.67 (br s, 1H). APCIMS m/z: [M+H]$^+$ 384. mp: 234-235° C.

Reference Example 103

1-(tert-Butoxycarbonyl)-N-[4-(2-furyl)-5-(pyridin-2-ylcarbonyl)thiazol-2-yl]piperidine-4-carboxamide (Compound 103)

$^1$H NMR (DMSO-d$_6$, δ ppm): 1.30-1.59 (m, 2H), 1.41 (s, 9H), 1.81-1.93 (m, 2H), 2.67-2.89 (m, 3H), 3.92-4.11 (m, 2H), 6.62 (dd, J=1.6, 3.2. Hz, 1H), 7.42 (dd, J=0.5, 3.2 Hz, 1H), 7.62-7.71 (m, 1H), 7.68 (d, J=1.6 Hz, 1H), 8.02-8.10 (m, 2H), 8.66-8.70 (m, 1H), 12.76 (br s, 1H).

Reference Example 104

N-[4-(2-Furyl)-5-(pyridin-2-ylcarbonyl)thiazol-2-yl]piperidine-4-carboxamide (Compound 104)

$^1$H NMR (DMSO-d$_6$, δ ppm): 1.74-1.92 (m, 2H), 1.98-2.12 (m, 2H), 2.79-3.02 (m, 3H), 3.29-3.40 (m, 2H), 6.62 (dd, J=1.6, 3.5 Hz, 1H), 7.42 (d, J=3.5 Hz, 1H), 7.63-7.70 (m, 1H), 7.68 (d, J=1.6 Hz, 1H), 8.02-8.11 (m, 2H), 8.66-8.70 (m, 1H).

Reference Example 105

N-[4-(2-Furyl)-5-(pyridin-2-ylcarbonyl)thiazol-2-yl]-1-(pyridin-3-ylmethyl)piperidine-4-carboxamide (Compound 105)

$^1$H NMR (DMSO-d$_6$, δ ppm): 1.57-1.75 (m, 2H), 1.77-1.89 (m, 2H), 1.94-2.07 (m, 2H), 2.38-2.68 (m, 1H), 2.79-2.91 (m, 2H), 3.52 (s, 2H), 6.61 (dd, J=1.6, 3.2 Hz, 1H), 7.36 (dd, J=4.9, 7.8 Hz, 1H), 7.41 (d, J=3.2 Hz, 1H), 7.64 (dd, J=4.6, 4.6 Hz, 1H), 7.67 (d, J=1.6 Hz, 1H), 7.72 (d, J=7.8 Hz, 1H), 8.03-8.09 (m, 2H), 8.47 (d, J=4.9 Hz, 1H), 8.50 (s, 1H), 8.67 (d, J=4.6 Hz, 1H), 12.67 (br s, 1H). APCIMS m/z: [M+H]$^+$ 474. mp: 208-209° C.

Reference Example 106

N-[4-(2-Furyl)-5-(pyridin-2-ylcarbonyl)thiazol-2-yl]-1-(pyridin-4-ylmethyl)piperidine-4-carboxamide (Compound 106)

$^1$H NMR (DMSO-d$_6$, δ ppm): 1.61-1.79 (m, 2H), 1.89-1.92 (m, 2H), 1.96-2.08 (m, 2H), 2.41-2.63 (m, 1H), 2.79-2.88 (m, 2H), 3.52 (s, 2H), 6.61 (dd, J=1.8, 3.3 Hz, 1H), 7.33 (d, J=5.7 Hz, 2H), 7.42 (d, J=3.3 Hz, 1H), 7.66 (dd, J=3.9, 4.8 Hz, 1H), 7.68 (d, J=1.8 Hz, 1H), 8.05-8.10 (m, 2H), 8.51 (d, J=5.7 Hz, 2H), 8.69 (d, J=4.8 Hz, 1H), 12.71 (br s, 1H). APCIMS m/z: [M+H]$^+$ 474. mp: 240-241° C.

Reference Example 107

N-[4-(2-Furyl)-5-(pyridin-2-ylcarbonyl)thiazol-2-yl]-benzamide (Compound 107)

$^1$H NMR (CDCl$_3$, δ ppm): 6.58 (dd, J=1.9, 3.8 Hz, 1H), 7.48-7.59 (m, 4H), 7.60-7.69 (m, 1H), 7.87-8.00 (m, 4H), 8.22 (d, J=7.6 Hz, 1H), 8.78 (d, J=4.9 Hz, 1H), 9.79 (br s, 1H). APCIMS m/z: [M+H]$^+$ 376. mp: 165-171° C.

Reference Example 108

N-[4-(2-Furyl)-5-(pyridin-2-ylcarbonyl)thiazol-2-yl]-2-methoxybenzamide (Compound 108)

$^1$H NMR (CDCl$_3$, δ ppm): 4.13 (s, 3H), 6.57 (dd, J=1.6, 3.5 Hz, 1H), 7.08 (d, J=8.4 Hz, 1H), 7.16 (dd, J=6.8, 7.8 Hz, 1H), 7.48 (ddd, J=1.4, 4.9, 7.6 Hz, 1H), 7.56 (d, J=1.6 Hz, 1H), 7.58 (ddd, J=1.9, 6.8, 7.8 Hz, 1H), 7.81 (d, J=3.5 Hz, 1H), 7.89 (ddd, J=1.6, 7.6, 7.8 Hz, 1H), 8.17 (ddd, J=0.8, 1.4, 7.8 Hz, 1H), 8.31 (dd, J=1.9, 7.8 Hz, 1H), 8.75 (ddd, J=0.8, 1.6, 4.9 Hz, 1H), 11.44 (br s, 1H). APCIMS m/z: [M+]$^+$ 406. mp: 205-208° C.

Reference Example 109

N-[4-(2-Furyl)-5-(pyridin-2-ylcarbonyl)thiazol-2-yl]-3-methoxybenzamide (Compound 109)

$^1$H NMR (CDCl$_3$, δ ppm): 3.88 (s, 3H), 6.56 (dd, J=1.9, 3.8 Hz, 1H), 7.16 (ddd, J=1.4, 2.4, 5.6 Hz, 1H), 7.43 (dd, J=5.6, 5.6 Hz, 1H), 7.46-7.57 (m, 3H), 7.54 (dd, J=0.8, 1.9 Hz, 1H), 7.87-7.95 (m, 1H), 7.91 (dd, J=0.8, 3.8 Hz, 1H), 8.22 (d, J=7.8 Hz, 1H), 8.77 (d, J=4.9 Hz, 1H), 9.85 (br s, 1H). APCIMS m/z: [M+H]$^+$ 406. mp: 165-166° C.

Reference Example 110

N-[4-(2-Furyl)-5-(pyridin-2-ylcarbonyl)thiazol-2-yl]-4-methoxybenzamide (Compound 110)

$^1$H NMR (CDCl$_3$, δ ppm): 3.90 (s, 3H), 6.57 (dd, J=1.9, 3.8 Hz, 1H), 7.02 (d, J=8.6 Hz, 2H), 7.50 (dd, J=4.9, 7.8 Hz, 1H), 7.54 (d, J=1.9 Hz, 1H), 7.86-7.97 (m, 2H), 7.93 (d, J=8.6 Hz, 2H), 8.21 (d, J=7.8 Hz, 1H), 8.77 (d, J=4.9 Hz, 1H), 9.75 (br s, 1H). APCIMS m/z: [M+H]+ 406. mp: 187-188° C.

Reference Example 111

N-[4-(2-Furyl)-5-(pyridin-2-ylcarbonyl)thiazol-2-yl]-3,4-dimethoxybenzamide (Compound 111)

$^1$H NMR (DMSO-$d_6$, δ ppm): 3.86 (s, 3H), 3.88 (s, 3H), 6.63 (dd, J=1.9, 3.5 Hz, 1H), 7.14 (d, J=8.4 Hz, 1H), 7.44 (d, J=3.5 Hz, 1H), 7.64-7.72 (m, 1H), 7.70 (d, J=1.9 Hz, 1H), 7.82 (d, J=2.2 Hz, 1H), 7.85 (dd, J=2.2, 8.4 Hz, 1H), 8.06-8.11 (m, 2H), 8.68-8.73 (m, 1H), 13.04 (br s, 1H). APCIMS m/z: [M+H]+ 436. mp: 169-170° C.

Reference Example 112

N-[4-(2-Furyl)-5-(pyridin-2-ylcarbonyl)thiazol-2-yl]-3,4,5-trimethoxybenzamide (Compound 112)

$^1$H NMR (DMSO-$d_6$, δ ppm): 3.77 (s, 3H), 3.90 (s, 6H), 6.64 (dd, J=1.6, 3.2 Hz, 1H), 7.47 (d, J=3.2 Hz, 1H), 7.58 (s, 2H), 7.65-7.73 (m, 1H), 7.72 (d, J=1.6 Hz, 1H), 8.04-8.12 (m, 2H), 8.69-8.74 (m, 1H), 13.16 (br s, 1H). APCIMS m/z: [M+H]+ 466. mp: 172-180° C. (dec.).

Reference Example 113

3-Cyano-N-[4-(2-furyl)-5-(pyridin-2-ylcarbonyl)thiazol-2-yl]benzamide (Compound 113)

$^1$H NMR (CDCl$_3$, δ ppm): 6.50 (dd, J=1.6, 3.2 Hz, 1H), 7.46 (d, J=1.6 Hz, 1H), 7.52 (ddd, J=1.1, 4.9, 7.6 Hz, 1H), 7.62 (dd, J=8.0, 8.1 Hz, 1H), 7.86 (d, J=8.0 Hz, 1H), 7.88 (d, J=3.2 Hz, 1H), 7.92 (ddd, J=1.6, 7.6, 7.8 Hz, 1H), 8.13 (d, J=8.1 Hz, 1H), 8.22 (ddd, J=0.8, 1.1, 7.8 Hz, 1H), 8.26 (s, 1H), 8.78 (ddd, J=0.8, 1.6, 4.9 Hz, 1H). APCIMS m/z: [M+H]+ 401. mp: 234-237° C.

Reference Example 114

4-Cyano-N-[4-(2-furyl)-5-(pyridin-2-ylcarbonyl)thiazol-2-yl]benzamide (Compound 114)

$^1$H NMR (CDCl$_3$, δ ppm): 6.51 (dd, J=1.6, 3.5 Hz, 1H), 7.45 (d, J=1.6 Hz, 1H), 7.53 (dd, J=4.6, 7.6 Hz, 1H), 7.79 (d, J=8.1 Hz, 2H), 7.85 (d, J=3.5 Hz, 1H), 7.93 (dd, J=7.6, 8.1 Hz, 1H), 8.03 (d, J=8.1 Hz, 2H), 8.24 (d, J=8.1 Hz, 1H), 8.78 (d, J=4.6 Hz, 1H), 10.50 (br s. 1H). APCIMS m/z: [M+H]+ 401. mp: 232-235° C.

Reference Example 115

3-Acetyl-N-[4-(2-furyl)-5-(pyridin-2-ylcarbonyl)thiazol-2-yl]benzamide (Compound 115)

$^1$H NMR (DMSO-$d_6$, δ ppm): 2.70 (s, 3H), 6.64 (dd, J=1.3, 3.5 Hz, 1H), 7.46 (d, J=3.5 Hz, 1H), 7.63-7.78 (m, 3H), 8.03-8.13 (m, 2H), 8.20 (d, J=7.0 Hz, 1H), 8.37 (d, J=6.8 Hz, 1H), 8.68-8.74 (m, 1H), 8.77 (s, 1H), 13.43 (br s, 1H). APCIMS m/z: [M+H]+ 418. mp: 168-169° C.

Reference Example 116

4-Acetyl-N-[4-(2-furyl)-5-(pyridin-2-ylcarbonyl)thiazol-2-yl]benzamide (Compound 116)

$^1$H NMR (DMSO-$d_6$, δ ppm): 2.66 (s, 3H), 6.64 (dd, J=1.6, 3.2 Hz, 1H), 7.46 (d, J=3.2 Hz, 1H), 7.65-7.75 (m, 1H), 7.72 (d, J=1.6 Hz, 1H), 8.04-8.14 (m, 2H), 8.11 (d, J=8.4 Hz, 2H), 8.28 (d, J=8.4 Hz, 2H), 8.69-8.75 (m, 1H), 13.40 (br s, 1H). APCIMS m/z: [M+H]+ 418. mp: 204-206° C.

Reference Example 117

N-[4-(2-Furyl)-5-(pyridin-2-ylcarbonyl)thiazol-2-yl]-3,4-methylenedioxybenzamide (Compound 117)

$^1$H NMR (DMSO-$d_6$, δ ppm): 6.17 (s, 2H), 6.63 (dd, J=1.6, 3.5 Hz, 1H), 7.09 (d, J=8.4 Hz, 1H), 7.44 (dd, J=0.8, 3.5 Hz, 1H), 7.64-7.72 (m, 1H), 7.70 (dd, J=0.8, 1.6 Hz, 1H), 7.73 (d, J=1.9 Hz, 1H), 7.82 (dd, J=1.9, 8.4 Hz, 1H), 8.05-8.11 (m, 2H), 8.68-8.73 (m, 1H), 12.99 (br s; 1H). APCIMS m/z: [M+H]+ 420. mp: 235-236° C.

Reference Example 118

N-[4-(2-Furyl)-5-(pyridin-2-ylcarbonyl)thiazol-2-yl]-1,4-benzodioxane-6-carboxamide (Compound 118)

$^1$H NMR (DMSO-$d_6$, δ ppm): 4.28-4.38 (m, 4H), 6.63 (dd, J=1.9, 3.5 Hz, 1H), 7.02 (d, J=8.6 Hz, 1H), 7.44 (dd, J=0.5, 3.5 Hz, 1H), 7.63-7.73 (m, 1H), 7.71 (dd, J=0.5, 1.9 Hz, 1H), 7.74 (dd, J=2.2, 8.6 Hz, 1H), 7.77 (d, J=2.2 Hz, 1H), 8.03-8.11 (m, 2H), 8.68-8.73 (m, 1H), 13.00 (br s, 1H). APCIMS m/z: [M+H]+ 434. mp: 189-191° C.

Reference Example 119

N-[4-(2-Furyl)-5-(pyridin-2-ylcarbonyl)thiazol-2-yl]-1,4-benzodioxane-2-carboxamide (Compound 119)

$^1$H NMR (DMSO-$d_6$, δ ppm): 4.44 (dd, J=3.0, 12.2 Hz, 1H), 4.53 (dd, J=3.8, 12.2 Hz, 1H), 5.24 (dd, J=3.0, 3.8 Hz, 1H), 6.63 (dd, J=1.9, 3.5 Hz, 1H), 6.84-6.95 (m, 3H), 6.99-7.05 (m, 1H), 7.46 (dd, J=0.8, 3.5 Hz, 1H), 7.62-7.69 (m, 1H), 7.71 (dd, J=0.8, 1.9 Hz, 1H), 8.02-8.11 (m, 2H), 8.66-8.70 (m, 1H), 13.10 (br s, 1H). APCIMS m/z: [M+H]+ 434. mp: 103-104° C.

Reference Example 120

N-[4-(2-Furyl)-5-(pyridin-2-ylcarbonyl)thiazol-2-yl]-2-methylpyridine-4-carboxamide (Compound 120)

$^1$H NMR (DMSO-$d_6$, δ ppm): 2.59 (s, 3H), 6.65 (dd, J=1.9, 3.5 Hz, 1H), 7.46 (dd, J=0.8, 3.5 Hz, 1H), 7.66-7.75 (m, 1H), 7.73 (dd, J=0.8, 1.9 Hz, 1H), 7.85 (dd, J=1.1, 5.1 Hz, 1H), 7.94 (d, J=1.1 Hz, 1H), 8.05-8.14 (m, 2H), 8.69 (d, J=5.1 Hz, 1H), 8.69-8.74 (m, 1H), 13.43 (br s, 1H). APCIMS m/z: [M+H]+ 391. mp: 187-188° C.

Reference Example 121

N-[4-(2-Furyl)-5-(pyridin-2-ylcarbonyl)thiazol-2-yl]-2-(4-methoxybenzyloxy)pyridine-4-carboxamide (Compound 121)

$^1$H NMR (DMSO-$d_6$, δ ppm): 3.78 (s, 3H), 5.31 (s, 2H), 6.42 (dd, J=1.8, 3.6 Hz, 1H), 6.86 (d, J=8.9 Hz, 2H), 7.21 (dd, J=1.0, 1.6 Hz, 1H), 7.31 (dd, J=1.6, 5.4 Hz, 1H), 7.35 (d, J=8.9 Hz, 2H), 7.36 (dd, J=0.7, 1.8 Hz, 1H), 7.51 (ddd, J=1.2, 4.8, 7.6 Hz, 1H), 7.70 (dd, J=0.7, 3.6 Hz, 1H), 7.91 (ddd, J=1.8, 7.6, 7.9 Hz, 1H), 8.04 (br s, 1H), 8.19 (ddd, J=1.0, 1.2, 7.9 Hz, 1H), 8.27 (dd, J=1.0, 5.4 Hz, 1H), 8.77 (ddd, J=1.0, 1.8, 4.8 Hz, 1H).

Reference Example 122

2-Chloro-N-[4-(2-furyl)-5-(pyridin-2-ylcarbonyl)thiazol-2-yl]pyridine-4-carboxamide (Compound 122)

$^1$H NMR (DMSO-$d_6$, δ ppm): 6.65 (dd, J=1.6, 3.2 Hz, 1H), 7.47 (d, J=3.2 Hz, 1H), 7.66-7.73 (m, 1H), 7.74 (d, J=1.6 Hz, 1H), 8.04 (dd, J=1.6, 5.4 Hz, 1H), 8.08-8.14 (m, 2H), 8.20 (d, J=1.6 Hz, 1H), 8.68 (d, J=5.4 Hz, 1H), 8.70-8.75 (m, 1H), 13.57 (br s, 1H). APCIMS m/z: [$^{35}$ClM+H]$^+$ 411, [$^{37}$ClM+H]$^+$ 413. mp: 219-225° C.

Reference Example 123

3-Chloro-N-[4-(2-furyl)-5-(pyridin-2-ylcarbonyl)thiazol-2-yl]pyridine-4-carboxamide (Compound 123)

$^1$H NMR (DMSO-$d_6$, δ ppm): 6.64 (dd, J=1.6, 3.5 Hz, 1H), 7.46 (d, J=3.5 Hz, 1H), 7.65-7.74 (m, 1H), 7.73 (d, J=1.6 Hz, 1H), 7.78 (d, J=4.9 Hz, 1H), 8.06-8.17 (m, 2H), 8.72 (d, J=4.9 Hz, 1H), 8.72-8.76 (m, 1H), 8.84 (s, 1H), 13.57 (br s, 1H). APCIMS m/z: [$^{35}$ClM+H]$^+$ 411, [$^{37}$ClM+H]$^+$ 413. mp: 206-207° C.

Reference Example 124

2,6-Dichloro-N-[4-(2-furyl)-5-(pyridin-2-ylcarbonyl)thiazol-2-yl]pyridine-4-carboxamide (Compound 124)

$^1$H NMR (DMSO-$d_6$, δ ppm): 6.65 (dd, J=1.6, 3.5 Hz, 1H), 7.48 (d, J=0.5 Hz, 1H), 7.66-7.72 (m, 1H), 7.74 (d, J=0.5 Hz, 1H), 8.05-8.15 (m, 2H), 8.19 (s, 2H), 8.69-8.75 (m, 1H), 13.59 (br s, 1H). APCIMS m/z: [$^{35}$Cl$^{35}$ClM+H]$^+$ 445, [$^{35}$Cl$^{37}$ClM+H]$^+$ 447. mp: 254-258° C.

Reference Example 125

N-[4-(2-Furyl)-5-(pyridin-2-ylcarbonyl)thiazol-2-yl]-2-[N-(2-methoxyethyl)-N-methylamino]pyridine-4-carboxamide (Compound 125)

$^1$H NMR (CDCl$_3$, δ ppm): 3.17 (s, 3H), 3.34 (s, 3H), 3.61 (t, J=5.4 Hz, 2H), 3.82 (t, J=5.4 Hz, 2H), 6.56 (dd, J=1.9, 3.8 Hz, 1H), 6.91 (d, J=5.1 Hz, 1H), 7.04-7.08 (m, 1H), 7.50 (ddd, J=1.6, 4.9, 7.3 Hz, 1H), 7.54 (d, J=1.9 Hz, 1H), 7.90 (ddd, J=1.6, 7.3, 7.8 Hz, 1H), 7.91 (d, J=3.8 Hz, 1H), 8.21 (d, J=7.8 Hz, 1H), 8.29 (d, J=5.1 Hz, 1H), 8.75 (dd, J=1.6, 4.9 Hz, 1H). APCIMS m/z: [M+H]$^+$ 464. mp: 114-117° C.

Reference Example 126

N-[4-(2-Furyl)-5-(pyridin-2-ylcarbonyl)thiazol-2-yl]-2-piperidinopyridine-4-carboxamide (Compound 126)

$^1$H NMR (CDCl$_3$, δ ppm): 1.50-1.82 (m, 6H), 3.53-3.80 (m, 4H), 6.55 (dd, J=1.9, 3.8 Hz, 1H), 6.88 (d, J=5.1 Hz, 1H), 7.14 (s, 1H), 7.50 (ddd, J=1.4, 4.9, 7.8 Hz, 1H), 7.52 (dd, J=0.5, 1.9 Hz, 1H), 7.90 (ddd, J=1.9, 7.8, 7.8 Hz, 1H), 7.90 (dd, J=0.5, 3.8 Hz, 1H), 8.21 (ddd, J=0.8, 1.4, 7.8 Hz, 1H), 8.29 (d, J=5.1 Hz, 1H), 8.75 (ddd, J=0.8, 1.9, 4.9 Hz, 1H), 9.97 (br s, 1H). APCIMS m/z: [M+H]$^+$ 460. mp: 136-141° C.

Reference Example 127

N-[4-(2-Furyl)-5-(pyridin-2-ylcarbonyl)thiazol-2-yl]-2-morpholinopyridine-4-carboxamide (Compound 127)

$^1$H NMR (CDCl$_3$, δ ppm): 3.59-3.67 (m, 4H), 3.79-3.87 (m, 4H), 6.57 (dd, J=1.6, 3.5 Hz, 1H), 7.04 (d, J=4.6 Hz, 1H), 7.21 (s, 1H), 7.52 (dd, J=4.9, 7.6 Hz, 1H), 7.56 (d, J=1.6 Hz, 1H), 7.92 (ddd, J=1.9, 7.6, 7.8 Hz, 1H), 7.95 (d, J=3.5 Hz, 1H), 8.22 (d, J=7.8 Hz, 1H), 8.35 (d, J=4.6 Hz, 1H), 8.76 (dd, J=1.9, 4.9 Hz, 1H). APCIMS m/z: [M+H]$^+$ 462. mp: 216-217° C.

Reference Example 128

N-[4-(2-Furyl)-5-(pyridin-2-ylcarbonyl)thiazol-2-yl]pyridine-3-carboxamide (Compound 128)

$^1$H NMR (DMSO-$d_6$, δ ppm): 6.65 (dd, J=1.9, 3.5 Hz, 1H), 7.48 (d, J=3.5 Hz, 1H), 7.62 (dd, J=5.1, 8.1 Hz, 1H), 7.66-7.73 (m, 1H), 7.73 (d, J=1.9 Hz, 1H), 8.05-8.14 (m, 2H), 8.50 (ddd, J=1.4, 2.2, 8.1 Hz, 1H), 8.71-8.75 (m, 1H), 8.83 (dd, J=1.4, 5.1 Hz, 1H), 9.28 (d, J=2.2 Hz, 1H), 13.43 (br s, 1H). APCIMS m/z: [M+H]$^+$ 377.

Reference Example 129

N-[4-(2-Furyl)-5-(pyridin-2-ylcarbonyl)thiazol-2-yl]-2-methylpyridine-3-carboxamide (Compound 129)

$^1$H NMR (DMSO-$d_6$, δ ppm): 2.63 (s, 3H), 6.63 (dd, J=1.9, 3.5 Hz, 1H), 7.38 (dd, J=4.9, 7.8 Hz, 1H), 7.44 (dd, J=0.8, 3.5 Hz, 1H), 7.65-7.73 (m 1H), 7.71 (dd, J=0.8, 1.9 Hz, 1H), 8.04-8.14 (m, 2H), 8.05 (dd, J=1.6, 7.8 Hz, 1H), 8.61 (dd, J=1.6, 4.9 Hz, 1H), 8.71-8.75 (m 1H), 12.67 (br s, 1H). APCIMS m/z: [M+H]$^+$ 391. mp: 186-187° C.

Reference Example 130

N-[4-(2-Furyl)-5-(pyridin-2-ylcarbonyl)thiazol-2-yl]-2-methylpyridine-5-carboxamide (Compound 130)

$^1$H NMR (DMSO-$d_6$, δ ppm): 2.58 (s, 3H), 6.64 (dd, J=1.6, 3.5 Hz, 1H), 7.46 (d, J=7.8 Hz, 1H), 7.46 (dd, J=0.8, 3.5 Hz, 1H), 7.65-7.74 (m, 1H), 7.72 (dd, J=0.8, 1.6 Hz, 1H), 8.04-8.13 (m, 2H), 8.38 (dd, J=2.4, 7.8 Hz, 1H), 8.69-8.74 (m, 1H), 9.17 (d, J=2.4 Hz, 1H), 13.31 (br s, 1H). APCIMS m/z: [M+H]$^+$ 391. mp: 210-215° C.

Reference Example 131

N-[4-(2-Furyl)-5-(pyridin-2-ylcarbonyl)thiazol-2-yl]-5-methylpyridine-3-carboxamide (Compound 131)

$^1$H NMR (DMSO-$d_6$, δ ppm): 2.41 (s, 3H), 6.64 (dd, J=1.9, 3.5 Hz, 1H), 7.46 (dd, J=0.8, 3.5 Hz, 1H), 7.65-7.75 (m, 1H), 7.73 (dd, J=0.8, 1.9 Hz, 1H), 8.05-8.14 (m, 2H), 8.33 (dd, J=1.4, 1.9 Hz, 1H), 8.67 (d, J=1.4 Hz, 1H), 8.70-8.73 (m, 1H), 9.08 (d, J=1.9 Hz, 1H), 13.35 (br s, 1H). APCIMS m/z: [M+H]+ 391. mp: 245-248° C.

Reference Example 132

N-[4-(2-Furyl)-5-(pyridin-2-ylcarbonyl)thiazol-2-yl]-2,6-dimethoxypyridine-3-carboxamide (Compound 132)

$^1$H NMR (DMSO-d$_6$, δ ppm): 3.97 (s, 3H), 4.09 (s, 3H), 6.58 (d, J=8.6 Hz, 1H), 6.63 (dd, J=1.9, 3.2 Hz 1H), 7.45 (d, J=3.2 Hz, 1H), 7.64-7.71 (m, 1H), 7.71 (d, J=1.9 Hz, 1H), 8.03-8.12 (m, 2H), 8.18 (d, J=8.6 Hz, 1H), 8.69-8.73 (m, 1H), 11.97 (br s, 1H). APCIMS m/z: [M+H]+ 437. mp: 201-202° C.

Reference Example 133

2-Chloro-N-[4-(2-furyl)-5-(pyridin-2-ylcarbonyl)thiazol-2-yl]pyridine-5-carboxamide (Compound 133)

$^1$H NMR (DMSO-d$_6$, δ ppm): 6.64 (dd, J=1.6, 3.2 Hz, 1H), 7.47 (d, J=3.2 Hz, 1H), 7.65-7.74 (m, 1H), 7.72 (d, J=1.6 Hz, 1H), 7.76 (d, J=8.4 Hz, 1H), 8.04-8.14 (m, 2H), 8.52 (dd, J=2.4, 8.4 Hz, 1H), 8.70-8.74 (m, 1H), 9.12 (d, J=2.4 Hz, 1H), 13.47 (br s, 1H). mp: 136-138° C.

Reference Example 134

5-Bromo-N-[4-(2-furyl)-5-(pyridin-2-ylcarbonyl)thiazol-2-yl]pyridine-3-carboxamide (Compound 134)

$^1$H NMR (DMSO-d$_6$, δ ppm): 6.65 (dd, J=1.9, 3.8 Hz, 1H), 7.48 (dd, J=0.8, 3.8 Hz, 1H), 7.65-7.72 (m, 1H), 7.73 (dd, J=0.8, 1.9 Hz, 1H), 8.06-8.15 (m, 2H), 8.71-8.77 (m, 1H), 8.75 (dd, J=1.9, 2.2 Hz, 1H), 8.97 (d, J=2.2 Hz, 1H), 9.22 (d, J=1.9 Hz, 1H), 13.46 (br s. 1H). APCIMS m/z: [$^{79}$BrM+H]+ 455, [$^{81}$BrM+H]+ 457. mp: 259-262° C.

Reference Example 135

N-[4-(2-Furyl)-5-(pyridin-2-ylcarbonyl)thiazol-2-yl]pyridazine-4-carboxamide (Compound 135)

$^1$H NMR (DMSO-d$_6$, δ ppm): 6.66 (dd, J=1.9, 3.5 Hz, 1H), 7.51 (d, J=3.5 Hz, 1H), 7.66-7.73 (m, 1H), 7.75 (d, J=1.9 Hz, 1H), 8.05-8.16 (m, 2H), 8.30 (dd, J=2.4, 5.4 Hz, 1H), 8.71-8.77 (m, 1H), 9.56 (dd, J=1.1, 5.4 Hz, 1H), 9.78 (dd, J=1.1, 2.4 Hz, 1H), 13.73 (br s, 1H). APCIMS m/z: [M+H]+ 378. mp: 270-274° C.

Reference Example 136

N-[4-(2-Furyl)-5-(pyridin-2-ylcarbonyl)thiazol-2-yl]-2-methylpyrimidine-5-carboxamide (Compound 136)

$^1$H NMR (DMSO-d$_6$, δ ppm): 2.73 (s, 3H), 6.65 (dd, J=1.6, 3.5 Hz, 1H), 7.50 (dd, J=0.8, 3.5 Hz, 1H), 7.66-7.73 (m, 1H), 7.74 (dd, J=0.8, 1.6 Hz, 1H), 8.05-8.15 (m, 2H), 8.70-8.75 (m, 1H), 9.32 (s, 2H), 13.51 (br s, 1H). APCIMS m/z: [M+H]+ 392. mp: 255-265° C. (dec.).

Reference Example 137

2-Cyclopropyl-N-[4-(2-furyl)-5-(pyridin-2-ylcarbonyl)thiazol-2-yl]pyrimidine-5-carboxamide (Compound 137)

$^1$H NMR (DMSO-d$_6$, δ ppm): 1.09-1.24 (m, 4H), 2.27-2.39 (m, 1H), 6.64 (dd, J=1.6, 3.5 Hz, 1H), 7.49 (d, J=3.5 Hz, 1H), 7.65-7.73 (m, 1H), 7.73 (d, J=1.6 Hz, 1H), 8.04-8.15 (m, 2H), 8.70-8.75 (m, 1H), 9.26 (s, 2H). APCIMS m/z: [M+H]+ 418. mp: 150-154° C.

Reference Example 138

N-[4-(2-Furyl)-5-(pyridin-2-ylcarbonyl)thiazol-2-yl]-5-methylpyrazine-2-carboxamide (Compound 138)

$^1$H NMR (DMSO-d$_6$, δ ppm): 2.65 (s, 3H), 6.63 (dd, J=1.6, 3.2 Hz, 1H), 7.41 (d, J=3.2 Hz, 1H), 7.66-7.74 (m, 1H), 7.71 (d, J=1.6 Hz, 1H), 8.07-8.14 (m, 2H), 8.69-8.74 (m, 1H), 8.75 (s, 1H), 9.22 (s, 1H), 12.94 (br s, 1H). APCIMS m/z: [M+H]+ 392. mp: 208-209° C.

Reference Example 139

N-[4-(2-Furyl)-5-(pyridin-2-ylcarbonyl)thiazol-2-yl]-2-oxo-1,2-dihydropyridine-4-carboxamide (Compound 139)

$^1$H NMR (DMSO-d$_6$, δ ppm): 6.64 (dd, J=1.9, 3.5 Hz, 1H), 6.69 (dd, J=1.9, 6.8 Hz, 1H), 7.09 (d, J=1.9 Hz, 1H), 7.46 (d, J=3.5 Hz, 1H), 7.56 (d, J=6.8 Hz, 1H), 7.65-7.75 (m, 1H), 7.73 (d, J=1.9 Hz, 1H), 8.04-8.15 (m, 2H), 8.68-8.77 (m, 1H), 13.27 (br s, 1H). APCIMS m/z: [M+H]+ 393. mp: 170-180° C. (dec.).

Reference Example 140

1-Benzyl-N-[4-(2-furyl)-5-(pyridin-2-ylcarbonyl)thiazol-2-yl]-2-oxo-1,2-dihydropyridine-4-carboxamide (Compound 140)

$^1$H NMR (DMSO-d$_6$, δ ppm): 5.12 (s, 2H), 6.64 (dd, J=1.9, 3.5 Hz, 1H), 6.78 (dd, J=1.6, 7.3 Hz, 1H), 7.20 (d, J=1.6 Hz, 1H), 7.28-7.41 (m, 5H), 7.45 (dd, J=0.5, 3.5 Hz, 1H), 7.65-7.74 (m, 1H), 7.72 (dd, J=0.5, 1.9 Hz, 1H), 8.00 (d, J=7.3 Hz, 1H), 8.04-8.13 (m, 2H), 8.69-8.74 (m, 1H), 13.35 (br s, 1H). APCIMS m/z: [M+H]+ 483. mp: 269-270° C.

Reference Example 141

N-[4-(2-Furyl)-5-(pyridin-2-ylcarbonyl)thiazol-2-yl]-1-methyl-2-oxo-1,2-dihydropyridine-4-carboxamide (Compound 141)

$^1$H NMR (DMSO-d$_6$, δ ppm): 3.54 (s, 3H), 6.64 (dd, J=1.9, 3.5 Hz, 1H), 6.74 (dd, J=2.2, 7.0 Hz, 1H), 7.15 (d, J=2.2 Hz, 1H), 7.46 (dd, J=0.8, 3.5 Hz, 1H), 7.65-7.72 (m, 1H), 7.73 (dd, J=0.8, 1.9 Hz, 1H), 7.88 (d, J=7.0 Hz, 1H), 8.04-8.14 (m, 2H), 8.70-8.74 (m, 1H), 13.36 (br s, 1H). APCIMS m/z: [M+H]+ 407. mp: 280-285° C.

Reference Example 142

N-[4-(2-Furyl)-5-(pyridin-2-ylcarbonyl)thiazol-2-yl] furan-2-carboxamide (Compound 142)

$^1$H NMR (CDCl$_3$, δ ppm): 6.57 (dd, J=1.9, 3.8 Hz, 1H), 6.62 (dd, J=1.9, 3.8 Hz, 1H), 7.41 (dd, J=0.8, 3.8 Hz, 1H), 7.49 (ddd, J=1.4, 4.9, 7.6 Hz, 1H), 7.56 (dd, J=0.8, 1.9 Hz, 1H), 7.59 (dd, J=0.8, 1.9 Hz, 1H), 7.89 (ddd, J=1.9, 7.6, 8.1 Hz, 1H), 7.92 (dd, J=0.8, 3.8 Hz, 1H), 8.19 (ddd, J=0.8, 1.4, 8.1 Hz, 1H), 8.74 (ddd, J=0.8, 1.9, 4.9 Hz, 1H), 10.11 (br s, 1H). APCIMS m/z: [M+H]$^+$ 366. mp: 184-185° C.

Reference Example 143

5-Bromo-N-[4-(2-furyl)-5-(pyridin-2-ylcarbonyl) thiazol-2-yl]furan-2-carboxamide (Compound 143)

$^1$H NMR (DMSO-d$_6$, δ ppm): 6.63 (dd, J=1.9, 3.5 Hz, 1H), 6.92 (d, J=3.5 Hz, 1H), 7.45 (dd, J=0.5, 3.5 Hz, 1H), 7.64-7.73 (m, 1H), 7.70 (dd, J=0.5, 1.9 Hz, 1H), 7.81 (d, J=3.5 Hz, 1H), 8.03-8.13 (m, 2H), 8.67-8.72 (m, 1H), 13.23 (br s, 1H). APCIMS m/z: [$^{79}$BrM+H]$^+$ 444, [$^{81}$BrM+H]$^+$ 446. mp: 211-212° C.

Reference Example 144

N-[4-(2-Furyl)-5-(pyridin-2-ylcarbonyl)thiazol-2-yl]-5-nitrofuran-2-carboxamide (Compound 144)

$^1$H NMR (DMSO-d$_6$, δ ppm): 6.65 (dd, J=1.6, 3.5 Hz, 1H), 7.48 (dd, J=0.5, 1.6 Hz, 1H), 7.66-7.74 (m, 1H), 7.73 (dd, J=0.5, 1.6 Hz, 1H), 7.85 (d, J=4.1 Hz, 1H), 7.98 (d, J=4.1 Hz, 1H), 8.05-8.14 (m, 2H), 8.69-8.73 (m, 1H), 13.72 (br s, 1H). APCIMS m/z: [M+H]$^+$ 411. mp: 278-283° C. (dec.).

Reference Example 145

N-[4-(2-Furyl)-5-(pyridin-2-ylcarbonyl)thiazol-2-yl]-3-methylfuran-2-carboxamide (Compound 145)

$^1$H NMR (DMSO-d$_6$, δ ppm): 2.40 (s, 3H), 6.62 (dd, J=1.9, 3.5 Hz, 1H), 6.67 (d, J=1.6 Hz, 1H), 7.40 (dd, J=0.5, 3.5 Hz, 1H), 7.62-7.72 (m, 1H), 7.70 (dd, J=0.5, 1.9 Hz, 1H), 7.88 (d, J=1.6 Hz, 1H), 8.03-8.11 (m, 2H), 8.69-8.73 (m, 1H), 12.87 (br s, 1H). APCIMS m/z: [M+H]$^+$ 380. mp: 174-176° C.

Reference Example 146

N-[4-(2-Furyl)-5-(pyridin-2-ylcarbonyl)thiazol-2-yl] furan-3-carboxamide (Compound 146)

$^1$H NMR (DMSO-d$_6$, δ ppm): 6.63 (dd, J=1.6, 3.2 Hz, 1H), 7.14 (d, J=1.9 Hz, 1H), 7.44 (d, J=3.2 Hz, 1H), 7.67 (ddd, J=2.3, 4.6, 4.9 Hz, 1H), 7.69 (d, J=1.6 Hz, 1H), 7.87 (dd, J=1.9, 1.9 Hz, 1H), 8.03-8.11 (m, 2H), 8.64-8.68 (m, 1H), 8.69 (d, J=4.6 Hz, 1H), 13.00 (br s, 1H). APCIMS m/z: [M+H]$^+$ 366. mp: 187-189° C.

Reference Example 147

N-[4-(2-Furyl)-5-(pyridin-2-ylcarbonyl)thiazol-2-yl]-2-methylfuran-3-carboxamide (Compound 147)

$^1$H NMR (DMSO-d$_6$, δ ppm): 2.63 (s, 3H), 6.63 (dd, J=1.6, 3.5 Hz, 1H), 7.37 (d, J=2.2 Hz, 1H), 7.44 (d, J=1.0, 3.5 Hz, 1H), 7.64-7.75 (m, 1H), 7.65 (d, J=2.2 Hz, 1H), 7.70 (dd, J=1.0, 1.6 Hz, 1H), 8.03-8.11 (m, 2H), 8.69-8.74 (m, 1H), 12.74 (br s, 1H). APCIMS m/z: [M+H]$^+$ 380. mp: 183-186° C.

Reference Example 148

N-[4-(2-Furyl)-5-(pyridin-2-ylcarbonyl)thiazol-2-yl]-2,5-dimethylfuran-3-carboxamide (Compound 148)

$^1$H NMR (DMSO-d$_6$, δ ppm): 2.27 (s, 3H), 2.58 (s, 3H), 6.62 (dd, J=1.9, 3.5 Hz, 1H), 6.96 (s, 1H), 7.44 (dd, J=0.5, 3.5 Hz, 1H), 7.62-7.72 (m, 1H), 7.70 (dd, J=0.5, 1.9 Hz, 1H), 8.03-8.11 (m, 2H), 8.69-8.73 (m, 1H), 12.65 (br s, 1H). APCIMS m/z: [M+H]$^+$ 394. mp: 195-198° C.

Reference Example 149

N-[4-(2-Furyl)-5-(pyridin-2-ylcarbonyl)thiazol-2-yl]-thiophene-2-carboxamide (Compound 149)

$^1$H NMR (CDCl$_3$, δ ppm): 6.55 (dd, J=1.9, 3.5 Hz, 1H), 7.16 (dd, J=4.1, 5.1 Hz, 1H), 7.49 (ddd, J=1.1, 4.9, 7.6 Hz, 1H), 7.53 (dd, J=1.1, 1.9 Hz, 1H), 7.66 (d, J=5.1 Hz, 1H), 7.74 (dd, J=1.1, 3.5 Hz, 1H), 7.89 (ddd, J=1.6, 7.6, 7.6 Hz, 1H), 7.92 (d, J=4.1 Hz, 1H), 8.19 (ddd, J=0.8, 1.1, 7.6 Hz, 1H), 8.75 (ddd, J=0.8, 1.6, 4.9 Hz, 1H). APCIMS m/z: [M+H]$^+$ 382. mp: 197-199° C.

Reference Example 150

N-[4-(2-Furyl)-5-(pyridin-2-ylcarbonyl)thiazol-2-yl] isoxazole-5-carboxamide (Compound 150)

$^1$H NMR (DMSO-d$_6$, δ ppm): 6.64 (dd, J=1.9, 3.5 Hz, 1H), 7.46 (d, J=3.5 Hz, 1H), 7.61 (d, J=1.9 Hz, 1H), 7.69 (ddd, J=2.4, 4.9, 6.5 Hz, 1H), 7.72 (d, J=1.9 Hz, 1H), 8.05-8.15 (m, 2H), 8.72 (d, J=4.9 Hz, 1H), 8.88 (d, J=1.9 Hz, 1H). APCIMS m/z: [M+H]$^+$ 367. mp: 223-230° C.

Reference Example 151

N-[4-(2-Furyl)-5-(pyridin-2-ylcarbonyl)thiazol-2-yl]-5-methylisoxazole-3-carboxamide (Compound 151)

$^1$H NMR (DMSO-d$_6$, δ ppm): 2.53 (s, 3H), 6.63 (dd, J=1.6, 3.5 Hz, 1H), 6.90 (s, 1H), 7.42 (dd, J=0.5, 3.5 Hz, 1H), 7.65-7.74 (m, 1H), 7.72 (dd, J=0.5, 1.6 Hz, 1H), 8.04-8.13 (m, 2H), 8.68-8.74 (m, 1H), 13.47 (br s, 1H). APCIMS m/z: [M+H]$^+$ 381. mp: 209-213° C.

Reference Example 152

N-[4-(2-Furyl)-5-(pyridin-2-ylcarbonyl)thiazol-2-yl]-1,2,3-benzothiadiazole-5-carboxamide (Compound 152)

$^1$H NMR (DMSO-d$_6$, δ ppm): 6.65 (dd, J=1.6, 3.2 Hz, 1H), 7.48 (dd, J=0.5, 3.2 Hz, 1H), 7.66-7.73 (m, 1H), 7.74 (dd, J=0.5, 1.6 Hz, 1H), 8.05-8.15 (m, 2H), 8.47 (dd, J=1.6, 8.6 Hz, 1H), 8.60 (dd, J=0.8, 8.6 Hz, 1H), 8.72-8.77 (m, 1H), 9.56

(dd, J=0.8, 1.6 Hz, 1H), 13.58 (br s, 1H). APCIMS m/z: [M+H]⁺ 434. mp: 213-218° C.

Reference Example 153

N-[4-(2-Furyl)-5-(pyridin-2-ylcarbonyl)thiazol-2-yl]-1-methyl-1H-benzotriazole-6-carboxamide (Compound 153)

¹H NMR (DMSO-d₆, δ ppm): 4.37 (s, 3H), 6.64 (dd, J=1.6, 3.5 Hz, 1H), 7.46 (d, J=3.5 Hz, 1H), 7.65-7.74 (m, 1H), 7.72 (d, J=1.6 Hz, 1H), 8.03 (d, J=8.6 Hz, 1H), 8.07-8.13 (m, 2H), 8.29 (dd, J=1.4, 8.6 Hz, 1H), 8.70-8.75 (m, 1H), 8.97 (d, J=1.4 Hz, 1H), 13.38 (br s, 1H). APCIMS m/z: [M+H]⁺ 431. mp: 230-231° C.

Reference Example 154

N-[4-(2-Furyl)-5-(pyridin-2-ylcarbonyl)thiazol-2-yl]-2-(1-hydroxyethyl)-1-benzofuran-5-carboxamide (Compound 154)

¹H NMR (DMSO-d₆, δ ppm): 1.50 (d, J=6.6 Hz, 3H), 4.89 (dq, J=5.3, 6.6 Hz, 1H), 5.63 (d, J=5.3 Hz, 1H), 6.64 (dd, J=1.6, 3.2 Hz, 1H), 6.88 (s, 1H), 7.45 (d, J=3.2 Hz, 1H), 7.65-7.75 (m, 1H), 7.72 (d, J=7.8 Hz, 1H), 7.72 (d, J=1.6 Hz, 1H), 8.07-8.14 (m, 2H), 8.11 (dd, J=1.6, 7.8 Hz, 1H), 8.49 (d, J=1.6 Hz, 1H), 8.70-8.75 (m, 1H), 13.19 (br s, 1H). APCIMS m/z: [M+H]⁺ 460. mp: 246-249° C.

Reference Example 155

N-[4-(2-Furyl)-5-(pyridin-2-ylcarbonyl)thiazol-2-yl]-2-(1-hydroxy-1-methylethyl)-1-benzofuran-5-carboxamide (Compound 155)

¹H NMR (DMSO-d₆, δ ppm): 1.55 (s, 6H), 5.52 (br s, 1H), 6.64 (dd, J=1.6, 3.2 Hz, 1H), 6.84 (s, 1H), 7.45 (d, J=3.2 Hz, 1H), 7.65-7.75 (m, 1H), 7.71 (d, J=8.9 Hz, 1H), 7.72 (d, J=1.6 Hz, 1H), 8.04-8.12 (m, 2H), 8.09 (dd, J=1.4, 8.9 Hz, 1H), 8.48 (d, J=1.4 Hz, 1H), 8.69-8.74 (m, 1H), 13.19 (br s, 1H). APCIMS m/z: [M+H]⁺ 474. mp: 230-231° C.

Reference Example 156

N-[4-(2-Furyl)-5-(pyridin-2-ylcarbonyl)thiazol-2-yl]-furo[2,3-b]pyridine-5-carboxamide (Compound 156)

¹H NMR (DMSO-d₆, δ ppm): 6.65 (dd, J=1.9, 3.5 Hz, 1H), 7.21 (d, J=2.4 Hz, 1H), 7.47 (d, J=3.5 Hz, 1H), 7.65-7.75 (m, 1H), 7.73 (d, J=1.9 Hz, 1H), 8.05-8.14 (m, 2H), 8.28 (d, J=2.4 Hz, 1H), 8.70-8.76 (m, 1H), 8.89 (d, J=1.9 Hz, 1H), 9.07 (d, J=1.9 Hz, 1H). APCIMS m/z: [M+H]⁺ 417. mp: 234-235° C.

Reference Example 157

Methyl N-[4-(2-furyl)-5-(pyridin-2-ylcarbonyl)thiazol-2-yl]carbamate (Compound 157)

¹H NMR (CDCl₃, δ ppm): 3.85 (s, 3H), 6.56 (dd, J=1.6, 3.2 Hz, 1H), 7.44-7.53 (m, 2H), 7.82-7.93 (m, 2H), 8.19 (d, J=7.8 Hz, 1H), 8.71 (d, J=4.5 Hz, 1H), 8.98 (br s, 1H). APCIMS m/z: [M+H]⁺ 330.

Reference Example 158

Ethyl N-[4-(2-furyl)-5-(pyridin-2-ylcarbonyl)thiazol-2-yl]carbamate (Compound 158)

¹H NMR (CDCl₃, δ ppm): 1.30 (t, J=7.0 Hz, 3H), 4.28 (q, J=7.0 Hz, 2H), 6.55 (dd, J=1.9, 3.5 Hz, 1H), 7.48 (ddd, J=0.8, 4.6, 7.6 Hz, 1H), 7.51 (dd, J=0.8, 1.9 Hz, 1H), 7.85 (dd, J=0.8, 3.5 Hz, 1H), 7.89 (ddd, J=1.9, 7.6, 7.8 Hz, 1H), 8.19 (ddd, J=0.8, 0.8, 7.8 Hz, 1H), 8.71 (ddd, J=0.8, 1.9, 4.6 Hz, 1H), 9.24 (br s, 1H). APCIMS m/z: [M+H]⁺ 344. mp: 158-159° C.

Reference Example 159

Cyclobutyl N-[4-(2-furyl)-5-(pyridin-2-ylcarbonyl)thiazol-2-yl]carbamate (Compound 159)

¹H NMR (CDCl₃, δ ppm): 1.54-1.90 (m, 2H), 2.04-2.22 (m, 2H), 2.32-2.46 (m, 2H), 5.01-5.15 (m, 1H), 6.57 (dd, J=1.8, 3.5 Hz, 1H), 7.49 (ddd, J=1.0, 4.8, 7.6 Hz, 1H), 7.54 (d, J=1.8 Hz, 1H), 7.90 (ddd, J=1.6, 7.6, 7.9 Hz, 1H), 7.91 (d, J=3.5 Hz, 1H), 8.19 (ddd, J=0.9, 1.0, 7.9 Hz, 1H), 8.72 (ddd, J=0.9, 1.6, 4.8 Hz, 1H). APCIMS m/z: [M+H]⁺ 370. mp: 152-153° C.

Reference Example 160

Cyclopentyl N-[4-(2-furyl)-5-(pyridin-2-ylcarbonyl)thiazol-2-yl]carbamate (Compound 160)

¹H NMR (CDCl₃, δ ppm): 1.55-2.01 (m, 8H), 5.25-5.35 (m, 1H), 6.57 (dd, J=1.6, 3.5 Hz, 1H), 7.49 (ddd, J=1.2, 4.6, 7.4 Hz, 1H), 7.54 (dd, J=0.7, 1.6 Hz, 1H), 7.90 (ddd, J=1.7, 7.4, 7.9 Hz, 1H), 7.90 (dd, J=0.7, 3.5 Hz, 1H), 8.19 (ddd, J=1.0, 1.2, 7.9 Hz, 1H), 8.72 (ddd, J=1.0, 1.7, 4.6 Hz, 1H). APCIMS m/z: [M+H]⁺ 384. mp: 162-163° C.

Reference Example 161

4-Tetrahydropyranyl N-[4-(2-furyl)-5-(pyridin-2-ylcarbonyl)thiazol-2-yl]carbamate (Compound 161)

¹H NMR (CDCl₃, δ ppm): 1.71-1.86 (m, 2H), 1.97-2.09 (m, 2H), 3.51-3.62 (m 2H), 3.89-4.00 (m, 2H), 5.01-5.12 (m, 1H), 6.58 (dd, J=1.8, 3.5 Hz, 1H), 7.50 (ddd, J=1.3, 4.8, 7.6 Hz, 1H), 7.56 (dd, J=0.7, 1.8 Hz, 1H), 7.91 (d, J=0.7, 3.5 Hz, 1H), 7.92 (ddd, J=1.7, 7.6, 7.9 Hz, 1H), 8.21 (ddd, J=0.8, 1.3, 7.9 Hz, 1H), 8.72 (ddd, J=0.8, 1.7, 4.8 Hz, 1H). APCIMS m/z: [M+H]⁺ 400. mp: 144-145° C.

Reference Example 162

1-Methylpiperidine-4-yl N-[4-(2-furyl)-5-(pyridin-2-ylcarbonyl)thiazol-2-yl]carbamate (Compound 162)

¹H NMR (DMSO-d₆, δ ppm): 1.59-1.74 (m, 2H), 1.87-1.99 (m, 2H), 2.11-2.25 (m, 2H), 2.19 (s, 3H), 2.59-2.70 (m, 2H), 4.70-4.81 (m, 1H), 6.61 (dd, J=1.6, 3.2 Hz, 1H), 7.41 (dd, J=0.5, 3.2 Hz, 1H), 7.60-7.70 (m, 1H), 7.68 (dd, J=0.5, 1.6 Hz, 1H), 8.03-8.08 (m, 2H), 8.64-8.69 (m, 1H). APCIMS m/z: [M+H]⁺ 413. mp: 222-225° C.

Reference Example 163

2-Fluoro-1-(fluoromethyl)ethyl N-[4-(2-furyl)-5-(pyridin-2-ylcarbonyl)thiazol-2-yl]carbamate (Compound 163)

¹H NMR (CDCl₃, δ ppm): 4.56-4.61 (m, 2H), 4.73-4.79 (m, 2H), 5.21-5.43 (m, 1H), 6.58 (dd, J=1.8, 3.6 Hz, 1H), 7.51

(ddd, J=1.3, 4.8, 7.6 Hz, 1H), 7.56 (dd, J=0.7, 1.8 Hz, 1H), 7.90 (ddd, J=1.5, 7.6, 8.1 Hz, 1H), 7.90 (dd, J=0.7, 3.6 Hz, 1H), 8.22 (ddd, J=0.8, 1.3, 8.1 Hz, 1H), 8.73 (ddd, J=0.8, 1.5, 4.8 Hz, 1H). APCIMS m/z: [M+H]⁺ 394. mp: 158-159° C.

Reference Example 164

N-[4-(2-Furyl)-5-(pyridin-2-ylcarbonyl)thiazol-2-yl] morpholine-4-carboxamide (Compound 164)

¹H NMR (CDCl₃, δ ppm): 3.51-3.59 (m, 4H), 3.68-3.75 (m, 4H), 6.58 (dd, J=1.8, 3.6 Hz, 1H), 7.48 (ddd, J=1.2, 4.8, 7.6 Hz, 1H), 7.55 (d, J=1.8 Hz, 1H), 7.89 (ddd, J=1.7, 7.6, 7.9 Hz, 1H), 7.96 (d, J=3.6 Hz, 1H), 8.18 (ddd, J=0.8, 1.2, 7.9 Hz, 1H), 8.74 (ddd, J=0.8, 1.7, 4.8 Hz, 1H). APCIMS m/z: [M+H]⁺ 385. mp: 144-145° C.

Reference Example 165

N-[4-(2-Furyl)-5-(pyridin-2-ylcarbonyl)thiazol-2-yl] piperidine-1-carboxamide (Compound 165)

¹H NMR (CDCl₃, δ ppm): 1.57-1.71 (m, 6H), 3.48-3.56 (m, 4H), 6.57 (dd, J=1.7, 3.5 Hz, 1H), 7.46 (ddd, J=1.0, 4.6, 7.6 Hz, 1H), 7.55 (d, J=1.7 Hz, 1H), 7.88 (ddd, J=1.7, 7.6, 7.9 Hz, 1H), 7.94 (d, J=3.5 Hz, 1H), 8.17 (ddd, J=1.0, 1.1, 7.9 Hz, 1H), 8.73 (ddd, J=1.1, 1.7, 4.6 Hz, 1H). APCIMS m/z: [M+H]⁺ 383. mp: 182-185° C.

Reference Example 166

N-[4-(2-Furyl)-5-(pyridin-2-ylcarbonyl)thiazol-2-yl]-N'-isopropylurea (Compound 166)

¹H NMR (DMSO-d₆, δ ppm): 1.51 (d, J=6.5 Hz, 3H), 3.30 (d, J=6.5 Hz, 3H), 3.75-3.87 (m, 1H), 6.50 (br d, J=7.3 Hz, 1H), 6.58 (dd, J=1.9, 3.5 Hz, 1H), 7.37 (dd, J=0.8, 3.5 Hz, 1H), 7.59-7.66 (m, 1H), 7.63 (dd, J=0.8, 1.9 Hz, 1H), 7.99-8.08 (m, 2H), 8.62-8.66 (m, 1H), 10.90 (br s, 1H). APCIMS m/z: [M+H]⁺ 357. mp: 182-186° C.

Reference Example 167

N-tert-Butyl-N'-[4-(2-furyl)-5-(pyridin-2-ylcarbonyl) thiazol-2-yl]urea (Compound 167)

¹H NMR (DMSO-d₆, δ ppm): 1.33 (s, 9H), 6.49 (br s, 1H), 6.59 (dd, J=1.9, 3.5 Hz, 1H), 7.40 (dd, J=0.8, 3.5 Hz, 1H), 7.59-7.62 (m, 1H), 7.65 (dd, J=0.8, 1.9 Hz, 1H), 8.00-8.09 (m, 2H), 8.65-8.69 (m, 1H), 10.71 (br s, 1H). APCIMS m/z: [M+H]⁺ 371. mp: 123-124° C.

Reference Example 168

N-[4-(2-Furyl)-5-(pyridin-2-ylcarbonyl)thiazol-2-yl]-N'-(2-methoxyethyl)urea (Compound 168)

¹H NMR (DMSO-d₆, δ ppm): 3.27-3.38 (m, 2H), 3.29 (s, 3H), 3.42 (t, J=4.9 Hz, 2H), 6.59 (dd, J=1.9, 3.5 Hz, 1H), 6.74 (t, J=5.4 Hz, 1H), 7.38 (dd, J=0.5, 3.5 Hz, 1H), 7.59-7.66 (m, 1H), 7.63 (dd, J=0.5, 1.9 Hz, 1H), 8.00-8.09 (m, 2H), 8.01-8.07 (m, 1H), 11.09 (br s, 1H). APCIMS m/z: [M+H]⁺ 373. mp: 150-151° C.

Reference Example 169

N-[4-(2-Furyl)-5-(pyridin-2-ylcarbonyl)thiazol-2-yl]-N'-(3-methoxypropyl)urea (Compound 169)

¹H NMR (DMSO-d₆, δ ppm): 1.65-1.76 (m, 2H), 3.17-3.26 (m, 2H), 3.25 (s, 3H), 3.37 (t, J=6.2 Hz, 2H), 6.58 (dd, J=1.6, 3.2 Hz, 1H), 6.67 (t, J=6.3 Hz, 1H), 7.38 (dd, J=0.8, 3.2 Hz, 1H), 7.59-7.66 (m, 1H), 7.63 (dd, J=0.8, 1.6 Hz, 1H), 7.99-8.08 (m 2H), 8.62-8.66 (m, 1H), 11.18 (br s, 1H). APCIMS m/z: [M+H]⁺ 387. mp: 169-170° C.

Reference Example 170

2-Chloro-N-[4-(2-furyl)-5-(pyridin-2-ylcarbonyl) thiazol-2-yl]acetamide (Compound 170)

¹H NMR (CDCl₃, δ ppm): 4.30 (s, 2H), 6.57 (dd, J=1.6, 3.5 Hz, 1H), 7.49 (ddd, J=1.1, 4.6, 7.6 Hz, 1H), 7.55 (dd, J=0.8, 1.6 Hz, 1H), 7.85 (dd, J=0.8, 3.5 Hz, 1H), 7.89 (ddd, J=1.9, 7.6, 8.1 Hz, 1H), 8.19 (ddd, J=1.0, 1.1, 8.1 Hz, 1H), 8.72 (ddd, J=1.0, 1.9, 4.6 Hz, 1H), 10.10 (br s, 1H). APCIMS m/z: [³⁵ClM+H]⁺ 348, [³⁷ClM+H]⁺ 350. mp: 184-185° C.

Reference Example 171

2-Bromo-N-[4-(2-furyl)-5-(pyridin-2-ylcarbonyl) thiazol-2-yl]acetamide (Compound 171)

¹H NMR (CDCl₃, δ ppm): 4.05 (s, 2H), 6.56 (dd, J=1.6, 3.5 Hz, 1H), 7.46 (ddd, J=1.4, 4.6, 7.6 Hz, 1H), 7.52 (dd, J=0.8, 1.6 Hz, 1H), 7.78 (dd, J=0.8, 3.5 Hz, 1H), 7.89 (ddd, J=1.9, 7.6, 7.8 Hz, 1H), 8.17 (ddd, J=0.8, 1.4, 7.8 Hz, 1H), 8.71 (ddd, J=0.8, 1.6, 4.6 Hz, 1H).

Reference Example 172

N-[4-(2-Furyl)-5-(pyridin-2-ylcarbonyl)thiazol-2-yl] morpholinoacetamide (Compound 172)

¹H NMR (DMSO-d₆, δ ppm): 2.48-2.62 (m, 4H), 3.36 (s, 2H), 3.58-3.64 (m, 4H), 6.62 (dd, J=1.9, 3.5 Hz, 1H), 7.41 (dd, J=0.8, 3.5 Hz, 1H), 7.63-7.70 (m, 1H), 7.68 (dd, J=0.8, 1.9 Hz, 1H), 8.05-8.10 (m, 2H), 8.66-8.70 (m, 1H). APCIMS m/z: [M+H]⁺ 399. mp: 170-171° C.

Reference Example 173

2-(cis-2,6-Dimethylmorpholino)-N-[4-(2-furyl)-5-(pyridin-2-ylcarbonyl)thiazol-2-yl]acetamide (Compound 173)

¹H NMR (DMSO-d₆, δ ppm): 1.05 (d, J=6.3 Hz, 6H), 1.84-1.97 (m, 2H), 2.74-2.82 (m, 2H), 3.34 (s, 2H), 3.55-3.68 (m, 2H), 6.61 (dd, J=1.6, 3.5 Hz, 1H), 7.40 (d, J=3.5 Hz, 1H), 7.71-7.79 (m, 2H), 8.03-8.08 (m, 2H), 8.64-8.70 (m, 1H). APCIMS m/z: [M+H]⁺ 427. mp: 188-191° C.

Reference Example 174

N-[4-(2-Furyl)-5-(pyridin-2-ylcarbonyl)thiazol-2-yl]-2-(4-methylpiperidino)acetamide (Compound 174)

¹H NMR (DMSO-d₆, δ ppm): 0.90 (d, J=6.1 Hz, 3H), 1.10-1.41 (m, 3H), 1.52-1.63 (m, 2H), 2.13-2.24 (m, 2H), 2.80-2.90 (m, 2H), 3.33 (s, 2H), 6.62 (dd, J=1.6, 3.5 Hz, 1H), 7.41 (d, J=3.5 Hz, 1H), 7.63-7.71 (m, 2H), 8.02-8.11 (m, 2H), 8.66-8.70 (m, 1H). APCIMS m/z: [M+H]+ 411. mp: 104-106° C.

Reference Example 175

N-[4-(2-Furyl)-5-(pyridin-2-ylcarbonyl)thiazol-2-yl]-2-(4-methoxypiperidino)acetamide hydrochloride (Compound 175)

$^1$H NMR (DMSO-$d_6$, δ ppm): 1.62-2.24 (m, 4H), 3.13-3.68 (m, 8H), 4.33 (s, 2H), 6.65 (dd, J=1.6, 3.5 Hz, 1H), 7.47 (d, J=3.5 Hz, 1H), 7.66-7.74 (m, 1H), 7.73 (d, J=1.6 Hz, 1H), 8.05-8.15 (m, 2H), 8.68-8.73 (m, 1H). APCIMS m/z: [M+H]+ 427. mp: 220-232° C. (dec.).

Reference Example 176

2-[3-(N,N-Diethylcarbamoyl)piperidino]-N-[4-(2-furyl)-5-(pyridin-2-ylcarbonyl)thiazol-2-yl]acetamide hydrochloride (Compound 176)

$^1$H NMR (DMSO-$d_6$, δ ppm): 1.06 (t, J=7.0 Hz, 3H), 1.17 (t, J=6.8 Hz, 3H), 1.43-2.15 (m, 4H), 3.08-3.83 (m, 9H), 4.36 (s, 2H), 6.65 (dd, J=1.9, 3.5 Hz, 1H), 7.48 (d, J=3.5 Hz, 1H), 7.66-7.77 (m, 2H), 8.05-8.15 (m, 2H), 8.70-8.76 (m, 1H). APCIMS m/z: [M+H]+ 496. mp: 180-185° C.

Reference Example 177

2-(1,4-Dioxa-8-azaspiro[4.5]decan-8-yl)-N-[4-(2-furyl)-5-(pyridin-2-ylcarbonyl)thiazol-2-yl]acetamide (Compound 177)

$^1$H NMR (DMSO-$d_6$, δ ppm): 1.62-1.70 (m, 4H), 2.58-2.66 (m, 4H), 3.39 (s, 2H), 3.86 (s, 4H), 6.62 (dd, J=1.6, 3.0 Hz, 1H), 7.42 (d, J=3.0 Hz, 1H), 7.64-7.71 (m, 2H), 8.03-8.10 (m, 2H), 8.67-8.71 (m, 1H). APCIMS m/z: [M+H]+ 455. mp: 188-204° C.

Reference Example 178

N-[4-(2-Furyl)-5-(pyridin-2-ylcarbonyl)thiazol-2-yl]-2-(4-piperidinopiperidino)acetamide (Compound 178)

$^1$H NMR (DMSO-$d_6$, δ ppm): 1.22-2.01 (m, 14H), 2.16-2.42 (m, 2H), 2.91-3.12 (m, 3H), 3.39 (s, 2H), 6.62 (dd, J=1.9, 3.5 Hz, 1H), 7.41 (d, J=3.5 Hz, 1H), 7.63-7.71 (m, 2H), 8.05-8.12 (m, 2H), 8.65-8.70 (m, 1H). APCIMS m/z: [M+H]+ 480. mp: 214-220° C. (dec.).

Reference Example 179

N-[4-(2-Furyl)-5-(pyridin-2-ylcarbonyl)thiazol-2-yl]-2-(4-morpholinopiperidino)acetamide (Compound 179)

$^1$H NMR (DMSO-$d_6$, δ ppm): 1.35-1.63 (m, 2H), 1.63-1.90 (m, 2H), 2.06-2.35 (m, 3H), 2.35-2.67 (m, 1H), 2.79-3.02 (m, 2H), 3.22-3.49 (m, 5H), 3.49-3.73 (m, 4H), 6.62 (dd, J=1.6, 3.5 Hz, 1H), 7.42 (d, J=3.5 Hz, 1H), 7.63-7.70 (m, 2H), 8.03-8.11 (m, 2H), 8.66-8.70 (m, 1H). APCIMS m/z: [M+H]+ 482. mp: 149-150° C.

Reference Example 180

N-[4-(2-Furyl)-5-(pyridin-2-ylcarbonyl)thiazol-2-yl]-2-(4-methylpiperazin-1-yl)acetamide (Compound 180)

$^1$H NMR (DMSO-$d_6$, δ ppm): 2.68 (s, 3H), 2.61-3.24 (m, 8H), 3.49 (s, 2H), 6.60-6.64 (m, 1H), 7.40-7.44 (m, 1H), 7.63-7.71 (m, 2H), 8.03-8.12 (m, 2H), 8.65-8.71 (m, 1H). APCIMS m/z: [M+H]+ 412. mp: 136-145° C.

Reference Example 181

2-(4-Ethylpiperazin-1-yl)-N-[4-(2-furyl)-5-(pyridin-2-ylcarbonyl)thiazol-2-yl]acetamide (Compound 181)

$^1$H NMR (DMSO-$d_6$, δ ppm): 0.99 (t, J=7.0 Hz, 3H), 2.32 (g, J=7.0 Hz, 2H), 2.49-2.60 (m, 4H), 3.21-3.44 (m, 4H), 3.34 (s, 2H), 6.61 (dd, J=1.9, 4.1 Hz, 1H), 7.41 (d, J=4.1 Hz, 1H), 7.62-7.70 (m, 1H), 7.68 (d, J=1.9 Hz, 1H), 8.04-8.10 (m, 2H), 8.66-8.70 (m, 1H). APCIMS m/z: [M+H]+ 426. mp: 142-144° C.

Reference Example 182

N-[4-(2-Furyl)-5-(pyridin-2-ylcarbonyl)thiazol-2-yl]-2-(4-isopropylpiperazin-1-yl)acetamide (Compound 182)

$^1$H NMR (DMSO-$d_6$, δ ppm): 0.97 (d, J=6.5 Hz, 6H), 2.43-2.68 (m, 5H), 3.25-3.36 (m, 4H), 3.33 (s, 2H), 6.61 (dd, J=1.9, 3.5 Hz, 1H), 7.41 (d, J=3.5 Hz, 1H), 7.63-7.71 (m, 2H), 8.04-8.09 (m, 2H), 8.66-8.70 (m, 1H). APCIMS m/z: [M+H]+ 440. mp: 154-155° C.

Reference Example 183

2-(4-Acetylpiperazin-1-yl)-N-[4-(2-furyl)-5-(pyridin-2-ylcarbonyl)thiazol-2-yl]acetamide (Compound 183)

$^1$H NMR (DMSO-$d_6$, δ ppm): 1.99 (s, 3H), 2.53-2.61 (m, 2H), 3.27-3.35 (m, 2H), 3.40-3.51 (m, 4H), 3.42 (s, 2H), 6.62 (dd, J=1.9, 3.5 Hz, 1H), 7.43 (d, J=3.5 Hz, 1H), 7.62-7.71 (m, 1H), 7.69 (d, J=1.9 Hz, 1H), 8.05-8.11 (m, 2H), 8.67-8.71 (m, 1H). APCIMS m/z: [M+H]+ 440. mp: 170-171° C.

Reference Example 184

N-[4-(2-Furyl)-5-(pyridin-2-ylcarbonyl)thiazol-2-yl]-2-(4-phenylpiperazin-1-yl)acetamide (Compound 184)

$^1$H NMR (DMSO-$d_6$, δ ppm): 2.66-2.74 (m, 4H), 3.13-3.21 (m, 4H), 3.43 (s, 2H), 6.61 (dd, J=1.9, 3.2 Hz, 1H), 6.78 (t, J=7.6 Hz, 1H), 6.94 (d, J=8.9 Hz, 2H), 7.21 (dd, J=7.6, 8.9 Hz, 2H), 7.40 (d, J=3.2 Hz, 1H), 7.62-7.69 (m, 2H), 8.05-8.09 (m, 2H), 8.66-8.70 (m, 1H). APCIMS m/z: [M+H]+ 474. mp: 203-204° C.

Reference Example 185

N-[4-(2-Furyl)-5-(pyridin-2-ylcarbonyl)thiazol-2-yl]-2-[4-(2-pyridyl)piperazin-1-yl]acetamide (Compound 185)

$^1$H NMR (DMSO-$d_6$, δ ppm): 2.61-2.69 (m, 4H), 3.43 (s, 2H), 3.49-3.57 (m, 4H), 6.60-6.70 (m, 2H), 6.82 (d, J=8.9 Hz, 1H), 7.42 (d, J=3.5 Hz, 1H), 7.48-7.57 (m, 1H), 7.63-7.71 (m, 2H), 8.05-8.13 (m, 3H), 8.67-8.72 (m, 1H). APCIMS m/z: [M+H]$^+$ 475. mp: 215-218° C.

Reference Example 186

N-[4-(2-Furyl)-5-(pyridin-2-ylcarbonyl)thiazol-2-yl]-2-[4-(2-pyrimidinyl)piperazin-1-yl]acetamide (Compound 186)

$^1$H NMR (DMSO-d$_6$, δ ppm): 2.55-2.65 (m, 4H), 3.43 (s, 2H), 3.73-3.82 (m, 4H), 6.62 (t, J=4.9 Hz, 1H), 6.62 (dd, J=1.9, 3.5 Hz, 1H), 7.42 (d, J=3.5 Hz, 1H), 7.63-7.70 (m, 1H), 7.68 (d, J=1.9 Hz, 1H), 8.05-8.10 (m, 2H), 8.36 (d, J=4.9 Hz, 2H), 8.67-8.71 (m, 1H), 12.60 (br s, 1H). APCIMS m/z: [M+H]$^+$ 476. mp: 199-200° C.

Reference Example 187

N-[4-(2-Furyl)-5-(pyridin-2-ylcarbonyl)thiazol-2-yl]-2-[4-(tetrahydropyran-4-yl)piperazin-1-yl]acetamide (Compound 187)

$^1$H NMR (DMSO-d$_6$, δ ppm): 1.28-1.47 (m, 2H), 1.64-1.76 (m, 2H), 2.22-2.66 (m, 7H), 3.14-3.42 (m, 6H), 3.82-3.92 (m, 2H), 6.62 (dd, J=1.6, 3.2 Hz, 1H), 7.42 (d, J=3.2 Hz, 1H), 7.63-7.71 (m, 2H), 8.02-8.11 (m, 2H), 8.66-8.70 (m, 1H). APCIMS m/z: [M+H]$^+$ 482. mp: 172-188° C.

Reference Example 188

N-[4-(2-Furyl)-5-(pyridin-2-ylcarbonyl)thiazol-2-yl]-2-(1-methyl-2-oxopiperazin-4-yl)acetamide hydrochloride (Compound 188)

$^1$H NMR (DMSO-d$_6$, δ ppm): 2.89 (s, 3H), 3.38-3.69 (m, 4H), 3.84-3.90 (m, 2H), 4.22-4.32 (m, 2H), 6.64 (dd, J=1.9, 3.5 Hz, 1H), 7.48 (d, J=3.5 Hz, 1H), 7.65-7.75 (m, 2H), 8.05-8.15 (m, 2H), 8.68-8.73 (m, 1H). APCIMS m/z: [M+H]$^+$ 426. mp: 170-188° C.

Reference Example 189

N-[4-(2-Furyl)-5-(pyridin-2-ylcarbonyl)thiazol-2-yl]-2-(1,3-thiazolidin-3-yl)acetamide (Compound 189)

$^1$H NMR (DMSO-d$_6$, δ ppm): 2.82-2.90 (m, 2H), 3.07-3.15 (m, 2H), 3.36-3.48 (m, 2H), 4.11 (s, 2H), 6.62 (dd, J=1.9, 3.5 Hz, 1H), 7.42 (d, J=3.5 Hz, 1H), 7.62-7.72 (m, 2H), 8.05-8.12 (m, 2H), 8.67-8.71 (m, 1H). APCIMS m/z: [M+H]$^+$ 401. mp: 153-155° C.

Reference Example 190

N-[4-(2-Furyl)-5-(pyridin-2-ylcarbonyl)thiazol-2-yl]-2-thiomorpholinoacetamide (Compound 190)

$^1$H NMR (DMSO-d$_6$, δ ppm): 2.60-2.69 (m, 4H), 2.78-2.86 (m, 4H), 3.41 (s, 2H), 6.62 (dd, J=1.9, 3.5 Hz, 1H), 7.42 (d, J=3.5 Hz, 1H), 7.62-7.72 (m, 2H), 8.02-8.10 (m, 2H), 8.66-8.71 (m, 1H). APCIMS m/z: [M+H]$^+$ 415. mp: 148-149° C.

Reference Example 191

N-[4-(2-Furyl)-5-(6-methoxypyridin-2-ylcarbonyl)thiazol-2-yl]pyridine-4-carboxamide (Compound 191)

$^1$H NMR (DMSO-d$_6$, δ ppm): 4.02 (s, 3H), 6.66 (dd, J=1.7, 3.5 Hz, 1H), 7.15 (d, J=8.3 Hz, 1H), 7.51 (d, J=3.5 Hz, 1H), 7.74-7.77 (m, 2H), 7.98 (dd, J=8.3, 8.3 Hz, 1H), 8.03 (d, J=6.1 Hz, 2H), 8.83 (d, J=6.1 Hz, 2H), 13.49 (br s, 1H). APCIMS m/z: [M+H]$^+$ 407. mp: 247-250° C.

Reference Example 192

N-[4-(2-Furyl)-5-(6-methylpyridin-2-ylcarbonyl)thiazol-2-yl]pyridine-4-carboxamide (Compound 192)

$^1$H NMR (DMSO-d$_6$, δ ppm): 2.56 (s, 3H), 6.64 (dd, J=1.7, 3.6 Hz, 1H), 7.44 (d, J=3.6 Hz, 1H), 7.52-7.55 (m, 1H), 7.71 (d, J=1.7 Hz, 1H), 7.89-7.99 (m, 2H), 8.05 (d, J=5.9 Hz, 2H), 8.84 (d, J=5.9 Hz, 2H), 13.49 (br s, 1H). APCIMS m/z: [M+H]$^+$ 391. mp: 238-241° C.

Reference Example 193 tert-Butyl N-[4-(2-furyl)-5-(6-methylpyridin-2-ylcarbonyl)thiazol-2-yl]carbamate (Compound 193)

$^1$H NMR (CDCl$_3$, δ ppm): 1.48 (s, 9H), 2.68 (s, 3H), 6.54 (dd, J=1.7, 3.3 Hz, 1H), 7.31 (d, J=7.6 Hz, 1H), 7.49 (d, J=1.7 Hz, 1H), 7.75 (t, J=7.6 Hz, 1H), 7.82 (d, J=3.3 Hz, 1H), 7.95 (d, J=7.6 Hz, 1H), 9.33 (br s, 1H).

Reference Example 194

2-Amino-4-(2-furyl)thiazol-5-yl 6-methylpyridin-2-yl ketone (Compound 194)

$^1$H NMR (DMSO-d$_6$, δ ppm): 2.45 (s, 3H), 6.53 (dd, J=1.8, 3.3 Hz, 1H), 7.36 (d, J=3.3 Hz, 1H), 7.39-7.42 (m, 1H), 7.54 (d, J=1.8 Hz, 1H), 7.73-7.89 (m, 2H), 8.00 (br s, 2H).

Reference Example 195

N-[4-(2-Furyl)-5-(6-methylpyridin-2-ylcarbonyl)thiazol-2-yl]-2-morpholinoacetamide (Compound 195)

$^1$H NMR (DMSO-d$_6$, δ ppm): 2.51 (s, 3H), 2.54 (t, J=4.6 Hz, 4H), 3.36 (s, 2H), 3.62 (t, J=4.6 Hz, 4H), 6.61 (dd, J=1.7, 3.5 Hz, 1H), 7.38 (d, J=3.5 Hz, 1H), 7.51 (d, J=7.6 Hz, 1H), 7.66 (d, J=1.7 Hz, 1H), 7.85-7.97 (m, 2H), 12.5 (br s, 1H). APCIMS m/z: [M+H]$^+$ 413.

Reference Example 196

N-[4-(2-Furyl)-5-(6-methylpyridin-2-ylcarbonyl)thiazol-2-yl]-2-(4-hydroxypiperidino)acetamide (Compound 196)

$^1$H NMR (CDCl$_3$, δ ppm): 1.65-1.78 (m, 2H), 1.95-2.05 (m, 2H), 2.41-2.50 (m, 2H), 2.69 (s, 3H), 2.80-2.88 (m, 2H), 3.29 (s, 2H), 3.79-3.85 (m, 1H), 6.58 (dd, J=1.7, 3.5 Hz, 1H), 7.33 (d, J=7.9 Hz, 1H), 7.56 (dd, J=0.7, 1.7 Hz, 1H), 7.77 (dd, J=7.9, 7.9 Hz, 1H), 7.85 (dd, J=0.7, 3.5 Hz, 1H), 7.98 (d, J=7.9 Hz, 1H). APCIMS m/z: [M+H]+ 427.

Reference Example 197

N-[4-(2-Furyl)-5-(6-methylpyridin-2-ylcarbonyl) thiazol-2-yl]-2-(4-methylpiperazin-1-yl)acetamide dihydrochloride (Compound 197)

$^1$H NMR (DMSO-d$_6$, δ ppm): 2.52 (s, 3H), 2.77 (s, 2H), 2.79 (s, 3H), 2.93-3.89 (m, 8H), 6.62 (dd, J=1.7, 3.3 Hz, 1H), 7.41 (d, J=3.3 Hz, 1H), 7.51-7.54 (m, 1H), 7.68 (d, J=1.7 Hz, 1H), 7.87-7.98 (m, 2H). APCIMS m/z: [M+H]+ 426.

Reference Example 198

2-(4-Ethylpiperazin-1-yl)-N-[4-(2-furyl)-5-(6-methylpyridin-2-ylcarbonyl)thiazol-2-yl]acetamide dihydrochloride (Compound 198)

$^1$H NMR (DMSO-d$_6$, δ ppm): 1.23-1.28 (m, 3H), 2.52 (s, 3H), 3.05-3.81 (m, 12H), 6.63 (dd, J=1.8, 3.3 Hz, 1H), 7.41 (d, J=3.3 Hz, 1H), 7.52-7.54 (m, 1H), 7.68 (d, J=1.8 Hz, 1H), 7.87-7.98 (m, 2H). APCIMS m/z: [M+H]+ 440.

Reference Example 199

2-(4-Acetylpiperazin-1-yl)-N-[4-(2-furyl)-5-(6-methylpyridin-2-ylcarbonyl)thiazol-2-yl]acetamide (Compound 199)

$^1$H NMR (CDCl$_3$, δ ppm): 2.12 (s, 3H), 2.70 (s, 3H), 2.59-2.64 (m, 4H), 3.33 (s, 2H), 3.56-3.74 (m, 4H), 6.58 (dd, J=1.7, 3.5 Hz, 1H), 7.34 (d, J=7.7 Hz, 1H), 7.57 (d, J=1.7 Hz, 1H), 7.78 (dd, J=7.7, 7.7 Hz, 1H), 7.88 (d, J=3.5 Hz, 1H), 7.99 (d, J=7.7 Hz, 1H), 10.39 (br s, 1H). APCIMS m/z: [M+H]+ 454.

Reference Example 200

N-[4-(2-Furyl)-5-(6-methylpyridin-2-ylcarbonyl) thiazol-2-yl]-2-[4-(2-pyridyl)piperazin-1-yl]acetamide (Compound 200)

$^1$H NMR (DMSO-d$_6$, δ ppm): 2.70 (s, 3H), 2.74 (t, J=5.1 Hz, 4H), 3.36 (s, 2H), 3.66 (t, J=5.1 Hz, 4H), 6.57 (dd, J=1.7, 3.5 Hz, 1H), 6.65-6.68 (m, 2H), 7.34 (, J=7.8 Hz, 1H), 7.48-7.54 (m, 1H), 7.55 (d, J=1.7 Hz, 1H), 7.77 (t, J=7.8 Hz, 1H), 7.85 (d, J=3.5 Hz, 1H), 7.99 (d, J=7.8 Hz, 1H), 8.20-8.22 (m, 1H), 10.45 (br s, 1H). APCIMS m/z: [M+H]+ 489.

Reference Example 201

N-[4-(2-Furyl)-5-(6-methylpyridin-2-ylcarbonyl) thiazol-2-yl]-2-(4-morpholinopiperidino)acetamide (Compound 201)

$^1$H NMR (CDCl$_3$, δ ppm): 1.58-1.87 (m, 5H), 2.28-2.36 (m, 2H), 2.57 (t, J=4.5 Hz, 4H), 2.69 (s, 3H), 2.94-2.98 (m, 2H), 3.27 (s, 2H), 3.74 (t, J=4.5 Hz, 4H), 6.57 (dd, J=1.7, 3.5 Hz, 1H), 7.33 (d, J=7.8 Hz, 1H), 7.56 (d, J=1.7 Hz, 1H), 7.77 (dd, J=7.8, 7.8 Hz, 1H), 7.84 (d, J=3.5 Hz, 1H), 7.98 (d, J=7.8 Hz, 1H). APCIMS m/z: [M+H]+ 496.

Reference Example 202

N-[4-(2-Furyl)-5-(5-methylpyridin-2-ylcarbonyl) thiazol-2-yl]pyridine-4-carboxamide (Compound 202)

$^1$H NMR (DMSO-d$_6$, δ ppm): 2.43 (s, 3H), 6.66 (dd, J=1.7, 3.5 Hz, 1H), 7.49 (dd, J=0.7, 3.5 Hz, 1H), 7.76 (dd, J=0.7, 1.7 Hz, 1H), 7.88-7.92 (m, 1H), 8.03-8.06 (m, 3H), 8.59-8.60 (m, 1H), 8.84 (d, J=6.1 Hz, 2H). APCIMS m/z: [M+H]+ 391. mp: 255-257° C.

Reference Example 203

N-[4-(2-Furyl)-5-(4-methylpyridin-2-ylcarbonyl) thiazol-2-yl]pyridine-4-carboxamide (Compound 203)

$^1$H NMR (DMSO-d$_6$, δ ppm): 2.46 (s, 3H), 6.65 (dd, J=1.7, 3.5 Hz, 1H), 7.48 (dd, J=0.7, 3.5 Hz, 1H), 7.52 (d, J=4.8 Hz, 1H), 7.75 (dd, J=0.7, 1.7 Hz, 1H), 7.96 (s, 1H), 8.05 (d, J=6.1 Hz, 2H), 8.59 (d, J=4.8 Hz, 1H), 8.84 (d, J=6.1 Hz, 2H), 13.49 (br s, 1H). APCIMS m/z: [M+H]+ 391. mp: 240-245° C.

Reference Example 204 tert-Butyl N-[4-(2-furyl)-5-(5-methoxypyridin-2-ylcarbonyl)thiazol-2-yl]carbamate (Compound 204)

$^1$H NMR (CDCl$_3$, δ ppm): 1.57 (s, 9H), 3.95 (s, 3H), 6.54 (dd, J=1.6, 3.4 Hz, 1H), 7.32 (dd, J=3.0, 8.8 Hz, 1H), 7.51 (dd, J=0.8, 1.6 Hz, 1H), 7.70 (dd, J=0.8, 3.4 Hz, 1H), 8.18 (dd, J=0.7, 8.8 Hz, 1H), 8.39 (dd, J=0.7, 3.0 Hz, 1H).

Reference Example 205

2-amino-4-(2-Furyl)thiazol-5-yl 5-methoxypyridin-2-yl ketone (Compound 205)

$^1$H NMR (DMSO-d$_6$, δ ppm): 3.91 (s, 3H), 6.56 (dd, J=1.7, 3.5 Hz, 1H), 7.44 (dd, J=0.7, 3.5 Hz, 1H), 7.56 (dd, J=3.0, 8.7 Hz, 1H), 7.63 (dd, J=0.7, 1.7 Hz, 1H), 7.92 (br s, 2H), 8.02 (d, J=9.2 Hz, 1H), 8.26 (d, J=3.0 Hz, 1H).

Reference Example 206

N-[4-(2-Furyl)-5-(5-methoxypyridin-2-ylcarbonyl) thiazol-2-yl]pyridine-4-carboxamide (Compound 206)

$^1$H NMR (DMSO-d$_6$, δ ppm): 3.97 (s, 3H), 6.64 (dd, J=1.8, 3.5 Hz, 1H), 7.43 (d, J=3.5 Hz, 1H), 7.64 (dd, J=3.0, 8.8 Hz, 1H), 7.75 (d, J=1.8 Hz, 1H), 8.05 (dd, J=1.7, 4.5 Hz, 2H), 8.15 (d, J=8.8 Hz, 1H), 8.43 (d, J=3.0 Hz, 1H), 8.84 (dd, J=1.7, 4.5 Hz, 2H), 13.46 (br s, 1H).

Reference Example 207

N-[5-(6-Bromopyridin-2-ylcarbonyl)-4-(2-furyl) thiazol-2-yl]pyridine-4-carboxamide (Compound 207)

Reference Example 208

N-[4-(2-Furyl)-5-(6-morpholinopyridin-2-ylcarbonyl)thiazol-2-yl]pyridine-4-carboxamide (Compound 208)

$^1$H NMR (DMSO-d$_6$, δ ppm): 3.60-3.64 (m, 4H), 3.75-3.79 (m, 4H), 6.66 (dd, J=1.6, 3.5 Hz, 1H), 7.15 (d, J=8.6 Hz, 1H), 7.43 (d, J=7.3 Hz 1H), 7.55 (d, J=3.5 Hz, 1H), 7.78 (d, J=1.6 Hz, 1H), 7.81 (dd, J=7.3, 8.6 Hz, 1H), 8.04 (dd, J=0.8, 5.4 Hz, 2H), 8.83 (dd, J=0.8, 5.4 Hz, 2H), 13.47 (br s, 1H). APCIMS m/z: [M+H]$^+$ 450. mp: 258-262° C.

Reference Example 209 tert-Butyl N-[4-(2-furyl)-5-(pyridin-3-ylcarbonyl)thiazol-2-yl]carbamate (Compound 209)

$^1$H NMR (CDCl$_3$, δ ppm): 1.51 (s, 9H), 6.25 (dd, J=1.9, 3.4 Hz, 1H), 6.68 (d, J=3.4 Hz, 1H), 7.03 (d, J=1.9 Hz, 1H), 7.37 (dd, J=4.9, 7.9 Hz, 1H), 8.12 (dd, J=1.9, 7.9 Hz, 1H), 8.65 (dd, J=1.9, 4.9 Hz, 1H), 9.10 (s, 1H), 10.32 (br s, 1H).

Reference Example 210

2-Amino-4-(2-furyl)thiazol-5-yl 3-pyridyl ketone (Compound 210)

$^1$H NMR (CDCl$_3$, δ ppm): 6.32 (dd, J=1.8, 3.3 Hz, 1H), 6.91 (d, J=3.3 Hz, 1H), 7.10 (d, J=1.8 Hz, 1H), 7.27-7.31 (m, 1H), 7.93-7.96 (m, 1H), 8.62-8.64 (m, 1H), 8.83-8.84 (m, 1H).

Reference Example 211

N-[4-(2-Furyl)-5-(pyridin-3-ylcarbonyl)thiazol-2-yl]pyridine-4-carboxamide (Compound 211)

$^1$H NMR (DMSO-d$_6$, δ ppm): 6.50 (dd, J=1.8, 3.5 Hz, 1H), 6.97 (d, J=3.5 Hz, 1H), 7.46 (d, J=1.8 Hz, 1H), 7.44-7.48 (m, 1H), 8.01-8.06 (m, 1H), 8.02 (d, J=6.2 Hz, 2H), 8.04-8.07 (m, 1H), 8.70-8.72 (m, 1H), 8.80-8.81 (m, 1H), 8.83 (d, J=6.2 Hz, 2H). APCIMS m/z: [M+H]$^+$ 377. mp: 245-248° C.

Reference Example 212

N-[4-(2-Furyl)-5-(pyridin-3-ylcarbonyl)thiazol-2-yl]cyclopropanecarboxamide (Compound 212)

$^1$H NMR (CDCl$_3$, δ ppm): 0.92-0.98 (m, 2H), 1.15-1.19 (m, 2H), 1.50-1.59 (m, 1H), 6.30-6.31 (m, 1H), 6.80 (s, 1H), 7.12 (s, 1H), 7.41 (dd, J=4.8, 8.0 Hz, 1H), 8.17 (dd, J=1.5, 8.0 Hz, 1H), 8.70 (dd, J=1.5, 4.8 Hz, 1H), 9.14 (s, 1H). ESIMS m/z: [M+H]$^+$ 340. mp: 231-233° C.

Reference Example 213

4-Cyano-N-[4-(2-furyl)-5-(pyridin-3-ylcarbonyl)thiazol-2-yl]benzamide (Compound 213)

$^1$H NMR (DMSO-d$_6$, δ ppm): 6.51 (dd, J=1.7, 3.2 Hz, 1H), 6.98 (d, J=3.2 Hz, 1H), 7.45-7.49 (m, 2H), 8.04-8.05 (m, 1H), 8.06 (d, J=8.1 Hz, 2H), 8.28 (d, J=8.1 Hz, 2H), 8.71 (d, J=4.8 Hz, 1H), 8.80-8.81 (m, 1H). ESIMS m/z: [M+H]$^+$ 401. mp: 288-290° C.

Reference Example 214

N-[4-(2-Furyl)-5-(pyridin-3-ylcarbonyl)thiazol-2-yl]furan-2-carboxamide (Compound 214)

$^1$H NMR (DMSO-d$_6$, δ ppm): 6.50 (dd, J=2.0, 3.3 Hz, 1H), 6.78 (dd, J=1.6, 3.5 Hz, 1H), 6.96 (d, J=3.5 Hz, 1H), 7.43-7.48 (m, 2H), 7.79 (s, 1H), 8.03 (d, J=7.9 Hz, 1H), 8.07 (s, 1H), 8.70 (dd, J=1.6, 4.9 Hz, 1H), 8.80 (d, J=2.2 Hz, 1H), 13.34 (br s, 1H). ESIMS m/z: [M+H]$^+$ 366. mp: 234-236° C.

Reference Example 215 tert-Butyl N-[4-(2-furyl)-5-(2-methylpyridin-3-ylcarbonyl)thiazol-2-yl]carbamate (Compound 215)

$^1$H NMR (CDCl$_3$, δ ppm): 1.43 (s, 9H), 2.61 (s, 3H), 6.41 (dd, J=1.8, 3.5 Hz, 1H), 7.05-7.10 (m, 1H), 7.24 (d, J=1.8 Hz, 1H), 7.40 (d, J=3.5 Hz, 1H), 7.57-7.60 (m, 1H), 8.52-8.54 (m, 1H).

Reference Example 216

2-Amino-4-(2-furyl)thiazol-5-yl 2-methylpyridin-3-yl ketone (Compound 216)

$^1$H NMR (CDCl$_3$, δ ppm): 2.53 (s, 3H), 6.12-6.14 (m, 1H), 6.93-7.05 (m, 2H), 7.44-7.47 (m, 1H), 8.19-8.21 (m, 1H), 8.51-8.54 (m, 1H).

Reference Example 217

N-[4-(2-Furyl)-5-(2-methylpyridin-3-ylcarbonyl)thiazol-2-yl]pyridine-4-carboxamide (Compound 217)

$^1$H NMR (DMSO-d$_6$, δ ppm): 2.53 (s, 3H), 6.53 (dd, J=1.7, 3.5 Hz, 1H), 7.15 (dd, J=0.7, 3.5 Hz, 1H), 7.21 (dd, J=4.8, 7.7 Hz, 1H), 7.55 (dd, J=0.7, 1.7 Hz, 1H), 7.75 (dd, J=1.8, 7.7 Hz, 1H), 8.01 (d, J=6.1 Hz, 2H), 8.53 (dd, J=1.8, 4.8 Hz, 1H), 8.84 (d, J=6.1 Hz, 2H), 13.7 (br s, 1H). APCIMS m/z: [M+H]$^+$ 391. mp: 230-234° C.

Reference Example 218 tert-Butyl N-[4-(2-furyl)-5-(2-methylpyridine-5-ylcarbonyl)thiazol-2-yl]carbamate (Compound 218)

$^1$H NMR (CDCl$_3$, δ ppm): 1.49 (s, 9H), 3.31 (s, 3H), 6.48 (dd, J=1.7, 3.3 Hz, 1H), 6.91 (d, J=3.3 Hz, 1H), 7.29 (d, J=8.3 Hz, 1H), 7.46 (d, J=1.7 Hz, 1H), 7.89 (dd, J=2.3, 8.3 Hz, 1H), 8.65 (d, J=2.3 Hz, 1H), 12.2 (br s, 1H).

Reference Example 219

2-Amino-4-(2-furyl)thiazol-5-yl 2-methylpyridine-5-yl ketone (Compound 219)

$^1$H NMR (DMSO-d$_6$, δ ppm): 2.45 (s, 3H), 6.41 (dd, J=1.7, 3.3 Hz, 1H), 6.79 (d, J=3.3 Hz, 1H), 7.20 (d, J=7.9 Hz, 1H), 7.32 (d, J=1.7 Hz, 1H), 7.75 (dd, J=2.3, 7.9 Hz, 1H), 8.51 (d, J=2.3 Hz, 1H).

Reference Example 220

N-[4-(2-Furyl)-5-(2-methylpyridin-5-ylcarbonyl)thiazol-2-yl]pyridine-4-carboxamide (Compound 220)

$^1$H NMR (DMSO-d$_6$, δ ppm): 2.51 (s, 3H), 6.52 (dd, J=1.8, 3.5 Hz, 1H), 6.97 (dd, J=0.7, 3.5 Hz, 1H), 7.32 (d, J=8.1 Hz, 1H), 7.50 (dd, J=0.7, 1.8 Hz, 1H), 7.95 (dd, J=2.3, 8.1 Hz, 1H), 8.02 (d, J=6.1 Hz, 2H), 8.70 (d, J=2.3 Hz, 1H), 8.83 (d, J=6.1 Hz, 2H), 13.6 (s, 1H). APCIMS m/z: [M+H]$^+$ 391. mp: 230-232° C. (dec.).

Reference Example 221

4-Cyano-N-[4-(2-furyl)-5-(2-methylpyridin-5-ylcarbonyl)thiazol-2-yl]benzamide (Compound 221)

$^1$H NMR (DMSO-d$_6$, δ ppm): 2.51 (s, 3H), 6.52 (dd, J=1.7, 3.5 Hz, 1H), 6.97 (dd, J=0.8, 3.5 Hz, 1H), 7.32 (d, J=8.1 Hz, 1H), 7.51 (dd, J=0.8, 1.7 Hz, 1H), 7.95 (dd, J=2.3, 8.1 Hz, 1H), 8.06 (d, J=8.4 Hz, 2H), 8.26 (d, J=8.4 Hz, 2H), 8.70 (d, J=2.3 Hz, 1H), 13.6 (br s, 1H). APCIMS m/z: [M+H]$^+$ 415. mp: 261-265° C.

Reference Example 222

N-[4-(2-Furyl)-5-(2-methylpyridin-5-ylcarbonyl)thiazol-2-yl]furan-2-carboxamide (Compound 222)

$^1$H NMR (DMSO-d$_6$, δ ppm): 2.51 (s, 3H), 6.50 (dd, J=1.8, 3.3 Hz, 1H), 6.76 (dd, J=1.8, 3.5 Hz, 1H), 6.94 (d, J=3.3 Hz, 1H), 7.30 (d, J=8.1 Hz, 1H), 7.48 (d, J=1.8 Hz, 1H), 7.77 (d, J=3.5 Hz, 1H), 7.92 (dd, J=2.1, 8.1 Hz, 1H), 8.05 (d, J=1.8 Hz, 1H), 8.68 (d, J=2.1 Hz, 1H), 13.3 (br s, 1H). APCIMS m/z: [M+H]$^+$ 380. mp: 197-209° C.

Reference Example 223

N-[4-(2-Furyl)-5-(2-methylpyridin-5-ylcarbonyl)thiazol-2-yl]furan-3-carboxamide (Compound 223)

$^1$H NMR (DMSO-d$_6$, δ ppm): 2.47 (s, 3H), 6.50 (dd, J=1.8, 3.5 Hz, 1H), 6.94 (d, J=3.5 Hz, 1H), 7.11-7.12 (m, 1H), 7.30 (d, J=8.1 Hz, 1H), 7.47 (d, J=1.8 Hz, 1H), 7.84-7.86 (m, 1H), 7.92 (dd, J=2.3, 8.1 Hz, 1H), 8.63-8.64 (m, 1H), 8.67 (d, J=2.3 Hz, 1H). APCIMS m/z: [M+H]$^+$ 380. mp: 229-231° C.

Reference Example 224 tert-Butyl N-[4-(2-furyl)-5-(2-methoxypyridin-5-ylcarbonyl)thiazol-2-yl]carbamate (Compound 224)

$^1$H NMR (CDCl$_3$, δ ppm): 1.47 (s, 9H), 3.99 (s, 3H), 6.39 (dd, J=1.8, 3.3 Hz, 1H), 6.74 (dd, J=0.9, 8.4 Hz, 1H), 6.98 (d, J=0.6, 3.3 Hz, 1H), 7.23 (dd, J=0.9, 2.4 Hz, 1H), 8.02 (dd, J=2.4, 8.4 Hz, 1H), 8.66 (dd, J=0.6, 1.8 Hz, 1H), 9.48 (br s, 1H). APCIMS m/z: [M+H]$^+$ 402.

Reference Example 225

2-Amino-4-(2-furyl)thiazol-5-yl 2-methoxypyridine-5-yl ketone (Compound 225)

$^1$H NMR (DMSO-d$_6$, δ ppm): 3.85 (s, 3H), 6.43 (dd, J=1.6, 3.2 Hz, 1H), 6.74 (d, J=8.7 Hz, 1H), 6.77 (d, J=3.2 Hz, 1H), 7.37 (d, J=1.6 Hz, 1H), 7.81 (dd, J=2.4, 8.7 Hz, 1H), 8.03 (br s, 2H), 8.32 (d, J=2.4 Hz, 1H). APCIMS m/z: [M+H]$^+$ 302.

Reference Example 226

N-[4-(2-Furyl)-5-(2-methoxypyridin-5-ylcarbonyl)thiazol-2-yl]pyridine-4-carboxamide (Compound 226)

$^1$H NMR (DMSO-d$_6$, δ ppm): 3.91 (s, 3H), 6.54 (dd, J=1.9, 3.5 Hz, 1H), 6.87 (dd, J=0.8, 8.4 Hz, 1H), 6.95 (dd, J=0.8, 3.5 Hz, 1H), 7.54 (dd, J=0.8, 1.9 Hz, 1H), 8.01 (dd, J=2.7, 8.4 Hz, 1H), 8.03 (dd, J=1.3, 5.4 Hz, 2H), 8.52 (dd, J=0.8, 2.7 Hz, 1H), 8.81 (dd, J=1.3, 5.4 Hz, 2H), 13.60 (br s, 1H). APCIMS m/z: [M+H]$^+$ 407. mp: 246-257° C. (dec.).

Reference Example 227 tert-Butyl N-[5-(2-chloropyrimidin-5-ylcarbonyl)-4-(2-furyl)thiazol-2-yl]carbamate (Compound 227)

$^1$H NMR (CDCl$_3$, δ ppm): 1.53 (s, 9H), 6.41 (dd, J=1.9, 3.5 Hz, 1H), 7.02 (dd, J=0.5, 3.5 Hz, 1H), 7.21 (dd, J=0.5, 1.9 Hz, 1H), 7.34 (dd, 0.5, 8.1 Hz, 1H), 7.98 (dd, J=2.4, 8.1 Hz, 1H), 8.59 (br s, 1H), 8.71 (dd, J=0.5, 2.4 Hz, 1H).

Reference Example 228

2-Amino-4-(2-furyl)thiazol-5-yl 2-chloropyridine-5-yl ketone (Compound 228)

$^1$H NMR (DMSO-d$_6$, δ ppm): 6.45 (dd, J=1.6, 3.2 Hz, 1H), 6.79 (d, J=3.2 Hz, 1H), 7.35 (d, J=1.6 Hz, 1H), 7.47 (d, J=8.1 Hz, 1H), 7.90 (dd, J=2.2, 8.1 Hz, 1H), 8.22 (br s, 2H), 8.45 (d, J=2.2 Hz, 1H). APCIMS m/z: [M+H]$^+$ 306.

Reference Example 229

N-[5-(2-Chloropyridin-5-ylcarbonyl)-4-(2-furyl)thiazol-2-yl]pyridine-4-carboxamide (Compound 229)

$^1$H NMR (DMSO-d$_6$, δ ppm): 6.54 (dd, J=1.6, 3.2 Hz, 1H), 6.93 (d, J=1.6 Hz, 1H), 7.50-7.56 (m, 2H), 7.67-7.69 (m, 1H), 8.02 (d, J=6.0 Hz, 2H), 8.33-8.35 (m, 1H), 8.63 (d, J=6.0 Hz, 2H), 13.65 (br s, 1H). APCIMS m/z: [$^{35}$ClM−H]$^-$ 409, [$^{37}$ClM−H]$^-$ 411.

Reference Example 230

N-{5-[2-(Dimethylamino)pyridin-5-ylcarbonyl]-4-(2-furyl)thiazol-2-yl}pyridine-4-carboxamide (Compound 230)

$^1$H NMR (DMSO-d$_6$, δ ppm): 3.12 (s, 6H), 6.55 (dd, J=1.6, 3.2 Hz, 1H), 6.67 (d, J=8.6 Hz, 1H), 6.88 (d, J=3.2 Hz, 1H), 7.61 (d, J=1.6 Hz, 1H), 7.86 (dd, J=2.4, 8.6 Hz, 1H), 8.03 (dd, J=1.6, 4.6 Hz, 2H) 8.47 (d, J=2.4 Hz, 1H), 8.84 (dd, J=1.6, 4.6 Hz, 2H), 13.51 (br s, 1H). APCIMS m/z: [M+H]$^+$ 420. mp: 260-265° C. (dec.).

Reference Example 231

N-[4-(2-Furyl)-5-(2-morpholinopyridin-5-ylcarbonyl)thiazol-2-yl]pyridine-4-carboxamide (Compound 231)

$^1$H NMR (DMSO-d$_6$, δ ppm): 3.25-3.35 (m, 4H), 3.60-3.70 (m, 4H), 6.55 (dd, J=1.9, 3.2 Hz, 1H), 6.86 (d, J=9.2 Hz, 1H), 6.90 (dd, J=0.8, 3.2 Hz, 1H), 7.61 (dd, J=0.8, 1.9 Hz, 1H), 7.88 (dd, J=2.4, 9.2 Hz, 1H), 8.03 (dd, J=1.6, 6.2 Hz, 2H), 8.48 (d, J=2.4 Hz, 1H), 8.84 (dd, J=1.6, 6.2 Hz, 2H), 13.52 (br s, 1H). APCIMS m/z: [M+H]$^+$ 462. mp: 195-20° C.

Reference Example 232

N-{4-(2-Furyl)-5-[2-(4-methylpiperazin-1-yl)pyridin-5-ylcarbonyl]thiazol-2-yl}pyridine-4-carboxamide (Compound 232)

$^1$H NMR (DMSO-d$_6$, δ ppm): 2.28 (s, 3H), 2.47-2.50 (m, 4H), 3.65-3.75 (m, 4H), 6.55 (dd, J=1.6, 3.2 Hz, 1H), 6.87 (d, J=9.2 Hz, 1H), 6.90 (d, J=3.2 Hz, 1H), 7.60 (d, J=1.6 Hz, 1H), 7.86 (dd, J=2.4, 9.2 Hz, 1H), 8.02 (dd, J=1.4, 4.5 Hz, 2H), 8.47 (d, J=2.4 Hz, 1H), 8.81 (dd, J=1.4, 4.5 Hz, 2H). APCIMS m/z: [M+H]⁺ 475. mp: 195-205° C.

Reference Example 233

N-{4-(2-Furyl)-5-[2-(4-hydroxypiperidino)pyridin-5-ylcarbonyl]thiazol-2-yl}pyridine-4-carboxamide (Compound 233)

¹H NMR (DMSO-d₆, δ ppm): 1.28-1.41 (m, 2H), 1.75-1.80 (m, 2H), 3.16-3.17 (m, 2H), 3.72-3.78 (m, 1H), 4.06-4.12 (m, 2H), 4.76 (d, J=4.0 Hz, 1H), 6.55 (dd, J=1.6, 3.5 Hz, 1H), 6.86 (d, J=9.2 Hz, 1H), 6.88 (dd, J=0.8, 3.5 Hz, 1H), 7.60 (dd, J=0.8, 1.6 Hz, 1H), 7.83 (dd, J=2.4, 9.2 Hz, 1H), 8.03 (dd, J=1.6, 4.6 Hz, 2H), 8.45 (d, J=2.4 Hz, 1H), 8.84 (dd, J=1.6, 4.6 Hz, 2H), 13.51 (br s, 1H). APCIMS m/z: [M+H]⁺ 476. mp: 264-268° C.

Reference Example 234 tert-Butyl N-[4-(2-furyl)-5-(pyridin-4-ylcarbonyl)thiazol-2-yl]carbamate (Compound 234)

¹H NMR (CDCl₃, δ ppm): 1.51 (s, 9H), 6.40 (dd, J=1.7, 3.3 Hz, 1H), 7.14 (d, J=3.3 Hz, 1H), 7.16 (d, J=1.7 Hz, 1H), 7.55 (d, J=6.1 Hz, 2H), 8.67 (d, J=6.1 Hz, 2H).

Reference Example 235

2-Amino-4-(2-furyl)thiazol-5-yl 4-pyridyl ketone (Compound 235)

¹H NMR (CDCl₃, δ ppm): 5.68 (br s, 2H), 6.35 (dd, J=1.8, 3.3 Hz, 1H), 6.98 (d, J=3.3 Hz, 1H), 7.04 (d, J=1.8 Hz, 1H), 7.51 (d, J=6.1 Hz, 2H), 8.62 (d, J=6.1 Hz, 2H).

Reference Example 236

N-[4-(2-Furyl)-5-(pyridin-4-ylcarbonyl)thiazol-2-yl]pyridine-4-carboxamide (Compound 236)

¹H NMR (DMSO-d₆, δ ppm): 6.53 (dd, J=1.8, 3.5 Hz, 1H), 7.05 (dd, J=0.7, 3.5 Hz, 1H), 7.47 (dd, J=0.7, 1.8 Hz, 1H), 7.55 (d, J=5.8 Hz, 2H), 8.03 (d, J=6.1 Hz, 2H), 8.65 (d, J=5.8 Hz, 2H), 8.84 (d, J=6.1 Hz, 2H). APCIMS m/z: [M+H]⁺ 377. mp: 276-285° C.

Reference Example 237 tert-Butyl N-[4-(2-furyl)-5-(2-methylpyridin-4-ylcarbonyl)thiazol-2-yl]carbamate (Compound 237)

¹H NMR (CDCl₃, δ ppm): 1.53 (s, 9H), 2.57 (s, 3H), 6.42 (dd, J=1.7, 3.5 Hz, 1H), 7.20 (d, J=3.5 Hz, 1H), 7.24 (d, J=1.7 Hz, 1H), 7.30 (d, J=5.1 Hz, 1H), 7.35 (s, 1H), 8.56 (d, J=5.1 Hz, 1H).

Reference Example 238

2-Amino-4-(2-furyl)thiazol-5-yl 2-methylpyridin-4-yl ketone (Compound 238)

¹H NMR (CDCl₃, δ ppm): 2.53 (s, 3H), 5.67 (br s, 2H), 6.36 (dd, J=1.8, 3.5 Hz, 1H), 7.03 (d, J=3.5 Hz, 1H), 7.14 (d, J=1.8 Hz, 1H), 7.24 (d, J=5.1 Hz, 1H), 7.28 (s, 1H), 8.50 (d, J=5.1 Hz, 1H).

Reference Example 239

N-[4-(2-Furyl)-5-(2-methylpyridin-4-ylcarbonyl)thiazol-2-yl]pyridine-4-carboxamide (Compound 239)

¹H NMR (CDCl₃, δ ppm): 2.59 (s, 3H), 6.38 (dd, J=1.7, 3.5 Hz, 1H), 7.17 (d, J=3.5 Hz, 1H), 7.22 (d, J=1.7 Hz, 1H), 7.35 (d, J=5.1 Hz, 1H), 7.40 (s, 1H), 7.76 (d, J=6.1 Hz, 2H), 8.59 (d, J=5.1 Hz, 1H), 8.85 (d, J=6.1 Hz, 2H). APCIMS m/z: [M+H]⁺ 391. mp: 223-225° C.

Reference Example 240

N-[4-(2-Furyl)-5-(2-methylpyridin-4-ylcarbonyl)thiazol-2-yl]-2-methylpyridine-4-carboxamide (Compound 240)

¹H NMR (DMSO-d₆, δ ppm): 2.47 (s, 3H), 2.59 (s, 3H), 6.54 (dd, J=1.8, 3.3 Hz, 1H), 7.05 (d, J=3.3 Hz, 1H), 7.35 (d, J=5.1 Hz, 1H), 7.40 (s, 1H), 7.48 (d, J=1.8 Hz, 1H), 7.83 (d, J=5.0 Hz, 1H), 7.92 (s, 1H), 8.54 (d, J=5.0 Hz, 1H), 8.69 (d, J=5.1 Hz, 1H), 13.6 (br s, 1H). APCIMS m/z: [M+H]⁺ 405. mp: 205-229° C.

Reference Example 241 tert-Butyl N-[4-(2-furyl)-5-(2-methoxypyridin-4-ylcarbonyl)thiazol-2-yl]carbamate (Compound 241)

¹H NMR (CDCl₃, δ ppm): 1.47 (s, 9H), 3.94 (s, 3H), 6.44 (dd, J=1.9, 3.5 Hz, 1H), 6.96 (dd, J=0.8, 1.4 Hz, 1H), 7.09 (dd, J=1.4, 5.1 Hz, 1H), 7.28-7.34 (m, 2H), 8.21 (dd, J=0.8, 5.1 Hz, 1H), 9.26 (br s, 1H). APCIMS m/z: [M+H]⁺ 402.

Reference Example 242

2-Amino-4-(2-furyl)thiazol-5-yl 2-methoxypyridin-4-yl ketone (Compound 242)

¹H NMR (DMSO-d₆, δ ppm): 3.82 (s, 3H), 6.45 (dd, J=1.6, 3.2 Hz, 1H), 6.75 (dd, J=0.8, 1.4 Hz, 1H), 6.92 (dd, J=0.5, 3.2 Hz, 1H), 6.96 (dd, J=1.4, 5.1 Hz, 1H), 7.35 (dd, J=0.5, 1.6 Hz, 1H), 8.13 (dd, J=0.8, 5.1 Hz, 1H), 8.22 (br s, 2H). APCIMS m/z: [M+H]⁺ 302.

Reference Example 243

N-[4-(2-Furyl)-5-(2-methoxypyridin-4-ylcarbonyl)thiazol-2-yl]pyridine-4-carboxamide (Compound 243)

¹H NMR (DMSO-d₆, δ ppm): 3.87 (s, 3H), 6.54-6.58 (m, 1H), 6.96 (s, 1H), 7.12 (d, J=3.2 Hz, 1H), 7.16 (d, J=5.1 Hz, 1H), 7.55 (s, 1H), 8.03 (d, J=4.9 Hz, 2H), 8.26 (d, J=5.1 Hz, 1H), 8.84 (d, J=4.9 Hz, 2H), 13.69 (br s, 1H). APCIMS m/z: [M+H]⁺ 407. mp: 237-239° C.

Reference Example 244 tert-Butyl N-[4-(2-furyl)-5-(2-morpholinopyridin-4-ylcarbonyl)thiazol-2-yl]carbamate (Compound 244)

¹H NMR (CDCl₃, δ ppm): 1.49 (s, 9H), 3.49 (t, J=4.8 Hz, 4H), 3.80 (t, J=4.8 Hz, 4H), 6.44 (dd, J=1.8, 3.6 Hz, 1H), 6.82-6.84 (m, 1H), 6.86 (dd, J=1.8, 4.8 Hz, 1H), 7.24-7.27 (m, 1H), 7.30-7.32 (m, 1H), 8.23 (dd, J=0.6, 4.8 Hz, 1H), 9.11 (br s, 1H). APCIMS m/z: [M+H]⁺ 457.

Reference Example 245

2-Amino-4-(2-furyl)thiazol-5-yl 2-morpholinopyridin-4-yl ketone (Compound 245)

¹H NMR (DMSO-d₆, δ ppm): 3.33 (t, J=5.1 Hz, 4H), 3.64 (t, J=5.1 Hz, 4H), 6.46 (dd, J=1.6, 3.5 Hz, 1H), 6.70 (dd, J=0.8, 3.5 Hz, 1H), 6.71-6.72 (m, 1H), 6.92 (d, J=3.5 Hz, 1H), 7.36-7.38 (m, 1H), 8.12 (d, J=5.1 Hz, 1H), 8.16 (br s, 2H). APCIMS m/z: [M+H]⁺ 357.

Reference Example 246

N-[4-(2-Furyl)-5-(2-morpholinopyridin-4-ylcarbonyl)thiazol-2-yl]pyridine-4-carboxamide (Compound 246)

¹H NMR (DMSO-d₆, δ ppm): 3.40 (dd, J=4.1, 5.1 Hz, 4H), 3.66 (dd, J=4.1, 5.1 Hz, 4H), 6.57 (dd, J=1.6, 3.2 Hz, 1H), 6.86 (d, J=4.9 Hz, 1H), 6.93 (s, 1H), 7.10 (d, J=3.2 Hz, 1H), 7.56 (d, J=1.6 Hz, 1H), 8.03 (dd. J=1.6, 4.4 Hz, 2H), 8.22 (d, J=4.9 Hz, 1H), 8.84 (dd, J=1.6, 4.4 Hz, 2H), 13.67 (br s, 1H). APCIMS m/z: [M+H]⁺ 462. mp: 270-273° C.

Reference Example 247 tert-Butyl N-[4-(furan-2-yl)-5-(furan-2-ylcarbonyl)thiazol-2-yl]carbamate (Compound 247)

¹H NMR (CDCl₃, δ ppm): 1.51 (s, 9H), 6.47 (dd, J=1.8, 3.3 Hz, 1H), 6.53 (dd, J=1.7, 3.5 Hz, 1H), 7.28 (d, J=3.3 Hz, 1H), 7.45-7.46 (m, 2H), 7.60 (d, J=1.7 Hz, 1H).

Reference Example 248

2-Amino-4-(furan-2-yl)thiazol-5-yl furan-2-yl ketone (Compound 248)

¹H NMR (CDCl₃, δ ppm): 6.45-6.46 (m, 1H), 6.49-6.51 (m, 1H), 7.17-7.18 (m, 1H), 7.40-7.44 (m, 2H), 7.51-7.52 (m, 1H).

Reference Example 249

N-[4-(Furan-2-yl)-5-(furan-2-ylcarbonyl)thiazol-2-yl]pyridine-4-carboxamide (Compound 249)

¹H NMR (DMSO-d₆, δ ppm): 6.60 (dd, J=1.8, 3.7 Hz, 1H), 6.73 (dd, J=1.5, 3.7 Hz, 1H), 7.09 (d, J=3.7 Hz, 1H), 7.32 (d, J=3.7 Hz, 1H), 7.68 (d, J=1.8 Hz, 1H), 8.00 (d, J=1.5 Hz, 1H), 8.01 (d, J=5.5 Hz, 2H), 8.82 (d, J=5.5 Hz, 2H). APCIMS m/z: [M+H]⁺ 366. mp: 245-248° C.

Reference Example 250

N-[4-(2-Furyl)-5-(5-methylfuran-2-ylcarbonyl)thiazol-2-yl]pyridine-4-carboxamide (Compound 250)

¹H NMR (DMSO-d₆, δ ppm): 2.41 (s, 3H), 6.21 (d, J=3.5 Hz, 1H), 6.44 (dd, J=1.8, 3.5 Hz, 1H), 7.26 (d, J=3.5 Hz, 1H), 7.32 (dd, J=0.7, 3.5 Hz, 1H), 7.41 (dd, J=0.7, 1.8 Hz, 1H), 7.75 (d, J=6.1 Hz, 2H), 8.85 (d, J=6.1 Hz, 2H). APCIMS m/z: [M+H]⁺ 380. mp: 185-189° C.

Reference Example 251 tert-Butyl N-[4-(furan-2-yl)-5-(furan-3-ylcarbonyl)thiazol-2-yl]carbamate (Compound 251)

¹H NMR (CDCl₃, δ ppm): 1.50 (s, 9H), 6.44-6.48 (m, 1H), 6.82-6.83 (m, 1H), 7.31-7.45 (m, 3H), 7.94-7.96 (m, 1H), 8.67 (br s, 1H).

Reference Example 252

2-Amino-4-(2-furyl)thiazol-5-yl furan-3-yl ketone (Compound 252)

¹H NMR (CDCl₃, δ ppm): 6.39 (dd, J=1.8, 3.7 Hz, 1H), 6.67 (dd, J=0.7, 1.8 Hz, 1H), 7.21 (dd, J=0.7, 3.7 Hz, 1H), 7.32-7.33 (m, 1H), 7.34-7.35 (m, 1H), 7.78-7.79 (m, 1H).

Reference Example 253

N-[4-(Furan-2-yl)-5-(furan-3-ylcarbonyl)thiazol-2-yl]pyridine-4-carboxamide (Compound 253)

¹H NMR (DMSO-d₆, δ ppm): 6.61 (dd, J=1.8, 3.5 Hz, 1H), 6.83-6.84 (m, 1H), 7.09 (dd, J=0.8, 3.5 Hz, 1H), 7.71 (dd, J=0.8, 1.8 Hz, 1H), 7.83-7.84 (m, 1H), 8.03 (d, J=5.9 Hz, 2H), 8.31-8.32 (m, 1H), 8.84 (d, J=5.9 Hz, 2H). APCIMS m/z: [M+H]⁺ 366. mp: 217-231° C.

Reference Example 254

N-[4-(2-Furyl)-5-(thiophen-2-ylcarbonyl)thiazol-2-yl]-pyridine-4-carboxamide (Compound 254)

¹H NMR (DMSO-d₆, δ ppm): 6.59 (dd, J=1.8, 3.5 Hz, 1H), 7.02 (d, J=3.5 Hz, 1H), 7.20 (dd, J=3.9, 5.2 Hz, 1H), 7.67 (d, J=1.8 Hz, 1H), 7.68 (dd, J=1.1, 3.9 Hz, 1H), 8.03 (d, J=6.1 Hz, 2H), 8.09 (dd, J=1.1, 5.2 Hz, 1H), 8.84 (d, J=6.1 Hz, 2H), 13.6 (br s, 1H). APCIMS m/z: [M+H]⁺ 382. mp: 208-210° C.

Reference Example 255

N-[4-(2-Furyl)-5-(thiazol-2-ylcarbonyl)thiazol-2-yl]pyridine-4-carboxamide (Compound 255)

¹H NMR (DMSO-d₆, δ ppm): 6.72 (dd, J=1.7, 3.5 Hz, 1H), 7.73 (d, J=3.5 Hz, 1H), 7.89 (d, J=1.7 Hz, 1H), 8.06 (d, J=6.1 Hz, 2H), 8.26 (d, J=3.1 Hz, 1H), 8.30 (d, J=3.1 Hz, 1H), 8.85 (d, J=6.1 Hz, 2H), 13.7 (br s, 1H). APCIMS m/z: [M+H]⁺ 383. mp: 228-240° C.

Reference Example 256

N-[4-(2-Furyl)-5-(5-methylthiazol-2-ylcarbonyl)thiazol-2-yl]pyridine-4-carboxamide (Compound 256)

¹H NMR (DMSO-d₆, δ ppm): 2.59 (s, 3H), 6.71 (dd, J=1.8, 3.5 Hz, 1H), 7.71 (d, J=3.5 Hz, 1H), 7.88 (d, J=1.8 Hz, 1H), 7.96 (s, 1H), 8.05 (d, J=6.1 Hz, 2H), 8.85 (d, J=6.1 Hz, 2H), 13.6 (br s, 1H). APCIMS m/z: [M+H]⁺ 397. mp: 275-277° C. (dec.).

Reference Example 257

N-[4-(2-Furyl)-5-(4-methylthiazol-2-ylcarbonyl)thiazol-2-yl]pyridine-4-carboxamide (Compound 257)

$^1$H NMR (DMSO-d$_6$, δ ppm): 2.50 (s, 3H), 6.69 (dd, J=1.8, 3.5 Hz, 1H), 7.64 (d, J=3.5 Hz, 1H), 7.83-7.85 (m, 2H), 8.04 (d, J=6.1 Hz, 2H), 8.83 (d, J=6.1 Hz, 2H), 13.6 (br s, 1H). APCIMS m/z: [M+H]$^+$ 397. mp: 250-255° C.

Reference Example 258

N-[5-(4,5-Dimethylthiazol-2-ylcarbonyl)-4-(2-furyl)thiazol-2-yl]pyridine-4-carboxamide (Compound 258)

$^1$H NMR (DMSO-d$_6$, δ ppm): 2.41 (s, 3H), 2.48 (s, 3H), 6.69 (dd, J=1.8, 3.5 Hz, 1H), 7.64 (dd, J=0.7, 3.5 Hz, 1H), 7.86 (dd, J=0.7, 1.8 Hz, 1H), 8.05 (d, J=6.1 Hz, 2H), 8.84 (d. J=6.1 Hz, 2H), 13.6 (br s, 1H). APCIMS m/z: [M+H]$^+$ 411. mp: 270-272° C. (dec.).

Reference Example 259

N-{4-(2-Furyl)-5-[1-(triisopropylsilyl)pyrrol-3-ylcarbonyl]thiazol-2-yl}pyridine-4-carboxamide (Compound 259)

$^1$H NMR (DMSO-d$_6$, δ ppm): 0.96-1.03 (m, 18H), 1.41-1.49 (m, 3H), 6.52 (dd, J=1.8, 3.5 Hz, 1H), 6.64-6.65 (m, 1H), 6.91-6.92 (m, 2H), 7.31-7.32 (m, 1H), 7.80 (dd, J=0.7, 1.8 Hz, 1H), 8.00 (d, J=6.1 Hz, 2H), 8.80 (d, J=6.1 Hz, 2H).

Reference Example 260

N-[4-(2-Furyl)-5-(pyrrol-3-ylcarbonyl)thiazol-2-yl]pyridine-4-carboxamide (Compound 260)

$^1$H NMR (DMSO-d$_6$, δ ppm): 6.51-6.54 (m, 1H), 6.57 (dd, J=1.8, 3.3 Hz, 1H), 6.89-6.90 (m, 1H), 6.97 (d, J=3.3 Hz, 1H), 7.41-7.42 (m, 1H), 7.68 (d, J=1.8 Hz, 1H), 8.03 (d, J=6.1 Hz, 2H), 8.83 (d, J=6.1 Hz, 2H), 11.6 (br s, 1H), 13.5 (br s, 1H). mp: 259-260° C.

Reference Example 261

N-[4-(2-Furyl)-5-(1-methylpyrrol-3-ylcarbonyl)thiazol-2-yl]pyridine-4-carboxamide (Compound 261)

$^1$H NMR (DMSO-d$_6$, δ ppm): 3.69 (s, 3H), 6.36 (dd, J=1.8, 3.5 Hz, 1H), 6.61-6.62 (m, 1H), 6.71-6.72 (m, 1H), 7.16 (d, J=3.5 Hz, 1H), 7.29 (d, J=1.8 Hz, 1H), 7.33-7.34 (m, 1H), 7.74 (d, J=6.1 Hz, 2H), 8.82 (d, J=6.1 Hz, 2H), 10.7 (br s, 1H). APCIMS m/z: [M+H]$^+$ 379. mp: 209-211° C.

Reference Example 262

N-[5-(1-Ethylpyrrol-3-ylcarbonyl)-4-(2-furyl)thiazol-2-yl]pyridine-4-carboxamide (Compound 262)

$^1$H NMR (DMSO-d$_6$, δ ppm): 1.44 (t, J=7.3 Hz, 3H), 3.94 (q, J=7.3 Hz, 2H), 6.34 (dd, J=1.7, 3.3 Hz, 1H), 6.66-6.72 (m, 2H), 7.11 (d, J=3.3 Hz, 1H), 7.31 (d, J=1.7 Hz, 1H), 7.33-7.34 (m, 1H), 7.73 (d, J=6.1 Hz, 2H), 8.80 (d, J=6.1 Hz, 2H), 10.9 (br s, 1H). APCIMS m/z: [M+H]$^+$ 393. mp: 127-134° C.

Reference Example 263

N-[5-(1-Benzylpyrrol-3-ylcarbonyl)-4-(2-furyl)thiazol-2-yl]pyridine-4-carboxamide (Compound 263)

$^1$H NMR (DMSO-d$_6$, δ ppm): 5.06 (s, 2H), 6.35 (dd, J=1.8, 3.5 Hz, 1H), 6.65-6.75 (m, 2H), 7.11-7.14 (m, 3H), 7.31-7.37 (m, 5H), 7.73 (d, J=6.1 Hz, 2H), 8.81 (d, J=6.1 Hz, 2H), 10.6 (br s, 1H). APCIMS m/z: [M+H]$^+$ 455. mp: 175-178° C.

Reference Example 264

N-[5-(5-tert-Butyl-1,3,4-oxadiazol-2-ylcarbonyl)-4-(2-furyl)thiazol-2-yl]pyridine-4-carboxamide (Compound 264)

$^1$H NMR (DMSO-d$_6$, δ ppm): 1.40 (s, 9H), 6.71 (dd, J=1.9, 3.5 Hz, 1H), 7.59 (d, J=3.5 Hz, 1H), 7.84 (d, J=1.9 Hz, 1H), 8.05 (dd, J=1.6, 6.2 Hz, 2H), 8.85 (dd, J=1.6, 6.2 Hz, 2H), 13.77 (br s, 1H). ESIMS m/z: [M+H]$^+$ 424. mp: 190-255° C. (dec.).

Reference Example 265

2-Amino-4-(2-furyl)thiazol-5-yl 2-oxo-1,2-dihydropyridine-5-yl ketone (Compound 265)

$^1$H NMR (DMSO-d$_6$, δ ppm): 6.18 (d, J=9.5 Hz, 1H), 6.50 (dd, J=1.6, 3.2 Hz, 1H), 6.73 (d, J=3.2 Hz, 1H), 7.54 (d, J=1.6 Hz, 1H), 7.60 (dd, J=2.4, 9.5 Hz, 1H), 7.74 (d, J=2.4 Hz, 1H), 7.83 (br s, 2H).

Reference Example 266

2-Amino-4-(2-furyl)thiazol-5-yl 1-methyl-2-oxo-1,2-dihydropyridine-5-yl ketone (Compound 266)

$^1$H NMR (DMSO-d$_6$, δ ppm): 3.30 (s, 3H), 6.30 (d, J=9.7 Hz, 1H), 6.51 (dd, J=1.6, 3.2 Hz, 1H), 6.74 (dd, J=0.5, 3.2 Hz, 1H), 7.51 (dd, J=0.5, 1.6 Hz, 1H), 7.60 (dd, J=2.7, 9.7 Hz, 1H), 7.94 (br s, 2H), 8.11 (d, J=2.7 Hz, 1H). ESIMS m/z: [M+H]$^+$ 302.

Reference Example 267

N-[4-(2-Furyl)-5-(1-methyl-2-oxo-1,2-dihydropyridin-5-ylcarbonyl)thiazol-2-yl]pyridine-4-carboxamide (Compound 267)

$^1$H NMR (DMSO-d$_6$, δ ppm): 3.33 (s, 3H), 6.41 (d, J=9.7 Hz, 1H), 6.59 (dd, J=2.2, 3.2 Hz, 1H), 6.88 (d, J=3.2 Hz, 1H), 7.65 (d, J=2.2 Hz, 1H), 7.77 (dd, J=2.4, 9.7 Hz 1H), 8.03 (dd, J=1.6, 4.6 Hz, 2H), 8.37 (d, J=2.4 Hz, 1H), 8.84 (dd, J=1.6, 4.6 Hz, 2H), 13.58 (br s, 1H). APCIMS m/z: [M+H]$^+$ 407. mp: 294-295° C.

Reference Example 268

2-Amino-4-(2-furyl)thiazol-5-yl 1-ethyl-2-oxo-1,2-dihydropyridine-5-yl ketone (Compound 268)

$^1$H NMR (DMSO-d$_6$, δ ppm): 1.01 (t, J=6.5 Hz, 3H), 3.79 (q, J=6.5 Hz, 2H), 6.34 (d, J=9.5 Hz, 1H), 6.50 (dd, J=1.6, 3.2 Hz, 1H), 6.74 (d, J=3.2 Hz, 1H), 7.51 (d, J=1.6 Hz, 1H), 7.64 (dd, J=2.4, 9.5 Hz, 1H), 7.93 (br s, 2H), 8.11 (d, J=2.4 Hz, 1H). APCIMS m/z: [M+H]$^+$ 316.

Reference Example 269

N-[5-(1-Ethyl-2-oxo-1,2-dihydropyridin-5-ylcarbonyl)-4-(2-furyl)thiazol-2-yl]pyridine-4-carboxamide (Compound 269)

$^1$H NMR (DMSO-d$_6$, δ ppm): 1.04 (t, J=7.3 Hz, 3H), 3.85 (q, J=7.3 Hz, 2H), 6.43 (d, J=9.7 Hz, 1H), 6.58 (dd, J=1.6, 3.2 Hz, 1H), 6.88 (d, J=3.2 Hz, 1H), 7.64 (d, J=1.6 Hz, 1H), 7.98 (dd, J=2.7, 9.7 Hz, 1H), 8.04 (dd, J=1.6, 4.4 Hz, 2H), 8.32 (d, J=2.7 Hz, 1H), 8.85 (dd, J=1.6, 4.4 Hz, 2H), 13.59 (br s, 1H). APCIMS m/z: [M+H]$^+$ 421. mp: 295-296° C.

Reference Example 270

2-Amino-4-(2-furyl)thiazol-5-yl 1-benzyl-2-oxo-1,2-dihydropyridine-5-yl ketone (Compound 270)

$^1$H NMR (DMSO-d$_6$, δ ppm): 5.02 (s, 2H), 6.36 (d, J=9.7 Hz, 1H), 6.45 (dd, J=1.6, 3.2 Hz, 1H), 6.70 (dd, J=0.5, 3.2 Hz, 1H), 7.10 (dd, J=1.6, 7.5 Hz, 2H), 7.20-7.30 (m, 3H), 7.43 (dd, J=0.5, 1.6 Hz, 1H), 7.64 (dd, J=2.7, 9.7 Hz, 1H), 7.90 (br s, 2H), 8.29 (d, J=2.7 Hz, 1H). APCIMS m/z: [M+H]$^+$ 378.

Reference Example 271

N-[5-(1-Benzyl-2-oxo-1,2-dihydropyridin-5-ylcarbonyl)-4-(2-furyl)thiazol-2-yl]pyridine-4-carboxamide (Compound 271)

$^1$H NMR (DMSO-d$_6$, δ ppm): 5.05 (s, 2H), 6.45 (d, J=9.5 Hz, 1H), 6.54 (dd, J=1.9, 3.2 Hz, 1H), 6.83 (d, J=3.2 Hz, 1H), 7.04-7.12 (m, 2H), 7.24-7.30 (m, 3H), 7.58 (d, J=1.9 Hz, 1H), 7.82 (dd, J=2.7, 9.5 Hz, 1H), 8.02 (dd, J=1.6, 4.6 Hz, 2H), 8.51 (d, J=2.7 Hz, 1H), 8.83 (dd, J=1.6, 4.6 Hz, 2H), 13.57 (br s, 1H). APCIMS m/z: [M+H]$^+$ 483. mp: 265-282° C. (dec.).

Reference Example 272

2-Amino-4-(2-furyl)thiazol-5-yl 2-oxo-1,2-dihydropyridin-4-yl ketone (Compound 272)

$^1$H NMR (DMSO-d$_6$, δ ppm): 6.15 (dd, J=1.6, 6.2 Hz, 1H), 6.22 (d, J=1.6 Hz, 1H), 6.51 (dd, J=1.9, 3.5 Hz, 1H), 6.98 (d, J=3.5 Hz, 1H), 7.33 (d, J=6.2 Hz, 1H), 7.52 (d, J=1.9 Hz, 1H), 11.65 (br s, 1H). APCIMS m/z: [M+H]$^+$ 288.

Reference Example 273

2-Amino-4-(2-furyl)thiazol-5-yl 1-methyl-2-oxo-1,2-dihydropyridin-4-yl ketone (Compound 273)

$^1$H NMR (DMSO-d$_6$, δ ppm): 3.39 (s, 3H), 6.19 (dd, J=1.9, 7.0 Hz, 1H), 6.30 (d, J=1.9 Hz, 1H), 6.51 (dd, J=1.9, 3.5 Hz, 1H), 7.00 (dd J=0.8, 3.5 Hz, 1H), 7.51 (dd, J=0.8, 1.9 Hz, 1H), 7.66 (d, J=7.0 Hz, 1H), 8.20 (br s. 2H). APCIMS m/z: [M+H]$^+$ 302.

Reference Example 274

N-[4-(2-Furyl)-5-(1-methyl-2-oxo-1,2-dihydropyridin-4-ylcarbonyl)thiazol-2-yl]pyridine-4-carboxamide (Compound 274)

$^1$H NMR (DMSO-d$_6$, δ ppm): 3.44 (s, 3H), 6.38 (dd, J=1.9, 7.0 Hz, 1H), 6.53 (d, J=1.9 Hz, 1H), 6.62 (dd, J=1.6, 3.5 Hz, 1H), 7.19 (dd, J=0.5, 3.5 Hz, 1H), 7.70-7.77 (m, 2H), 8.03 (dd, J=1.6, 4.6 Hz, 2H), 8.84 (dd, J=1.6, 4.6 Hz, 2H), 13.69 (br s, 1H). APCIMS m/z: [M+H]$^+$ 407. mp: 243-255° C. (dec.).

Reference Example 275

2-Amino-4-(2-furyl)thiazol-5-yl 1-ethyl-2-oxo-1,2-dihydropyridin-4-yl ketone (Compound 275)

$^1$H NMR (DMSO-d$_6$, δ ppm): 1.18 (t, J=7.3 Hz, 3H), 3.86 (q, J=7.3 Hz, 2H), 6.20 (dd, J=1.6, 4.9 Hz, 1H), 6.26 (d, J=1.6 Hz, 1H), 6.49 (dd, J=1.6, 3.2 Hz, 1H), 6.95 (dd, J=0.5, 3.2 Hz, 1H), 7.48 (dd, J=0.5, 1.6 Hz, 1H), 7.66 (d, J=4.9 Hz, 1H), 8.21 (br s, 2H). APCIMS m/z: [M+H]$^+$ 316.

Reference Example 276

N-[5-(1-Ethyl-2-oxo-1,2-dihydropyridin-4-ylcarbonyl)-4-(2-furyl)thiazol-2-yl]pyridine-4-carboxamide (Compound 276)

$^1$H NMR (DMSO-d$_6$, δ ppm): 1.21 (t, J=7.0 Hz, 3H), 3.91 (q, J=7.0 Hz, 2H), 6.38 (dd, J=1.9, 7.3 Hz, 1H), 6.50 (d, J=1.9 Hz, 1H), 6.60 (dd, J=1.9, 3.2 Hz, 1H), 7.15 (dd, J=0.8, 3.2 Hz, 1H), 7.65 (dd, J=0.8, 1.9 Hz, 1H), 7.78 (d, J=7.3 Hz, 1H), 8.02 (dd, J=1.6, 4.4 Hz, 2H), 8.84 (dd, J=1.6, 4.4 Hz, 2H), 13.69 (br s, 1H). APCIMS m/z: [M+H]$^+$ 421. mp: 277-281° C.

Reference Example 277

2-Amino-4-(2-furyl)thiazol-5-yl 1-benzyl-2-oxo-1,2-dihydropyridin-4-yl ketone (Compound 277)

$^1$H NMR (DMSO-d$_6$, δ ppm): 5.07 (s, 2H), 6.23 (dd, J=2.2, 7.0 Hz, 1H), 6.32 (d, J=2.2 Hz, 1H), 6.42 (dd, J=1.9, 3.5 Hz, 1H), 6.91 (dd, J=0.8, 3.5 Hz, 1H), 7.20-7.24 (m, 2H), 7.29-7.41 (m, 4H), 7.74 (d, J=7.0 Hz, 1H), 8.22 (br s, 2H). APCIMS m/z: [M+H]$^+$ 378.

Reference Example 278

N-[5-(1-Benzyl-2-oxo-1,2-dihydropyridin-4-ylcarbonyl)-4-(2-furyl)thiazol-2-yl]pyridine-4-carboxamide (Compound 278)

$^1$H NMR (DMSO-d$_6$, δ ppm): 5.11 (s, 2H), 6.41 (dd, J=1.9, 6.7 Hz, 1H), 6.54 (d, J=1.9 Hz, 1H), 6.55 (dd, J=1.9, 3.5 Hz, 1H), 7.09 (dd, J=0.8, 3.5 Hz, 1H), 7.20-7.41 (m, 5H), 7.55 (dd, J=0.8, 1.9 Hz, 1H), 7.85 (d, J=6.7 Hz, 1H), 8.02 (dd, J=1.6, 4.3 Hz, 2H), 8.83 (dd, J=1.6, 4.3 Hz, 2H), 13.68 (br s, 1H). APCIMS m/z: [M+H]$^+$ 483. mp: 288-291° C.

Reference Example 279 tert-Butyl N-[4-(2-furyl)-5-(pyrazine-2-ylcarbonyl)thiazol-2-yl]carbamate (Compound 279)

$^1$H NMR (CDCl$_3$, δ ppm): 1.53 (s, 9H), 6.54 (dd, J=1.8, 3.7 Hz, 1H), 7.47 (d, J=1.8 Hz, 1H), 7.82 (d, J=3.7 Hz, 1H), 8.63-8.64 (m, 1H), 8.72-8.73 (m, 1H), 9.34-9.35 (m, 1H).

Reference Example 280

2-Amino-4-(2-furyl)thiazol-5-yl pyrazine-2-yl ketone (Compound 280)

$^1$H NMR (CDCl$_3$, δ ppm): 6.48 (dd, J=1.8, 3.5 Hz, 1H), 7.42 (d, J=1.8 Hz, 1H), 7.84 (d, J=3.5 Hz, 1H), 8.49 (dd, J=1.5, 2.5 Hz, 1H), 8.66 (d, J=2.5 Hz, 1H), 9.29 (d, J=1.5 Hz, 1H).

Reference Example 281

N-[4-(2-Furyl)-5-(pyrazin-2-ylcarbonyl)thiazol-2-yl]pyridine-4-carboxamide (Compound 281)

$^1$H NMR (DMSO-d$_6$, δ ppm): 6.63 (dd, J=1.8, 3.5 Hz, 1H), 7.40 (d, J=3.5 Hz, 1H), 7.66 (d, J=1.8 Hz, 1H), 8.05 (d, J=5.9 Hz, 2H), 8.74 (dd, J=1.3, 2.5 Hz, 1H), 8.85 (d, J=5.9 Hz, 2H), 8.89 (d, J=2.5 Hz, 1H), 9.23 (d, J=1.3 Hz, 1H). APCIMS m/z: [M+H]$^+$ 378. mp: >300° C.

Reference Example 282

N-[4-(2-Furyl)-5-(pyrimidine-4-ylcarbonyl)thiazol-2-yl]pyridine-4-carboxamide (Compound 282)

$^1$H NMR (DMSO-d$_6$, δ ppm): 6.64 (dd, J=1.8, 3.5 Hz, 1H), 7.42 (dd, J=0.7, 3.5 Hz, 1H), 7.66 (dd, J=0.7, 1.8 Hz, 1H), 8.02-8.03 (m, 1H), 8.05 (d, J=6.1 Hz, 2H), 8.85 (d, J=6.1 Hz, 2H), 9.12-9.14 (m, 1H), 9.33-9.34 (m, 1H), 13.6 (br s, 1H). APCIMS m/z: [M+H]$^+$ 378. mp: >300° C.

Reference Example 283

N-[4-(2-Furyl)-5-(pyridazine-3-ylcarbonyl)thiazol-2-yl]pyridine-4-carboxamide (Compound 283)

$^1$H NMR (DMSO-d$_6$, δ ppm): 6.36 (d, J=9.6 Hz, 1H), 6.46 (dd, J=1.8, 3.3 Hz 1H), 6.94 (dd, J=0.7, 3.3 Hz, 1H), 7.38-7.53 (m, 4H), 7.65 (d, J=6.1 Hz, 2H), 8.05 (dd, J=2.5, 9.6 Hz, 1H). APCIMS m/z: [M+H]$^+$ 378. mp: 280-281° C.

Reference Example 284

N-[5-Acetyl-4-(2-furyl)thiazol-2-yl]pyridine-4-carboxamide (Compound 284)

$^1$H NMR (DMSO, δ ppm): 3.33 (s, 3H), 6.71 (dd, J=1.8, 3.5 Hz, 1H), 7.43 (dd, J=0.7, 3.5 Hz, 1H), 7.91 (dd, J=0.7, 1.8 Hz, 1H), 8.02 (d, J=4.4 Hz, 2H), 8.83 (d, J=4.4 Hz, 2H), 13.55 (br s, 1H). ESIMS m/z: [M+H]$^+$ 314. mp: 252-259° C. (dec.).

Reference Example 285 tert-Butyl N-[4-(2-furyl)-5-(trifluoroacetyl)thiazol-2-yl]carbamate (Compound 285)

$^1$H NMR (CDCl$_3$, δ ppm): 1.53 (s, 9H), 6.61 (dd, J=1.6, 3.5 Hz, 1H), 7.61 (dd, J=0.8, 1.6 Hz, 1H), 8.06 (dd, J=0.8, 3.5 Hz, 1H), 8.90 (br s, 1H). ESIMS m/z: [M–H]$^-$ 361.

Reference Example 286

2-Amino-4-(2-furyl)thiazol-5-yl trifluoromethyl ketone (Compound 286)

$^1$H NMR (DMSO-d$_6$, δ ppm): 6.71 (dd, J=1.6, 3.5 Hz, 1H), 7.83 (d, J=3.5 Hz, 1H), 7.92 (d, J=1.6 Hz, 1H), 8.75 (br s, 2H) APCIMS m/z: [M+H]$^+$ 263.

Reference Example 287

N-[4-(2-Furyl)-5-(trifluoroacetyl)thiazol-2-yl]pyridine-4-carboxamide (Compound 287)

$^1$H NMR (DMSO-d$_6$, δ ppm): 6.79 (dd, J=1.6, 3.5 Hz, 1H), 7.81 (d, J=0.8, 3.5 Hz, 1H), 8.01 (dd, J=0.8, 1.6 Hz, 1H), 8.05 (dd, J=1.6, 4.3 Hz, 2H), 8.86 (dd, J=1.6, 4.3 Hz, 2H). APCIMS m/z: [M–H]$^+$ 366. mp: 268-270° C.

Reference Example 288

N-[4-(2-Furyl)-5-propionylthiazol-2-yl]pyridine-4-carboxamide (Compound 288)

$^1$H NMR (DMSO, δ ppm): 1.08 (t, J=7.2 Hz, 3H), 2.88 (q, J=7.2 Hz, 2H), 6.70 (dd, J=1.8, 3.7 Hz, 1H), 7.46 (dd, J=0.7, 3.7 Hz, 1H), 7.89 (dd, J=0.7, 1.8 Hz, 1H), 8.02 (d, J=4.4 Hz, 2H), 8.83 (d, J=4.4 Hz, 2H), 13.52 (br s, 1H). ESIMS m/z: [M+H]$^-$ 328. mp: 225-240° C. (dec.).

Reference Example 289

N-[5-Butyryl-4-(2-furyl)thiazol-2-yl]pyridine-4-carboxamide (Compound 289)

$^1$H NMR (DMSO, δ ppm): 0.90 (t, J=7.3 Hz, 3H), 1.60-1.66 (m, 2H), 2.82 (t, J=7.3 Hz, 2H), 6.70 (dd, J=1.8, 3.5 Hz, 1H), 7.46 (dd, J=0.8, 3.5 Hz, 1H), 7.90 (dd, J=0.8, 1.8 Hz, 1H), 8.02 (d, J=4.5 Hz, 2H), 8.83 (d, J=4.5 Hz, 2H), 13.55 (br s, 1H). ESIMS m/z: [M–H]$^-$ 340. mp: 191-194° C.

Reference Example 290 tert-Butyl N-[5-butyryl-4-(2-furyl)thiazol-2-yl]carbamate (Compound 290)

$^1$H NMR (CDCl$_3$, δ ppm): 0.86 (t, J=7.3 Hz, 3H), 1.15-1.60 (m, 2H), 1.50 (s, 9H), 1.70-2.05 (m, 2H), 6.48 (dd, J=1.8, 3.3 Hz, 1H), 6.99 (dd, J=0.8, 1.8 Hz, 1H), 7.47 (dd, J=0.8, 3.3 Hz, 1H), 8.20 (br s, 1H). ESIMS m/z: [M+H]$^+$ 337.

Reference Example 291

2-Amino-4-(2-furyl)thiazol-5-yl propyl ketone (Compound 291)

$^1$H NMR (CDCl$_3$, δ ppm): 0.86 (t, J=7.3 Hz, 3H), 1.15-2.05 (m, 4H), 5.46 (br s, 2H), 6.53 (dd, J=1.8, 3.6 Hz, 1H), 7.54 (dd, J=0.7, 1.8 Hz, 1H), 7.66 (dd, J=0.7, 3.6 Hz, 1H). ESIMS m/z: [M+H]$^+$ 237.

Reference Example 292

N-[5-Butyryl-4-(2-furyl)thiazol-2-yl]cyclopropanecarboxamide (Compound 292)

$^1$H NMR (CDCl$_3$, δ ppm): 0.92-1.02 (m, 2H), 0.95 (t, J=7.3 Hz, 3H), 1.16-1.25 (m, 2H), 1.42-1.53 (m, 1H), 1.73-1.79 (m, 2H), 2.81 (t, J=7.3 Hz, 2H), 6.56 (dd, J=1.8, 3.7 Hz, 1H), 7.56 (dd, J=0.7, 1.8 Hz, 1H), 7.84 (dd, J=0.7, 3.7 Hz, 1H), 9.95 (br s, 1H). ESIMS m/z: [M+H]$^+$ 305. mp: 170-172° C.

Reference Example 293

N-[5-Butyryl-4-(2-furyl)thiazol-2-yl]furan-2-carboxamide (Compound 293)

$^1$H NMR (CDCl$_3$, δ ppm): 1.00 (t, J=7.3 Hz, 3H), 1.76-1.82 (m, 2H), 2.85 (t, J=7.3 Hz, 1H), 6.57 (dd, J=1.7, 3.3 Hz, 1H), 6.65 (dd, J=1.8, 3.7 Hz, 1H), 7.41 (dd, J=0.7, 3.7 Hz, 1H), 7.59 (dd, J=0.7, 1.8 Hz, 1H), 7.60 (dd, J=0.7, 1.8 Hz, 1H), 7.82 (dd, J=0.7 Hz, 3.3 Hz, 1H), 9.80 (br s, 1H). ESIMS m/z: [M+H]⁺ 331. mp: 172-176° C.

Reference Example 294

N-[5-Butyryl-4-(2-furyl)thiazol-2-yl]-2-(chloromethyl)pyridine-4-carboxamide (Compound 294)

¹H NMR (CDCl₃, δ ppm): 1.02 (t, J=7.4 Hz, 3H), 1.78-1.84 (m, 2H), 2.87 (t, J=7.4 Hz, 2H), 4.71 (s, 2H), 6.44 (dd, J=1.8, 3.6 Hz, 1H), 7.38 (dd, J=0.7, 1.8 Hz, 1H), 7.61-7.71 (m, 1H), 7.74 (dd, J=0.7, 3.6 Hz, 1H), 7.88 (s, 1H), 8.73 (d, J=5.1 Hz, 1H).

Reference Example 295

N-[5-Butyryl-4-(2-furyl)thiazol-2-yl]-2-(methoxymethyl)-pyridine-4-carboxamide (Compound 295)

¹H NMR (CDCl₃, δ ppm): 1.01 (t, J=7.3 Hz, 3H), 1.77-1.83 (m, 2H), 2.87 (t, J=7.3 Hz, 2H), 4.60 (s, 2H), 6.43 (d, J=1.8, 3.5 Hz, 1H), 7.39 (d, J=1.8 Hz, 1H), 7.61-7.71 (m, 1H), 7.73 (d, J=3.5 Hz, 1H), 7.79 (s, 1H), 8.71 (d, J=5.0 Hz, 1H). APCIMS m/z: [M+H]⁺ 386.

Reference Example 296

N-[5-Butyryl-4-(2-furyl)thiazol-2-yl]-2-[2-(dimethylamino)ethoxymethyl]pyridine-4-carboxamide hydrochloride (Compound 296)

¹H NMR (DMSO-d₆, δ ppm): 0.88 (t, J=7.4 Hz, 3H), 1.57-1.63 (m, 2H), 2.64 (t, J=7.4 Hz, 2H), 3.16 (s, 6H), 3.53 (t, J=5.0 Hz, 2H), 3.95 (t, J=5.0 Hz, 2H), 4.76 (s, 2H), 6.60 (dd, J=1.8, 3.3 Hz, 1H), 7.34 (dd, J=0.8, 3.3 Hz, 1H), 7.77 (dd, J=0.8, 1.8 Hz, 1H), 8.05-8.15 (m, 1H), 8.35 (s, 1H), 8.77 (d, J=5.0 Hz, 1H). APCIMS [M+H]⁺ 443.

Reference Example 297

N-[5-Butyryl-4-(2-furyl)thiazol-2-yl]-2-morpholinoacetamide (Compound 297)

¹H NMR (CDCl₃, δ ppm): 0.987 (t, J=7.4 Hz, 3H), 1.74-1.80 (m, 2H), 2.67 (t, J=4.6 Hz, 4H), 2.82 (t, J=7.4 Hz, 2H), 3.79 (t, J=4.6 Hz, 4H), 6.57 (dd, J=1.7, 3.5 Hz, 1H), 7.59 (dd, J=0.7, 1.7 Hz, 1H), 7.80 (dd, J=0.7, 3.5 Hz, 1H). APCIMS m/z: [M+H]⁺ 364.

Reference Example 298 tert-Butyl N-[4-(2-furyl)-5-isobutyrylthiazol-2-yl]carbamate (Compound 298)

¹H NMR (CDCl₃, δ ppm): 1.22 (d, J=7.0 Hz, 6H), 1.54 (s, 9H), 3.16 (septet, J=7.0 Hz, 1H), 6.54 (dd, J=1.8, 3.7 Hz, 1H), 7.55 (dd, J=0.7, 1.8 Hz, 1H), 7.79 (dd, J=0.7, 3.7 Hz, 1H), 8.52 (br s, 1H). ESIMS m/z: [M+H]⁺ 337.

Reference Example 299

2-Amino-4-(2-furyl)thiazol-5-yl isopropyl ketone (Compound 299)

¹H NMR (CDCl₃, δ ppm): 1.18 (d, J=6.8 Hz, 6H), 3.00 (septet, J=6.8 Hz, 2H), 5.46 (br s, 2H), 6.53 (dd, J=1.8, 3.6 Hz, 1H), 7.54 (dd, J=0.7, 1.8 Hz, 1H), 7.66 (dd, J=0.7, 3.6 Hz, 1H). ESIMS m/z: [M+H]⁺ 237. mp: 195-199° C.

Reference Example 300

N-[4-(2-Furyl)-5-isobutyrylthiazol-2-yl]pyridine-4-carboxamide (Compound 300)

¹H NMR (CDCl₃, δ ppm): 1.27 (d, J=6.6 Hz, 6H), 3.26 (septet, J=6.6 Hz, 1H), 6.53 (dd, J=1.8, 3.7 Hz, 1H), 7.52 (dd, J=0.8, 1.8 Hz, 1H), 7.74 (d, J=4.4 Hz, 2H), 7.82 (dd, J=0.8, 3.7 Hz, 1H), 8.87 (d, J=4.4 Hz, 2H), 10.17 (br s, 1H). ESIMS m/z: [M+H]⁺ 342. mp: 179-182° C.

Reference Example 301

N-[4-(2-Furyl)-5-isobutyrylthiazol-2-yl]cyclopropanecarboxamide (Compound 301)

¹H NMR (CDCl₃, δ ppm): 0.93-1.03 (m, 2H), 1.15-1.25 (m, 2H), 1.23 (d. J=7.0 Hz, 6H), 1.43-1.53 (m, 1H), 3.16 (septet, J=7.0 Hz, 1H), 6.55 (dd, J=1.8, 3.7 Hz, 1H), 7.56 (dd, J=0.7, 1.8 Hz, 1H), 7.85 (dd, J=0.7, 3.7 Hz, 1H), 10.07 (br s, 1H). ESIMS m/z: [M+H]⁺ 305. mp: 178-182° C.

Reference Example 302 tert-Butyl N-[4-(2-furyl)-5-valerylthiazol-2-yl]carbamate (Compound 302)

¹H NMR (CDCl₃, δ ppm): 0.93 (t, J=7.3 Hz, 3H), 1.31-1.42 (m, 2H), 1.53 (s, 9H), 1.62-1.77 (m, 2H), 2.82 (t, J=7.3 Hz, 2H), 6.55 (dd, J=1.8, 3.4 Hz, 1H), 7.55 (dd, J=0.8, 1.8 Hz, 1H), 7.78 (d, J=0.8, 3.4 Hz, 1H), 8.62 (br s, 1H).

Reference Example 303

2-Amino-4-(2-furyl)thiazol-5-yl butyl ketone (Compound 303)

¹H NMR (CDCl₃, δ ppm): 0.91 (t, J=7.3 Hz, 3H), 1.29-1.41 (m, 2H), 1.61-1.72 (m, 2H), 2.69 (t, J=7.3 Hz, 2H), 5.99 (br s, 2H), 6.55 (dd, J=1.8, 3.5 Hz, 1H), 7.56 (dd, J=1.0, 1.8 Hz, 1H), 7.62 (dd, J=1.0, 3.5 Hz, 1H).

Reference Example 304 tert-Butyl N-[4-(2-furyl)-5-pivaloylthiazol-2-yl]carbamate (Compound 304)

¹H NMR (CDCl₃, δ ppm): 1.33 (s, 9H), 1.51 (s, 9H), 6.47 (dd, J=1.8, 3.5 Hz, 1H), 7.10 (d, J=3.5 Hz, 1H), 7.46 (d, J=1.8 Hz, 1H), 8.63 (br s, 1H). ESIMS m/z: [M+H]⁺ 351.

Reference Example 305

2-Amino-4-(2-furyl)thiazol-5-yl tert-butyl ketone (Compound 305)

¹H NMR (CDCl₃, δ ppm): 1.30 (s, 9H), 5.26 (br s, 2H), 6.47 (dd, J=1.8, 3.5 Hz, 1H), 7.30 (d, J=3.5 Hz, 1H), 7.47 (d, J=1.8 Hz, 1H). ESIMS m/z: [M+H]⁺ 251.

Reference Example 306

N-[4-(2-Furyl)-5-pivaloylthiazol-2-yl]pyridine-4-carboxamide (Compound 306)

¹H NMR (CDCl₃, δ ppm): 1.36 (s, 9H), 6.45 (dd, J=1.8, 3.5 Hz, 1H), 7.09 (dd, J=0.5, 3.5 Hz, 1H), 7.44 (dd, J=0.5 Hz, 1.8 Hz, 1H), 7.75 (d, J=4.5 Hz, 2H), 8.86 (d, J=4.5 Hz, 2H), 10.05 (br s, 1H). ESIMS m/z: [M+H]$^+$ 356. mp: 240-245° C.

Reference Example 307

N-[4-(2-Furyl)-5-pivaloylthiazol-2-yl]cyclopropan-ecarboxamide (Compound 307)

$^1$H NMR (CDCl$_3$, δ ppm): 0.88-0.98 (m, 2H), 1.13-1.20 (m, 2H), 1.32 (s, 9H), 1.40-1.50 (m, 1H), 6.48 (dd, J=1.8, 3.7 Hz, 1H), 7.16 (dd, J=0.7, 3.7 Hz, 1H), 7.48 (dd, J=0.7, 1.8 Hz, 1H), 10.15 (br s, 1H). ESIMS m/z: [M+H]$^+$ 319. mp: 133-134° C.

Reference Example 308 tert-Butyl N-[4-(2-furyl)-5-(methoxyacetyl)thiazol-2-yl]carbamate (Compound 308)

$^1$H NMR (CDCl$_3$, δ ppm): 1.46 (s, 9H), 3.47 (s, 3H), 4.41 (s, 2H), 6.54 (dd, J=1.7, 3.5 Hz, 1H), 7.53 (d, J=1.7 Hz, 1H), 7.80 (d, J=3.5 Hz, 1H).

Reference Example 309

2-Amino-4-(2-furyl)thiazol-5-yl methoxymethyl ketone (Compound 309)

$^1$H NMR (CDCl$_3$, δ ppm): 3.43 (s, 3H), 4.29 (s, 2H), 6.54 (dd, J=1.8, 3.5 Hz, 1H), 7.55 (d, J=1.8 Hz, 1H), 7.69 (d, J=3.5 Hz, 1H).

Reference Example 310

2-Chloro-N-[4-(2-furyl)-5-(methoxyacetyl)thiazol-2-yl]pyridine-5-carboxamide (Compound 310)

$^1$H NMR (CDCl$_3$, δ ppm): 3.51 (s, 3H), 4.44 (s, 2H), 6.48 (dd, J=1.8, 3.7 Hz, 1H), 7.44-7.46 (m, 2H), 7.77 (d, J=3.7 Hz, 1H), 8.18 (dd, J=2.2, 8.4 Hz, 1H), 8.92 (d, J=2.2 Hz, 1H). APCIMS m/z: [M+H]$^+$ 378. mp: 174-183° C.

Reference Example 311

4-Fluoro-N-[4-(2-furyl)-5-(methoxyacetyl)thiazol-2-yl]benzamide (Compound 311)

$^1$H NMR (CDCl$_3$, δ ppm): 3.50 (s, 3H), 4.45 (s, 2H), 6.51 (dd, J=1.8, 3.3 Hz, 1H), 7.15-7.21 (m, 2H), 7.50 (d, J=1.8 Hz, 1H), 7.82 (d, J=3.3 Hz, 1H), 7.93-7.97 (m, 2H). APCIMS m/z: [M+H]$^+$ 361. mp: 166-167° C.

Reference Example 312 tert-Butyl N-[5-(ethoxyacetyl)-4-(2-furyl)thiazol-2-yl]carbamate (Compound 312)

$^1$H NMR (CDCl$_3$, δ ppm): 1.27 (t, J=6.9 Hz, 3H), 1.51 (s, 9H), 3.61 (q, J=6.9 Hz, 2H), 4.44 (s, 2H), 6.54 (dd, J=1.8, 3.5 Hz, 1H), 7.55 (d, J=1.8 Hz, 1H), 7.81 (d, J=3.5 Hz, 1H).

Reference Example 313

2-Amino-4-(2-furyl)thiazol-5-yl ethoxymethyl ketone (Compound 313)

$^1$H NMR (CDCl$_3$, δ ppm): 1.24 (t, J=7.1 Hz, 3H), 3.57 (q, J=7.1 Hz, 2H), 4.31 (s, 2H), 6.54 (dd, J=1.8, 3.5 Hz, 1H), 7.56 (d, J=1.8 Hz, 1H), 7.75 (d, J=3.5 Hz, 1H).

Reference Example 314 tert-Butyl N-[5-acryloyl-4-(2-furyl)thiazol-2-yl]carbamate (Compound 314)

$^1$H NMR (CDCl$_3$, δ ppm): 1.45 (s, 9H), 5.76 (dd, J=1.7, 10.2 Hz, 1H), 6.42 (dd, J=1.7, 16.8 Hz, 1H), 6.53 (dd, J=1.8, 3.5 Hz, 1H), 6.83 (dd, J=10.2, 16.8 Hz, 1H), 7.53 (d, J=1.8 Hz, 1H), 7.56 (d, J=3.5 Hz, 1H).

Reference Example 315 tert-Butyl N-[4-(2-furyl)-5-(2-methoxyethylcarbonyl)thiazol-2-yl]carbamate (Compound 315)

$^1$H NMR (CDCl$_3$, δ ppm): 1.47 (s, 9H), 3.07 (t, J=6.1 Hz, 2H), 3.33 (s, 3H), 3.76 (t, J=6.1 Hz, 2H), 6.52 (dd, J=1.8, 3.5 Hz, 1H), 7.53 (d, J=1.8 Hz, 1H), 7.72 (d, J=3.5 Hz, 1H).

Reference Example 316

2-Amino-4-(2-furyl)thiazol-5-yl 2-methoxyethyl ketone (Compound 316)

$^1$H NMR (CDCl$_3$, δ ppm): 2.96 (t, J=6.2 Hz, 2H), 3.33 (s, 3H), 3.72 (t, J=6.2 Hz, 2H), 5.61 (br s, 2H), 6.52 (dd, J=1.8, 3.5 Hz, 1H), 7.53-7.54 (m, 2H).

Reference Example 317 tert-Butyl N-[5-(2-ethoxyethylcarbonyl)-4-(2-furyl)thiazol-2-yl]carbamate (Compound 317)

$^1$H NMR (CDCl$_3$, δ ppm): 1.16 (t, J=6.9 Hz, 3H), 3.08 (t, J=6.4 Hz, 2H), 3.49 (q, J=6.9 Hz, 2H), 3.80 (t, J=6.4 Hz, 2H), 6.52 (dd, J=1.8, 3.6 Hz, 1H), 7.53 (d, J=1.8 Hz, 1H), 7.70 (d, J=3.6 Hz, 1H).

Reference Example 318

2-Amino-4-(2-furyl)thiazol-5-yl 2-ethoxyethyl ketone (Compound 318)

$^1$H NMR (CDCl$_3$, δ ppm): 1.16 (t, J=7.0 Hz, 3H), 2.97 (t, J=6.6 Hz, 2H), 3.48 (q, J=7.0 Hz, 2H), 3.76 (t, J=6.6 Hz, 2H), 5.70 (br s, 2H), 6.51 (dd, J=1.8, 3.5 Hz, 1H), 7.53 (dd, J=0.7, 1.8 Hz, 1H), 7.56 (dd, J=0.7, 3.5 Hz, 1H).

Reference Example 319

N-[4-(2-Furyl)-5-(3-methoxyprop-1-ynylcarbonyl)thiazol-2-yl]pyridine-4-carboxamide (Compound 319)

$^1$H NMR (DMSO-d$_6$, δ ppm): 3.37 (s, 3H), 4.45 (s, 2H), 6.74 (dd, J=1.7, 3.5 Hz, 1H), 7.76 (dd, J=0.8, 3.5 Hz, 1H), 7.95 (dd, J=0.8, 1.7 Hz, 1H), 8.04 (dd, J=1.6, 4.5 Hz, 2H), 8.84 (dd, J=1.6, 4.5 Hz, 2H), 13.80 (br s, 1H). ESIMS m/z: [M+H]⁺ 368. mp: 198-200° C.

Reference Example 320

N-[4-(2-Furyl)-5-(3-methoxyprop-1-ynylcarbonyl) thiazol-2-yl]tert-butyl Carbamate (Compound 320)

¹H NMR (CDCl₃, δ ppm): 1.55 (s, 9H), 3.47 (s, 3H), 4.34 (s, 2H), 6.58 (dd, J=1.8, 3.0 Hz, 1H), 7.59 (dd, J=1.2, 1.8 Hz, 1H), 8.02 (dd, J=1.2, 3.0 Hz, 1H), 8.67 (br s, 1H).

Reference Example 321 tert-Butyl N-[4-(2-furyl)-5-(3-methoxypropylcarbonyl)thiazol-2-yl]carbamate (Compound 321)

¹H NMR (CDCl₃, δ ppm): 1.48 (s, 9H), 1.98-2.03 (m, 2H), 2.93 (t, J=7.0 Hz, 2H), 3.32 (s, 3H), 3.43 (t, J=7.0 Hz, 2H), 6.55 (dd, J=1.0, 3.3 Hz, 1H), 7.54 (d, J=1.0 Hz, 1H), 7.79 (d, J=3.3 Hz, 1H), 9.28 (br s, 1H).

Reference Example 322

2-Amino-4-(2-furyl)thiazol-5-yl 3-methoxypropyl ketone (Compound 322)

¹H NMR (CDCl₃, δ ppm): 1.96 (t, J=7.0 Hz, 2H), 2.76-2.81 (m, 2H), 3.31 (s, 3H), 3.42 (t, J=7.0 Hz, 2H), 6.00 (br s, 2H), 6.54 (dd, J=1.8, 3.3 Hz, 1H), 7.55 (d, J=1.8 Hz, 1H), 7.63 (d, J=3.3 Hz, 1H).

Reference Example 323

N-[5-(Cyclopropylcarbonyl)-4-(2-furyl)thiazol-2-yl] pyridine-4-carboxamide (Compound 323)

¹H NMR (CDCl₃, δ ppm): 1.03-1.10 (m, 2H), 1.29-1.34 (m, 2H), 2.35-2.43 (m, 1H), 6.50 (dd, J=1.7, 3.5 Hz, 1H), 7.50 (dd, J=0.7 Hz, 3.5 Hz, 1H), 7.61 (dd, J=0.7 Hz, 1.7 Hz, 1H), 7.76 (d, J=4.4 Hz, 2H), 8.85 (d, J=4.4 Hz, 2H), 10.34 (br s, 1H). ESIMS m/z: [M+H]⁺ 340. mp: 225-230° C. (dec.).

Reference Example 324 tert-Butyl N-[5-(cyclopropylcarbonyl)-4-(2-furyl) thiazol-2-yl]carbamate (Compound 324)

¹H NMR (CDCl₃, δ ppm): 0.90-1.03 (m, 2H), 1.16-1.36 (m, 2H), 1.52 (s, 9H), 1.78-1.99 (m, 1H), 6.53 (dd, J=1.7 Hz, 3.3 Hz, 1H). 6.74 (d, J=3.3 Hz, 1H), 7.55 (d, J=1.7 Hz, 1H), 8.30 (br s, 1H). ESIMS m/z: [M+H]⁺ 335.

Reference Example 325

2-Amino-4-(2-furyl)thiazol-5-yl cyclopropyl ketone (Compound 325)

¹H NMR (CDCl₃, δ ppm): 1.03-1.10 (m, 2H), 1.28-1.35 (m, 2H), 2.35-2.45 (m, 1H), 5.46 (br s, 2H), 6.53 (dd, J=1.8, 3.6 Hz, 1H), 7.54 (d, J=0.7, 1.8 Hz, 1H), 7.66 (dd, J=0.7, 3.6 Hz, 1H). ESIMS m/z: [M+H]⁺ 235.

Reference Example 326

N-[5-(Cyclopropylcarbonyl)-4-(2-furyl)thiazol-2-yl]-2-methoxybenzamide (Compound 326)

¹H NMR (CDCl₃, δ ppm): 0.80-1.07 (m, 2H), 1.24-1.32 (m, 2H), 2.37-2.42 (m, 1H), 4.12 (s, 3H), 6.55 (dd, J=1.8, 3.5 Hz, 1H), 7.08 (d, J=8.4 Hz, 1H), 7.18 (ddd, J=1.0 Hz, 7.4 Hz, 7.8 Hz, 1H), 7.55-7.65 (m, 3H), 8.32 (dd, J=1.8 Hz, 7.8 Hz, 1H), 11.23 (br s, 1H). ESIMS m/z: [M+H]⁺ 369. mp: 150-154° C.

Reference Example 327

N-[5-(Cyclopropylcarbonyl)-4-(2-furyl)thiazol-2-yl]-2-morpholinoacetamide (Compound 327)

¹H NMR (CDCl₃, δ ppm): 1.00-1.03 (m, 2H), 1.22-1.18 (m, 2H), 2.30-2.38 (m, 1H), 2.61 (t, J=4.6 Hz, 4H), 3.77 (t, J=4.6 Hz, 4H), 6.53 (dd, J=1.8, 3.5 Hz, 1H), 7.56 (dd, J=0.7, 1.8 Hz, 1H), 7.60 (J=0.7, 3.5 Hz, 1H). APCIMS m/z: [M+H]⁺ 362.

Reference Example 328 tert-Butyl N-[5-(cyclobutylcarbonyl)-4-(2-furyl)thiazol-2-yl]carbamate (Compound 328)

¹H NMR (CDCl₃, δ ppm): 1.48 (s, 9H), 1.80-2.10 (m, 2H), 2.15-2.33 (m, 2H), 2.35-2.48 (m, 2H), 3.70-3.77 (m, 1H), 6.55 (dd, J=1.8, 3.5 Hz, 1H), 7.55 (dd, J=0.7, 1.8 Hz, 1H), 7.87 (dd, J=0.7, 3.5 Hz, 1H), 9.28 (br s, 1H).

Reference Example 329

2-Amino-4-(2-furyl)thiazol-5-yl cyclobutyl ketone (Compound 329)

¹H NMR (CDCl₃, δ ppm): 1.80-2.05 (m, 2H), 2.10-2.22 (m, 2H), 2.30-2.45 (m, 2H), 3.55-3.61 (m, 1H), 5.56 (br s, 2H), 6.55 (dd, J=1.8, 3.5 Hz, 1H), 7.55 (dd, J=0.8, 1.8 Hz, 1H), 7.70 (dd, J=0.8, 3.5 Hz, 1H). ESIMS m/z: [M+H]⁺ 249. mp: 125-160° C. (dec.).

Reference Example 330

N-[5-(Cyclobutylcarbonyl)-4-(2-furyl)thiazol-2-yl] pyridine-4-carboxamide (Compound 330)

¹H NMR (CDCl₃, δ ppm): 1.85-2.18 (m, 2H), 2.25-2.40 (m, 2H), 2.40-2.55 (m, 2H), 3.76-3.82 (m, 1H), 6.53 (dd, J=1.8, 3.5 Hz, 1H), 7.50 (dd, J=0.8, 1.8 Hz, 1H), 7.73 (d, J=4.5 Hz, 2H), 7.85 (dd, J=0.8, 3.5 Hz, 1H), 8.84 (d, J=4.5 Hz, 1H), 8.85 (d, J=4.5 Hz, 1H), 10.27 (br s, 1H). ESIMS m/z: [M+H]⁺ 354. mp: 227-235° C. (dec.)

Reference Example 331

N-[5-(Cyclobutylcarbonyl)-4-(2-furyl)thiazol-2-yl] furan-2-carboxamide (Compound 331)

¹H NMR (CDCl₃, δ ppm): 1.93-2.13 (m, 2H), 2.23-2.50 (m, 4H), 3.74-3.80 (m, 1H), 6.58 (dd, J=1.8, 3.7 Hz, 1H), 6.64 (dd, J=1.8, 3.7 Hz, 1H), 7.39-7.41 (m, 3H), 7.90 (dd, J=0.7, 3.7 Hz, 1H), 9.81 (br s, 1H). ESIMS m/z: [M+H]⁺ 343. mp: 188-192° C.

Reference Example 332

4-Cyano-N-[5-(cyclobutylcarbonyl)-4-(2-furyl)thiazol-2-yl]benzamide (Compound 332)

¹H NMR (CDCl₃, δ ppm): 1.85-2.14 (m, 2H), 2.24-2.50 (m, 4H), 3.76-3.82 (m, 1H), 6.51 (dd, J=1.8, 3.7 Hz, 1H), 7.47

(dd, J=0.7, 1.8 Hz, 1H), 7.80 (d, J=8.8 Hz, 2H), 7.85 (dd, J=0.7, 3.7 Hz, 1H), 8.01 (d, J=8.8 Hz, 2H), 10.41 (br s, 1H). ESIMS m/z: [M−H]⁻ 376. mp: 220-225° C.

Reference Example 333

N-[5-(Cyclobutylcarbonyl)-4-(2-furyl)thiazol-2-yl] cyclopropanecarboxamide (Compound 333)

¹H NMR (CDCl₃, δ ppm): 0.91-0.99 (m, 2H), 1.15-1.25 (m, 2H), 1.80-2.10 (m, 2H), 2.20-2.49 (m, 5H), 3.69-3.75 (m, 1H), 6.56 (dd, J=1.7, 3.5 Hz, 1H), 7.56 (dd, J=0.7, 1.7 Hz, 1H), 7.91 (dd, J=0.7, 3.5 Hz, 1H), 10.09 (br s, 1H). ESIMS m/z: [M+H]⁺ 317. mp: 200-205° C.

Reference Example 334 tert-Butyl N-[4-(2-furyl)-5-(3-methyloxetan-3-ylcarbonyl)thiazol-2-yl]carbamate (Compound 334)

¹H NMR (CDCl₃, δ ppm): 1.38 (s, 9H), 1.77 (s, 3H), 4.44 (d, J=6.1 Hz, 2H), 5.05 (d, J=6.1 Hz, 2H), 6.50 (dd, J=1.8, 3.6 Hz, 1H), 7.48 (dd, J=0.8, 1.8 Hz, 1H), 7.84 (dd, J=0.8, 3.6 Hz, 1H).

Reference Example 335

2-Amino-4-(2-furyl)thiazol-5-yl 3-methyloxetane-3-yl ketone (Compound 335)

¹H NMR (CDCl₃, δ ppm): 1.75 (s, 3H), 4.37 (d, J=6.1 Hz, 2H), 5.02 (d, J=6.1 Hz, 2H), 6.56 (dd, J=1.8, 3.6 Hz, 1H), 7.57 (d, J=1.8 Hz, 1H), 7.88 (d, J=3.6 Hz, 1H).

Reference Example 336

N-[5-(Cyclopentylcarbonyl)-4-(2-furyl)thiazol-2-yl] pyridine-4-carboxamide (Compound 336)

¹H NMR (CDCl₃, δ ppm): 1.62-1.84 (m, 4H), 1.90-2.03 (m, 4H), 3.42-3.48 (m, 1H), 6.53 (dd, J=1.8, 3.5 Hz, 1H), 7.52 (dd, J=0.7, 3.5 Hz, 1H), 7.74 (d, J=4.4 Hz, 2H), 7.85 (dd, J=0.7, 1.8 Hz, 1H), 8.86 (d, J=4.4 Hz, 1H), 8.88 (d, J=4.4 Hz, 1H), 10.16 (br s, 1H). ESIMS m/z: [M+H]⁺ 368. mp: 168-181° C.

Reference Example 337 tert-Butyl N-[5-(cyclopentylcarbonyl)-4-(2-furyl)thiazol-2-yl]carbamate (Compound 337)

¹H NMR (CDCl₃, δ ppm): 1.20-2.10 (m, 8H), 1.51 (s, 9H), 2.96-3.02 (m, 1H), 6.45 (dd, J=1.8, 3.3 Hz, 1H), 6.65 (d, J=3.3 Hz, 1H), 7.41 (d, J=1.8 Hz, 1H), 8.45 (br s, 1H). ESIMS m/z: [M+H]⁺ 363.

Reference Example 338

2-Amino-4-(2-furyl)thiazol-5-yl cyclopentyl ketone (Compound 338)

¹H NMR (CDCl₃, δ ppm): 1.20-2.10 (m, 8H), 2.96-3.02 (m, 1H), 5.46 (br s, 2H), 6.53 (dd, J=1.8, 3.6 Hz, 1H), 7.54 (dd, J=0.7, 1.8 Hz, 1H), 7.66 (dd, J=0.7, 3.6 Hz, 1H). ESIMS m/z: [M+H]⁺ 263.

Reference Example 339

N-[5-(Cyclopentylcarbonyl)-4-(2-furyl)thiazol-2-yl] cyclopropanecarboxamide (Compound 339)

¹H NMR (CDCl₃, δ ppm): 0.94-1.04 (m, 2H), 1.16-1.25 (m, 2H), 1.46-1.82 (m, 6H), 1.86-1.99 (m, 3H), 3.32-3.41 (m, 1H), 6.55 (dd, J=1.8, 3.5 Hz, 1H), 7.56 (dd, J=0.7, 1.8 Hz, 1H), 7.87 (dd, J=0.7, 3.5 Hz, 1H), 9.83 (br s, 1H). ESIMS m/z: [M+H]⁺ 331. mp: 182-187° C.

Reference Example 340

N-[5-(Cyclopentylcarbonyl)-4-(2-furyl)thiazol-2-yl] morpholine-4-carboxamide (Compound 340)

¹H NMR (CDCl₃, δ ppm): 1.55-1.80 (m, 4H), 1.85-2.00 (m, 4H), 3.35-3.41 (m, 1H), 3.45-3.53 (m, 4H), 3.65-3.73 (m, 4H), 6.56 (dd, J=1.8, 3.5 Hz, 1H), 7.52 (dd, J=0.7, 1.8 Hz, 1H), 7.93 (dd, J=0.7, 3.5 Hz, 1H), 9.23 (br s, 1H). ESIMS m/z: [M+H]⁺ 376. mp: 108-110° C.

Reference Example 341 tert-Butyl N-[5-(1-cyclohexyl-1-hydroxymethyl)-4-(2-furyl)thiazol-2-yl]carbamate (Compound 341)

¹H NMR (CDCl₃, δ ppm): 0.86-1.40 (m, 6H), 1.45 (s, 9H), 1.50-1.80 (m, 4H), 2.05-2.15 (m, 1H), 5.21 (d, J=8.1 Hz, 1H), 6.46 (dd, J=1.9, 3.5 Hz, 1H), 6.65 (dd, J=0.8, 3.5 Hz, 1H), 7.45 (dd, J=0.8, 1.9 Hz, 1H), 8.55 (br s, 1H).

Reference Example 342 tert-Butyl N-[5-(cyclohexylcarbonyl)-4-(2-furyl)thiazol-2-yl]carbamate (Compound 342)

¹H NMR (CDCl₃, δ ppm): 1.15-1.35 (m, 4H), 1.56 (s, 9H), 1.65-1.95 (m, 6H), 2.85 (tt, J=3.4, 11.0 Hz, 1H), 6.53 (dd, J=0.9, 1.8 Hz, 1H), 7.54 (dd, J=0.9, 3.3 Hz, 1H), 7.75 (dd, J=1.7, 3.3 Hz, 1H).

Reference Example 343

2-Amino-4-(2-furyl)thiazol-5-yl cyclohexyl ketone (Compound 343)

¹H NMR (DMSO-d₆, δ ppm): 1.10-1.45 (m, 4H), 1.50-1.80 (m, 6H), 2.80-2.95 (m, 1H), 6.64 (dd, J=1.8, 3.5 Hz, 1H), 7.21 (d, J=3.5 Hz, 1H), 7.82 (d, J=1.8 Hz, 1H), 7.87 (br s, 1H).

Reference Example 344

N-[5-(Cyclohexylcarbonyl)-4-(2-furyl)thiazol-2-yl] pyridine-4-carboxamide (Compound 344)

¹H NMR (DMSO-d₆, δ ppm): 1.05-1.45 (m, 4H), 1.55-1.90 (m, 6H), 2.86-2.94 (m, 1H), 6.70 (dd, J=1.6, 3.2 Hz, 1H), 7.40 (d, J=3.2 Hz, 1H), 7.89 (d, J=1.6 Hz 1H), 8.02 (dd, J=1.9, 4.3 Hz, 2H), 8.83 (dd, J=1.9, 4.3 Hz, 2H), 13.54 (br s, 1H). mp: 197-199° C.

Reference Example 345 tert-Butyl N-[4-(2-furyl)-5-(4-methoxycyclohexyl-carbonyl)thiazol-2-yl]carbamate (Compound 345)

$^1$H NMR (CDCl$_3$, δ ppm): 1.23-2.17 (m, 19H), 3.30-3.36 (m, 4H), 6.53 (dd, J=1.7, 3.5 Hz, 1H), 7.54 (d, J=1.7, Hz, 1H), 7.76 (d, J=3.5 Hz, 1H).

Reference Example 346

2-Amino-4-(2-furyl)thiazol-5-yl 4-methoxycyclohexyl ketone (Compound 346)

$^1$H NMR (CDCl$_3$, δ ppm): 1.26-2.02 (m, 8H), 2.70-2.78 (m, 1H), 3.29-3.36 (m, 3H), 5.57-5.60 (m, 2H), 6.52-6.55 (m, 1H), 7.53-7.54 (m, 1H), 7.59-7.60 (m, 1H).

Reference Example 347

N-[4-(2-Furyl)-5-(4-methoxycyclohexylcarbonyl)thiazol-2-yl]pyridine-4-carboxamide (Compound 347)

$^1$H NMR (DMSO-d$_6$, δ ppm): 1.08-2.08 (m, 8H), 2.84-3.01 (m, 1H), 3.20-3.23 (m, 3H), 6.68-6.71 (m, 1H), 7.39-7.42 (m, 1H), 7.89-7.90 (m, 1H), 8.02 (d, J=5.9 Hz, 2H), 8.82 (d, J=5.9 Hz, 2H), 13.6 (br s, 1H). APCIMS m/z: [M+H]$^+$ 412. mp: 180-187° C.

Reference Example 348

4-Cyano-N-[4-(2-furyl)-5-(4-methoxycyclohexylcarbonyl)-thiazol-2-yl]benzamide (Compound 348)

$^1$H NMR (DMSO-d$_6$, δ ppm): 1.10-2.17 (m, 9H), 2.88-2.97 (m, 1H), 3.20-3.23 (m, 3H), 6.69-6.71 (m, 1H), 7.40-7.43 (m, 1H), 7.88-7.91 (m, 1H), 8.06 (d, J=8.3 Hz, 2H), 8.26 (d, J=8.3 Hz, 2H), 13.5 (br s, 1H). APCIMS m/z: [M+H]$^+$ 436. mp: 105-109° C.

Reference Example 349

2-Amino-4-(2-furyl)thiazol-5-yl 4-hydroxycyclohexyl ketone (Compound 349)

$^1$H NMR (CDCl$_3$, δ ppm): 1.55-2.15 (m, 10H), 5.82-5.92 (m, 2H), 6.52-6.54 (m, 1H), 7.54-7.59 (m, 2H).

Reference Example 350 tert-Butyl N-[5-(1,4-dioxaspiro[4,5]decane-8-ylcarbonyl)-4-(2-furyl)-thiazol-2-yl]carbamate (Compound 350)

$^1$H NMR (CDCl$_3$, δ ppm): 1.52 (s, 9H), 1.57-1.64 (m, 2H), 1.82-1.95 (m, 6H), 2.85-3.00 (m, 1H), 3.95 (s, 4H), 6.54 (dd, J=1.8, 3.3 Hz, 1H), 7.53 (d, J=1.8 Hz, 1H), 7.73 (d, J=3.3 Hz, 1H).

Reference Example 351

2-Amino-4-(2-furyl)thiazol-5-yl 1,4-dioxaspiro[4,5]decane-8-yl ketone (Compound 351)

$^1$H NMR (DMSO-d$_6$, δ ppm): 1.35-1.73 (m. 8H), 2.67-2.74 (m, 1H), 3.84 (s, 3H), 6.65 (dd, J=1.8, 3.5 Hz, 1H), 7.22 (dd, J=0.7, 3.5 Hz, 1H), 7.84 (dd, J=0.7, 1.8 Hz, 1H), 7.97 (br s, 2H).

Reference Example 352

2-Amino-4-(2-furyl)thiazol-5-yl 4-oxocyclohexyl ketone (Compound 352)

$^1$H NMR (DMSO-d$_6$, δ ppm): 1.70-1.79 (m, 2H), 2.01-2.08 (m, 2H), 2.20-2.36 (m, 4H), 3.18-3.26 (m, 1H), 6.64 (dd, J=1.8, 3.5 Hz, 1H), 7.28 (dd, J=0.8, 3.5 Hz, 1H), 7.85 (dd, J=0.8, 1.8 Hz, 1H), 8.01 (br s, 2H).

Reference Example 353

N-[4-(2-Furyl)-5-(4-oxocyclohexylcarbonyl)thiazol-2-yl]-pyridine-4-carboxamide (Compound 353)

$^1$H NMR (DMSO-d$_6$, δ ppm): 2.07-2.60 (m, 8H), 3.36-3.23 (m, 1H), 6.56 (dd, J=1.8, 3.5 Hz, 1H), 7.54 (dd, J=0.7, 1.8 Hz, 1H), 7.75 (dd, J=0.7, 3.5 Hz, 1H), 7.80 (d, J=6.1 Hz, 2H), 8.88 (d, J=6.1 Hz, 2H). APCIMS m/z: [M+H]$^+$ 396. mp: 206-212° C.

Reference Example 354

N-[4-(2-Furyl)-5-(4-oxocyclohexylcarbonyl)thiazol-2-yl]-2-methylpyridine-4-carboxamide (Compound 354)

$^1$H NMR (CDCl$_3$, δ ppm): 2.04-2.60 (m, 8H), 2.66 (s, 3H), 3.35-3.43 (m, 1H), 6.54 (dd, J=1.8, 3.6 Hz, 1H), 7.52 (dd, J=0.7, 1.8 Hz, 1H), 7.57 (d, J=5.1 Hz, 1H), 7.62 (s, 1H), 7.75 (dd, J=0.7, 3.6 Hz, 1H), 8.72 (d, J=5.1 Hz, 1H). APCIMS m/z: [M+H]$^+$ 410. mp: 108-115° C.

Reference Example 355

N-[4-(2-Furyl)-5-(4-oxocyclohexylcarbonyl)thiazol-2-yl]-furan-2-carboxamide (Compound 355)

$^1$H NMR (CDCl$_3$, δ ppm): 2.03-2.57 (m, 8H), 3.30-3.39 (m, 1H), 6.57 (dd, J=1.8, 3.5 Hz, 1H), 6.64 (dd, J=1.7, 3.6 Hz, 1H), 7.42 (d, J=3.6 Hz, 1H), 7.59-7.60 (m, 2H), 7.79 (d, J=3.5 Hz, 1H). APCIMS m/z: [M+H]$^+$ 385. mp: 232-235° C.

Reference Example 356

N-[4-(2-Furyl)-5-(4-oxocyclohexylcarbonyl)thiazol-2-yl]-3-methoxybenzamide (Compound 356)

$^1$H NMR (CDCl$_3$, δ ppm): 2.06-2.58 (m, 8H), 3.33-3.41 (m, 1H), 3.88 (s, 3H), 6.56 (dd, J=1.7, 3.6 Hz, 1H), 7.16-7.20 (m, 1H), 7.41-7.51 (m, 3H), 7.58 (d, J=1.7 Hz, 1H), 7.82 (d, J=3.6 Hz, 1H). APCIMS m/z: [M+H]$^+$ 425. mp: 176-183° C.

Reference Example 357

4-Cyano-N-[4-(2-furyl)-5-(4-oxocyclohexylcarbonyl)-thiazole-2-yl]benzamide (Compound 357)

$^1$H NMR (CDCl$_3$, δ ppm): 2.06-2.58 (m, 8H), 3.32-3.40 (m, 1H), 6.51 (dd, J=1.8, 3.5 Hz, 1H), 7.48 (dd, J=0.7, 1.8 Hz, 1H), 7.74 (dd, J=0.7, 3.5 Hz, 1H), 7.81 (d, J=8.6 Hz, 2H), 8.06 (d, J=8.6 Hz, 2H). APCIMS m/z: [M–H]⁺ 418. mp: 211-212° C.

Reference Example 358 tert-Butyl N-[4-(2-furyl)-5-(tetrahydropyran-4-ylcarbonyl)thiazol-2-yl]carbamate (Compound 358)

¹H NMR (CDCl₃, δ ppm): 1.53 (s, 9H), 1.76-1.94 (m, 4H), 3.06-3.18 (m, 1H), 3.46 (ddd, J=2.7, 11.6, 11.6 Hz, 2H), 4.03 (ddd, J=2.7, 4.0, 11.6 Hz, 2H), 6.55 (dd, J=1.9, 3.5 Hz, 1H), 7.55 (dd, J=0.8, 1.9 Hz, 1H), 7.76 (dd, J=0.8, 3.5 Hz, 1H), 8.68 (br s, 1H). APCIMS m/z: [M+H]⁺ 379.

Reference Example 359

2-Amino-4-(2-furyl)thiazol-5-yl tetrahydropyran-4-yl ketone (Compound 359)

¹H NMR (DMSO-d₆, δ ppm): 1.52-1.64 (m, 4H), 2.89-3.03 (m, 1H), 3.24 (ddd, J=3.8, 11.3, 11.3 Hz, 2H), 3.85 (ddd, J=2.7, 3.8, 11.3 Hz, 2H), 6.65 (dd, J=1.9, 3.5 Hz, 1H), 7.24 (d, J=3.5 Hz, 1H), 7.84 (d, J=1.9 Hz, 1H), 7.96 (br s, 2H). APCIMS m/z: [M+H]⁺ 279.

Reference Example 360

N-[4-(2-Furyl)-5-(tetrahydropyran-4-ylcarbonyl)thiazol-2-yl]pyridine-4-carboxamide (Compound 360)

¹H NMR (DMSO-d₆, δ ppm): 1.50-1.90 (m, 4H), 3.15-3.25 (m, 1H), 3.35 (ddd, J=2.7, 11.6, 11.6 Hz, 2H), 3.89 (ddd, J=2.7, 4.0, 11.6 Hz, 2H), 6.71 (dd, J=1.9, 3.5 Hz, 1H), 7.43 (dd, J=0.8, 3.5 Hz, 1H), 7.91 (dd, J=0.8, 1.9 Hz, 1H), 8.02 (dd, J=1.6, 4.6 Hz, 2H), 8.84 (dd, J=1.6, 4.6 Hz, 2H), 13.56 (br s, 1H). APCIMS m/z: [M+H]⁺ 384. mp: 202-209° C.

Reference Example 361

N-[4-(2-Furyl)-5-(tetrahydropyran-4-ylcarbonyl)thiazol-2-yl]cyclopropanecarboxamide (Compound 361)

¹H NMR (DMSO-d₆, δ ppm): 0.90-1.04 (m, 4H), 1.50-1.76 (m, 4H), 1.92-2.03 (m, 1H), 3.07-3.21 (m, 1H), 3.25-3.40 (m, 2H), 3.83-3.91 (m, 2H), 6.69 (dd, J=1.9, 3.5 Hz, 1H), 7.41 (d, J=3.5 Hz, 1H), 7.88 (d, J=1.9 Hz, 1H), 13.04 (br s, 1H). APCIMS m/z: [M+H]⁺ 347. mp: 182-183° C.

Reference Example 362

N-[4-(2-Furyl)-5-(tetrahydropyran-4-ylcarbonyl)thiazol-2-yl]benzamide (Compound 362)

¹H NMR (DMSO-d₆, δ ppm): 1.50-1.80 (m, 4H), 3.13-3.26 (m, 1H), 3.36 (ddd, J=2.2, 11.3, 11.3 Hz, 2H), 3.84-3.93 (m, 2H), 6.70 (dd, J=1.6, 3.5 Hz, 1H), 7.44 (d, J=3.5 Hz, 1H), 7.53-7.61 (m, 2H), 7.64-7.72 (m, 1H), 7.91 (d, J=1.6 Hz, 1H), 8.11-8.18 (m, 2H), 13.27 (br s, 1H). APCIMS m/z: [M+H]⁺ 383. mp: 221-222° C.

Reference Example 363

N-[4-(2-Furyl)-5-(tetrahydropyran-4-ylcarbonyl)thiazol-2-yl]-2-methylbenzamide (Compound 363)

¹H NMR (DMSO-d₆, δ ppm): 1.55-1.85 (m, 4H), 2.44 (s, 3H), 3.14-3.26 (m, 1H), 3.36 (ddd, J=2.2, 11.9, 11.9 Hz, 2H), 3.84-3.92 (m, 2H), 6.69 (dd, J=1.9, 3.5 Hz, 1H), 7.27-7.51 (m, 4H), 7.60-7.66 (m, 1H), 7.89 (d, J=1.9 Hz, 1H), 13.14 (br s, 1H). APCIMS m/z: [M+H]⁺ 397. mp: 204-206° C.

Reference Example 364

N-[4-(2-Furyl)-5-(tetrahydropyran-4-ylcarbonyl)thiazol-2-yl]-3-methylbenzamide (Compound 364)

¹H NMR (DMSO-d₆, δ ppm): 1.52-1.74 (m, 4H), 2.38 (s, 3H), 3.03-3.16 (m, 1H), 3.34 (ddd, J=2.4, 11.3, 11.3 Hz, 2H), 3.84-3.94 (m, 2H), 6.62 (dd, J=1.9, 3.5 Hz, 1H), 7.20-7.37 (m, 2H), 7.40 (dd, J=0.5. 3.5 Hz, 1H), 7.80 (dd, J=0.5, 1.9 Hz, 1H), 7.90-7.95 (m, 1H), 7.97-8.01 (m, 1H), 13.17 (br s, 1H). APCIMS m/z: [M+H]⁺ 397. mp: 197-201° C.

Reference Example 365

N-[4-(2-Furyl)-5-(tetrahydropyran-4-ylcarbonyl)thiazol-2-yl]-4-methylbenzamide (Compound 365)

¹H NMR (DMSO-d₆, δ ppm): 1.54-1.76 (m, 4H), 2.40 (s, 3H), 3.13-3.26 (m, 1H), 3.36 (ddd, J=2.2, 11.3, 11.3 Hz, 2H), 3.84-3.94 (m, 2H), 6.70 (dd, J=1.9, 3.5 Hz, 1H), 7.38 (d, J=8.4 Hz, 2H), 7.44 (d, J=3.5 Hz, 1H), 7.91 (d, J=1.9 Hz, 1H), 8.06 (d, J=8.4 Hz, 2H), 13.18 (br s, 1H). APCIMS m/z: [M+H]⁺ 397. mp: 190-192° C.

Reference Example 366

N-[4-(2-Furyl)-5-(tetrahydropyran-4-ylcarbonyl)thiazol-2-yl]-2-methoxybenzamide (Compound 366)

¹H NMR (DMSO-d₆, δ ppm): 1.55-1.80 (m, 4H), 3.15-3.25 (m, 1H), 3.35 (ddd, J=2.2, 11.6, 11.6 Hz, 2H), 3.80-3.95 (m, 2H), 3.92 (s, 3H), 6.69 (dd, J=1.6, 3.2 Hz, 1H), 7.05-7.15 (m, 1H), 7.16-7.24 (m, 1H), 7.41 (d, J=3.2 Hz, 1H), 7.55-7.63 (m, 1H), 7.70 (dd, J=1.3, 8.6 Hz, 1H), 7.90 (d, J=1.6 Hz, 1H), 12.47 (br s, 1H). APCIMS m/z: [M+H]⁺ 413. mp: 181-184° C.

Reference Example 367

N-[4-(2-Furyl)-5-(tetrahydropyran-4-ylcarbonyl)thiazol-2-yl]-3-methoxybenzamide (Compound 367)

¹H NMR (DMSO-d₆, δ ppm): 1.55-1.80 (m, 4H), 3.14-3.24 (m, 1H), 3.36 (ddd, J=2.4, 11.3, 11.3 Hz, 2H), 3.86 (s, 3H), 3.87-3.92 (m, 2H), 6.70 (dd, J=1.6, 3.5 Hz, 1H), 7.20-7.26 (m, 1H), 7.45 (dd, J=0.8, 3.5 Hz, 1H), 7.43-7.53 (m, 1H), 7.69-7.77 (m, 2H), 7.91 (dd, J=0.8, 1.6 Hz, 1H), 13.27 (br s, 1H). APCIMS m/z: [M+H]⁺ 413. mp: 198-200° C.

Reference Example 368

N-[4-(2-Furyl)-5-(tetrahydropyran-4-ylcarbonyl)thiazol-2-yl]-4-methoxybenzamide (Compound 368)

¹H NMR (DMSO-d₆, δ ppm): 1.54-1.76 (m, 4H), 3.13-3.24 (m, 1H), 3.36 (ddd, J=2.2, 11.3, 11.3 Hz, 2H), 3.86 (s, 3H), 3.89-3.91 (m, 2H), 6.70 (dd, J=1.6, 3.2 Hz, 1H), 7.10 (dd, J=1.9, 8.9 Hz, 2H), 7.45 (dd, J=0.5, 3.2 Hz, 1H), 7.90 (dd, J=0.5, 1.6 Hz, 1H), 8.15 (dd, J=1.9, 8.9 Hz), 13.10 (br s, 1H). APCIMS m/z: [M+H]$^+$ 413. mp: 184-188° C.

Reference Example 369

3-(Dimethylamino)-N-[4-(2-furyl)-5-(tetrahydropyran-4-ylcarbonyl)thiazol-2-yl]benzamide (Compound 369)

$^1$H NMR (DMSO-d$_6$, δ ppm): 1.55-1.75 (m, 4H), 2.99 (s, 6H), 3.13-3.23 (m, 1H), 3.35 (ddd, J=2.2, 11.6, 11.6 Hz, 2H), 3.89 (ddd, J=2.2, 3.8, 11.6 Hz, 2H), 6.70 (dd, J=1.9, 3.5 Hz, 1H), 6.99 (ddd, J=1.4, 2.7, 8.1 Hz, 1H), 7.31-7.48 (m, 4H), 7.90 (dd, J=0.8, 1.9 Hz, 1H), 13.19 (br s, 1H). APCIMS m/z: [M+H]$^+$ 426. mp: 239-243° C.

Reference Example 370

4-(Dimethylamino)-N-[4-(2-furyl)-5-(tetrahydropyran-4-ylcarbonyl)thiazol-2-yl]benzamide (Compound 370)

$^1$H NMR (DMSO-d$_6$, δ ppm): 1.55-1.80 (m, 4H), 3.03 (s, 6H), 3.11-3.22 (m, 1H), 3.35 (ddd, J=2.2, 11.6, 11.6 Hz, 2H), 3.85-3.93 (m, 2H), 6.69 (dd, J=1.6, 3.5 Hz, 1H), 6.77 (d, J=9.2 Hz, 2H), 7.45 (dd, J=0.8, 3.5 Hz, 1H), 7.89 (dd, J=0.8, 1.6 Hz, 1H), 8.05 (d, J=9.2 Hz, 2H), 12.81 (br s, 1H). APCIMS m/z: [M+H]$^+$ 426. mp: 238-240° C.

Reference Example 371

2-Fluoro-N-[4-(2-furyl)-5-(tetrahydropyran-4-ylcarbonyl)-thiazol-2-yl]benzamide (Compound 371)

$^1$H NMR (DMSO-d$_6$, δ ppm): 1.54-1.76 (m, 4H), 3.15-3.25 (m, 1H), 3.36 (ddd, J=2.2, 11.3, 11.3 Hz, 2H), 3.84-3.93 (m, 2H), 6.69 (dd, J=1.9, 3.5 Hz, 1H), 7.35-7.50 (m, 3H) 7.61-7.71 (m, 1H), 7.75-7.83 (m, 1H), 7.89 (d, J=1.9 Hz, 1H), 13.23 (br s, 1H). APCIMS m/z: [M+H]$^+$ 401. mp: 172-176° C.

Reference Example 372

3-Fluoro-N-[4-(2-furyl)-5-(tetrahydropyran-4-ylcarbonyl)-thiazol-2-yl]benzamide (Compound 372)

$^1$H NMR (DMSO-d$_6$, δ ppm): 1.50-1.80 (m, 4H), 3.15-3.25 (m, 1H), 3.36 (ddd, J=2.2, 11.6, 11.6 Hz, 2H), 3.89 (ddd, J=2.2, 4.0, 11.6 Hz, 2H), 6.70 (dd, J=1.6, 3.2 Hz, 1H), 7.44 (d, J=3.2 Hz, 1H), 7.49-7.68 (m, 2H), 7.90 (dd, J=0.8, 1.6 Hz, 1H), 7.94-8.02 (m, 2H), 13.34 (br s, 1H). APCIMS m/z: [M+H]$^+$ 401. mp: 229-231° C.

Reference Example 373

4-Fluoro-N-[4-(2-furyl)-5-(tetrahydropyran-4-ylcarbonyl)-thiazol-2-yl]benzamide (Compound 373)

$^1$H NMR (DMSO-d$_6$, δ ppm): 1.58-1.78 (m, 4H), 3.15-3.25 (m, 1H), 3.35-3.55 (m, 2H), 3.88 (ddd, J=1.9, 3.8, 11.3 Hz, 2H), 6.70 (dd, J=1.6, 3.2 Hz, 1H), 7.37-7.46 (m, 3H), 7.90 (dd, J=0.8, 1.6 Hz, 1H), 8.20-8.26 (m, 2H), 13.27 (br s, 1H). APCIMS m/z: [M+H]$^+$ 401. mp: 131-132° C.

Reference Example 374

2-Chloro-N-[4-(2-furyl)-5-(tetrahydropyran-4-ylcarbonyl)-thiazol-2-yl]benzamide (Compound 374)

$^1$H NMR (DMSO-d$_6$, δ ppm): 1.55-1.85 (m, 4H), 3.15-3.25 (m, 1H), 336 (ddd, J=2.4, 11.3, 11.3 Hz, 2H), 3.88 (ddd, J=2.4, 3.8, 11.3 Hz, 2H), 6.69 (dd, J=1.6, 3.5 Hz, 1H), 7.39 (d, J=3.5 Hz, 1H), 7.45-7.70 (m, 5H), 7.89 (dd, J=0.8, 1.6 Hz, 1H), 13.34 (br s, 1H). APCIMS m/z: [$^{35}$ClM+H]$^+$ 417, [$^{37}$ClM+H]$^+$ 419. mp: 160-162° C.

Reference Example 375

3-Chloro-N-[4-(2-furyl)-5-(tetrahydropyran-4-ylcarbonyl)-thiazol-2-yl]benzamide (Compound 375)

$^1$H NMR (DMSO-d$_6$, δ ppm): 1.55-1.80 (m, 4H), 3.12-3.25 (m, 1H), 3.36 (ddd, J=2.2, 12.1, 12.1 Hz, 2H), 3.86-3.92 (m, 2H), 6.70 (dd, J=1.9, 3.5 Hz, 1H), 7.43 (d, J=3.5 Hz, 1H), 7.60 (dd, J=7.8, 7.8 Hz, 1H), 7.72-7.76 (m, 1H), 7.90 (d, J=1.9 Hz, 1H), 8.09 (dd, J=1.1, 7.8 Hz, 1H), 8.19-8.20 (m, 1H), 13.36 (br s, 1H). APCIMS m/z: [$^{35}$ClM+H]$^+$ 417, [$^{37}$ClM+H]$^+$ 419. mp: 210-212° C.

Reference Example 376

4-Chloro-N-[4-(2-furyl)-5-(tetrahydropyran-4-ylcarbonyl)-thiazol-2-yl]benzamide (Compound 376)

$^1$H NMR (DMSO-d$_6$, δ ppm): 1.55-1.85 (m, 4H), 3.15-3.25 (m, 1H), 3.34-3.42 (m, 2H), 3.84-3.93 (m, 2H), 6.70 (dd, J=1.9, 3.5 Hz, 1H), 7.44 (dd, J=0.8, 3.5 Hz, 1H), 7.65 (dd, J=1.6, 8.4 Hz, 2H), 7.90 (dd, J=0.8, 1.9 Hz, 1H), 8.15 (dd, J=1.6, 8.4 Hz, 2H), 13.35 (br s, 1H). APCIMS m/z: [$^{35}$ClM+H]$^+$ 417, [$^{37}$ClM+H]$^+$ 419. mp: 204-206° C.

Reference Example 377

2-Cyano-N-[4-(2-furyl)-5-(tetrahydropyran-4-ylcarbonyl)-thiazol-2-yl]benzamide (Compound 377)

$^1$H NMR (DMSO-d$_6$, δ ppm): 1.50-1.80 (m, 4H), 3.12-3.22 (m, 1H), 3.28-3.38 (m, 2H), 3.88 (ddd. J=2.2, 11.3, 11.3 Hz, 2H), 6.73 (dd, J=1.9, 3.5 Hz, 1H), 7.50 (d, J=3.5 Hz, 1H), 7.80-8.20 (m, 5H), 11.27 (br s, 1H). APCIMS m/z: [M+H]$^+$ 408. mp: 221-224° C.

Reference Example 378

3-Cyano-N-[4-(2-furyl)-5-(tetrahydropyran-4-ylcarbonyl)-thiazol-2-yl]benzamide (Compound 378)

$^1$H NMR (DMSO-d$_6$, δ ppm): 1.55-1.76 (m, 4H), 3.15-3.25 (m, 1H), 3.37 (ddd, J=1.6, 11.6, 11.6 Hz, 2H), 3.80-3.91 (m, 2H), 6.71 (dd, J=1.6, 3.2 Hz, 1H), 7.45 (d, J=3.2 Hz, 1H), 7.79 (dd, J=7.8, 7.8 Hz, 1H), 7.92 (d, J=1.6 Hz, 1H), 8.14 (d, J=7.8 Hz, 1H), 8.40 (d, J=7.8 Hz, 1H), 8.58 (s, 1H), 13.47 (br s, 1H). APCIMS m/z: [M+H]$^+$ 408. mp: 257-260° C.

Reference Example 379

4-Cyano-N-[4-(2-furyl)-5-(tetrahydropyran-4-ylcarbonyl)-thiazol-2-yl]benzamide (Compound 379)

$^1$H NMR (DMSO-d$_6$, δ ppm): 1.50-1.80 (m, 4H), 3.10-3.30 (m, 1H), 3.35-3.50 (m, 2H), 3.84-3.93 (m, 2H), 6.70 (dd, J=1.9, 3.5 Hz, 1H), 7.44 (d, J=3.5 Hz, 1H), 7.90 (d, J=1.9 Hz, 1H), 8.05 (d, J=8.4 Hz, 2H), 8.26 (d, J=8.4 Hz, 2H), 13.53 (br s, 1H). APCIMS m/z: [M−H]⁻ 406. mp: 231-234° C.

Reference Example 380

N-[4-(2-Furyl)-5-(tetrahydropyran-4-ylcarbonyl) thiazol-2-yl]-2-(trifluoromethoxy)benzamide (Compound 380)

¹H NMR (DMSO-d$_6$, δ ppm): 1.50-1.80 (m, 4H), 3.10-3.22 (m, 1H), 3.36 (ddd, J=2.2, 11.3, 11.3 Hz, 2H), 3.85-3.92 (m, 2H), 6.70 (dd, J=1.6, 3.5 Hz, 1H), 7.41 (d, J=3.5 Hz, 1H), 7.52-7.60 (m, 2H), 7.73 (ddd, J=1.6, 7.6, 7.6 Hz 1H), 7.83 (dd, J=1.6, 7.6 Hz, 1H), 7.89 (d, J=1.6 Hz, 1H), 13.41 (br s, 1H). APCIMS m/z: [M+H]⁺ 467. mp: 131-134° C.

Reference Example 381

N-[4-(2-Furyl)-5-(tetrahydropyran-4-ylcarbonyl) thiazol-2-yl]-3-(trifluoromethoxy)benzamide (Compound 381)

¹H NMR (DMSO-d$_6$, δ ppm): 1.50-1.80 (m, 4H), 3.10-3.25 (m, 1H), 3.36 (ddd, J=2.2, 11.6, 11.6 Hz, 2H), 3.85-3.93 (m, 1H), 7.68-7.75 (m, 2H), 7.90 (d, J=1.6 Hz, 1H), 8.12-8.21 (m, 2H), 13.49 (br s, 1H). APCIMS m/z: [M+H]⁺ 467. mp: 197-198° C.

Reference Example 382

N-[4-(2-Furyl)-5-(tetrahydropyran-4-ylcarbonyl) thiazol-2-yl]-4-(trifluoromethoxy)benzamide (Compound 382)

¹H NMR (DMSO-d$_6$, δ ppm): 1.50-1.80 (m, 4H), 3.15-3.25 (m, 1H), 3.36 (ddd, J=2.2, 11.6, 11.6 Hz, 2H), 3.85-3.94 (m, 2H), 6.70 (dd, J=1.6, 3.2 Hz, 1H), 7.44 (d, J=3.2 Hz, 1H), 7.57 (d, J=8.1 Hz, 2H), 7.90 (d, J=1.6 Hz, 1H), 8.27 (d, J=8.1 Hz, 2H), 13.39 (br s, 1H). APCIMS m/z: [M+H]⁺ 467. mp: 177-180° C.

Reference Example 383

4-(Chloromethyl)-N-[4-(2-furyl)-5-(tetrahydropyran-4-ylcarbonyl)thiazol-2-yl]benzamide (Compound 383)

¹H NMR (DMSO-d$_6$, δ ppm): 1.55-1.78 (m, 4H), 3.13-3.27 (m, 1H), 3.36 (ddd, J=2.4, 11.3, 11.3 Hz, 2H), 3.89 (ddd, J=2.4, 3.8, 11.3 Hz, 2H), 4.86 (s, 2H), 6.70 (dd, J=1.9, 3.5 Hz, 1H), 7.44 (dd, J=0.5, 3.5 Hz, 1H), 7.63 (d, J=8.4 Hz, 2H), 7.90 (dd, J=0.5, 1.9 Hz, 1H), 8.14 (d, J=8.4 Hz, 2H), 13.30 (br s, 1H). APCIMS m/z: [³⁵ClM+H]⁺ 431, [³⁷ClM+H]⁺ 433.

Reference Example 384

4-(Dimethylaminomethyl)-N-[4-(2-furyl)-5-(tetrahydropyran-4-ylcarbonyl)thiazol-2-yl]benzamide (Compound 384)

¹H NMR (DMSO-d$_6$, δ ppm): 1.55-1.80 (m, 4H), 2.20 (s, 6H), 3.10-3.20 (m, 1H), 3.36 (ddd, J=2.4, 11.6, 11.6 Hz, 2H), 3.52 (s, 2H), 3.85-3.93 (m, 2H), 6.70 (dd, J=1.9, 3.5 Hz, 1H), 7.44 (d, J=3.5 Hz, 1H), 7.48 (d, J=8.1 Hz, 2H), 7.90 (d, J=1.9 Hz, 1H), 8.12 (d, J=8.1 Hz, 2H), 13.06 (br s, 1H). APCIMS m/z: [M+H]⁺ 440. mp: 109-112° C.

Reference Example 385

N-[4-(2-Furyl)-5-(tetrahydropyran-4-ylcarbonyl) thiazol-2-yl]-4-(piperidinomethyl)benzamide (Compound 385)

¹H NMR (DMSO-d$_6$, δ ppm): 1.20-1.50 (m, 6H), 1.50-1.80 (m, 6H), 2.30-2.45 (m, 2H), 3.10-3.25 (m, 1H), 3.30-3.45 (m, 2H), 3.55 (s, 2H), 3.85-3.93 (m, 2H), 6.69 (dd, J=1.6, 3.2 Hz, 1H), 7.44 (d, J=3.2 Hz, 1H), 7.48 (d, J=8.1 Hz, 2H), 7.90 (d, J=1.6 Hz, 1H), 8.11 (d, J=8.1 Hz, 2H), 13.07 (br s, 1H). APCIMS m/z: [M+H]⁺ 480. mp: 160-162° C.

Reference Example 386

N-[4-(2-Furyl)-5-(tetrahydropyran-4-ylcarbonyl) thiazol-2-yl]-4-(4-hydroxypiperidinomethyl)benzamide (Compound 386)

¹H NMR (DMSO-d$_6$, δ ppm): 1.40-1.50 (m, 2H), 1.65-1.85 (m, 4H), 2.00-2.10 (m, 2H), 2.85-2.90 (m, 2H), 2.84 (ddd, J=3.5, 9.4, 11.3 Hz, 2H), 3.05-3.20 (m, 1H), 3.20-3.40 (m, 3H), 3.45 (s, 2H), 3.70-3.80 (m, 1H), 3.85-3.95 (m, 2H), 4.45-4.50 (m, 1H), 6.63 (dd, J=1.6, 3.5 Hz, 1H), 7.35 (d, J=8.4 Hz, 2H), 7.41 (d, J=3.5 Hz, 1H), 7.80 (d, J=1.6 Hz, 1H), 8.09 (d, J=8.4 Hz, 2H). APCIMS m/z: [M+H]⁺ 496. mp: 194-195° C.

Reference Example 387

N-[4-(2-Furyl)-5-(tetrahydropyran-4-ylcarbonyl) thiazol-2-yl]-4-(morpholinomethyl)benzamide (Compound 387)

¹H NMR (DMSO-d$_6$, δ ppm): 1.50-1.80 (m, 4H), 2.38 (t, J=4.3 Hz, 4H), 3.10-3.25 (m, 1H), 3.36 (ddd, J=2.4, 11.3, 11.3 Hz, 2H), 3.56 (s, 2H), 3.59 (t, J=4.3 Hz, 4H), 3.85-3.93 (m, 2H), 6.69 (dd, J=1.9, 3.5 Hz, 1H), 7.44 (dd, J=0.8, 3.5 Hz, 1H), 7.49 (d, J=8.4 Hz, 2H), 7.89 (dd, J=0.8, 1.9 Hz, 1H), 8.12 (d, J=8.4 Hz, 2H), 12.67 (br s, 1H). APCIMS m/z: [M+H]⁺ 482. mp: 92-96° C.

Reference Example 388

N-[4-(2-Furyl)-5-(tetrahydropyran-4-ylcarbonyl) thiazol-2-yl]-2,3-dimethoxybenzamide (Compound 388)

¹H NMR (DMSO-d$_6$, δ ppm): 1.50-1.75 (m, 4H), 3.15-3.25 (m, 1H), 3.36 (ddd, J=2.4, 11.3, 11.3 Hz, 2H), 3.83 (s, 3H), 3.84-3.94 (m, 2H), 3.87 (s, 3H), 6.69 (dd, J=1.9, 3.5 Hz, 1H), 7.17-7.21 (m, 2H), 7.23-7.30 (m, 1H), 7.41 (dd, J=0.5, 3.5 Hz, 1H), 7.89 (dd, J=0.5, 1.9 Hz, 1H), 12.80 (br s, 1H). APCIMS m/z: [M+H]⁺ 443. mp: 198-200° C.

Reference Example 389

N-[4-(2-Furyl)-5-(tetrahydropyran-4-ylcarbonyl) thiazol-2-yl]-2,4-dimethoxybenzamide (Compound 389)

¹H NMR (DMSO-d$_6$, δ ppm): 1.54-1.75 (m, 4H), 3.12-3.22 (m, 1H), 3.34 (ddd, J=2.4, 11.3, 11.3 Hz, 2H), 3.89 (s, 3H), 3.90-3.95 (m, 2H), 3.97 (s, 3H), 6.69 (dd, J=1.9, 3.2 Hz, 1H), 6.72-6.77 (m, 2H), 7.41 (d, J=3.2 Hz, 1H), 7.80 (dd, J=3.0, 8.4 Hz, 1H), 7.89 (d, J=1.9 Hz, 1H), 11.94 (br s, 1H). APCIMS m/z: [M+H]⁺ 443. mp: 219-222° C.

Reference Example 390

N-[4-(2-Furyl)-5-(tetrahydropyran-4-ylcarbonyl) thiazol-2-yl]-2,5-dimethoxybenzamide (Compound 390)

¹H NMR (DMSO-d₆, δ ppm): 1.50-1.80 (m, 4H), 3.10-3.25 (m, 1H), 3.35 (ddd, J=2.2, 11.3, 11.3 Hz, 2H), 3.77 (s, 3H), 3.80-3.92 (m, 2H), 3.88 (s, 3H), 6.69 (dd, J=1.9, 3.5 Hz, 1H), 7.15-7.24 (m, 2H), 7.25-7.31 (m, 1H), 7.41 (d, J=3.5 Hz, 1H), 7.90 (d, J=1.9 Hz, 1H), 12.44 (br s, 1H). APCIMS m/z: [M+H]⁺ 443. mp: 107-110° C.

Reference Example 391

N-[4-(2-Furyl)-5-(tetrahydropyran-4-ylcarbonyl) thiazol-2-yl]-2,6-dimethoxybenzamide (Compound 391)

¹H NMR (DMSO-d₆, δ ppm): 1.54-1.76 (m, 4H), 3.12-3.24 (m, 1H), 3.32-3.42 (m, 2H), 3.76 (s, 6H), 3.84-3.92 (m, 2H), 6.68 (dd, J=1.6, 3.0 Hz, 1H), 6.75 (d, J=8.4 Hz, 2H), 7.37 (d, J=3.0 Hz, 1H), 7.42 (t, J=8.4 Hz, 1H), 7.88 (d, J=1.6 Hz, 1H), 12.93 (br s, 1H). APCIMS m/z: [M+H]⁺ 443. mp: 152-156° C.

Reference Example 392

N-[4-(2-Furyl)-5-(tetrahydropyran-4-ylcarbonyl) thiazol-2-yl]-3,4-dimethoxybenzamide (Compound 392)

¹H NMR (DMSO-d₆, δ ppm): 1.55-1.80 (m, 4H), 3.10-3.25 (m, 1H), 3.35 (ddd, J=2.2, 11.3, 11.3 Hz, 2H), 3.86 (s, 3H), 3.87 (s, 3H), 3.88-3.92 (m, 2H), 6.70 (dd, J=1.6, 3.2 Hz, 1H), 7.13 (d, J=8.4 Hz, 1H), 7.45 (d, J=3.2 Hz, 1H), 7.78-7.82 (m, 2H), 7.84 (d, J=1.6 Hz, 1H), 13.11 (br s, 1H). APCIMS m/z: [M+H]⁺ 443. mp: 289-292° C.

Reference Example 393

N-[4-(2-Furyl)-5-(tetrahydropyran-4-ylcarbonyl) thiazol-2-yl]-3,5-dimethoxybenzamide (Compound 393)

¹H NMR (DMSO-d₆, δ ppm): 1.50-1.80 (m, 4H), 3.10-3.25 (m, 1H), 3.36 (ddd, J=2.2, 11.3, 11.3 Hz, 2H), 3.84 (s, 6H), 3.80-3.92 (m, 2H), 6.70 (dd, J=1.9, 3.5 Hz, 1H), 6.78 (t, J=2.7 Hz, 1H), 7.35 (d, J=2.7 Hz, 2H), 7.45 (dd, J=0.8, 3.5 Hz, 1H), 7.91 (dd, J=0.8, 1.9 Hz, 1H), 13.25 (br s, 1H). APCIMS m/z: [M+H]⁺ 443. mp: 278-280° C.

Reference Example 394

2,3-Difluoro-N-[4-(2-furyl)-5-(tetrahydropyran-4-ylcarbonyl)thiazol-2-yl]benzamide (Compound 394)

¹H NMR (DMSO-d₆, δ ppm): 1.50-1.80 (m, 4H), 3.15-3.25 (m, 1H), 3.36 (ddd, J=2.4, 11.3, 11.3 Hz, 2H), 3.84-3.93 (m, 2H), 6.70 (dd, J=1.6, 3.5 Hz, 1H), 7.34-7.41 (m, 1H), 7.42 (dd, J=0.8, 3.5 Hz, 1H), 7.57-7.77 (m, 2H), 7.90 (dd, J=0.8, 1.6 Hz, 1H), 13.42 (br s, 1H). APCIMS m/z: [M+H]⁺ 419. mp: 154-160° C.

Reference Example 395

2,4-Difluoro-N-[4-(2-furyl)-5-(tetrahydropyran-4-ylcarbonyl)thiazol-2-yl]benzamide (Compound 395)

¹H NMR (DMSO-d₆, δ ppm): 1.50-1.80 (m, 4H), 3.15-3.25 (m, 1H), 3.36 (ddd, J=2.2, 11.3, 11.3 Hz, 2H), 3.84-3.93 (m, 2H), 6.70 (dd, J=1.6, 3.5 Hz, 1H), 7.22-7.32 (m, 1H), 7.42 (dd, J=0.8, 3.5 Hz, 1H), 7.44-7.52 (m, 1H), 7.85-7.92 (m, 2H), 13.28 (br s, 1H). APCIMS m/z: [M+H]⁺ 419. mp: 213-215° C.

Reference Example 396

2,5-Difluoro-N-[4-(2-furyl)-5-(tetrahydropyran-4-ylcarbonyl)thiazol-2-yl]benzamide (Compound 396)

¹H NMR (DMSO-d₆, δ ppm): 1.50-1.80 (m, 4H), 3.15-3.25 (m, 1H), 3.36 (ddd, J=2.2, 11.3, 11.3 Hz, 2H), 3.88 (ddd, J=2.2, 4.3, 11.3 Hz, 2H), 6.70 (dd, J=1.9, 3.5 Hz, 1H), 7.41 (dd, J=0.8, 3.5 Hz, 1H), 7.43-7.58 (m, 2H), 7.68 (ddd, J=3.0, 5.4, 8.4 Hz, 1H), 7.90 (dd, J=0.8, 1.9 Hz, 1H), 13.37 (br s, 1H). APCIMS m/z: [M+H]⁺ 419. mp: 172-174° C.

Reference Example 397

2,6-Difluoro-N-[4-(2-furyl)-5-(tetrahydropyran-4-ylcarbonyl)thiazol-2-yl]benzamide (Compound 397)

¹H NMR (DMSO-d₆, δ ppm): 1.50-1.80 (m, 4H), 3.15-3.25 (m, 1H), 3.36 (ddd, J=2.4, 11.6, 11.6 Hz, 2H), 3.83-3.92 (m, 2H), 6.70 (dd, J=1.6, 3.5 Hz, 1H), 7.29 (t, J=8.1 Hz, 1H), 7.40 (d, J=3.5 Hz, 1H), 7.60-7.73 (m, 2H), 7.90 (d, J=1.9 Hz, 1H), 13.60 (br s, 1H). APCIMS m/z: [M+H]⁺ 419. mp: 168-170° C.

Reference Example 398

3,4-Difluoro-N-[4-(2-furyl)-5-(tetrahydropyran-4-ylcarbonyl)thiazol-2-yl]benzamide (Compound 398)

¹H NMR (DMSO-d₆, δ ppm): 1.50-1.80 (m, 4H), 3.15-3.25 (m, 1H), 3.36 (ddd, J=2.4, 11.6, 11.6 Hz, 2H), 3.83-3.92 (m, 2H), 6.70 (dd, J=1.9, 3.5 Hz, 1H), 7.45 (d, J=3.5 Hz, 1H), 7.63-7.73 (m, 1H), 7.90 (d, J=1.9 Hz, 1H), 8.02-8.08 (m, 1H), 8.24 (ddd, J=2.2, 7.5, 11.3 Hz, 1H), 13.37 (br s, 1H). APCIMS m/z: [M+H]⁺ 419. mp: 208-210° C.

Reference Example 399

3,5-Difluoro-N-[4-(2-furyl)-5-(tetrahydropyran-4-ylcarbonyl)thiazol-2-yl]benzamide (Compound 399)

¹H NMR (DMSO-d₆, δ ppm): 1.50-1.80 (m, 4H), 3.15-3.25 (m, 1H), 3.36 (ddd, J=2.4, 11.3, 11.3 Hz, 2H), 3.83-3.93 (m, 2H), 6.71 (dd, J=1.9, 3.5 Hz, 1H), 7.44 (dd, J=0.8, 3.5 Hz, 1H), 7.58-7.67 (m, 1H), 7.84-7.90 (m, 2H), 7.91 (dd, J=0.8, 1.9 Hz, 1H), 13.43 (br s, 1H). APCIMS m/z: [M+H]⁺ 419. mp: 259-265° C.

Reference Example 400

N-[4-(2-Furyl)-5-(tetrahydropyran-4-ylcarbonyl) thiazol-2-yl]-1,4-benzodioxane-5-carboxamide (Compound 400)

¹H NMR (DMSO-d₆, δ ppm): 1.50-1.80 (m, 4H), 3.10-3.22 (m, 1H), 3.35 (ddd, J=2.4, 11.6, 11.6 Hz, 2H), 3.83-3.93 (m, 2H), 4.29-4.34 (m, 2H), 4.39-4.43 (m, 2H), 6.69 (dd, J=1.6, 3.2 Hz, 1H), 6.96 (dd, J=7.8, 7.8 Hz, 1H), 7.09 (dd, J=1.6, 7.8 Hz, 1H), 7.23 (dd, J=1.6, 7.8 Hz, 1H), 7.42 (d, J=3.2 Hz, 1H), 7.89 (d, J=1.6 Hz, 1H), 12.52 (br s, 1H). APCIMS m/z: [M+H]$^+$ 441. mp: 188-190° C.

Reference Example 401

N-[4-(2-Furyl)-5-(tetrahydropyran-4-ylcarbonyl)thiazol-2-yl]-1,3-benzodioxol-5-carboxamide (Compound 401)

$^1$H NMR (DMSO-d$_6$, δ ppm): 1.50-1.80 (m, 4H), 3.15-3.25 (m, 1H), 3.36 (ddd, J=2.4, 11.6, 11.6 Hz, 2H), 3.83-3.93 (m, 2H), 6.16 (s, 2H), 6.70 (dd, J=1.6, 3.2 Hz, 1H), 7.09 (d, J=8.1 Hz, 1H), 7.45 (d, J=3.2 Hz, 1H), 7.70 (d, J=1.9 Hz, 1H), 7.79 (dd, J=1.9, 8.1 Hz, 1H), 7.90 (d, J=1.6 Hz, 1H), 13.07 (br s, 1H). APCIMS m/z: [M+H]$^+$ 427. mp: 194-196° C.

Reference Example 402

2,2-Difluoro-N-[4-(2-furyl)-5-(tetrahydropyran-4-ylcarbonyl)thiazol-2-yl]-1,3-benzodioxol-4-carboxamide (Compound 402)

$^1$H NMR (DMSO-d$_6$, δ ppm): 1.50-1.80 (m, 4H), 3.10-3.30 (m, 1H), 3.36 (ddd, J=2.2, 11.6, 11.6 Hz, 2H), 3.85-3.92 (m, 2H), 6.70 (dd, J=1.6, 3.2 Hz, 1H), 7.37 (dd, J=8.1, 8.1 Hz, 1H), 7.45 (d, J=3.2 Hz, 1H), 7.69 (dd, J=0.8, 8.1 Hz, 1H), 7.82 (dd, J=0.8, 8.1 Hz, 1H), 7.90 (d, J=1.6 Hz, 1H), 13.43 (br s, 1H). APCIMS m/z: [M+H]$^+$ 463. mp: 206-207° C.

Reference Example 403

2,2-Difluoro-N-[4-(2-furyl)-5-(tetrahydropyran-4-ylcarbonyl)thiazol-2-yl]-1,3-benzodioxol-5-carboxamide (Compound 403)

$^1$H NMR (DMSO-d$_6$, δ ppm): 1.50-1.80 (m, 4H), 3.15-3.25 (m, 1H), 3.36 (ddd, J=2.4, 11.6, 11.6 Hz, 2H), 3.85-3.92 (m, 2H), 6.70 (dd, J=1.6, 3.5 Hz, 1H), 7.45 (d, J=3.5 Hz, 1H), 7.63 (d, J=8.6 Hz, 1H), 7.90 (d, J=1.6 Hz, 1H), 8.08 (dd, J=1.6, 8.6 Hz, 1H), 8.18 (d, J=1.6 Hz, 1H), 13.33 (br s, 1H). APCIMS m/z: [M+H]$^+$ 463. mp: 124-129° C.

Reference Example 404

2-Chloro-N-[4-(2-furyl)-5-(tetrahydropyran-4-ylcarbonyl)-thiazol-2-yl]pyridine-4-carboxamide (Compound 404)

$^1$H NMR (DMSO-d$_6$, δ ppm): 1.50-1.80 (m, 4H), 3.15-3.25 (m, 1H), 3.36 (ddd, J=2.7, 11.3, 11.3 Hz, 2H), 3.85-3.92 (m, 2H), 6.71 (dd, J=1.6, 3.5 Hz, 1H), 7.44 (dd, J=0.8, 3.5 Hz, 1H), 7.92 (dd, J=0.8, 1.6 Hz, 1H), 8.01 (dd, J=1.4, 5.1 Hz, 1H), 8.17 (dd, J=0.8, 1.4 Hz, 1H), 8.67 (dd, J=0.8, 5.1 Hz, 1H), 13.64 (br s, 1H). APCIMS m/z: [$^{35}$ClM+H]$^+$ 418, [$^{37}$ClM+H]$^+$ 420. mp: 185-186° C.

Reference Example 405

N-[4-(2-Furyl)-5-(tetrahydropyran-4-ylcarbonyl)thiazol-2-yl]-2-methylpyridine-4-carboxamide (Compound 405)

$^1$H NMR (DMSO-d$_6$, δ ppm): 1.50-1.80 (m, 4H), 2.58 (s, 3H), 3.15-3.25 (m, 1H), 3.35-3.38 (m, 2H), 3.83-3.93 (m, 2H), 6.71 (dd, J=1.9, 3.5 Hz, 1H), 7.43 (dd, J=0.8, 3.5 Hz, 1H), 7.81 (dd, J=1.1, 5.1 Hz, 1H), 7.89-7.92 (m, 2H), 8.68 (d, J=5.1 Hz, 1H), 13.48 (br s, 1H). APCIMS m/z: [M+H]$^+$ 398. mp: 169-173° C.

Reference Example 406

N-[4-(2-Furyl)-5-(tetrahydropyran-4-ylcarbonyl)thiazol-2-yl]pyridine-3-carboxamide (Compound 406)

$^1$H NMR (DMSO-d$_6$, δ ppm): 1.54-1.76 (m, 4H), 3.15-3.25 (m, 1H), 3.36 (ddd, J=2.2, 11.3, 11.3 Hz, 2H), 3.84-3.93 (m, 2H), 6.71 (dd, J=1.9, 3.5 Hz, 1H), 7.45 (d, J=3.5 Hz, 1H), 7.61 (dd, J=4.9, 8.4 Hz, 1H), 7.90 (d, J=1.9 Hz, 1H), 8.46 (ddd, J=2.2, 2.2, 8.4 Hz, 1H), 8.80 (dd, J=2.2, 4.9 Hz, 1H), 9.25 (d, J=2.2 Hz, 1H), 13.50 (br s, 1H). APCIMS m/z: [M+H]$^+$ 384. mp: 209-212° C.

Reference Example 407

2-Chloro-N-[4-(2-furyl)-5-(tetrahydropyran-4-ylcarbonyl)-thiazol-2-yl]pyridine-5-carboxamide (Compound 407)

$^1$H NMR (DMSO-d$_6$, δ ppm): 1.50-1.80 (m, 4H), 3.15-3.27 (m, 1H), 3.36 (ddd, J=2.2, 11.6, 11.6 Hz, 2H), 3.89 (ddd, J=2.2, 4.0, 11.6 Hz, 2H), 6.71 (dd, J=1.9, 3.5 Hz, 1H), 7.44 (dd, J=0.5, 3.5 Hz, 1H), 7.76 (dd, J=0.5, 8.6 Hz, 1H), 7.91 (dd, J=0.5, 1.9 Hz, 1H), 8.49 (dd, J=2.7, 8.6 Hz, 1H), 9.90 (dd, J=0.5, 2.7 Hz, 1H), 13.55 (br s, 1H). APCIMS m/z: [$^{35}$ClM+H]$^+$ 416, [$^{37}$ClM+H]$^+$ 418. mp: 233-235° C.

Reference Example 408

N-[4-(2-Furyl)-5-(tetrahydropyran-4-ylcarbonyl)thiazol-2-yl]-2-morpholinopyridine-5-carboxamide (Compound 408)

$^1$H NMR (DMSO-d$_6$, δ ppm): 1.50-1.75 (m, 4H), 3.12-3.23 (m, 1H), 3.35 (ddd, J=2.4, 11.6, 11.6 Hz, 2H), 3.60-3.70 (m, 8H), 3.83-3.93 (m, 2H), 6.69 (dd, J=1.6, 3.2 Hz, 1H), 6.94 (d, J=9.4 Hz, 1H), 7.45 (d, J=3.2 Hz, 1H), 7.89 (d, J=1.6, Hz, 1H), 8.24 (dd, J=2.4, 9.4 Hz, 1H), 8.90 (d, J=2.4 Hz, 1H), 12.98 (br s, 1H). APCIMS m/z: [M+H]$^+$ 469. mp: 166-170° C.

Reference Example 409

N-[4-(2-Furyl)-5-(tetrahydropyran-4-ylcarbonyl)thiazol-2-yl]-2-methylpyridine-5-carboxamide (Compound 409)

$^1$H NMR (DMSO-d$_6$, δ ppm): 1.54-1.78 (m, 4H), 2.57 (s, 3H), 3.16-3.25 (m, 1H), 3.32-3.48 (m, 2H), 3.84-3.93 (m, 2H), 6.70 (dd, J=1.9, 3.5 Hz, 1H), 7.43-7.49 (m, 2H), 7.91 (d, J=1.9 Hz, 1H), 8.35 (dd, J=2.4, 8.1 Hz, 1H), 9.14 (d, J=2.4 Hz, 1H), 13.40 (br s, 1H). APCIMS m/z: [M+H]$^+$ 398. mp: 209-211° C.

Reference Example 410

N-[4-(2-Furyl)-5-(tetrahydropyran-4-ylcarbonyl)thiazol-2-yl]-2-(trifluoromethyl)pyridine-5-carboxamide (Compound 410)

$^1$H NMR (DMSO-d$_6$, δ ppm): 1.50-1.80 (m, 4H), 3.15-3.25 (m, 1H), 3.37 (ddd, J=2.4, 11.3, 11.3 Hz, 2H), 3.89 (ddd, J=2.4, 4.3, 11.3 Hz, 2H), 6.72 (dd, J=1.9, 3.5 Hz, 1H), 7.45 (dd, J=0.8, 3.5 Hz, 1H), 7.92 (dd, J=0.8, 1.9 Hz, 1H), 8.15 (dd, J=0.8, 8.1 Hz, 1H), 8.72 (dd, J=1.6, 8.1 Hz, 1H), 9.39 (dd, J=0.8, 1.6 Hz, 1H), 13.71 (br s, 1H). APCIMS m/z: [M+H]$^+$ 452. mp: 217-222° C.

Reference Example 411

N-[4-(2-Furyl)-5-(tetrahydropyran-4-ylcarbonyl) thiazol-2-yl]-5-methylpyridine-3-carboxamide-411)

$^1$H NMR (DMSO-d$_6$, δ ppm): 1.50-1.80 (m, 4H), 2.40 (s, 3H), 3.15-3.25 (m, 1H), 3.36 (ddd, J=2.4, 11.6, 11.6 Hz, 2H), 3.89 (ddd, J=2.2, 4.4, 11.6 Hz, 2H), 6.71 (dd, J=1.9, 3.2 Hz, 1H), 7.43 (dd, J=0.8, 3.2 Hz, 1H), 7.91 (dd, J=0.8, 1.9 Hz, 1H), 8.28-8.31 (m, 1H), 8.67 (d, J=1.6 Hz, 1H), 9.05 (d, J=1.6 Hz, 1H), 13.42 (br s, 1H). APCIMS m/z: [M+H]$^+$ 398. mp: 239-243° C.

Reference Example 412

N-[4-(2-Furyl)-5-(tetrahydropyran-4-ylcarbonyl) thiazol-2-yl]pyridine-2-carboxamide (Compound 412)

$^1$H NMR (DMSO-d$_6$, δ ppm): 1.53-1.78 (m, 4H), 3.15-3.27 (m, 1H), 3.35 (ddd, J=2.4, 11.6, 11.6 Hz, 2H), 3.88 (ddd, J=2.4, 4.3, 11.6 Hz, 2H), 6.71 (dd, J=1.6, 3.2 Hz, 1H), 7.37 (dd, J=0.8, 3.2 Hz, 1H), 7.74 (ddd, J=1.3, 4.9, 7.5 Hz, 1H), 7.92 (dd, J=0.8, 1.6 Hz, 1H), 8.11 (dd, J=1.6, 7.5, 7.5 Hz, 1H), 8.20 (ddd, J=1.3, 1.3, 7.5 Hz, 1H), 8.78 (ddd, J=1.3, 1.6, 4.9 Hz, 1H), 12.62 (br s, 1H). APCIMS m/z: [M+H]$^+$ 384. mp: 185-186° C.

Reference Example 413

N-[4-(2-Furyl)-5-(tetrahydropyran-4-ylcarbonyl) thiazol-2-yl]-2-methylpyrimidine-5-carboxamide (Compound 413)

$^1$H NMR (DMSO-d$_6$, δ ppm): 1.55-176 (m, 4H), 2.73 (S, 3H), 3.16-3.30 (m, 1H), 3.30-3.50 (m, 2H), 3.80-3.93 (m, 2H), 6.71 (dd, J=1.6, 3.2 Hz, 1H), 7.44 (d, J=3.2 Hz, 1H), 7.92 (d, J=1.6 Hz, 1H), 9.29 (s, 2H), 13.58 (br s, 1H). APCIMS m/z: [M+H]$^+$ 399.

Reference Example 414

N-[4-(2-Furyl)-5-(tetrahydropyran-4-ylcarbonyl) thiazol-2-yl]pyrazine-2-carboxamide (Compound 414)

$^1$H NMR (DMSO-d$_6$, δ ppm): 1.50-1.80 (m, 4H), 3.10-3.30 (m, 1H), 3.35 (ddd, J=2.2, 11.3, 11.3 Hz, 2H), 3.85-3.94 (m, 2H), 6.71 (dd, J=1.9, 3.5 Hz, 1H), 7.39 (d, J=3.5 Hz, 1H), 7.92 (d, J=1.9 Hz, 1H), 8.85 (dd, J=1.3, 2.4 Hz, 1H), 8.96 (d, J=2.4 Hz, 1H), 9.33 (d, J=1.3 Hz, 1H), 13.18 (br s, 1H). APCIMS m/z: [M+H]$^+$ 385. mp: 200-205° C.

Reference Example 415

N-[4-(2-Furyl)-5-(tetrahydropyran-4-ylcarbonyl) thiazol-2-yl]-5-methylpyrazine-2-carboxamide (Compound 415)

$^1$H NMR (DMSO-d$_6$, δ ppm): 1.50-1.80 (m, 4H), 2.65 (s, 3H), 3.15-3.25 (m, 1H), 3.35 (ddd, J=2.2, 11.3, 11.3 Hz, 2H), 3.85-3.93 (m, 2H), 6.71 (dd, J=1.9, 3.5 Hz, 1H), 7.38 (dd, J=0.5, 3.5 Hz, 1H), 7.92 (dd, J=0.5, 1.9 Hz, 1H), 8.74 (d, J=1.1 Hz, 1H), 9.20 (d, J=1.1 Hz, 1H), 13.07 (br s, 1H). APCIMS m/z: [M+H]$^+$ 399. mp: 130-131° C.

Reference Example 416

N-[4-(2-Furyl)-5-(tetrahydropyran-4-ylcarbonyl) thiazol-2-yl]furan-2-carboxamide (Compound 416)

$^1$H NMR (DMSO-d$_6$, δ ppm): 1.54-1.74 (m, 4H), 3.13-3.24 (m, 1H), 3.26-3.40 (m, 2H), 3.84-3.92 (m, 2H), 6.70 (dd, J=1.6, 3.5 Hz, 1H), 6.77 (dd, J=1.6, 3.5 Hz, 1H), 7.42 (d, J=3.5 Hz, 1H), 7.78 (d, J=3.5 Hz, 1H), 7.90 (d, J=1.6 Hz, 1H), 8.06 (d, J=1.6 Hz, 1H), 13.22 (br s, 1H). APCIMS m/z: [M+H]$^+$ 373. mp: 196-198° C.

Reference Example 417

N-[4-(2-Furyl)-5-(tetrahydropyran-4-ylcarbonyl) thiazol-2-yl]-5-methylfuran-2-carboxamide (Compound 417)

$^1$H NMR (DMSO-d$_6$, δ ppm): 1.50-1.80 (m, 4H), 2.40 (s, 3H), 3.13-3.24 (m, 1H), 3.34 (ddd, J=2.4, 11.6, 11.6 Hz, 2H), 3.84-3.91 (m, 2H), 6.41 (d, J=3.5 Hz, 1H), 6.70 (dd, J=1.6, 3.5 Hz, 1H), 7.41 (dd, J=0.8, 3.5 Hz, 1H), 7.70 (d, J=3.5 Hz, 1H), 7.90 (dd, J=0.8, 1.9 Hz, 1H), 13.08 (br s, 1H). APCIMS m/z: [M+H]$^+$ 387. mp: 209-212° C.

Reference Example 418

5-Formyl-N-[4-(2-furyl)-5-(tetrahydropyran-4-ylcarbonyl)-thiazol-2-yl]furan-2-carboxamide (Compound 418)

$^1$H NMR (DMSO-d$_6$, δ ppm): 1.50-1.80 (m, 4H), 3.10-3.22 (m, 1H), 3.35 (ddd, J=2.2, 11.6, 11.6 Hz, 2H), 3.82-3.92 (m, 2H), 6.70 (dd, J=1.6, 3.5 Hz, 1H), 7.41 (d, J=3.5 Hz, 1H), 7.67 (d, J=3.8 Hz 1H), 7.87 (d, J=3.8 Hz, 1H), 7.90 (d, J=1.6 Hz, 1H), 9.78 (s, 1H), 13.63 (br s, 1H). APCIMS m/z: [M+H]$^+$ 401.

Reference Example 419

N-[4-(2-Furyl)-5-(tetrahydropyran-4-ylcarbonyl) thiazol-2-yl]-5-(hydroxyimino)furan-2-carboxamide (Compound 419)

Reference Example 420

5-Cyano-N-[4-(2-furyl)-5-(tetrahydropyran-4-ylcarbonyl)-thiazol-2-yl]furan-2-carboxamide (Compound 420)

$^1$H NMR (DMSO-d$_6$, δ ppm): 1.50-1.75 (m, 4H), 3.15-3.35 (m, 3H), 3.85-3.92 (m, 2H), 6.71 (dd, J=1.6, 3.2 Hz, 1H), 7.43 (d, J=3.2 Hz, 1H), 7.82 (d, J=4.1 Hz, 1H), 7.86 (d, J=4.1 Hz, 1H), 7.91 (d, J=1.6 Hz, 1H), 13.66 (br s, 1H). APCIMS m/z: [M+H]$^+$ 398. mp: 222-223° C.

Reference Example 421

N-[4-(2-Furyl)-5-(tetrahydropyran-4-ylcarbonyl) thiazol-2-yl]furan-3-carboxamide (Compound 421)

$^1$H NMR (DMSO-d$_6$, δ ppm): 1.53-1.73 (m, 4H), 3.13-3.24 (m, 1H), 3.40 (ddd, J=2.4, 11.3, 11.3 Hz, 2H), 3.88 (ddd, J=2.4, 4.0, 11.3 Hz, 2H), 6.70 (dd, J=1.9, 3.5 Hz, 1H), 7.12-7.14 (m, 1H), 7.43 (dd, J=0.8, 3.5 Hz, 1H), 7.85-7.89 (m, 1H), 7.90 (dd, J=0.8, 1.9 Hz, 1H), 8.65-8.69 (m, 1H), 13.08 (br s, 1H). APCIMS m/z: [M+H]$^+$ 373. mp: 236-238° C.

Reference Example 422

N-[4-(2-Furyl)-5-(tetrahydropyran-4-ylcarbonyl)thiazol-2-yl]thiophene-2-carboxamide (Compound 422)

$^1$H NMR (DMSO-d$_6$, δ ppm): 1.53-1.77 (m, 4H), 3.12-3.24 (m, 1H), 3.35 (ddd, J=2.4, 11.3, 11.3 Hz, 2H), 3.89 (ddd, J=2.4, 3.8, 11.3 Hz, 2H), 6.70 (dd, J=1.9, 3.5 Hz, 1H), 7.28 (dd, J=1.4, 4.9 Hz, 1H), 7.45 (dd, J=0.5, 3.5 Hz 1H), 7.90 (dd, J=0.5, 1.9 Hz, 1H), 8.04 (dd, J=0.8, 4.9 Hz, 1H), 8.34 (dd, J=0.8, 1.4 Hz, 1H), 13.35 (br s, 1H). APCIMS m/z: [M+H]$^+$ 389. mp: 231-232° C.

Reference Example 423

N-[4-(2-Furyl)-5-(tetrahydropyran-4-ylcarbonyl)thiazol-2-yl]thiophene-3-carboxamide (Compound 423)

$^1$H NMR (DMSO-d$_6$, δ ppm): 1.54-1.76 (m, 4H), 3.13-3.25 (m, 1H), 3.35 (ddd, J=2.2, 11.6, 11.6 Hz, 2H), 3.84-3.93 (m, 2H), 6.70 (dd, J=1.6, 3.2 Hz, 1H), 7.44 (d, J=3.2 Hz, 1H), 7.72 (dd, J=2.7, 5.1 Hz, 1H), 7.78 (dd, J=1.3, 2.7 Hz, 1H), 7.90 (d, J=1.6 Hz, 1H), 8.70 (dd, J=1.3, 2.7 Hz, 1H), 13.13 (br s, 1H). APCIMS m/z: [M+H]$^+$ 389. mp: 227-229° C.

Reference Example 424

N-[4-(2-Furyl)-5-(tetrahydropyran-4-ylcarbonyl)thiazol-2-yl]-1-methylpyrazole-4-carboxamide (Compound 424)

$^1$H NMR (DMSO-d$_6$, δ ppm): 1.50-1.75 (m, 4H), 3.10-3.20 (m, 1H), 3.35 (ddd, J=2.2, 11.3, 11.3 Hz, 2H), 3.88 (ddd, J=2.2, 4.1, 11.3 Hz, 2H), 3.92 (s, 3H), 6.70 (dd, J=1.6, 3.5 Hz, 1H), 7.44 (dd, J=0.8, 1.6 Hz, 1H), 7.90 (dd, J=0.8, 3.5 Hz, 1H), 8.22 (s, 1H), 8.53 (s, 1H), 12.94 (br s, 1H). APCIMS m/z: [M+H]$^+$ 387. mp: 243-247° C.

Reference Example 425

1-Ethyl-N-[4-(2-furyl)-5-(tetrahydropyran-4-ylcarbonyl)-thiazol-2-yl]pyrazole-4-carboxamide (Compound 425)

$^1$H NMR (DMSO-d$_6$, δ ppm): 1.41 (t, J=7.0 Hz, 3H), 1.50-1.80 (m, 4H), 3.10-3.25 (m, 1H), 3.30-3.45 (m, 2H), 3.83-3.92 (m, 2H), 4.21 (q, J=7.0 Hz, 2H), 6.70 (dd, J=1.6, 3.5 Hz, 1H), 7.43 (d, J=3.5 Hz, 1H), 7.90 (d, J=1.6 Hz, 1H), 8.23 (s, 1H), 8.58 (s, 1H). 12.93 (br s, 1H). APCIMS m/z: [M+H]$^+$ 401. mp: 170-174° C.

Reference Example 426

N-[4-(2-Furyl)-5-(tetrahydropyran-4-ylcarbonyl)thiazol-2-yl]-1-phenylpyrazole-4-carboxamide (Compound 426)

$^1$H NMR (DMSO-d$_6$, δ ppm): 1.50-1.80 (m, 4H), 3.20-3.30 (m, 1H), 3.30-3.45 (m, 2H), 3.82-3.92 (m, 2H), 6.71 (dd, J=1.6, 3.2 Hz, 1H), 7.38-7.44 (m, 2H), 7.43 (d, J=3.2 Hz, 1H), 7.55-7.62 (m, 2H), 7.85-7.93 (m, 2H), 8.50 (s, 1H), 9.30 (s, 1H), 13.08 (br s, 1H). APCIMS m/z: [M+H]$^+$ 449. mp: 217-220° C.

Reference Example 427

N-[4-(2-Furyl)-5-(tetrahydropyran-4-ylcarbonyl)thiazol-2-yl]isoxazole-5-carboxamide (Compound 427)

$^1$H NMR (DMSO-d$_6$, δ ppm): 1.53-1.79 (m, 4H), 3.15-3.26 (m, 1H), 3.36 (ddd, J=2.2, 11.6, 11.6 Hz, 2H), 3.83-3.92 (m, 2H), 6.71 (dd, J=1.6, 3.5 Hz, 1H), 7.42 (d, J=3.5 Hz, 1H), 7.59 (d, J=1.9 Hz, 1H), 7.91 (d, J=1.6 Hz, 1H) 8.87 (d, J=1.9 Hz, 1H), 13.78 (br s, 1H). APCIMS m/z: [M+H]$^+$ 372.

Reference Example 428

N-[4-(2-Furyl)-5-(tetrahydropyran-4-ylcarbonyl)thiazol-2-yl]tetrahydrofuran-2-carboxamide (Compound 428)

$^1$H NMR (DMSO-d$_6$, δ ppm): 1.50-1.75 (m, 4H), 1.80-2.20 (m, 3H), 2.20-2.30 (m, 1H), 3.10-3.25 (m, 1H), 3.33 (ddd, J=2.2, 11.3, 11.3 Hz, 2H), 3.77-4.02 (m, 4H), 4.58 (dd, J=5.4, 8.1 Hz, 1H), 6.69 (dd, J=1.9, 3.5 Hz, 1H), 7.38 (dd, J=0.8, 3.5 Hz, 1H), 7.89 (dd, J=0.8, 1.9 Hz, 1H), 12.66 (br s, 1H). APCIMS m/z: [M+H]$^+$ 377. mp: 115-117° C.

Reference Example 429

N-[4-(2-Furyl)-5-(tetrahydropyran-4-ylcarbonyl)thiazol-2-yl]tetrahydrofuran-3-carboxamide (Compound 429)

$^1$H NMR (DMSO-d$_6$, δ ppm): 1.50-1.80 (m, 4H), 2.05-2.15 (m, 2H), 3.10-3.25 (m, 1H), 3.30-3.45 (m, 3H), 3.70-4.00 (m, 6H), 6.69 (dd, J=1.9, 3.5 Hz, 1H), 7.40 (dd, J=0.8, 3.5 Hz, 1H), 7.89 (dd, J=0.8, 1.9 Hz, 1H), 12.90 (br s, 1H). APCIMS m/z: [M+H]$^+$ 377. mp: 164-166° C.

Reference Example 430

N-[4-(2-Furyl)-5-(tetrahydropyran-4-ylcarbonyl)thiazol-2-yl]-2-(tetrahydropyran-4-yl)acetamide (Compound 430)

$^1$H NMR (DMSO-d$_6$, δ ppm): 1.20-1.40 (m, 2H), 1.50-1.75 (m, 8H), 1.95-2.10 (m, 1H), 2.43 (d, J=7.0 Hz, 2H), 3.15-3.30 (m, 1H), 3.33 (ddd, J=2.2, 11.6, 11.6 Hz, 2H), 3.80-3.90 (m, 4H), 6.69 (dd, J=1.9, 3.5 Hz, 1H), 7.39 (dd, J=0.8, 3.5 Hz, 1H), 7.88 (dd, J=0.8, 1.9 Hz, 1H), 12.77 (br s, 1H). APCIMS m/z: [M+H]$^+$ 405. mp: 206-209° C.

Reference Example 431

N-[4-(2-Furyl)-5-(tetrahydropyran-4-ylcarbonyl)thiazol-2-yl]-2-phenylacetamide (Compound 431)

$^1$H NMR (DMSO-d$_6$, δ ppm): 1.49-1.75 (m, 4H), 3.08-3.20 (m, 1H), 3.36-3.50 (m, 2H), 3.82 (s, 2H), 3.83-3.90 (m, 2H), 6.69 (dd, J=1.9, 3.5 Hz, 1H), 7.20-7.35 (m, 5H), 7.40 (d, J=3.5

Reference Example 432

N-[4-(2-Furyl)-5-(tetrahydropyran-4-ylcarbonyl)thiazol-2-yl]-3-phenylpropanamide (Compound 432)

$^1$H NMR (DMSO-d$_6$, δ ppm): 1.50-1.67 (m, 4H), 2.81 (t, J=6.7 Hz, 2H), 2.94 (t, J=6.7 Hz, 2H), 3.10-3.22 (m, 1H), 3.34 (ddd, J=2.4, 10.8, 10.8 Hz, 2H), 3.83-3.93 (m, 2H), 6.68 (dd, J=1.9, 3.5 Hz, 1H), 7.15-7.29 (m, 5H), 7.38 (d, J=3.5 Hz, 1H), 7.88 (d, J=1.9 Hz, 1H), 12.78 (br s, 1H). APCIMS m/z: [M+H]$^+$ 411. mp: 161-164° C.

Reference Example 433

N-[4-(2-Furyl)-5-(tetrahydropyran-4-ylcarbonyl)thiazol-2-yl]-3-phenylacrylamide (Compound 433)

$^1$H NMR (DMSO-d$_6$, δ ppm): 1.50-1.75 (m, 4H), 3.10-3.30 (m, 1H), 3.35-3.45 (m, 2H), 3.83-3.93 (m, 2H), 6.70 (dd, J=1.6, 3.2 Hz, 1H), 6.92 (d, J=15.6 Hz, 1H), 7.40 (d, J=3.2 Hz, 1H), 7.45-7.51 (m, 3H), 7.63-7.69 (m, 2H), 7.80 (d, J=15.6 Hz, 1H), 7.91 (d, J=1.6 Hz, 1H), 13.04 (br s, 1H). APCIMS m/z: [M+H]$^+$ 409. mp: 253-256° C.

Reference Example 434

N-[4-(2-Furyl)-5-(tetrahydropyran-4-ylcarbonyl)thiazol-2-yl]-2-phenoxyacetamide (Compound 434)

$^1$H NMR (DMSO-d$_6$, δ ppm): 1.50-1.78 (m, 4H), 3.11-3.23 (m, 1H), 3.32-3.38 (m, 2H), 3.82-3.88 (m, 2H), 4.92 (s, 2H), 6.70 (dd, J=1.9, 3.5 Hz, 1H), 6.95-7.02 (m, 3H), 7.31 (dd, J=7.8, 7.8 Hz, 2H), 7.39 (d, J=3.5 Hz, 1H), 7.90 (d, J=1.9 Hz, 1H), 13.05 (br s, 1H). APCIMS m/z: [M+H]$^+$ 413. mp: 148-150° C.

Reference Example 435

N-[4-(2-Furyl)-5-(tetrahydropyran-4-ylcarbonyl)thiazol-2-yl]-2-methoxyacetamide (Compound 435)

$^1$H NMR (DMSO-d$_6$, δ ppm): 1.50-1.80 (m, 4H), 3.10-3.22 (m, 1H), 3.34 (ddd, J=2.2, 11.3, 11.3 Hz, 2H), 3.36 (s, 3H), 3.87 (ddd, J=2.2, 4.3, 11.3 Hz, 2H), 4.20 (s, 2H), 6.69 (dd, J=1.6, 3.2 Hz, 1H), 7.38 (dd, J=0.8, 3.2 Hz, 1H), 7.89 (dd, J=0.8, 1.6 Hz, 1H), 12.75 (br s, 1H). APCIMS m/z: [M+H]$^+$ 351. mp: 148-149° C.

Reference Example 436

2-Bromo-N-[4-(2-furyl)-5-(tetrahydropyran-4-ylcarbonyl)-thiazol-2-yl]acetamide (Compound 436)

$^1$H NMR (CDCl$_3$, δ ppm): 1.65-2.00 (m, 4H), 3.15 (tt, J=4.3, 10.7 Hz, 1H), 3.49 (ddd, J=2.8, 11.4, 11.4 Hz, 2H), 4.00-4.08 (m, 2H), 4.05 (s, 2H), 6.58 (dd, J=1.8, 3.6 Hz, 1H), 7.58 (dd, J=0.8, 1.8 Hz, 1H), 7.74 (dd, J=0.8, 3.6 Hz, 1H).

Reference Example 437

2-Ethoxy-N-[4-(2-furyl)-5-(tetrahydropyran-4-ylcarbonyl)-thiazol-2-yl]acetamide (Compound 437)

$^1$H NMR (DMSO-d$_6$, δ ppm): 1.16 (t, J=7.0 Hz, 3H), 1.50-1.75 (m, 4H), 3.10-3.25 (m, 1H), 3.34 (ddd, J=2.7, 11.6, 11.6 Hz, 2H), 3.56 (q, J=7.0 Hz, 2H), 3.87 (ddd, J=2.7, 4.3, 11.6 Hz, 2H), 4.23 (s, 2H), 6.69 (dd, J=1.9, 3.5 Hz, 1H), 7.38 (dd, J=0.8, 3.5 Hz, 1H), 7.89 (dd, J=0.8, 1.9 Hz, 1H), 12.70 (br s, 1H). APCIMS m/z: [M+H]$^+$ 365. mp: 121-126° C.

Reference Example 438

2-(Dimethylamino)-N-[4-(2-furyl)-5-(tetrahydropyran-4-ylcarbonyl)thiazol-2-yl]acetamide (Compound 438)

$^1$H NMR (DMSO-d$_6$, δ ppm): 1.50-1.75 (m, 4H), 2.32 (s, 6H), 3.10-3.22 (m, 1H), 3.30 (s, 2H), 3.30-3.45 (m, 2H), 3.83-3.92 (m, 2H), 6.68 (dd, J=1.6, 3.5 Hz, 1H), 7.38 (d, J=3.5 Hz, 1H), 7.88 (d, J=1.6 Hz, 1H). APCIMS m/z: [M+H]$^+$ 364. mp: 129-130° C.

Reference Example 439

N-[4-(2-Furyl)-5-(tetrahydropyran-4-ylcarbonyl)thiazol-2-yl]-2-[N-(2-methoxyethyl)-N-methylamino]acetamide (Compound 439)

$^1$H NMR (DMSO-d$_6$, δ ppm): 1.50-1.75 (m, 4H), 2.37 (s, 3H), 2.69 (t, J=5.4 Hz, 2H), 3.10-3.20 (m, 1H), 3.26 (s, 3H), 3.34 (ddd, J=2.4, 11.3, 11.3 Hz, 2H), 3.44 (s, 2H), 3.44 (q, J=5.4 Hz, 2H), 3.87 (ddd, J=2.4, 3.8, 11.3 Hz, 2H), 6.69 (dd, J=1.9, 3.5 Hz, 1H), 7.38 (d, J=3.5 Hz, 1H), 7.89 (d, J=1.9 Hz, 1H). APCIMS m/z: [M+H]$^+$ 408. mp: 103-105° C.

Reference Example 440

2-[N,N-bis(2-Methoxyethyl)amino]-N-[4-(2-furyl)-5-(tetrahydropyran-4-ylcarbonyl)thiazol-2-yl]acetamide (Compound 440)

$^1$H NMR (CDCl$_3$, δ ppm): 1.70-2.00 (m, 4H), 2.88 (t, J=5.1 Hz, 4H), 3.10-3.20 (m, 1H), 3.23 (s, 6H), 3.30-3.40 (m, 2H), 3.49 (t, J=5.1 Hz, 4H), 3.58 (s, 2H), 4.03 (ddd, J=2.7, 3.8, 11.3 Hz, 2H), 6.55 (dd, J=1.6, 3.5 Hz, 1H), 7.56 (dd, J=0.8, 1.6 Hz, 1H), 7.64 (dd, J=0.8, 3.5 Hz, 1H), 11.55 (br s, 1H). APCIMS m/z: [M+H]$^+$ 452.

Reference Example 441

N-[4-(2-Furyl)-5-(tetrahydropyran-4-ylcarbonyl)thiazol-2-yl]-2-(1-pyrrolidinyl)acetamide (Compound 441)

$^1$H NMR (DMSO-d$_6$, δ ppm): 1.50-1.80 (m, 6H), 2.63-2.71 (m, 4H), 3.10-3.22 (m, 1H), 3.25-3.40 (m, 4H), 3.51 (s, 2H), 3.87 (ddd, J=2.2, 4.0, 12.1 Hz, 2H), 6.68 (dd, J=1.9, 3.5 Hz, 1H), 7.38 (dd, J=0.8, 3.5 Hz, 1H), 7.87 (dd, J=0.8, 1.9 Hz, 1H). APCIMS m/z: [M+H]$^+$ 390. mp: 115-117° C.

Reference Example 442

N-[4-(2-Furyl)-5-(tetrahydropyran-4-ylcarbonyl)thiazol-2-yl]-2-[(2R)-2-(methoxymethyl)pyrrolidin-1-yl]acetamide (Compound 442)

$^1$H NMR (DMSO-d$_6$, δ ppm): 1.45-1.95 (m, 8H), 2.84-2.89 (m, 1H), 3.00-3.05 (m, 1H), 3.10-3.40 (m, 6H), 3.20 (s, 3H), 3.48 (d, J=16.7 Hz, 1H), 3.72 (d, J=16.7 Hz, 1H), 3.87 (ddd, J=2.4, 4.0, 11.6 Hz, 2H), 6.69 (dd, J=1.9, 3.5 Hz, 1H), 7.39

Reference Example 443

N-[4-(2-Furyl)-5-(tetrahydropyran-4-ylcarbonyl) thiazol-2-yl]-2-[(2S)-2-(methoxymethyl)pyrrolidin-1-yl]acetamide (Compound 443)

$^1$H NMR (DMSO-d$_6$, δ ppm): 1.45-1.95 (m, 8H), 2.84-2.89 (m, 1H), 3.00-3.05 (m, 1H), 3.10-3.40 (m, 6H), 3.20 (s, 3H), 3.48 (d, J=16.7 Hz, 1H), 3.72 (d, J=16.7 Hz, 1H), 3.87 (ddd, J=2.4, 4.0, 11.6 Hz, 2H), 6.69 (dd, J=1.9, 3.5 Hz, 1H), 7.39 (dd, J=0.8, 3.5 Hz, 1H), 7.89 (dd, J=0.8, 1.9 Hz, 1H). APCIMS m/z: [M+H]$^+$ 434. mp: 102-103° C.

Reference Example 444

N-[4-(2-Furyl)-5-(tetrahydropyran-4-ylcarbonyl) thiazol-2-yl]-2-[3-(dimethylamino)pyrrolidin-1-yl] acetamide (Compound 444)

$^1$H NMR (CDCl$_3$, δ ppm): 1.70-2.15 (m, 6H), 2.26 (m, 6H), 2.45-2.55 (m, 1H), 2.55-2.80 (m, 2H), 2.85-3.05 (m, 2H), 3.10-3.20 (m, 1H), 3.40-3.60 (m, 4H), 4.00-4.09 (m, 2H), 6.58 (dd, J=1.6, 3.2 Hz, 1H), 7.59 (d, J=1.6 Hz, 1H), 7.78 (d, J=3.2 Hz, 1H). APCIMS m/z: [M+H]$^+$ 433.

Reference Example 445

N-[4-(2-Furyl)-5-(tetrahydropyran-4-ylcarbonyl) thiazol-2-yl]-2-(isoindolin-2-yl)acetamide (Compound 445)

$^1$H NMR (CDCl$_3$, δ ppm): 1.70-2.00 (m, 4H), 3.10-3.20 (m, 1H), 3.49 (ddd, J=2.7, 11.3, 11.3 Hz, 2H), 3.73 (s, 2H), 4.04 (ddd, J=2.7, 3.5, 11.3 Hz, 2H), 4.16 (s, 4H), 6.55 (dd, J=1.9, 3.8 Hz, 1H), 7.20-7.30 (m, 4H), 7.54 (dd, J=0.8, 1.9 Hz, 1H), 7.77 (dd, J=0.8, 3.8 Hz, 1H). APCIMS m/z: [M+H]$^+$ 438.

Reference Example 446

N-[4-(2-Furyl)-5-(tetrahydropyran-4-ylcarbonyl) thiazol-2-yl]-2-(thiazolidin-3-yl)acetamide (Compound 446)

$^1$H NMR (CDCl$_3$, δ ppm): 1.75-2.00 (m, 4H), 2.96-3.03 (m, 2H), 3.10-3.20 (m, 3H), 3.37 (s, 2H), 3.49 (ddd, J=3.0, 11.6, 11.6 Hz, 2H), 4.04 (ddd, J=3.0, 4.0, 11.6 Hz, 2H), 4.04 (s, 2H), 6.58 (dd, J=1.9, 3.5 Hz, 1H), 7.59 (dd, J=0.8, 1.9 Hz, 1H), 7.82 (dd, J=0.8, 3.5 Hz, 1H), 10.71 (br s, 1H). APCIMS m/z: [M+H]$^+$ 408.

Reference Example 447

N-[4-(2-Furyl)-5-(tetrahydropyran-4-ylcarbonyl) thiazol-2-yl]-2-piperidinoacetamide (Compound 447)

$^1$H NMR (DMSO-d$_6$, δ ppm): 1.35-1.45 (m, 2H), 1.50-1.80 (m, 8H), 3.05-3.20 (m, 1H), 3.29 (s, 2H), 3.30-3.50 (m, 6H), 3.87 (ddd, J=2.4, 3.8, 11.6 Hz, 2H), 6.68 (dd, J=1.9, 3.5 Hz, 1H), 7.39 (dd, J=0.5, 3.5 Hz, 1H), 7.88 (dd, J=0.5, 1.9 Hz, 1H). APCIMS m/z: [M+H]$^+$ 404. mp: 146-147° C.

Reference Example 448

N-[4-(2-Furyl)-5-(tetrahydropyran-4-ylcarbonyl) thiazol-2-yl]-2-(4-hydroxypiperidino)acetamide (Compound 448)

$^1$H NMR (DMSO-d$_6$, δ ppm): 1.30-1.50 (m, 2H), 1.50-1.75 (m, 6H), 2.28 (ddd, J=2.4, 9.7, 12.1 Hz, 2H), 2.80-2.90 (m, 2H), 3.10-3.22 (m, 1H), 3.30-3.50 (m, 4H), 3.33 (s, 2H), 3.83-3.92 (m, 2H), 6.69 (dd, J=1.9, 3.5 Hz, 1H), 7.39 (dd, J=0.8, 3.5 Hz, 1H), 7.88 (dd, J=0.8, 1.9 Hz, 1H). APCIMS m/z: [M+H]$^+$ 420. mp: 178-180° C.

Reference Example 449

N-[4-(2-Furyl)-5-(tetrahydropyran-4-ylcarbonyl) thiazol-2-yl]-2-(3-hydroxypiperidino)acetamide (Compound 449)

$^1$H NMR (CDCl$_3$, δ ppm): 1.75-2.00 (m, 8H), 2.45-2.60 (m, 2H), 2.55-2.70 (m, 1H), 2.82 (dd, J=2.4, 8.1 Hz, 1H), 3.10-3.20 (m, 1H), 3.31 (s, 2H), 3.48 (ddd, J=2.7, 11.3, 11.3 Hz, 2H), 3.80-3.95 (m, 1H), 4.03 (ddd, J=2.4, 4.0, 11.3 Hz, 2H), 6.57 (dd, J=1.6, 3.2 Hz, 1H), 7.58 (d, J=1.6 Hz, 1H), 7.74 (d, J=3.2 Hz, 1H). APCIMS m/z: [M+H]$^+$ 420.

Reference Example 450

N-[4-(2-Furyl)-5-(tetrahydropyran-4-ylcarbonyl) thiazol-2-yl]-2-(4-methoxypiperidino)acetamide (Compound 450)

$^1$H NMR (DMSO-d$_6$, δ ppm): 1.40-1.85 (m, 8H), 2.32 (ddd, J=2.7, 9.2, 11.6 Hz, 2H), 2.70-2.80 (m, 2H), 3.22 (s, 3H), 3.30-3.80 (m, 4H), 3.34 (s, 2H), 3.87 (ddd, J=2.2, 4.3, 11.3 Hz, 2H), 6.69 (dd, J=1.6, 3.5 Hz, 1H), 7.39 (dd, J=0.8, 3.5 Hz, 1H), 7.88 (dd, J=0.8, 1.6 Hz, 1H). APCIMS m/z: [M+H]$^+$ 434. mp: 109-111° C.

Reference Example 451

N-[4-(2-Furyl)-5-(tetrahydropyran-4-ylcarbonyl) thiazol-2-yl]-2-(4-hydroxy-4-methylpiperidino)acetamide (Compound 451)

$^1$H NMR (CDCl$_3$, δ ppm): 1.11 (s, 3H), 1.45-1.75 (m, 8H), 2.50-2.55 (m, 4H), 3.10-3.20 (m, 1H), 3.34 (ddd, J=2.7, 11.3, 11.3 Hz, 2H), 3.34 (s, 2H), 3.87 (ddd, J=2.7, 4.3, 11.3 Hz, 2H), 6.68 (dd, J=1.6, 3.5 Hz, 1H), 7.39 (dd, J=0.5, 3.5 Hz, 1H), 7.88 (dd, J=0.5, 1.6 Hz, 1H). APCIMS m/z: [M+H]$^+$ 434. mp: 151-153° C.

Reference Example 452

N-[4-(2-Furyl)-5-(tetrahydropyran-4-ylcarbonyl) thiazol-2-yl]-2-(3-hydroxymethylpiperidino)acetamide (Compound 452)

$^1$H NMR (CDCl$_3$, δ ppm): 1.60-2.00 (m, 9H), 2.08-2.18 (m, 1H), 2.18-2.38 (m, 1H), 2.71-2.91 (m, 1H), 2.94 (dd, J=1.6, 10.8 Hz, 1H), 3.10-3.20 (m, 1H), 3.28 (s, 2H), 3.48 (ddd, J=3.0, 11.3, 11.3 Hz, 2H), 3.50-3.64 (m, 2H), 4.04 (ddd, J=3.0, 4.0, 11.3 Hz, 2H), 6.57 (dd, J=1.6, 3.5 Hz, 1H), 7.59 (dd, J=0.8, 1.6 Hz, 1H), 7.76 (dd, J=0.8, 3.5 Hz, 1H). APCIMS m/z: [M+H]$^+$ 434.

Reference Example 453

N-[4-(2-Furyl)-5-(tetrahydropyran-4-ylcarbonyl)thiazol-2-yl]-2-(4-hydroxymethylpiperidino)acetamide (Compound 453)

$^1$H NMR (CDCl$_3$, δ ppm): 1.30-1.60 (m, 3H), 1.70-2.00 (m, 8H), 2.31 (ddd, J=2.4, 11.9, 11.9 Hz, 2H), 2.86-2.96 (m, 2H), 3.10-3.20 (m, 1H), 3.28 (s, 2H), 3.48 (ddd, J=3.0, 11.6, 11.6 Hz, 2H), 3.55 (d, J=3.5 Hz, 2H), 4.04 (ddd, J=3.0, 4.0, 11.6 Hz, 2H), 6.58 (dd, J=1.6, 3.5 Hz, 1H), 7.59 (dd, J=0.8, 1.6 Hz, 1H), 7.77 (dd, J=0.8, 3.5 Hz, 1H). APCIMS m/z: [M+H]$^+$ 434.

Reference Example 454

N-[4-(2-Furyl)-5-(tetrahydropyran-4-ylcarbonyl)thiazol-2-yl]-2-[4-(2-hydroxypropan-2-yl)piperidino]acetamide (Compound 454)

$^1$H NMR (CDCl$_3$, δ ppm): 1.22 (s, 6H), 1.40-1.60 (m, 4H), 1.70-2.00 (m, 6H), 2.26 (ddd, J=2.2, 11.3, 11.3 Hz, 2H) 2.93-3.00 (m, 2H), 3.05-3.15 (m, 1H), 3.27 (s, 2H), 3.49 (ddd, J=2.7, 11.3, 11.3 Hz, 2H), 4.03 (ddd, J=2.7, 3.8, 11.3 Hz, 2H), 6.57 (dd, J=1.6, 3.5 Hz, 1H), 7.59 (dd, J=0.8, 1.6 Hz, 1H), 7.79 (dd, J=0.8, 3.5 Hz, 1H). APCIMS m/z: [M+H]$^+$ 462.

Reference Example 455

N-[4-(2-Furyl)-5-(tetrahydropyran-4-ylcarbonyl)thiazol-2-yl]-2-[4-(2-hydroxy-2-methylpropyl)piperidino]acetamide (Compound 455)

$^1$H NMR (CDCl$_3$, δ ppm): 1.26 (s, 6H), 1.40-1.70 (m, 3H), 1.70-2.00 (m, 8H), 2.27-2.34 (m, 2H), 2.80-2.90 (m, 2H), 3.10-3.20 (m, 1H), 3.25 (s, 2H), 3.42-3.54 (m, 3H), 3.99-4.09 (m, 2H), 6.57 (dd, J=1.6, 3.5 Hz, 1H), 7.59 (d, J=1.6 Hz, 1H), 7.78 (d, J=3.5 Hz, 1H). APCIMS m/z: [M+H]$^+$ 476.

Reference Example 456

N-[4-(2-Furyl)-5-(tetrahydropyran-4-ylcarbonyl)thiazol-2-yl]-2-[4-(1-pyrrolidinyl)piperidino]acetamide (Compound 456)

$^1$H NMR (DMSO-d$_6$, δ ppm): 1.30-1.75 (m, 12H), 1.95-2.05 (m, 1H), 2.10-2.20 (m, 2H), 2.70-2.85 (m, 2H), 3.10-3.20 (m, 1H), 3.25-3.40 (m, 8H), 3.83-3.93 (m, 2H), 6.68 (dd, J=1.6, 3.2 Hz, 1H), 7.39 (d, J=3.2 Hz, 1H), 7.88 (d, J=1.6 Hz, 1H). ESIMS m/z: [M+H]$^+$ 473. mp: 183-184° C.

Reference Example 457

N-[4-(2-Furyl)-5-(tetrahydropyran-4-ylcarbonyl)thiazol-2-yl]-2-(4-piperidinopiperidino)acetamide (Compound 457)

$^1$H NMR (DMSO-d$_6$, δ ppm): 1.30-1.75 (m, 12H), 2.13-2.20 (m, 2H), 2.50-2.60 (m, 3H), 2.80-2.95 (m, 2H), 3.15-3.25 (m, 1H), 3.25-3.40 (m, 6H), 3.33 (s, 2H), 3.83-3.93 (m, 2H), 6.69 (dd, J=1.6, 3.5 Hz, 1H), 7.39 (dd, J=0.8, 3.5 Hz, 1H), 7.88 (d, J=0.8, 1.6 Hz, 1H). APCIMS m/z: [M+H]$^+$ 487. mp: 177-179° C.

Reference Example 458

N-[4-(2-Furyl)-5-(tetrahydropyran-4-ylcarbonyl)thiazol-2-yl]-2-(4-morpholinopiperidino)acetamide (Compound 458)

$^1$H NMR (DMSO-d$_6$, δ ppm): 1.30-1.55 (m, 2H), 1.55-1.80 (m, 6H), 2.05-2.30 (m, 3H), 2.44 (t, J=4.3 Hz, 4H), 2.90 (d, J=11.6 Hz, 2H), 3.10-3.25 (m, 1H), 3.34 (ddd, J=2.2, 11.3, 11.3 Hz, 2H), 3.34 (s, 2H), 3.56 (t, J=4.3 Hz, 4H), 3.87 (ddd, J=2.2, 3.8, 11.3 Hz, 2H), 6.69 (dd, J=1.9, 3.5 Hz, 1H), 7.39 (dd, J=0.5, 3.5 Hz, 1H), 7.88 (dd, J=0.5, 1.9 Hz, 1H). APCIMS m/z: [M+H]$^+$ 489. mp: 193-195° C.

Reference Example 459

2-(1,4-Dioxa-8-azaspiro[4.5]decan-8-yl)-N-[4-(2-furyl)-5-(tetrahydropyran-4-ylcarbonyl)thiazol-2-yl]acetamide (Compound 459)

$^1$H NMR (DMSO-d$_6$, δ ppm): 1.52-1.75 (m, 8H), 2.55-2.70 (m, 4H), 3.15-3.25 (m, 1H), 3.25-3.35 (m, 2H), 3.37 (s, 2H), 3.86 (s, 4H), 3.86-3.93 (m, 2H), 6.69 (dd, J=1.9, 3.5 Hz, 1H), 7.39 (d, J=3.5 Hz, 1H), 7.89 (d, J=1.9 Hz, 1H). APCIMS m/z: [M+H]$^+$ 462. mp: 186-187° C.

Reference Example 460

2-(4-Cyanopiperidino)-N-[4-(2-furyl)-5-(tetrahydropyran-4-ylcarbonyl)thiazol-2-yl]acetamide (Compound 460)

$^1$H NMR (DMSO-d$_6$, δ ppm): 1.50-1.80 (m, 6H), 2.65-2.75 (m, 2H), 2.85-3.00 (m, 1H), 3.10-3.20 (m, 1H), 3.30-3.50 (m, 6H), 3.40 (s, 2H), 3.83-3.93 (m, 2H), 6.69 (dd, J=1.9, 3.5 Hz, 1H), 7.40 (d, J=3.5 Hz, 1H), 7.89 (d, J=1.9 Hz, 1H), 12.59 (br s, 1H). APCIMS m/z: [M+H]$^+$ 429.

Reference Example 461

2-(4,4-Difluoropiperidino)-N-[4-(2-furyl)-5-(tetrahydropyran-4-ylcarbonyl)thiazol-2-yl]acetamide (Compound 461)

$^1$H NMR (CDCl$_3$, δ ppm): 1.70-2.00 (m, 4H), 2.00-2.20 (m, 4H), 2.70-2.80 (m, 4H), 3.05-3.20 (m, 1H), 3.37 (s, 2H), 3.47 (ddd, J=2.7, 11.3, 11.3 Hz, 2H), 4.04 (ddd, J=2.7, 4.0, 11.3 Hz, 2H), 6.58 (dd, J=1.9, 3.8 Hz, 1H), 7.59 (d, J=1.9 Hz, 1H), 7.77 (d, J=3.8 Hz, 1H), 10.43 (br s, 1H). APCIMS m/z: [M+H]$^+$ 440.

Reference Example 462

N-[4-(2-Furyl)-5-(tetrahydropyran-4-ylcarbonyl)thiazol-2-yl]-2-(1,2,3,6-tetrahydropyridin-1-yl)acetamide (Compound 462)

$^1$H NMR (CDCl$_3$, δ ppm): 1.70-1.95 (m, 4H), 2.20-2.35 (m, 2H), 2.73-2.77 (m, 1H), 3.05-3.20 (m, 3H), 3.37 (s, 2H), 3.49 (ddd, J=2.7, 11.6, 11.6 Hz, 2H), 4.04 (ddd, J=2.7, 4.0, 11.6 Hz, 2H), 5.60-5.70 (m, 1H), 5.75-5.85 (m, 1H), 6.57 (dd, J=1.9, 3.5 Hz, 1H), 7.59 (d, J=1.9 Hz, 1H), 7.79 (d, J=3.5 Hz, 1H). APCIMS m/z: [M+H]⁺ 402.

Reference Example 463

N-[4-(2-Furyl)-5-(tetrahydropyran-4-ylcarbonyl)thiazol-2-yl]-2-morpholinoacetamide (Compound 463)

¹H NMR (DMSO-d₆, δ ppm): 1.50-1.80 (m, 4H), 3.15-3.25 (m, 1H), 3.33-3.38 (m, 6H), 3.39 (s, 2H), 3.60 (t, J=4.6 Hz, 4H), 3.87 (ddd, J=2.4, 4.0, 11.6 Hz, 2H), 6.71 (dd, J=1.6, 3.5 Hz, 1H), 7.39 (dd, J=0.8, 3.5 Hz, 1H), 7.89 (dd, J=0.8, 1.6 Hz, 1H), 12.63 (br s, 1H). APCIMS m/z: [M+H]⁺ 406. mp: 110-104° C.

Reference Example 464

2-(cis-2,6-Dimethylmorpholino)-N-[4-(2-furyl)-5-(tetrahydropyran-4-ylcarbonyl)thiazol-2-yl]acetamide (Compound 464)

¹H NMR (CDCl₃, δ ppm): 1.18 (d, J=6.2 Hz, 6H), 1.70-2.00 (m, 4H), 2.00-2.10 (m, 2H), 2.65-2.80 (m, 4H), 3.05-3.20 (m, 1H), 3.28 (s, 2H), 3.49 (ddd, J=3.0, 11.3, 11.3 Hz, 2H), 4.04 (ddd, J=3.0, 4.0, 11.3 Hz, 2H), 6.58 (dd, J=1.9, 3.8 Hz, 1H), 7.60 (dd, J=0.8, 1.9 Hz, 1H), 7.78 (dd, J=0.8, 3.8 Hz, 1H), 10.45 (br s, 1H). APCIMS m/z: [M+H]⁺ 434.

Reference Example 465

2-[4-(tert-Butoxycarbonyl)piperazin-1-yl]-N-[4-(2-furyl)-5-(tetrahydropyran-4-ylcarbonyl)thiazol-2-yl]acetamide (Compound 465)

¹H NMR (CDCl₃, δ ppm): 1.44 (s, 9H), 1.70-2.00 (m, 4H), 2.57 (t, J=4.9 Hz, 4H), 3.05-3.20 (m, 1H), 3.32 (s, 2H), 3.49 (ddd, J=2.7, 11.6, 11.6 Hz, 2H), 3.53 (t, J=4.9 Hz, 4H), 4.04 (ddd, J=2.7, 4.0, 11.6 Hz, 2H), 6.58 (dd, J=1.9, 3.8 Hz, 1H), 7.59 (dd, J=0.8, 1.9 Hz, 1H), 7.78 (dd, J=0.8, 3.8 Hz, 1H), 10.46 (br s, 1H). APCIMS m/z: [M+H]⁺ 505.

Reference Example 466

N-[4-(2-Furyl)-5-(tetrahydropyran-4-ylcarbonyl)thiazol-2-yl]-2-(1-piperazinyl)acetamide (Compound 466)

¹H NMR (CDCl₃, δ ppm): 1.50-1.80 (m, 4H), 2.74-2.80 (m, 4H), 3.10-3.20 (m, 1H), 3.34 (s, 2H), 3.35-3.45 (m, 8H), 3.87 (ddd, J=2.2, 4.3, 11.1 Hz, 2H), 6.67 (dd, J=1.9, 3.5 Hz, 1H), 7.38 (dd, J=0.5, 3.5 Hz, 1H), 7.87 (dd, J=0.5, 1.9 Hz, 1H). APCIMS m/z: [M+H]⁺ 405.

Reference Example 467

N-[4-(2-Furyl)-5-(tetrahydropyran-4-ylcarbonyl)thiazol-2-yl]-2-(4-methylpiperazin-1-yl)acetamide (Compound 467)

¹H NMR (DMSO-d₆, δ ppm): 1.40-1.75 (m, 4H), 2.30-2.45 (m, 4H), 3.10-3.22 (m, 1H), 3.33 (s, 3H), 3.34-3.50 (m, 8H), 3.87 (ddd, J=2.2, 12.1, 12.1 Hz, 2H), 6.69 (dd, J=1.9, 3.5 Hz, 1H), 7.39 (dd, J=0.8, 3.5 Hz, 1H), 7.89 (dd, J=0.8, 1.9 Hz, 1H). APCIMS m/z: [M+H]⁺ 419. mp: 106-112° C.

Reference Example 468

N-[4-(2-Furyl)-5-(tetrahydropyran-4-ylcarbonyl)thiazol-2-yl]-2-(4-isopropylpiperazin-1-yl)acetamide (Compound 468)

¹H NMR (DMSO-d₆, δ ppm): 1.08 (d, J=6.5 Hz, 6H), 1.70-2.00 (m, 4H), 2.65-2.80 (m, 9H), 3.05-3.20 (m, 1H), 3.30 (s, 2H), 3.49 (ddd, J=2.7, 11.3, 11.3 Hz, 2H), 3.95-4.05 (m, 2H), 6.58 (dd, J=1.6, 3.2 Hz, 1H), 7.59 (d, J=1.6 Hz, 1H), 7.79 (d, J=3.2 Hz, 1H). APCIMS m/z: [M+H]⁺ 447.

Reference Example 469

2-[4-(Ethoxycarbonyl)piperazin-1-yl]-N-[4-(2-furyl)-5-(tetrahydropyran-4-ylcarbonyl)thiazol-2-yl]acetamide (Compound 469)

¹H NMR (DMSO-d₆, δ ppm): 1.28 (t, J=7.0 Hz, 3H), 1.75-2.00 (m, 4H), 2.59 (dd, J=7.5, 7.8 Hz, 4H), 3.05-3.20 (m, 1H), 3.33 (s, 2H), 3.48 (ddd, J=3.0, 11.6, 11.6 Hz, 2H), 3.59 (dd, J=7.5, 7.8 Hz, 4H), 4.04 (ddd, J=3.0, 4.0, 11.6 Hz, 2H), 4.16 (q, J=7.0 Hz, 2H), 6.58 (dd, J=1.9, 3.8 Hz, 1H), 7.59 (dd, J=0.5, 1.9 Hz, 1H), 7.78 (dd, J=0.5, 3.8 Hz, 1H), 10.44 (br s, 1H). APCIMS m/z: [M+H]⁺ 477.

Reference Example 470

N-[4-(2-Furyl)-5-(tetrahydropyran-4-ylcarbonyl)thiazol-2-yl]-2-[4-(2-hydroxy-2-methylpropyl)piperazin-1-yl]acetamide (Compound 470)

¹H NMR (DMSO-d₆, δ ppm): 1.07 (s, 6H), 1.50-1.80 (m, 4H), 2.48-2.58 (m, 4H), 3.10-3.40 (m, 10H), 3.38 (s, 2H), 3.83-3.92 (m, 2H), 6.69 (dd, J=1.9, 3.5 Hz, 1H), 7.39 (d, J=3.5 Hz, 1H), 7.88 (d, J=1.9 Hz, 1H). APCIMS m/z: [M+H]⁺ 477. mp: 106-108° C.

Reference Example 471

N-[4-(2-Furyl)-5-(tetrahydropyran-4-ylcarbonyl)thiazol-2-yl]-2-[4-(2-methoxy-2-methylpropyl)piperazin-1-yl]acetamide (Compound 471)

¹H NMR (DMSO-d₆, δ ppm): 1.08 (s, 6H), 1.50-1.80 (m, 4H), 2.51-2.53 (m, 4H), 3.07 (s, 3H), 3.10-3.22 (m, 3H), 3.30-3.45 (m, 6H), 3.32 (s, 2H), 3.83-3.92 (m, 2H), 6.69 (dd, J=1.9, 3.5 Hz, 1H), 7.39 (d, J=3.5 Hz, 1H), 7.88 (d, J=1.9 Hz, 1H). APCIMS m/z: [M+H]⁺ 491. mp: 105-107° C.

Reference Example 472

N-[4-(2-Furyl)-5-(tetrahydropyran-4-ylcarbonyl)thiazol-2-yl]-2-{4-[(1-methoxycyclopropyl)methyl]piperazin-1-yl}acetamide (Compound 472)

¹H NMR (DMSO-d₆, δ ppm): 0.40-0.44 (m, 2H), 0.65-0.69 (m, 2H), 1.50-1.80 (m, 4H), 2.46 (s, 2H), 2.49-2.55 (m, 4H), 3.10-3.20 (m, 1H), 3.20 (s, 3H), 3.30-3.80 (m, 6H), 3.33 (s, 2H), 3.83-3.92 (m, 2H), 6.69 (dd, J=1.9, 3.5 Hz, 1H), 7.39 (d, J=3.5 Hz, 1H), 7.88 (d, J=1.9 Hz, 1H). APCIMS m/z: [M+H]⁺ 489. mp: 155-157° C.

Reference Example 473

N-[4-(2-Furyl)-5-(tetrahydropyran-4-ylcarbonyl)thiazol-2-yl]-2-[(7R,8aS)-7-methoxyoctahydropyrrolo[1,2-a]pyrazin-2-yl]acetamide (Compound 473)

$^1$H NMR (DMSO-d$_6$, δ ppm): 1.40-1.80 (m, 7H), 1.95-2.05 (m, 2H), 2.20-2.35 (m, 2H), 2.70-2.97 (m, 4H), 3.15-3.20 (m, 1H), 3.16 (s, 3H), 3.25-3.40 (m, 1H), 3.38 (s, 2H), 3.83-3.93 (m, 4H), 6.69 (dd, J=1.9, 3.5 Hz, 1H), 7.39 (d, J=3.5 Hz, 1H), 7.88 (d, J=1.9 Hz, 1H). APCIMS m/z: [M+H]$^+$ 475.

Reference Example 474

N-[4-(2-Furyl)-5-(tetrahydropyran-4-ylcarbonyl)thiazol-2-yl]-2-[(7S,8aS)-7-hydroxyoctahydropyrrolo[1,2-a]pyrazin-2-yl]acetamide (Compound 474)

$^1$H NMR (DMSO-d$_6$, δ ppm): 1.50-1.80 (m, 6H), 1.90-2.00 (m, 2H), 2.10-2.20 (m, 3H), 2.35-2.45 (m, 2H), 2.45-2.50 (m, 1H), 3.10-3.20 (m, 1H), 3.30-3.50 (m, 3H), 3.34 (s, 2H), 3.83-3.92 (m, 2H), 4.14-4.20 (m, 1H), 6.69 (dd, J=1.9, 3.5 Hz, 1H), 7.39 (d, J=3.5 Hz, 1H), 7.89 (d, J=1.9 Hz, 1H). APCIMS m/z: [M+H]$^+$ 461.

Reference Example 475

N-[4-(2-Furyl)-5-(tetrahydropyran-4-ylcarbonyl)thiazol-2-yl]-2-[octahydropyrazino[2,1-c][1,4]thiazin-8-yl]acetamide (Compound 475)

$^1$H NMR (DMSO-d$_6$, δ ppm): 1.50-1.80 (m, 4H), 1.95-2.00 (m, 1H), 2.05-2.40 (m, 6H), 2.55-2.80 (m, 4H), 2.95-3.05 (m, 1H), 3.10-3.20 (m, 1H), 3.30-3.50 (m, 5H), 3.83-3.93 (m, 2H), 6.69 (dd, J=1.6, 3.2 Hz, 1H), 7.39 (d, J=3.2 Hz, 1H), 7.88 (d, J=1.6 Hz, 1H), 12.60 (br s, 1H). APCIMS m/z: [M+H]$^+$ 477.

Reference Example 476

N-[4-(2-Furyl)-5-(tetrahydropyran-4-ylcarbonyl)thiazol-2-yl]-2-[4-(tetrahydropyran-4-yl)piperazin-1-yl]acetamide (Compound 476)

$^1$H NMR (CDCl$_3$, δ ppm): 1.75-2.00 (m, 6H), 2.75-2.85 (m, 45H), 3.05-3.20 (m, 1H), 3.31 (s, 2H), 3.36-3.54 (m, 6H), 4.00-4.10 (m, 8H), 6.58 (dd, J=1.9, 3.5 Hz, 1H), 7.60 (dd, J=0.8, 1.9 Hz, 1H), 7.79 (dd, J=0.8, 3.5 Hz, 1H). APCIMS m/z: [M+H]$^+$ 489.

Reference Example 477

N-[4-(2-Furyl)-5-(tetrahydropyran-4-ylcarbonyl)thiazol-2-yl]-2-(4-oxooctahydropyrazino[2,1-c][1,4]oxazin-8-yl)acetamide (Compound 477)

$^1$H NMR (CDCl$_3$, δ ppm): 1.75-2.00 (m, 4H), 2.29 (dd, J=11.0, 11.0 Hz, 1H), 2.41 (ddd, J=3.6, 11.0, 11.0 Hz, 1H), 2.75-2.88 (m, 1H), 2.88-3.00 (m, 2H), 3.05-3.20 (m, 1H), 3.37 (s, 2H), 3.49 (ddd, J=2.7, 11.0, 11.0 Hz, 2H), 3.55 (dd, J=7.0, 11.0 Hz, 1H), 3.65-3.80 (m, 1H), 3.96-4.08 (m, 3H), 4.18 (d, J=7.0 Hz, 2H), 4.66 (dd, J=2.7, 11.9 Hz, 1H), 6.59 (dd, J=1.9, 3.8 Hz, 1H), 7.60 (d, J=1.9 Hz, 1H), 7.78 (d, J=3.8 Hz, 1H), 10.35 (br s, 1H). APCIMS m/z: [M+H]$^+$ 475.

Reference Example 478

N-[4-(2-Furyl)-5-(tetrahydropyran-4-ylcarbonyl)thiazol-2-yl]-2-(octahydropyrazino[2,1-c][1,4]oxazin-8-yl)acetamide (Compound 478)

$^1$H NMR (CDCl$_3$, δ ppm): 1.70-2.00 (m, 4H), 2.11 (dd, J=13.2, 13.2 Hz, 1H), 2.35-2.85 (m, 8H), 3.05-3.20 (m, 1H), 3.23 (dd, J=13.2, 13.2 Hz, 1H), 3.30 (s, 2H), 3.48 (ddd, J=2.7, 11.3, 11.3 Hz, 2H), 3.60-3.72 (m, 2H), 3.88 (dd, J=3.5, 11.1 Hz, 1H), 4.04 (ddd, J=2.7, 4.0, 11.3 Hz, 2H), 6.58 (dd, J=1.6, 3.5 Hz, 1H), 7.60 (dd, J=0.8, 1.6 Hz, 1H), 7.78 (dd, J=0.8, 3.5 Hz, 1H), 10.46 (br s, 1H). APCIMS m/z: [M+H]$^+$ 461.

Reference Example 479

N-[4-(2-Furyl)-5-(tetrahydropyran-4-ylcarbonyl)thiazol-2-yl]-2-(1-methyl-2-oxopiperazin-4-yl)acetamide (Compound 479)

$^1$H NMR (CDCl$_3$, δ ppm): 1.75-2.00 (m, 4H), 2.92 (dd, J=5.1, 5.6 Hz, 2H), 3.02 (s, 3H), 3.10-3.20 (m, 1H), 3.32 (s, 2H), 3.41 (s, 2H), 3.45 (dd, J=5.1, 5.6 Hz, 2H), 3.48 (ddd, J=2.7, 11.3, 11.3 Hz, 2H), 4.04 (ddd, J=2.7, 4.0, 11.3 Hz, 2H), 6.57 (dd, J=1.9, 3.8 Hz, 1H), 7.59 (dd, J=0.8, 1.9 Hz, 1H), 7.79 (dd, J=0.8, 3.8 Hz, 1H), 10.40 (br s, 1H). APCIMS m/z: [M+H]$^+$ 433.

Reference Example 480

N-[4-(2-Furyl)-5-(tetrahydropyran-4-ylcarbonyl)thiazol-2-yl]-2-(1,4-perhydrooxazepin-4-yl)acetamide (Compound 480)

$^1$H NMR (CDCl$_3$, δ ppm): 1.70-2.00 (m, 6H), 2.86-2.93 (m, 4H), 3.10-3.20 (m, 1H), 3.47 (s, 2H), 3.48 (ddd, J=2.7, 11.1, 11.1 Hz, 2H), 3.75-3.87 (m, 4H), 4.03 (ddd, J=2.7, 3.7, 11.1 Hz, 2H), 6.57 (dd, J=1.9, 3.5 Hz, 1H), 7.59 (d, J=1.9 Hz, 1H), 7.78 (d, J=3.5 Hz, 1H). APCIMS m/z: [M+H]$^+$ 420.

Reference Example 481

N-[4-(2-Furyl)-5-(tetrahydropyran-4-ylcarbonyl)thiazol-2-yl]-2-(4-methyl-1,4-diazepan-1-yl)acetamide (Compound 481)

$^1$H NMR (DMSO-d$_6$, δ ppm): 1.50-1.80 (m, 4H), 1.85-2.00 (m, 2H), 2.78 (s, 3H), 2.80-2.90 (m, 2H), 2.95-3.05 (m, 2H), 3.10-3.20 (m, 1H), 3.30-3.45 (m, 6H), 3.62 (s, 2H), 3.83-3.93 (m, 2H), 6.69 (dd, J=1.6, 3.5 Hz, 1H), 7.40 (d, J=3.5 Hz, 1H), 7.89 (d, J=1.6 Hz, 1H). APCIMS m/z: [M+H]$^+$ 433. mp: 94-96° C.

Reference Example 482

N-[4-(2-Furyl)-5-(tetrahydropyran-4-ylcarbonyl)thiazol-2-yl]-2-(adamantan-1-ylamino)acetamide (Compound 482)

$^1$H NMR (DMSO-d$_6$, δ ppm): 1.50-1.80 (m, 16H), 2.00-2.05 (m, 3H), 3.10-3.25 (m, 1H), 3.35-3.50 (m, 2H), 3.53 (s, 2H), 3.87 (ddd, J=2.4, 4.0, 12.1 Hz, 2H), 6.66 (dd, J=1.6, 3.2

Hz, 1H), 7.33 (dd, J=0.8, 3.2 Hz, 1H), 7.84 (dd, J=0.8, 1.6 Hz, 1H). APCIMS m/z: [M+H]⁺ 470. mp: 168-170° C.

Reference Example 483

N-[4-(2-Furyl)-5-(tetrahydropyran-4-ylcarbonyl)thiazol-2-yl]-2-(3-hydroxyadamantan-1-ylamino)acetamide (Compound 483)

¹H NMR (DMSO-d₆, δ ppm): 1.25-1.75 (m, 16H), 2.10-2.15 (m, 2H), 3.05-3.20 (m, 1H), 3.30-3.40 (m, 2H), 3.51 (s, 2H), 3.84-3.90 (m, 2H), 6.66 (dd, J=1.9, 3.5 Hz, 1H), 7.34 (dd, J=0.5, 3.5 Hz, 1H), 7.85 (dd, J=0.5, 1.9 Hz, 1H). APCIMS m/z: [M+H]⁺ 486. mp: 176-178° C.

Reference Example 484

N-[4-(2-Furyl)-5-(tetrahydropyran-4-ylcarbonyl)thiazol-2-yl]-2-(1-imidazolyl)acetamide (Compound 484)

¹H NMR (CDCl₃, δ ppm): 1.70-2.00 (m, 4H), 3.05-3.20 (m, 1H), 3.40-3.50 (m, 2H), 3.90-4.10 (m, 2H), 4.98 (s, 2H), 6.54 (dd, J=1.6, 3.2 Hz, 1H), 7.07 (s, 1H), 7.18 (s, 1H), 7.53 (d, J=1.6 Hz, 1H), 7.65 (d, J=3.2 Hz, 1H), 7.73 (s, 1H). APCIMS m/z: [M+H]⁺ 387.

Reference Example 485

N-[4-(2-Furyl)-5-(tetrahydropyran-4-ylcarbonyl)thiazol-2-yl]-2-(2-methylimidazol-1-yl)acetamide (Compound 485)

¹H NMR (DMSO-d₆, δ ppm): 1.70-1.95 (m, 4H), 2.43 (s, 3H), 3.10-3.20 (m, 1H), 3.45 (ddd, J=2.7, 11.3, 11.3 Hz, 2H), 4.00-4.05 (m, 2H), 4.93 (s, 2H), 6.53 (dd, J=1.6, 3.2 Hz, 1H), 6.96 (d, J=0.5 Hz, 1H), 7.03 (d, J=0.5 Hz, 1H), 7.43 (d, J=1.6 Hz, 1H), 7.66 (d, J=3.2 Hz, 1H). APCIMS m/z: [M+H]⁺ 401.

Reference Example 486

Ethyl N-[4-(2-furyl)-5-(tetrahydropyran-4-ylcarbonyl)thiazol-2-yl]carbamate (Compound 486)

¹H NMR (DMSO-d₆, δ ppm): 1.27 (t, J=7.0 Hz, 3H), 1.50-1.76 (m, 4H), 3.05-3.18 (m, 1H), 3.22-3.40 (m, 2H), 3.82-3.92 (m, 2H), 4.25 (q, J=7.0 Hz, 2H), 6.68 (dd, J=1.6, 3.2 Hz, 1H), 7.36 (d, J=3.2 Hz, 1H), 7.88 (d, J=1.6 Hz, 1H), 12.39 (br s, 1H). APCIMS m/z: [M+H]⁺ 351. mp: 152-153° C.

Reference Example 487 tert-Butyl N-[4-(2-furyl)-5-(4-methyltetrahydropyran-4-ylcarbonyl)-thiazol-2-yl]carbamate (Compound 487)

¹H NMR (CDCl₃, δ ppm): 1.40 (s, 3H), 1.52 (s, 9H), 1.60-1.68 (m, 2H), 3.55-3.71 (m, 4H), 6.46 (dd, J=1.8, 3.5 Hz, 1H), 7.14 (d, J=3.5 Hz, 1H), 7.46 (d, J=1.8 Hz, 1H).

Reference Example 488

2-Amino-4-(2-furyl)thiazol-5-yl 4-methyltetrahydropyran-4-yl ketone (Compound 488)

¹H NMR (CDCl₃, δ ppm): 1.25 (s, 3H), 1.48-1.54 (m, 2H), 1.98-2.09 (m, 2H), 3.30-3.62 (m, 4H), 6.54 (dd, J=1.8, 3.5 Hz, 1H), 6.98 (d, J=0.8, 3.5 Hz, 1H), 7.68 (dd, J=0.8, 1.8 Hz, 1H), 7.72 (br s, 2H).

Reference Example 489 tert-Butyl N-[4-(2-furyl)-5-(4-methoxytetrahydropyran-4-ylcarbonyl)-thiazol-2-yl]carbamate (Compound 489)

¹H NMR (CDCl₃, δ ppm): 1.52 (s, 9H), 1.93-2.11 (m, 4H), 3.23 (s, 3H), 3.76-3.79 (m, 4H), 6.53 (dd, J=1.8, 3.3 Hz, 1H), 7.55 (d, J=1.8 Hz, 1H), 7.80 (d, J=3.3 Hz, 1H).

Reference Example 490

2-Amino-4-(2-furyl)thiazol-5-yl 4-methoxytetrahydropyran-4-yl ketone (Compound 490)

¹H NMR (CDCl₃, δ ppm): 1.85-2.09 (m, 4H), 3.22 (s, 3H), 3.73-3.78 (m, 4H), 5.64 (br s, 2H), 6.52 (dd, J=1.8, 3.6 Hz, 1H), 7.54 (dd, J=0.8, 1.8 Hz, 1H), 7.91 (dd, J=0.8, 3.6 Hz, 1H).

Reference Example 491 tert-Butyl N-[4-(2-furyl)-5-(tetrahydrothiopyran-4-ylcarbonyl)thiazol-2-yl]carbamate (Compound 491)

¹H NMR (CDCl₃, δ ppm): 1.42 (s, 9H), 1.95-2.26 (m, 4H), 2.69-2.94 (m, 5H), 6.55 (dd, J=1.8, 3.5 Hz, 1H), 7.52 (d, 1.8 Hz, 1H), 7.77 (d, J=3.5 Hz, 1H).

Reference Example 492

2-Amino-4-(2-furyl)thiazol-5-yl tetrahydrothiopyran-4-yl ketone (Compound 492)

¹H NMR (CDCl₃, δ ppm): 1.84-1.93 (m, 2H), 2.13-2.20 (m, 2H), 2.65-2.83 (m, 5H), 6.56 (dd, J=1.7, 3.3 Hz, 1H), 7.52 (d, J=3.3 Hz, 1H), 7.56 (d, J=1.7 Hz, 1H).

Reference Example 493

N-[4-(2-Furyl)-5-(tetrahydrothiopyran-4-ylcarbonyl)thiazol-2-yl]pyridine-4-carboxamide (Compound 493)

¹H NMR (CDCl₃, δ ppm): 1.88-2.05 (m, 2H), 2.22-2.29 (m, 2H), 2.68-2.84 (m, 4H), 2.94-3.03 (m, 1H), 6.51 (dd, J=1.8, 3.6 Hz, 1H), 7.48 (dd, J=0.7, 3.6 Hz, 1H), 7.71-7.48 (m, 3H), 8.85 (d, J=6.3 Hz, 2H), 10.6 (br s, 1H). APCIMS m/z: [M+H]⁺ 398. mp: 203-210° C.

Reference Example 494

N-[4-(2-Furyl)-5-(tetrahydrothiopyran-4-ylcarbonyl)thiazol-2-yl]-2-methylpyrimidine-5-carboxamide (Compound 494)

¹H NMR (DMSO-d₆, δ ppm): 1.65-1.69 (m, 2H), 2.13-2.17 (m, 2H), 2.65-2.73 (m, 4H), 2.73 (s, 3H), 3.04-3.20 (m, 1H), 6.71 (dd, J=1.7, 3.5 Hz, 1H), 7.43 (d, J=3.5 Hz, 1H), 7.92 (d, J=1.7 Hz, 1H), 9.29 (s, 2H). APCIMS m/z: [M+H]⁺ 415. mp: 238-240° C.

Reference Example 495 tert-Butyl N-[4-(2-furyl)-5-(1-oxotetrahydrothiopyran-4-ylcarbonyl)-thiazol-2-yl]carbamate (Compound 495)

$^1$H NMR (CDCl$_3$, δ ppm): 1.51 (s, 9H), 1.93-2.09 (m, 2H), 2.41-2.76 (m, 4H), 3.08-3.30 (m, 3H), 6.56 (dd, J=1.8, 3.3 Hz, 1H), 7.56 (d, J=1.8 Hz, 1H), 7.60 (d, J=3.3 Hz, 1H).

Reference Example 496

2-Amino-4-(2-furyl)thiazol-5-yl 1-oxotetrahydrothiopyran-4-yl ketone (Compound 496)

$^1$H NMR (DMSO-d$_6$, δ ppm): 1.62-1.75 (m, 2H), 2.01-2.26 (m, 2H), 2.51-2.68 (m, 2H), 2.85-3.24 (m, 3H), 6.64-6.67 (m, 1H), 7.26-7.32 (m, 1H), 7.84-7.89 (m, 1H), 8.02-8.04 (m, 2H).

Reference Example 497 tert-Butyl N-[4-(2-furyl)-5-(1,1-dioxotetrahydrothiopyran-4-ylcarbonyl)thiazol-2-yl]carbamate (Compound 497)

$^1$H NMR (CDCl$_3$, δ ppm): 1.51 (s, 9H), 2.29-2.48 (m, 4H), 2.96-3.01 (m, 2H), 3.15-3.28 (m, 3H), 6.56 (dd, J=1.7, 3.5 Hz, 1H), 7.55 (d, J=1.7 Hz, 1H), 7.63 (d, J=3.5 Hz 1H).

Reference Example 498

2-Amino-4-(2-furyl)thiazol-5-yl 1,1-dioxotetrahydrothiopyran-4-yl ketone (Compound 498)

$^1$H NMR (DMSO-d$_6$, δ ppm): 1.96-2.15 (m, 4H), 3.05-3.20 (m, 5H), 6.66 (dd, J=1.8, 3.5 Hz, 1H), 7.33 (d, J=3.5 Hz, 1H), 7.88 (d, J=1.8 Hz, 1H).

Reference Example 499 tert-Butyl N-[4-(2-furyl)-5-phenylacetylthiazol-2-yl]carbamate (Compound 499)

$^1$H NMR (CDCl$_3$, δ ppm): 1.54 (s, 9H), 4.13 (s, 2H), 6.53 (dd, J=1.8, 3.3 Hz, 1H), 7.20-7.40 (m, 5H), 7.56 (d, J=1.8 Hz, 1H), 7.79 (d, J=3.3 Hz, 1H), 8.60 (brs, 1H). ESIMS m/z: [M+H]$^+$ 385.

Reference Example 500

2-Amino-4-(2-furyl)thiazol-5-yl benzyl ketone (Compound 500)

$^1$H NMR (CDCl$_3$, δ ppm): 4.01 (s, 2H), 5.68 (br s, 2H), 6.53 (dd, J=1.7 Hz, 3.6 Hz, 1H), 7.18-7.35 (m, 5H), 7.55 (dd, J=0.7, 1.8 Hz, 1H), 7.68 (dd, J=0.7, 3.6 Hz, 1H). ESIMS m/z: [M+H]$^+$ 285.

Reference Example 501 tert-Butyl N-[4-(2-furyl)-5-[2-(2-methoxyphenyl)acetyl]thiazol-2-yl]carbamate (Compound 501)

$^1$H NMR (CDCl$_3$, δ ppm): 1.54 (s, 9H), 3.77 (s, 3H), 4.13 (s, 2H), 6.50 (dd, J=1.8, 3.7 Hz, 1H), 6.88 (dd, J=1.1 Hz, 8.4 Hz, 1H), 6.93 (ddd, J=1.1 Hz, 7.3 Hz, 7.4 Hz, 1H), 7.15 (dd, J=1.6 Hz, 7.3 Hz, 1H), 7.25 (ddd, J=1.6 Hz, 7.4 Hz, 7.5 Hz, 1H), 7.54 (dd, J=0.7 Hz, 1.8 Hz, 1H), 7.79 (dd, J=0.7 Hz, 3.7 Hz, 1H), 8.58 (brs, 1H). ESIMS m/z: [M+H]$^+$ 415.

Reference Example 502

2-Amino-4-(2-furyl)thiazol-5-yl 2-methoxybenzyl ketone (Compound 502)

$^1$H NMR (CDCl$_3$, δ ppm): 3.77 (s, 3H), 4.01 (s, 2H), 5.51 (brs, 2H), 6.49 (dd, J=1.8, 3.5 Hz, 1H), 6.82-6.95 (m, 2H), 7.10-7.29 (m, 2H), 7.59 (dd, J=0.7, 1.8 Hz, 1H), 7.75 (dd, J=0.7, 3.5 Hz, 1H). ESIMS m/z: [M+H]$^+$ 315.

Reference Example 503

2-(tert-Butoxycarbonylamino)-5-formyl-4-(2-furyl)thiazole (Compound 503)

$^1$H NMR (CDCl$_3$, δ ppm): 1.50 (s, 9H), 6.57 (dd, J=1.8, 3.4 Hz, 1H), 6.99 (dd, J=0.8, 3.4 Hz, 1H), 7.60 (dd, J=0.8, 1.8 Hz, 1H), 8.95 (br s, 1H), 10.52 (s; 1H).

Reference Example 504

N-[5-Carboxy-4-(2-furyl)thiazol-2-yl]pyridine-4-carboxamide (Compound 504)

$^1$H NMR (DMSO-d$_6$, δ ppm): 6.68 (dd, J=1.8, 3.5 Hz, 1H), 7.61 (dd, J=1.0, 3.5 Hz, 1H), 7.86 (dd, J=1.0, 1.8 Hz, 1H), 8.20 (dd, J=1.7, 4.8 Hz, 2H), 8.94 (dd, J=1.7, 4.8 Hz, 2H).

Reference Example 505

N-[4-(2-Furyl)-5-morpholinocarbonylthiazol-2-yl]pyridine-4-carboxamide (Compound 505)

$^1$H NMR (DMSO-d$_6$, δ ppm): 3.59-3.68 (m, 8H), 6.39 (dd, J=1.8, 3.3 Hz, 1H), 6.67 (dd, J=0.7, 3.3 Hz, 1H), 7.27 (dd, J=0.7, 1.8 Hz, 1H), 7.78 (dd, J=1.6, 4.5 Hz, 2H), 8.81 (dd, J=1.6, 4.5 Hz, 2H), 10.82 (br s, 1H). ESIMS m/z: [M−H]$^−$ 383.

Reference Example 506

N-[5-(N,N-Dimethylcarbamoyl)-4-(2-furyl)thiazol-2-yl]pyridine-4-carboxamide (Compound 506)

$^1$H NMR (DMSO-d$_6$, δ ppm): 2.81 (s, 3H), 3.01 (s, 3H), 6.62 (dd, J=1.8, 3.3 Hz, 1H), 6.74 (dd, J=0.7, 3.3 Hz, 1H), 7.77 (dd, J=0.7, 1.8 Hz, 1H), 7.94 (d, J=6.1 Hz, 2H), 8.81 (d, J=6.1 Hz, 2H). ESIMS m/z: [M−H]$^+$ 343.

Reference Example 507

N-[4-(2-Furyl)-5-(N-methoxy-N-methylcarbamoyl)thiazol-2-yl]pyridine-4-carboxamide (Compound 507)

$^1$H NMR (CDCl$_3$, δ ppm): 3.38 (s, 3H), 3.70 (s, 3H), 6.40 (dd, J=1.8, 3.5 Hz, 1H), 7.03 (dd, J=0.7, 3.5 Hz, 1H), 7.37 (dd, J=0.7, 1.8 Hz, 1H), 7.75 (dd, J=1.7, 4.6 Hz, 2H), 8.82 (dd, J=1.7, 4.6 Hz, 2H).

Reference Example 508

N-[5-Benzoyl-4-(2-furyl)thiazol-2-yl]pyridine-4-carboxamide (Compound 508)

$^1$H NMR (CDCl$_3$, δ ppm): 6.52 (dd, J=1.8, 3.5 Hz, 1H), 6.96 (dd, J=0.7, 3.5 Hz 1H), 7.44-7.49 (m, 2H), 7.50 (dd, J=0.7, 1.8 Hz, 1H), 7.58-7.63 (m, 1H), 7.72-7.75 (m, 2H), 8.03 (dd, J=1.7, 4.4 Hz, 2H), 8.84 (dd, J=1.7, 4.4 Hz, 2H). ESIMS m/z: [M+H]$^+$ 376.

Reference Example 516

4-(2-Furyl)-2-(indole-2-yl)thiazol-5-yl tetrahydropyran-4-yl ketone (Compound 516)

2-Bromo-4-(2-furyl)thiazol-5-yl tetrahydropyran-4-yl ketone (100 mg, 0.292 mmol) obtained in Reference Example 558 was dissolved in 1,4-dioxane (3 mL). To the solution was added 1H-indole-2-boronic acid (101 mg, 0.627 mmol), tetrakis(triphenylphosphine)palladium(0) (28.4 mg, 0.0245 mmol) and sodium carbonate (104 mg, 0.982 mmol), and the mixture was stirred at 60° C. for 1 hour. Water was added to the reaction mixture, and the mixture was extracted with ethyl acetate. The organic layer was dried over anhydrous magnesium sulfate, and the solvent was evaporated under reduced pressure. The resulting residue was purified by silica gel column chromatography (hexane:ethyl acetate=1:1) to give a title compound (17.0 mg, 15%).

$^1$H NMR (CDCl$_3$, δ ppm): 1.78-1.94 (m, 4H), 3.12-3.22 (m, 1H), 3.40-3.49 (m, 2H), 4.01-4.07 (m, 2H), 6.62 (dd, J=1.8, 3.6 Hz, 1H), 7.13-7.16 (m, 2H), 7.28-7.34 (m, 1H), 7.40-7.44 (m, 1H), 7.50 (dd, J=0.8, 3.6 Hz, 1H), 7.62 (dd, J=0.8, 1.8 Hz, 1H), 7.65-7.68 (m, 1H), 9.32 (br s, 1H). ESIMS m/z: [M+H]$^+$ 379.

Reference Example 517

2-(Benzoimidazol-2-yl)-4-(2-furyl)thiazol-5-yl tetrahydropyran-4-yl ketone (Compound 517)

Step 1: Methyl tetrahydropyran-4-carboxylate (1.33 mL, 10.0 mmol) was dissolved in THF (20 mL), and N,O-dimethylhydroxylamine hydrochloride (1.51 g, 15.5 mmol) added thereto, then the mixture was stirred. Under an argon atmosphere, THF solution of isopropyl magnesium chloride (2.0 mol/L; 15.0 mL, 30.0 mmol) was added dropwise to the reaction mixture at −30° C., and the mixture was stirred at −5° C. for 1 hour. Water was added to the reaction mixture, and the mixture was extracted with ethyl acetate. The organic layer was washed with brine and dried over anhydrous magnesium sulfate. The solvent was then evaporated under reduced pressure. The resulting residue was purified by distillation under reduced pressure to give N-methoxy-N-methyltetrahydropyran-4-carboxamide (1.00 g, 58%).

Boiling point: 125-129° C./8.0 hPa, $^1$H NMR (CDCl$_3$, δ ppm): 1.57-1.66 (m, 2H), 1.77-1.93 (m, 2H), 2.85-2.94 (m, 1H), 3.18 (s, 3H), 3.44 (ddd, J=2.4, 11.9, 11.9 Hz, 2H), 3.69 (s, 3H), 4.00 (ddd, J=2.4, 11.9, 11.9 Hz, 2H).

Step 2: 2-(Benzoimidazol-2-yl)-4-(2-furyl)thiazole (167 mg, 0.625 mmol) obtained in Reference Example 562 was dissolved in THF (5 mL). To the solution was added n-hexane solution of n-butyl lithium (1.58 mol/L; 1.01 mL, 1.56 mmol) at −78° C. under an argon atmosphere, and the mixture was stirred at −78° C. for 10 minutes. The THF solution (1 mL) of N-methoxy-N-methyltetrahydropyran-4-carboxamide (270 mg, 1.56 mmol) obtained in Step 1 was added dropwise to the mixture, and the mixture was stirred at room temperature for 1 hour. The reaction mixture was then poured into a saturated ammonium chloride aqueous solution, and the mixture was extracted with ethyl acetate. The organic layer was washed with brine and dried over anhydrous magnesium sulfate. The solvent was then evaporated under reduced pressure. The resulting residue was purified by silica gel column chromatography (hexane:ethyl acetate=1:1) to give a title compound (191 mg, 81%).

$^1$H NMR (DMSO-d$_6$, δ ppm): 1.51-1.67 (m, 4H), 3.21-3.38 (m, 3H), 3.80-3.86 (m, 2H), 6.74 (dd, J=1.8, 3.5 Hz, 1H), 7.29-7.32 (m, 2H), 7.41 (d, J=3.5 Hz, 1H), 7.63-7.66 (m, 2H), 7.94 (d, J=1.8 Hz, 1H). APCIMS m/z: [M+H]$^+$ 380. mp: 250-251° C.

Reference Example 518

4-(2-Furyl)-2-(imidazo[4,5-b]pyridin-2-yl)thiazol-5-yl tetrahydropyran-4-yl ketone (Compound 518)

The title compound (71.0 mg, 40%) was obtained in the same manner as in Reference Example 517 using 4-(2-furyl)-2-(imidazo[4,5-b]pyridin-2-yl)thiazole (125 mg, 0.466 mmol) obtained in Reference Example 478, instead of 2-(benzimidazol-2-yl)-4-(2-furyl)thiazole.

$^1$H NMR (DMSO-d$_6$, δ ppm): 1.57-1.91 (m, 4H), 3.26-3.41 (m, 3H), 3.86-3.93 (m, 2H), 6.77 (dd, J=1.8, 3.5 Hz, 1H), 7.33-7.39 (m, 1H), 7.41 (dd, J=0.8, 3.5H, 1H), 7.98 (dd, J=0.8, 1.8 Hz, 1H), 8.07-8.10 (m, 1H), 8.47-8.50 (m, 1H). APCIMS m/z: [M+H]$^+$ 381. mp: 265-268° C. (dec.).

Reference Example 519

4-(2-Furyl)-2-(imidazo[4,5-c]pyridin-2-yl)thiazol-5-yl tetrahydropyran-4-yl ketone (Compound 519)

The title compound (7.00 mg, 4%) was obtained in the same manner as in Reference Example 517 using 4-(2-furyl)-2-(imidazo[4,5-c]pyridin-2-yl)thiazole (137 mg, 0.511 mmol) obtained in Reference Example 564, instead of 2-(benzimidazol-2-yl)-4-(2-furyl)thiazole.

$^1$H NMR (CDCl$_3$, δ ppm): 1.89-1.95 (m, 4H), 3.18-3.21 (m, 1H), 3.42-3.52 (m, 2H), 4.04-4.11 (m, 2H), 6.61 (dd, J=1.8, 3.5 Hz, 1H), 7.59-7.62 (m, 3H), 8.54 (d, J=5.6 Hz, 1H), 9.19 (s, 1H). APCIMS m/z: [M+H]$^+$ 381.

Reference Example 520

4-(2-Furyl)-2-[4-(4-methoxyphenyl)imidazol-2-yl]thiazol-5-yl tetrahydropyran-4-yl ketone (Compound 520)

The title compound (113 mg, 84%) was obtained in the same manner as in Reference Example 517 using 4-(2-furyl)-2-[4-(4-methoxyphenyl)imidazol-2-yl]thiazole (100 mg, 0.309 mmol) obtained in Reference Example 566, instead of 2-(benzimidazol-2-yl)-4-(2-furyl)thiazole.

$^1$H NMR (DMSO-d$_6$, δ ppm): 1.53-1.78 (m, 4H), 3.23-3.39 (m, 3H), 3.78 (s, 3H), 3.86-3.90 (m, 2H), 6.73 (dd, J=1.7, 3.3 Hz, 1H), 6.96-6.99 (m, 2H), 7.42 (d, J=3.3 Hz, 1H), 7.79-7.82 (m, 3H), 7.94 (d, J=1.7 Hz, 1H). APCIMS m/z: [M+H]$^+$ 436. mp: 178-180° C.

Reference Example 521

4-(2-Furyl)-2-(4,5,6,7-tetrahydro-1H-benzimidazol-2-yl)-5-(tetrahydropyran-4-ylcarbonyl)thiazole (Compound 521)

The title compound (23.0 mg, 10%) was obtained in the same manner as in Reference Example 517 using 2-[4-(2-furyl)thiazol-2-yl)-4,5,6,7-tetrahydro-1H-benzimidazole (167 mg, 0.615 mmol) obtained in Reference Example 568, instead of 2-(benzimidazol-2-yl)-4-(2-furyl)thiazole. $^1$H NMR (CDCl$_3$, δ ppm): 1.84-1.96 (m, 12H), 3.08-3.15 (m, 1H), 3.40-3.49 (m, 2H), 4.01-4.07 (m, 2H), 6.58 (dd, J=1.7, 3.5 Hz, 1H), 7.58 (dd, J=0.7, 1.7 Hz, 1H), 7.70 (dd, J=0.7, 3.5 Hz, 1H).

Reference Example 523

4-(2-Furyl)-5-(tetrahydropyran-4-ylcarbonyl)-2-(3,4,6,7-tetrahydrothiopyrano[3,4-c]imidazol-2-yl)thiazole (Compound 523)

The title compound (17.0 mg, 9%) was obtained in the same manner as in Reference Example 517 using 2-[4-(2-furylthiazol-2-yl)-3,4,6,7-tetrahydrothiopyrano[3,4-d]imidazole (133 mg, 0.460 mmol) obtained in Reference Example 569, instead of 2-(benzimidazol-2-yl)-4-(2-furyl)thiazole.
$^1$H NMR (CDCl$_3$, δ ppm): 1.72-1.92 (m, 4H), 2.97 (s, 4H), 3.09-3.15 (m, 1H), 3.41-3.49 (m, 2H), 3.76 (s, 2H), 4.03-4.07 (m, 2H), 6.60 (dd, J=1.6, 3.3 Hz, 1H), 7.59 (d, J=1.6 Hz, 1H), 7.72 (d, J=3.3 Hz, 1H).

Reference Example 534

4-(2-Furyl)-5-(pyridin-2-ylcarbonyl)-2-(2-benzimidazolyl)thiazole (Compound 534)

The title compound (57.0 mg, 27%) was obtained in the same manner as in Reference Example 517 from 2-(benzimidazol-2-yl)-4-(2-furyl)thiazole (150 mg, 0.561 mmol), using N-methoxy-N-methyl-pyridine-2-carboxamide, instead of N-methoxy-N-methyl-tetrahydropyran-4-carboxamide.
$^1$H NMR (CDCl$_3$, δ ppm): 6.71 (dd, J=1.8, 3.5 Hz, 1H), 7.30-7.36 (m, 2H), 7.48 (dd, J=0.7, 3.5 Hz, 1H), 7.59-7.61 (m, 1H), 7.74-7.78 (m, 2H), 7.84 (dd, J=0.7, 1.8 Hz, 1H), 8.13-8.20 (m, 2H), 8.78-8.80 (m, 1H), 13.6 (br s, 1H).

Reference Example 540

4-(2-Furyl)-5-(pyridin-2-ylcarbonyl)-2-(3,4,6,7-tetrahydrothiopyrano[3,4-d]imidazol-2-yl)thiazole (Compound 540)

The title compound (36.0 mg, 19%) was obtained in the same manner as in Reference Example 517 using N-methoxy-N-methyl-pyridine-2-carboxamide instead of N-methoxy-N-methyl-tetrahydropyran-4-carboxamide, and using 2-[4-(2-furylthiazol-2-yl)-3,4,6,7-tetrahydrothiopyrano[3,4-d]imidazole (137 mg, 0.473 mmol) obtained in Reference Example 569 instead of 2-(benzimidazol-2-yl)-4-(2-furyl)thiazole.
$^1$H NMR (CDCl$_3$, δ ppm): 2.95 (m, 4H), 3.76-3.78 (m, 2H), 6.59 (dd, J=1.7, 3.5 Hz, 1H), 7.51-7.54 (m, 2H), 7.78 (dd, J=0.7, 3.5 Hz, 1H), 7.88-7.95 (m, 1H), 8.21-8.24 (m, 1H), 8.69-8.71 (m, 1H).

Reference Example 551

4-(2-Furyl)-N-phenyl-5-(tetrahydropyran-4-ylcarbonyl)thiazol-2-carboxamide (Compound 551)

The title compound (18.0 mg, 11%) was obtained in the same manner as in Reference Example 517 using 4-(2-furyl)-N-phenylthiazole-2-carboxamide (120 mg, 0.444 mmol) obtained in Reference Example 570, instead of 2-(benzimidazol-2-yl)-4-(2-furyl)thiazole.
$^1$H NMR (CDCl$_3$, δ ppm): 1.80-1.92 (m, 4H), 3.12-3.23 (m, 1H), 3.40-3.50 (m, 2H), 4.01-4.07 (m, 2H), 6.62 (dd, J=1.8, 3.6 Hz, 1H), 7.21-7.24 (m, 1H), 7.38-7.48 (m, 3H), 7.62 (d, J=1.8 Hz, 1H), 7.72-7.75 (m, 2H), 9.12 (br s, 1H).

Reference Example 552

4-(2-Furyl)-N-isobutyl-5-(tetrahydropyran-4-ylcarbonyl)thiazole-2-carboxamide (Compound 552)

The title compound (32.0 mg, 12%) was obtained in the same manner as in Reference Example 517 using 4-(2-furyl)-N-isobutylthiazole-2-carboxamide (186 mg, 0.743 mmol) obtained in Reference Example 571, instead of 2-(benzimidazol-2-yl)-4-(2-furyl)thiazole.
$^1$H NMR (CDCl$_3$, δ ppm): 1.00 (d, J=6.8 Hz, 6H), 1.82-2.05 (m, 5H), 3.12-3.16 (m, 1H), 3.29-3.49 (m, 4H), 3.99-4.06 (m, 2H), 6.59 (dd, J=1.7, 3.5 Hz, 1H), 7.44 (dd, J=0.8, 3.5 Hz, 1H), 7.59 (dd, J=0.8, 1.7 Hz, 1H).

Reference Example 554

4-(2-Furyl)-N-isobutyl-5-(pyridin-2-ylcarbonyl)thiazol-2-carboxamide (Compound 554)

The title compound (172 mg, 50%) was obtained in the same manner as in Reference Example 517 using N-methoxy-N-methyl-pyridine-2-carboxamide instead of N-methoxy-N-methyl-tetrahydropyran-4-carboxamide, and using 4-(2-furyl)-N-isobutylthiazole-2-carboxamide (241 mg, 0.963 mmol) obtained in Reference Example 571 instead of 2-(benzimidazol-2-yl)-4-(2-furyl)thiazole.
$^1$H NMR (CDCl$_3$, δ ppm): 1.00 (d, J=6.8 Hz, 6H), 1.92-1.97 (m, 1H), 3.29-3.34 (m, 2H), 6.54 (dd, J=1.7, 3.5 Hz, 1H), 7.45-7.54 (m, 3H), 7.88-7.94 (m, 1H), 8.19-8.22 (m, 1H), 8.65-8.67 (m, 1H).

Reference Example 555

2-Amino-5-bromo-4-(2-furyl)thiazole (Compound a)

Step 1: 2-Acetylfuran (5.10 g, 46.0 mmol) was dissolved in a mixed solvent of dichloromethane (50 mL) and methanol (50 mL), and N,N,N,N-tetra-n-butylammonium tribromide (22.3 g, 46.0 mmol) added thereto, then the solution was stirred at room temperature for 1 hour. The reaction mixture was concentrated under reduced pressure, and water was added to the resulting residue, then the mixture was extracted with ethyl acetate. The organic layer was washed with brine and dried over anhydrous magnesium sulfate. The solvent was then evaporated under reduced pressure. The resulting residue was dissolved in acetonitrile (60 mL), and thiourea (3.5 g, 46.0 mmol) added thereto, then the solution was stirred at room temperature for 30 minutes. The precipitated solid was collected by filtration, and to the resulting solid was added saturated sodium bicarbonate aqueous solution and ethyl acetate added, then the mixture was extracted. The organic layer was washed with brine and dried over anhydrous magnesium sulfate. The solvent was then evaporated under reduced pressure. The resulting residue was purified by silica gel column chromatography (hexane:ethyl acetate=3:1) to give 2-amino-4-(2-furyl)thiazole (1.53 g, 20%).

$^1$H NMR (CDCl$_3$, δ ppm): 5.17 (br s, 2H), 6.43 (dd, J=2.0, 3.3 Hz, 1H), 6.61 (d, J=3.3 Hz, 1H), 6.69 (s, 1H), 7.49 (d, J=2.0 Hz, 1H).

Step 2: 2-Amino-4-(2-furyl)thiazole (330 mg, 1.99 mmol) obtained in Step 1 was suspended in chloroform (4 mL). To the suspension was added N-bromosuccinimide (360 mg, 2.02 mmol), and the mixture was stirred at room temperature for 1 hour. Water was added to the reaction mixture, and the mixture was extracted with ethyl acetate. The organic layer was washed with brine and dried over anhydrous magnesium sulfate. The solvent was then evaporated under reduced pressure to give a title compound (438 mg, 90%).

$^1$H NMR (CDCl$_3$, δ ppm): 5.08 (br s, 2H), 6.48 (dd, J=2.0, 3.3 Hz, 1H), 6.96 (d, J=3.3 Hz, 1H), 7.48 (d, J=2.0 Hz, 1H).

Reference Example 556 tert-Butyl N-[5-bromo-4-(2-furyl)thiazol-2-yl]carbamate (Compound B)

Compound a (12.0 g, 49.0 mmol) obtained in Reference Example 555, di-tert-butyl dicarbonate (21.3 g, 97.9 mmol), triethylamine (17.1 mL, 122 mmol), and N,N-dimethylaminopyridine (0.60 g, 4.91 mmol) were dissolved in DMI (200 mL), and the mixture was stirred for overnight at room temperature. Water was added to the reaction mixture, and the mixture was extracted with ethyl acetate. The organic layer was washed with brine and dried over anhydrous magnesium sulfate. The solvent was then evaporated under reduced pressure. The resulting residue was purified by silica gel column chromatography (hexane:ethyl acetate=5:1) to give a title compound (14.2 g, 84%).

$^1$H NMR (DMSO-d$_6$, δ ppm): 1.49 (s, 9H), 6.64 (dd, J=2.0, 3.3 Hz, 1H), 6.91 (dd, J=0.7, 3.3 Hz, 1H), 7.80 (dd, J=0.7, 2.0 Hz, 1H).

Reference Example 557

2-Amino-4-(2-furyl)-5-(tetrahydropyran-4-ylcarbonyl)thiazole (Compound c)

Step 1: Tetrahydropyran-4-carboxylic acid (1.00 g, 7.69 mmol), phenol (651 mg, 6.92 mmol), and PyBOP (4.40 g, 8.45 mmol) were dissolved in DMF (15 mL). To the solution was added triethylamine (2.36 mL, 16.9 mmol), and the mixture was stirred at room temperature for 4 hours. The reaction mixture was poured into water, and the mixture was extracted with ethyl acetate. The organic layer was successively washed with saturated sodium bicarbonate aqueous solution and brine, and dried over anhydrous magnesium sulfate. The solvent was then evaporated under reduced pressure. The resulting residue was purified by silica gel column chromatography (hexane:ethyl acetate=3:2) to give phenyl tetrahydropyran-4-carboxylate (1.28 g, 81%).

$^1$H NMR (CDCl$_3$, δ ppm): 1.62-1.79 (m, 2H), 1.86-1.96 (m, 2H), 2.89 (tt, J=4.6, 11.0 Hz, 1H), 3.42 (ddd, J=2.4, 11.0, 11.0 Hz, 2H), 3.88 (ddd, J=2.4, 11.0, 11.0 Hz, 2H), 7.09-7.16 (m, 2H), 7.22-7.31 (m, 1H), 7.37-7.44 (m, 2H).

Step 2: Compound b (1.04 g, 3.00 mmol) obtained in Reference Example 556 was dissolved in THF (8 mL). To the solution was added n-hexane solution of n-butyl lithium (1.58 mol/L; 4.20 mL, 6.61 mmol) at −78° C. under an argon atmosphere, and the mixture was stirred at −78° C. for 10 minutes. The THF solution (4 mL) of phenyl tetrahydropyran-4-carboxylate (620 mg, 3.00 mmol) obtained in Step 1 was added dropwise to the mixture, and the mixture was stirred at room temperature for 1 hour. The reaction mixture was poured into a saturated ammonium chloride aqueous solution, and the mixture was extracted with ethyl acetate. The organic layer was washed with brine and dried over anhydrous magnesium sulfate. The solvent was then evaporated under reduced pressure. The resulting residue was purified by silica gel column chromatography (hexane:ethyl acetate=3:2) to give N-[4-(2-furyl)-5-(tetrahydropyran-4-ylcarbonyl)thiazol-2-yl]tert-butyl carbamate (350 mg, 31%).

$^1$H NMR (CDCl$_3$, δ ppm): 1.53 (s, 9H), 1.76-1.94 (m, 4H), 3.06-3.18 (m, 1H), 3.46 (ddd, J=2.7, 11.6, 11.6 Hz, 2H), 4.03 (ddd, J=2.7, 4.0, 11.6 Hz, 2H), 6.55 (dd, J=1.9, 3.5 Hz, 1H), 7.55 (dd, J=0.8, 1.9 Hz, 1H), 7.76 (dd, J=0.8, 3.5 Hz, 1H), 8.68 (br s, 1H).

Step 3: tert-Butyl N-[4-(2-furyl)-5-(tetrahydropyran-4-ylcarbonyl)thiazole-2-yl]carbamate (350 mg, 0.93 mmol) obtained in Step 2 was dissolved in trifluoroacetic acid (5 mL), and the mixture was stirred at room temperature for 1 hour. The reaction mixture was concentrated under reduced pressure, and ethyl acetate and saturated sodium bicarbonate aqueous solution were added thereto, then the mixture was extracted. The organic layer was washed with brine and dried over anhydrous magnesium sulfate. The solvent was then evaporated under reduced pressure. The resulting residue was purified by silica gel column chromatography (hexane:ethyl acetate=1:4) to give a title compound (212 mg, 72%).

$^1$H NMR (DMSO-d$_6$, δ ppm): 1.52-1.64 (m, 4H), 2.89-3.03 (m, 1H), 3.24 (ddd, J=3.8, 11.3, 11.3 Hz, 2H), 3.85 (ddd, J=2.7, 3.8, 11.3 Hz, 2H), 6.65 (dd, J=1.9, 3.5 Hz, 1H), 7.24 (d, J=3.5 Hz, 1H), 7.84 (d, J=1.9 Hz, 1H), 7.96 (br s, 2H).

Reference Example 558

2-Bromo-4-(2-furyl)thiazol-5-yl tetrahydropyran-4-yl ketone

Compound c (163 mg, 0.600 mmol) obtained in Reference Example 557 was dissolved in acetonitrile (5 mL). To the solution were added isoamyl nitrite (0.242 mL, 1.80 mmol) and copper (II) bromide (134 mg, 0.600 mmol), and the mixture was stirred at 60° C. for 1 hour. The reaction mixture was concentrated under reduced pressure, and the resulting residue was purified by silica gel column chromatography (hexane:ethyl acetate=3:1) to give a title, compound (85.0 mg, 41%).

$^1$H NMR (CDCl$_3$, δ ppm): 1.75-1.92 (m, 4H), 3.11-3.18 (m, 1H), 3.36-3.45 (m, 2H), 3.98-4.05 (m, 2H), 6.58 (dd, J=1.7, 3.6 Hz, 1H), 7.39 (dd, J=0.7, 3.6 Hz, 1H), 7.58 (dd, J=0.7, 1.7 Hz, 1H).

Reference Example 559

(2-Furoyl)methylthiocyanate

2-Acetylfuran (10.0 mL, 100 mmol) was dissolved in ethanol (200 mL). To the solution was added N,N,N,N-tetra-n-butylammonium tribromide (50.6 g, 105 mmol), and the mixture was stirred at 50° C. for 1 hour. Sodium thiocyanate (8.91 g, 110 mmol) was added to the reaction mixture, and the mixture was further stirred for 1 hour. A saturated sodium bicarbonate aqueous solution was added to the reaction mixture, and the mixture extracted with ethyl acetate. The organic layer was dried over anhydrous magnesium sulfate, and the solvent was evaporated under reduced pressure. The precipitated crystals were collected by filtration to give a title compound (11.2 g, 67%).

$^1$H NMR (CDCl$_3$, δ ppm): 4.44 (s, 2H), 6.65 (dd, J=1.6, 3.7 Hz, 1H), 7.38 (dd, J=0.7, 3.7 Hz, 1H), 7.68 (dd, J=0.7, 1.6 Hz, 1H).

Reference Example 560

2-Bromo-4-(2-furyl)thiazole (2-Furoyl)methylthiocyanate (896 mg, 5.20 mmol) obtained in Reference Example 559 was dissolved in ethyl acetate (25 mL). To the solution was added acetic acid solution of hydrogen bromide (1.85 mL, 10.4 mmol) at 0° C. under an argon atmosphere, and the mixture was stirred at room temperature for 2 hours. The reaction mixture was concentrated under reduced pressure, and a saturated sodium bicarbonate aqueous solution was added thereto. The mixture was then extracted with ethyl acetate. The organic layer was dried over anhydrous magnesium sulfate, and the solvent was evaporated under reduced pressure. The resulting residue was purified by silica gel column chromatography (hexane:ethyl acetate=3:1) to give a title compound (814 mg, 68%).

$^1$H NMR (CDCl$_3$, δ ppm): 6.48 (dd, J=1.7, 3.3 Hz, 1H), 6.83 (dd, J=0.7, 3.3 Hz, 1H), 7.34 (s, 1H), 7.43 (dd, J=0.7, 1.7 Hz, 1H).

Reference Example 561

2-Formyl-4-(2-furyl)thiazole

2-Bromo-4-(2-furyl)thiazole (3.00 g, 13.0 mmol) obtained in Reference Example 560 was dissolved in THF (65 mL). To the solution was added n-hexane solution of n-butyl lithium (1.58 mol/L; 9.11 mL, 14.3 mmol) at −78° C. under an argon atmosphere, and the mixture was stirred at −78° C. for 10 minutes. DMF (2.02 mL, 26.1 mmol) added dropwise thereto, and the mixture was stirred at room temperature for 1 hour. The reaction mixture was poured into a saturated ammonium chloride aqueous solution, and the mixture was extracted with ethyl acetate. The organic layer was washed with brine and dried over anhydrous magnesium sulfate. The solvent was then evaporated under reduced pressure. The resulting residue was purified by silica gel column chromatography (hexane:ethyl acetate=3:1) to give a title compound (1.49 g, 64%).

$^1$H NMR (CDCl$_3$, δ ppm): 6.54 (dd, J=1.8, 3.5 Hz, 1H), 6.93 (dd, J=0.7, 3.5 Hz, 1H), 7.51 (dd, J=0.7, 1.8 Hz, 1H), 7.81 (s, 1H), 10.04 (s, 1H).

Reference Example 562

2-(Benzoimidazol-2-yl)-4-(2-furyl)thiazole

2-Formyl-4-(2-furyl)thiazole (116 mg, 0.647 mmol) obtained in Reference Example 561 was dissolved in nitrobenzene (5 mL). To the solution was added ortho-phenylenediamine (77.0 mg, 0.712 mmol), and the mixture was stirred at 150° C. for 10 hours. The reaction mixture was directly purified by silica gel column chromatography (chloroform/methanol=95:5) to give a title compound (81.0 mg, 47%).

$^1$H NMR (CDCl$_3$, δ ppm): 6.53 (dd, J=1.8, 3.5 Hz, 1H), 6.86-6.88 (d, J=3.5 Hz, 1H), 7.26-7.34 (m, 2H), 7.49-7.58 (m, 3H), 7.85 (d, J=1.8 Hz, 1H).

Reference Example 563

4-(2-Furyl)-2-(imidazo[4,5-b]pyridin-2-yl)thiazole

The title compound (148 mg, 49%) was obtained in the same manner as in Reference Example 562 from 2-formyl-4-(2-furyl)thiazole (200 mg, 1.12 mmol), using 2,3-diaminopyridine instead of ortho-phenylenediamine.

$^1$H NMR (DMSO-d$_6$, δ ppm): 6.69 (dd, J=1.7, 3.3 Hz, 1H), 6.98 (d, J=3.3 Hz, 1H), 7.32-7.39 (m, 1H), 7.84 (d, J=1.7 Hz, 1H), 8.07-8.11 (m, 1H), 8.12 (s, 1H), 8.46-8.48 (m, 1H).

Reference Example 564

4-(2-Furyl)-2-(imidazo[4,5-c]pyridin-2-yl)thiazole

The title compound (137 mg, 46%) was obtained in the same manner as in Reference Example 562 from 2-formyl-4-(2-furyl)thiazole (200 mg, 1.12 mmol), using 3,4-diaminopyridine instead of ortho-phenylenediamine.

$^1$H NMR (DMSO-d$_6$, δ ppm): 6.68 (dd, J=1.8, 3.3 Hz, 1H), 6.97 (d, J=3.3 Hz, 1H), 7.60-7.63 (m, 1H), 7.84 (d, J=1.8 Hz, 1H), 8.11 (s, 1H), 8.35-8.37 (m, 1H), 9.00-9.01 (m, 1H).

Reference Example 565

4-(2-Furyl)thiazole-2-thioamide

The title compound (1.01 g, 48%) was obtained in the same manner as in Reference Example 559 from 2-acetylfuran (1.00 mL, 10.0 mmol) using rubeanic acid instead of sodium thiocyanate.

$^1$H NMR (DMSO-d$_6$, δ ppm): 6.64 (dd, J=1.7, 3.3 Hz, 1H), 6.91 (dd, J=0.7, 3.3 Hz, 1H), 7.79 (dd, J=0.7, 1.7 Hz, 1H), 8.06 (s, 1H), 10.21 (br s, 2H).

Reference Example 566

4-(2-Furyl)-2-[4-(4-methoxyphenyl)imidazol-2-yl]thiazole 4-(2-Furyl)thiazole-2-thioamide (210 mg, 1.00 mmol) obtained in Reference Example 565 was dissolved in THF (25 mL). To the solution was added methyl iodide (5 mL), and the mixture was stirred at room temperature for 3 days. The reaction mixture was concentrated under reduced pressure, and 2-amino-4'-methoxyacetophenone hydrochloride (807 mg, 4.00 mmol) added thereto and the mixture was stirred overnight at 50° C. A saturated sodium bicarbonate aqueous solution was added to the reaction mixture, and the mixture was extracted with ethyl acetate. The organic layer was dried over anhydrous magnesium sulfate, and the solvent was evaporated under reduced pressure. The resulting residue was purified by silica gel column chromatography (chloroform/methanol=97:3) to give a title compound (105 mg, 31%).

$^1$H NMR (DMSO-d$_6$, δ ppm): 3.78 (s, 3H), 6.65 (dd, J=1.8, 3.3 Hz, 1H), 6.89 (d, J=3.3 Hz, 1H), 6.92-7.02 (m, 2H), 7.73-7.85 (m, 5H).

Reference Example 567

Ethyl 4-(2-furyl)thiazol-2-carboxylate

The title compound (2.55 g, 30%) was obtained in the same manner as in Reference Example 559 from acetylfuran (3.77 mL, 37.5 mmol), using ethyl thiooxamate instead of sodium thiocyanate.

¹H NMR (CDCl₃, δ ppm): 1.46 (t, J=7.1 Hz, 3H), 4.51 (q, J=7.1 Hz, 2H), 6.51 (dd, J=1.7, 3.3 Hz, 1H), 6.98 (d, J=3.3 Hz, 1H), 7.47 (d, J=1.7 Hz, 1H), 7.68 (s, 1H).

Reference Example 568

2-[4-(2-Furyl)thiazol-2-yl]-4,5,6,7-tetrahydro-1H-benzimidazole

Step 1: Ethyl 4-(2-furyl)thiazol-2-carboxylate (335 mg, 1.50 mmol) obtained in Reference Example 567 was dissolved in methanol. To the solution was added 4 mol/L of sodium hydroxide aqueous solution (2.5 mL), and the mixture was stirred at 50° C. for 1 hour. After neutralization with hydrochloric acid, the solvent was evaporated under reduced pressure. The resulting residue was dissolved in DMF (5 mL), and 2-aminocyclohexanol (518 mg, 4.50 mmol), EDC hydrochloride (864 mg, 4.50 mmol), and 1-hydroxybenzotriazole monohydrate (689 mg, 4.50 mmol) were added thereto, then the mixture was stirred at room temperature for 3 hours. Water and ethyl acetate were added to the reaction mixture, and the mixture was extracted. The organic layer was washed with brine and dried over anhydrous magnesium sulfate. The solvent was then evaporated under reduced pressure. The resulting residue was purified by silica gel column chromatography (hexane:ethyl acetate=1:1) to give 4-(2-furyl)-N-(2-hydroxycyclohexyl)thiazole-2-carboxamide (413 mg, 94%).

¹H NMR (CDCl₃, δ ppm): 1.26-1.49 (m, 4H), 1.74-1.81 (m, 2H), 2.04-2.16 (m, 2H), 3.48-3.55 (m, 1H), 3.78-4.00 (m, 1H), 6.51 (dd, J=1.8, 3.3 Hz, 1H), 6.81 (dd, J=0.7, 3.3 Hz, 1H), 7.48 (dd, J=0.7, 1.8 Hz, 1H), 7.61 (s, 1H).

Step 2: Oxalyl chloride (0.776 mL, 1.55 mol) and dimethyl sulfoxide (0.240 mL, 3.38 mmol) were dissolved in dichloromethane (3 mL), and the mixture was stirred at −60° C. for 10 minutes. To the solution was added 4-(2-furyl)-N-(2-hydroxycyclohexyl)thiazole-2-carboxamide (413 mg, 1.41 mmol) obtained in Step 1 and the mixture was stirred for 15 minutes. Triethylamine (0.983 mL, 7.05 mmol) was added to the mixture, and the mixture was stirred at room temperature for 10 minutes, then water and ethyl acetate were added thereto and the mixture was extracted. The organic layer was washed with brine and dried over anhydrous magnesium sulfate. The solvent was then evaporated under reduced pressure, and the resulting residue was purified by silica gel column chromatography (hexane:ethyl acetate=1:1) to give 4-(2-furyl)-N-(2-oxocyclohexyl)thiazole-2-carboxamide (339 mg, 83%).

¹H NMR (CDCl₃, δ ppm): 1.54-1.96 (m, 4H), 2.16-2.19 (m, 1H), 2.42-2.78 (m, 3H), 4.62-4.72 (m, 1H), 6.52 (dd, J=1.8, 3.3 Hz, 1H), 6.90 (dd, J=0.7, 3.3 Hz, 1H), 7.47 (dd, J=0.7, 1.8 Hz, 1H), 7.62 (s, 1H), 8.12-8.14 (m, 1H).

Step 3: 4-(2-Furyl)-N-(2-oxocyclohexyl)thiazole-2-carboxamide (239 mg, 0.823 mmol) obtained in Step 2 and ammonium trifluoroacetate (1.00 g, 7.63 mmol) were stirred at 140° C. for 2 hours, and water and ethyl acetate were added thereto, then the mixture was extracted. The organic layer was washed with brine and dried over anhydrous magnesium sulfate. The solvent was then evaporated under reduced pressure, and the resulting residue was purified by silica gel column chromatography (hexane:ethyl acetate=1:1) to give a title compound (63.0 mg, 28%).

¹H NMR (CDCl₃, δ ppm): 1.81-1.86 (m, 4H), 2.57-2.65 (m, 4H), 6.48 (dd, J=1.8, 3.3 Hz, 1H), 6.76 (dd, J=0.7, 3.3 Hz, 1H), 7.31 (s, 1H), 7.46 (dd, J=0.7, 1.8 Hz, 1H).

Reference Example 569

2-[4-(2-Furyl)thiazol-2-yl]-3,4,6,7-tetrahydrothiopyrano][3,4-d]imidazole

Step 1: 4-Oxothiane (2.32 g, 20.0 mmol) was dissolved in ethanol. To the solution was added hydroxylamine hydrochloride (2.78 g, 40.0 mmol) and potassium carbonate (5.52 g, 40.0 mmol), and the mixture was heated to reflux for 1 hour. Water and ethyl acetate were added to the mixture, and the mixture was extracted. The organic layer was washed with brine and dried over anhydrous magnesium sulfate. The solvent was then evaporated under reduced pressure. The resulting residue was dissolved in pyridine (20 mL). p-Toluenesulfonyl chloride (6.46 g, 24.0 mmol) was added at −20° C., and the mixture was stirred at −20° C. for 1 hour. Water and ethyl acetate were added to the mixture, and the mixture was extracted. The organic layer was washed with brine and dried over anhydrous magnesium sulfate. The solvent was then evaporated under reduced pressure. The resulting residue was dissolved in ethanol, and an ethanol solution of potassium ethoxide (4 mol/L; 15.7 mL, 40.0 mmol) was added to the solution at 0° C., then the mixture was stirred for 1 hour. After stirring the mixture at 50° C. for another 1 hour, water and ethyl acetate were added thereto, and the mixture was extracted. The organic layer was washed with brine and dried over anhydrous magnesium sulfate. The solvent was then evaporated under reduced pressure. The resulting residue was purified by silica gel column chromatography (ethyl acetate) to give 3-amino-4,4-diethoxythiopyran (2.31 g, 56%).

¹H NMR (CDCl₃, δ ppm): 1.19 (t, J=7.1 Hz, 6H), 1.85-1.98 (m, 2H), 2.28-2.37 (m, 1H), 2.50-2.57 (m, 1H), 2.69-2.84 (m, 1H), 3.14-3.28 (m, 2H), 3.42 (q, J=7.1 Hz, 4H).

Step 2: 4-(2-Furyl)thiazol-2-thioamide (210 mg, 1.00 mmol) obtained in Reference Example 565 was dissolved in THF (25 mL). To the solution was added methyl iodide (5 mL), and the mixture was stirred at room temperature for 3 days. After evaporating the solvent under reduced pressure, 3-amino-4,4-diethoxythiopyran (821 mg, 4.00 mmol) obtained in Step 1 was added thereto and the mixture was stirred overnight at 50° C. The solvent was evaporated under reduced pressure. The resulting residue was dissolved in 2 mL of hydrochloric acid (6 mol/L); and the mixture was stirred at room temperature for 1 hour. After neutralizing the reaction mixture with sodium hydroxide, water and ethyl acetate were added thereto, and the mixture was extracted. The organic layer was dried over anhydrous magnesium sulfate, and the solvent was evaporated under reduced pressure. The solvent was evaporated under reduced pressure, and the resulting residue was purified by silica gel column chromatography (chloroform/methanol=97:3) to give a title compound (270 mg, 93%).

¹H NMR (CDCl₃, δ ppm): 2.88-3.25 (m, 4H), 3.72-3.90 (m, 2H), 6.48 (dd, J=1.8, 3.3 Hz, 1H), 6.75 (d, J=3.3 Hz, 1H), 7.41 (s, 1H), 7.46 (d, J=1.8 Hz, 1H).

Reference Example 570

4-(2-Furyl)-N-phenylthiazole-2-carboxamide

Ethyl 4-(2-furyl)thiazol-2-carboxylate (223 mg, 1.00 mmol) obtained in Reference Example 567 was dissolved in methanol. To the solution was added 2 mL of sodium hydroxide aqueous solution (4 mol/L), and the mixture was stirred at 50° C. for 1 hour. After neutralization with hydrochloric acid, the solvent was evaporated under reduced pressure. The resulting residue was dissolved in DMF (5 mL). To the solution were added aniline (0.273 mL, 3.00 mmol), EDC hydrochloride (576 mg, 3.00 mmol), and 1-hydroxybenzotriazole monohydrate (459 mg, 3.00 mmol), and the mixture was stirred at room temperature for 3 hours. Water was added to the reaction mixture, and precipitated crystals were collected by filtration to give a title compound (242 mg, 90%).

$^1$H NMR (CDCl$_3$, δ ppm): 6.54 (dd, J=1.8, 3.5 Hz, 1H), 6.90 (dd, J=0.7, 3.5 Hz, 1H), 7.16-7.22 (m, 1H), 7.38-7.43 (m, 2H), 7.50 (dd, J=0.7, 1.8 Hz, 1H), 7.69 (s, 1H), 7.73-7.76 (m, 2H).

Reference Example 571

4-(2-Furyl)-N-isobutylthiazol-2-carboxamide

The title compound (537 mg, 96%) was obtained in the same manner as in Reference Example 570 from ethyl 4-(2-furyl)thiazol-2-carboxylate (500 mg, 2.24 mmol), using isobutylamine instead of aniline.

$^1$H NMR (CDCl$_3$, δ ppm): 0.98-1.02 (m, 6H), 1.82-2.04 (m, 1H), 3.29-3.34 (m, 2H), 6.51 (dd, J=1.8, 3.5 Hz, 1H), 6.82 (d, J=3.5 Hz, 1H), 7.47 (d, J=1.8 Hz, 1H), 7.62 (s, 1H).

INDUSTRIAL APPLICABILITY

The present invention can provide therapeutic and/or preventive agents for a sleep disorder comprising a thiazole derivative or a pharmaceutically acceptable salt thereof as an active ingredient.

The invention claimed is:
1. A method for treating a sleep disorder selected from the group consisting of narcolepsy, hypersomnia and a circadian rhythm sleep disorder, which comprises administering an effective amount of a thiazole derivative represented by the general formula (I):

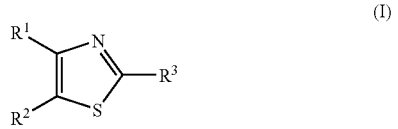

(I)

wherein $R^1$ represents a substituted or unsubstituted five-membered aromatic heterocyclic group having at least one oxygen atom,
$R^2$ represents halogen, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, substituted or unsubstituted aromatic heterocyclic alkyl, —NR$^4$R$^5$ (wherein R$^4$ and R$^5$ may be the same or different, and each represents a hydrogen atom, substituted or unsubstituted lower alkyl, substituted or unsubstituted lower alkenyl, substituted or unsubstituted lower alkynyl, substituted or unsubstituted lower alkanoyl, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, or substituted or unsubstituted aromatic heterocyclic alkyl, or R$^4$ and R$^5$ are combined together with the adjacent nitrogen atom thereto to represent a substituted or unsubstituted nitrogen-containing heterocyclic group), —COR$^6$ {wherein R$^6$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, substituted or unsubstituted aromatic heterocyclic alkyl, —NR$^7$R$^8$ (wherein R$^7$ and R$^8$ may be the same or different, and each represents a hydrogen atom, substituted or unsubstituted lower alkyl, substituted or unsubstituted lower alkenyl, substituted or unsubstituted lower alkynyl, substituted or unsubstituted lower alkanoyl, substituted or unsubstituted lower alkoxy, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, or substituted or unsubstituted aromatic heterocyclic alkyl, or R$^7$ and R$^8$ are combined together with the adjacent nitrogen atom thereto to represent a substituted or unsubstituted nitrogen-containing heterocyclic group), or —OR$^9$ (wherein R$^9$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, or substituted or unsubstituted aromatic heterocyclic alkyl)}, and $R^3$ represents —NR$^{10}$R$^{11}$ {wherein R$^{10}$ and R$^{11}$ may be the same or different, and each represents a hydrogen atom, substituted or unsubstituted lower alkyl, substituted or unsubstituted lower alkenyl, substituted or unsubstituted lower alkynyl, substituted or unsubstituted aralkyl, a substituted or unsubstituted aliphatic heterocyclic alkyl, substituted or unsubstituted aromatic heterocyclic alkyl, —COR$^{12}$ [wherein R$^{12}$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, substituted or unsubstituted aromatic heterocyclic alkyl, —NR$^{13}$R$^{14}$ (wherein R$^{13}$ and R$^{14}$ may be the same or different, and each represents a hydrogen atom, substituted or unsubstituted lower alkyl, substituted or unsubstituted lower alkenyl, substituted or unsubstituted lower alkynyl, substituted or unsubstituted lower alkanoyl, substituted or unsubstituted lower alkoxy, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, or substituted or unsubstituted aromatic heterocyclic alkyl, or $R^{13}$ and $R^{14}$ are combined together with the adjacent nitrogen atom thereto to represent a substituted or unsubstituted nitrogen-containing heterocyclic group), or $-OR^{15}$ (wherein $R^{15}$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, a substituted or unsubstituted aliphatic heterocyclic group, a substituted or unsubstituted aromatic heterocyclic group, substituted or unsubstituted aliphatic heterocyclic alkyl, or substituted or unsubstituted aromatic heterocyclic alkyl)], or $R^{10}$ and $R^{11}$ are combined together with the adjacent nitrogen atom thereto to represent a substituted or unsubstituted nitrogen-containing heterocyclic group}, $-CONHR^{16}$ (wherein $R^{16}$ represents a hydrogen atom, substituted or unsubstituted lower alkyl, substituted or unsubstituted lower alkenyl, substituted or unsubstituted lower alkynyl, substituted or unsubstituted lower alkanoyl, substituted or unsubstituted cycloalkyl, substituted or unsubstituted aryl, substituted or unsubstituted aralkyl, substituted or unsubstituted aroyl, a substituted or unsubstituted aliphatic heterocyclic group, a substituted or unsubstituted aromatic heterocyclic group, substituted or unsubstituted aliphatic heterocyclic alkyl, or substituted or unsubstituted aromatic heterocyclic alkyl), or the general formula (II)

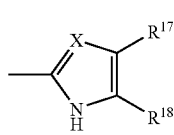

(II)

(wherein =X— represents =CH— or =N—, and $R^{17}$ and $R^{18}$ may be the same or different, and each represents a hydrogen atom, halogen, hydroxy, nitro, azido, amino, cyano, carboxy, formyl, substituted or unsubstituted lower alkyl, substituted or unsubstituted lower alkenyl, substituted or unsubstituted lower alkynyl, substituted or unsubstituted lower alkanoyl, substituted or unsubstituted lower alkoxy, substituted or unsubstituted cycloalkyl, substituted or unsubstituted lower alkylamino, substituted or unsubstituted di-(lower alkyl)amino, substituted or unsubstituted aryl, substituted or unsubstituted aralkyl, substituted or unsubstituted aroyl, a substituted or unsubstituted aliphatic heterocyclic group, a substituted or unsubstituted aromatic heterocyclic group, substituted or unsubstituted aliphatic heterocyclic alkyl, or substituted or unsubstituted aromatic heterocyclic alkyl, or $R^{17}$ and $R^{18}$ are combined together with the respectively adjacent two carbon atoms thereto to form a substituted or unsubstituted carbon ring or a substituted or unsubstituted heterocyclic ring),
or a pharmaceutically acceptable salt thereof, as an active ingredient.

2. The method according to claim 1, wherein $R^1$ is substituted or unsubstituted furyl.

3. The method according to claim 2, wherein $R^2$ is $-COR^6$.

4. The method according to claim 2, wherein $R^2$ is a substituted or unsubstituted aliphatic heterocyclic group.

5. The method according to claim 2, wherein $R^2$ is a substituted or unsubstituted aromatic heterocyclic group.

6. The method according to claim 3, wherein $R^6$ is substituted or unsubstituted cycloalkyl, substituted or unsubstituted aryl, a substituted or unsubstituted aromatic heterocyclic group, or a substituted or unsubstituted aliphatic heterocyclic group.

7. The method according to claim 3, wherein $R^6$ is a substituted or unsubstituted aromatic heterocyclic group.

8. The method according to claim 3, wherein $R^6$ is a substituted or unsubstituted aliphatic heterocyclic group.

9. The method according to claim 3, wherein $R^6$ is a substituted or unsubstituted aliphatic heterocyclic group having at least one oxygen atom.

10. The method according to claim 3, wherein $R^6$ is substituted or unsubstituted lower alkyl.

11. The method according to claim 1, wherein $R^3$ is $-NR^{10}R^{11}$.

12. The method according to claim 1, wherein $R^3$ is $-NHR^{11}$.

13. The method according to claim 12, wherein $R^{11}$ is $-COR^{12}$.

14. The method according to claim 13, wherein $R^{12}$ is substituted or unsubstituted aryl.

15. The method according to claim 13, wherein $R^{12}$ is a substituted or unsubstituted aromatic heterocyclic group.

16. The method according to claim 13, wherein $R^{12}$ is $-OR^{15}$.

17. The method according to claim 13, wherein $R^{12}$ is substituted or unsubstituted aromatic heterocyclic alkyl.

18. The method according to claim 13, wherein $R^{12}$ is substituted or unsubstituted aliphatic heterocyclic alkyl.

19. The method according to claim 1, wherein $R^3$ is $-CONHR^{16}$.

20. The method according to claim 1, wherein $R^3$ is the general formula (II)

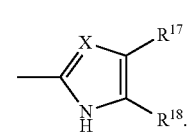

(II)

21. The method according to claim 2, wherein $R^3$ is $-NHR^{11}$.

22. The method according to claim 3, wherein $R^3$ is $-NHR^{11}$.

23. The method according to claim 21, wherein $R^{11}$ is $-COR^{12}$.

24. The method according to claim 22, wherein $R^{11}$ is $-COR^{12}$.

25. The method according to claim 1, wherein the thiazole derivative is a compound represented by any of formulae (1), (5), (7), (8), (11), (78), (95), (99), (114), (136), (142), (157), (336), (360), (361), (365), (367), (373) (376), (407), (409), (416), (420), (463), or (508):

(1)
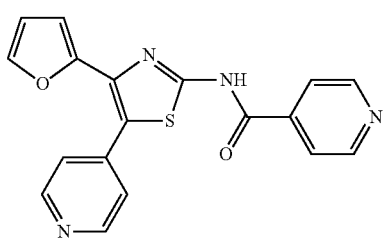
(5)
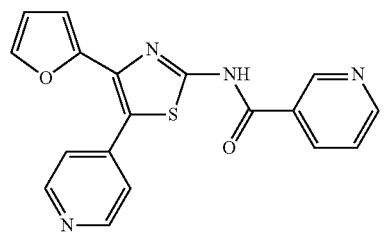
(7)
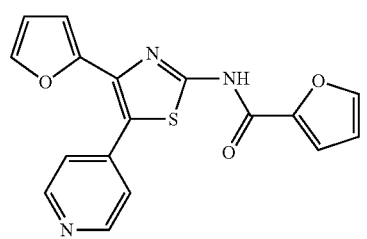
(8)
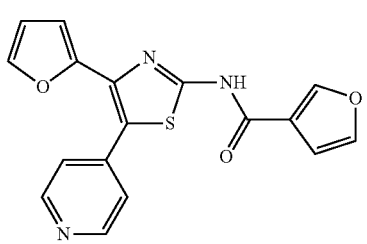
(11)
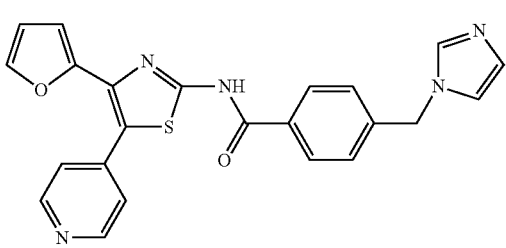
(78)
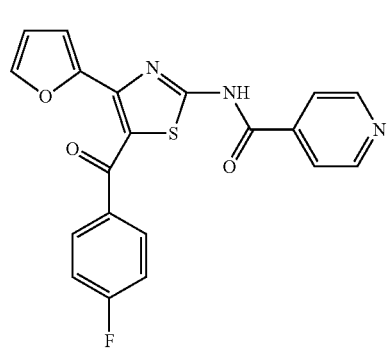
-continued
(95)
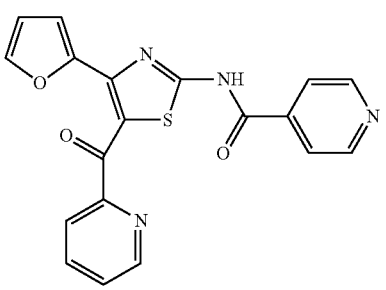
(99)
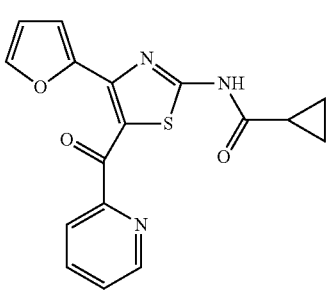
(114)
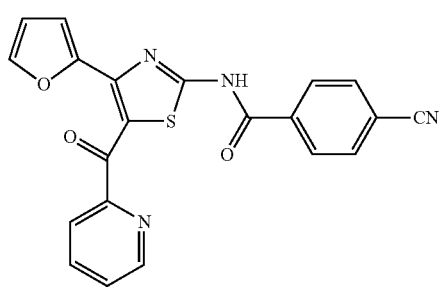
(136)
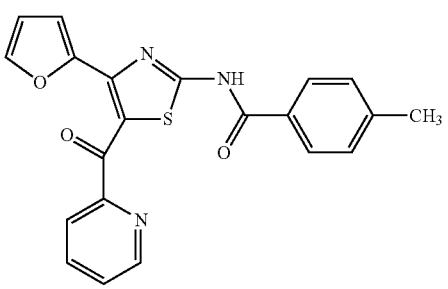
(142)
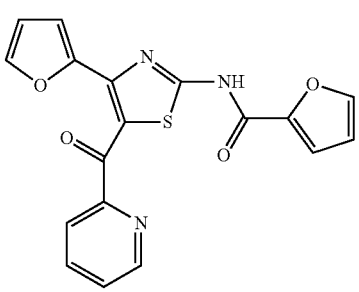

-continued
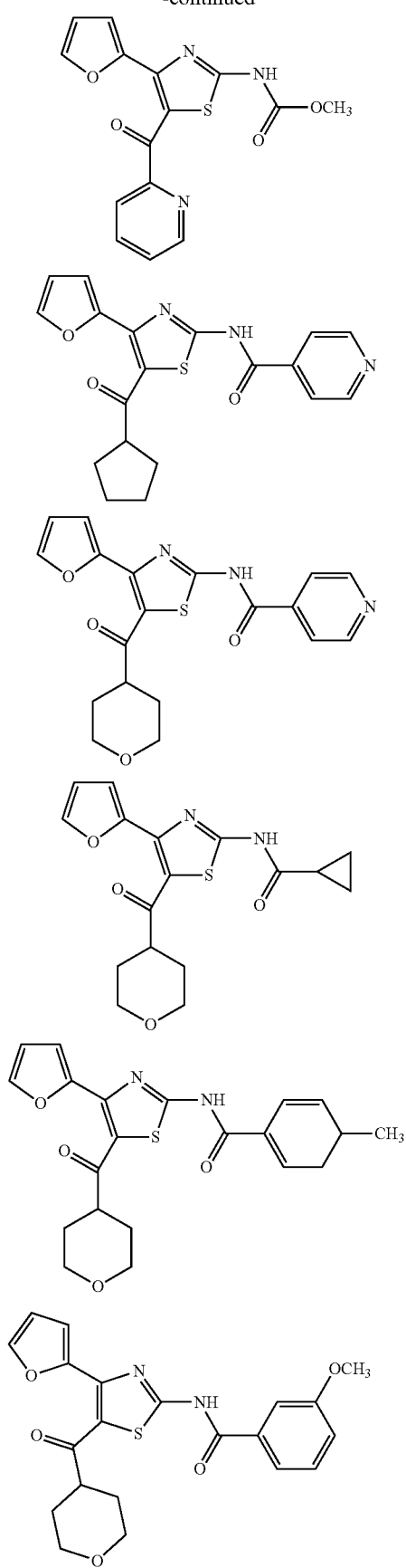
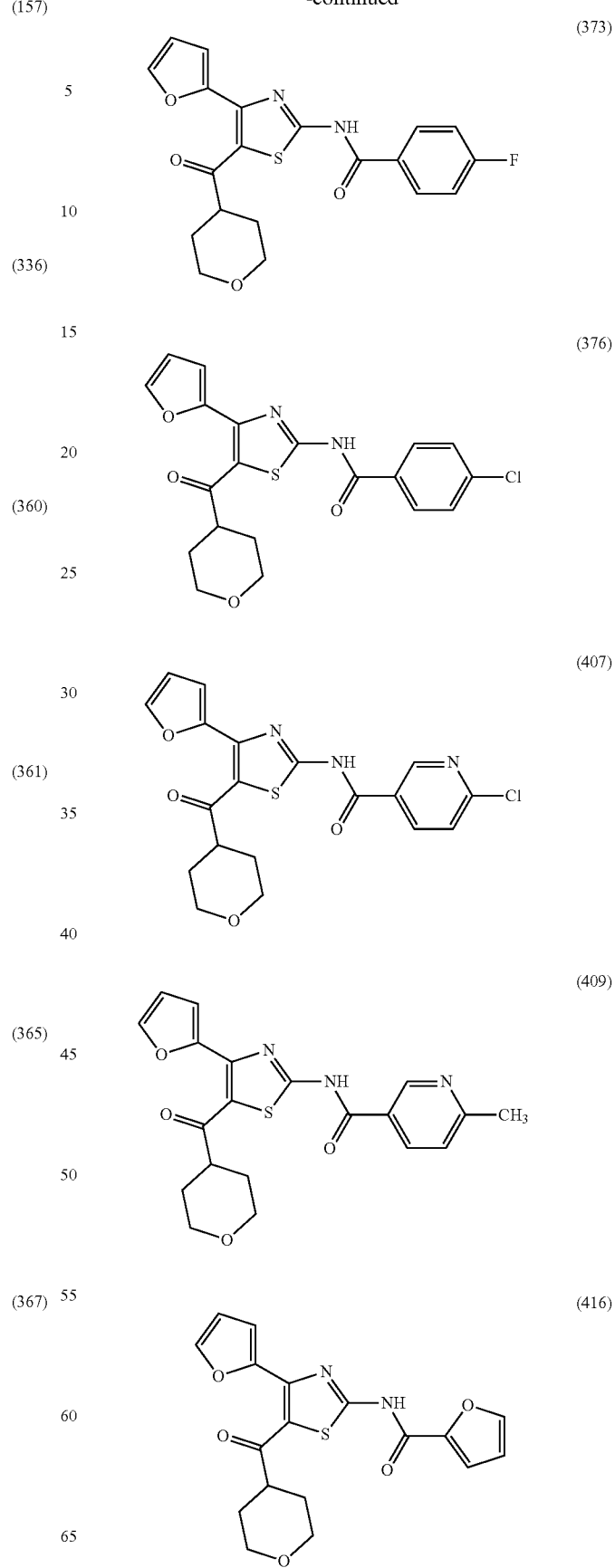

(420)

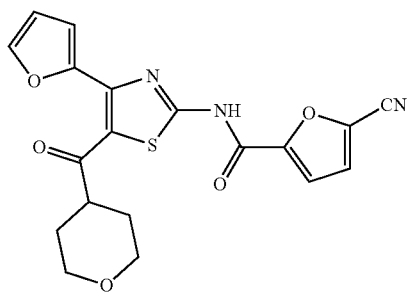

(463)

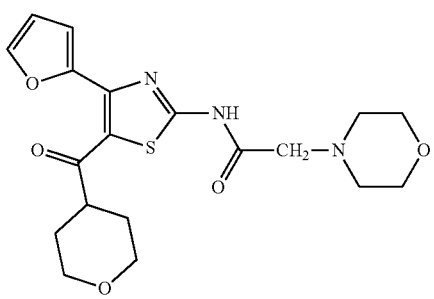

(508)

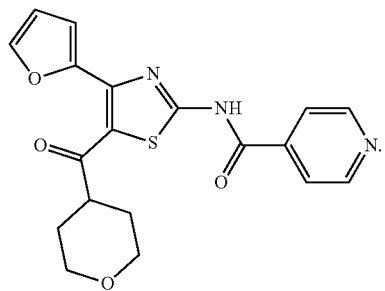

26. The method according to any one of claims 1 to 20 or 21-25, wherein the sleep disorder is a circadian rhythm sleep disorder.

27. The method according to any one of claims 1 to 20 or 21-25, wherein the sleep disorder is hypersomnia.

28. The method according to any one of claims 1 to 20 or 21-25, wherein the sleep disorder is narcolepsy.

29. The method according to claim 26, wherein the circadian rhythm sleep disorder is recurrent hypersomnia, idiopathic hypersomnia, or posttraumatic hypersomnia.

* * * * *

UNITED STATES PATENT AND TRADEMARK OFFICE
CERTIFICATE OF CORRECTION

| | | |
|---|---|---|
| PATENT NO. | : 7,928,098 B2 | |
| APPLICATION NO. | : 11/997585 | |
| DATED | : April 19, 2011 | |
| INVENTOR(S) | : Noriaki Uesaka et al. | |

It is certified that error appears in the above-identified patent and that said Letters Patent is hereby corrected as shown below:

COLUMN 2:

Line 61, "20040053982" should read --2004/0053982--.

COLUMN 7:

Line 2, "disorders." should read --disorder.--; and
Line 18, "disorders." should read --disorder.--.

COLUMN 15:

Line 8, "$R^{Y4}$" should read --$R^{Y3}$--.

COLUMN 17:

Line 37, "and the like;" should be deleted;
Line 44, "and the like;" should be deleted;
Line 48, "and" should be deleted; and
Line 49, "the like;" should be deleted.

COLUMN 18:

Line 2, "—$OR^{18}$" should read -- —$OR^{15}$--.

COLUMN 25:

Line 31, "Compound (Iei)" should read --Compound (Ie-i)--.

Signed and Sealed this
Eighteenth Day of September, 2012

David J. Kappos
*Director of the United States Patent and Trademark Office*

CERTIFICATE OF CORRECTION (continued)
U.S. Pat. No. 7,928,098 B2

COLUMN 29:

Line 38, "Step 21" should read --¶ Step 21--.

COLUMN 30:

Line 26, "Step 24" should read --¶ Step 24--.

COLUMN 36:

Line 14, "it" should read --they--.

COLUMN 132:

Line 6, "(3H-" should read --($^{3}$H- --; and
    Line 67, "a measurement of time" should read --measuring time for--.

COLUMN 133:

Line 49, "for" should read --of--;
    Line 51, "suppress" should read --suppresses--; and
    Line 55, "to" should read --for--.

COLUMN 139:

Line 45, "[M+H]$^{-}$ 338." should read --[M+H]$^{+}$ 338--.

COLUMN 152:

Line 2, "(dd, J=4.6Hz, 2H)," should read --(dd, J=1.6, 4.6Hz, 2H),--; and
    Line 13, "on/z:" should read --m/z:--.

COLUMN 154:

Line 65, "1H)," (first occurrence) should read --1H), 7.88 (dd, J=7.6, 7.8 Hz, 1H), 7.89
       (dd, J=0.8, 1.6 Hz,--.

COLUMN 170:

Line 18, "(g," should read --(q,--.

COLUMN 178:

Line 5, "(2-chloropyrimidin" should read --(2-chloropyridin--; and
    Line 58, "195-20°C." should read --195-205°C.--.

CERTIFICATE OF CORRECTION (continued)
U.S. Pat. No. 7,928,098 B2

COLUMN 188:

Line 2, "[M-H]$^+$" should read --[M-H]$^-$--.

COLUMN 193:

Line 6, "Carbamate" should read --carbamate--.

COLUMN 199:

Line 2, "[M-H]$^+$" should read --[M-H]$^-$--.

COLUMN 203:

Line 26, "3.85-3.93 (m," should read --3.85-3.93 (m, 2H), 6.71 (dd, J=1.6, 3.2 Hz, 1H), 7.45 (d, J=3.2 Hz,--.

COLUMN 209:

Line 41, "(S," should read --(s,--.

COLUMN 219:

Line 14, "110-" should read --101- --.

COLUMN 229:

Line 20, "6,7-tetrahydrothiopyrano[3,4-c]imidazol-2-yl)thiaz-" should read --6,7-tetrahydrothiopyrano[3,4-d]imidazol-2-yl)thiaz- --.

COLUMN 231:

Line 24, "(Compound B)" should read --(Compound b)--.

COLUMN 233:

Line 4, "(s, 211)," should read --(s, 2H),--.